United States Patent
Liao et al.

(10) Patent No.: US 10,358,446 B2
(45) Date of Patent: Jul. 23, 2019

(54) BRUTON'S TYROSINE KINASE INHIBITORS

(71) Applicants: Zibo Biopolar Changsheng Pharmaceutical Co. Ltd., Zibo, Shangdong (CN); Shanghai Institute of Materia Medica, Chinese Academy of Sciences, Shanghai (CN)

(72) Inventors: Xibin Liao, Edison, NJ (US); Jia Li, Shanghai (CN); Zhijian Lu, Plainfield, IN (US); Yubo Zhou, Shanghai (CN); Anhui Gao, Shanghai (CN)

(73) Assignees: ZIBO BIOPOLAR CHANGSHENG PHARMACEUTICAL CO., LTD., Zibo (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/763,095

(22) PCT Filed: Oct. 3, 2016

(86) PCT No.: PCT/US2016/055096
§ 371 (c)(1),
(2) Date: Mar. 24, 2018

(87) PCT Pub. No.: WO2017/066014
PCT Pub. Date: Apr. 20, 2017

(65) Prior Publication Data
US 2018/0222904 A1   Aug. 9, 2018

Related U.S. Application Data

(60) Provisional application No. 62/241,184, filed on Oct. 14, 2015.

(51) Int. Cl.
| | | |
|---|---|---|
| C07D 471/04 | (2006.01) | |
| A61K 31/437 | (2006.01) | |
| C07D 473/34 | (2006.01) | |
| A61K 31/52 | (2006.01) | |
| A61P 35/00 | (2006.01) | |
| A61P 29/00 | (2006.01) | |
| A61K 31/4184 | (2006.01) | |
| C07D 235/22 | (2006.01) | |
| C07D 487/04 | (2006.01) | |
| A61K 31/42 | (2006.01) | |
| A61K 31/4545 | (2006.01) | |
| A61K 31/501 | (2006.01) | |
| A61K 31/519 | (2006.01) | |
| A61K 31/5377 | (2006.01) | |
| A61K 31/56 | (2006.01) | |
| A61K 45/06 | (2006.01) | |

(52) U.S. Cl.
CPC ........ *C07D 471/04* (2013.01); *A61K 31/4184* (2013.01); *A61K 31/42* (2013.01); *A61K 31/437* (2013.01); *A61K 31/4545* (2013.01); *A61K 31/501* (2013.01); *A61K 31/519* (2013.01); *A61K 31/52* (2013.01); *A61K 31/5377* (2013.01); *A61K 31/56* (2013.01); *A61K 45/06* (2013.01); *A61P 29/00* (2018.01); *A61P 35/00* (2018.01); *C07D 235/22* (2013.01); *C07D 473/34* (2013.01); *C07D 487/04* (2013.01)

(58) Field of Classification Search
CPC ........................... A61K 31/437; C07D 471/04
See application file for complete search history.

(56) References Cited

U.S. PATENT DOCUMENTS

| | | |
|---|---|---|
| 6,489,338 B2 | 12/2002 | Yu et al. |
| 2015/0094299 A1 | 4/2015 | Yamamoto et al. |
| 2017/0129890 A1* | 5/2017 | Goldstein ............ C07D 471/04 |

FOREIGN PATENT DOCUMENTS

WO   2011152351 A1   12/2011

OTHER PUBLICATIONS

Stella (J. Pharmaceutical Sciences, 2010, 99(12), pp. 4755-4765).*
Singh et al. "The resurgence of covalent drugs", Nature Reviews Drug Discovery, Apr. 2011, vol. 10, pp. 307-317.

* cited by examiner

*Primary Examiner* — Susanna Moore
(74) *Attorney, Agent, or Firm* — SZDC Law P.C.

(57) ABSTRACT

Bruton's tyrosine kinase (Btk) inhibitors have the following Formula (I):

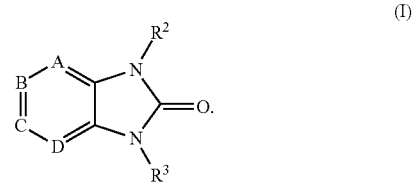

6 Claims, No Drawings

BRUTON'S TYROSINE KINASE INHIBITORS

This application is a national stage application of PCT/US2016/055096, filed on Oct. 3, 2016, which claims priority to U.S. Provisional Patent Application No. 62/241,184, filed on Oct. 14, 2015, which is incorporated by reference for all purposes as if fully set forth herein.

FIELD OF THE INVENTION

Described herein are Bruton's tyrosine kinase inhibitors, methods of making such inhibitors, and pharmaceutical compositions containing such inhibitors.

BACKGROUND OF THE INVENTION

Bruton's tyrosine kinase (Btk) plays an important role in signal transduction in B cells and is a factor that contributes to the survival, differentiation, proliferation, and activation of B cells. There is currently a need for methods of treating diseases in which B cells or mast cells participate. Btk is also known to participate in mast cell activation and in the physiological functions of platelets. Therefore, Btk inhibitors are effective for the treatment of diseases in which B cells or mast cells participate, for example, allergic diseases, autoimmune diseases, inflammatory diseases, thromboembolic diseases, and cancers.

SUMMARY OF THE INVENTION

The Btk inhibitors described herein have the following Formula (I):

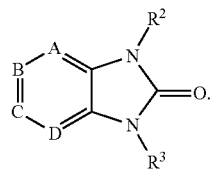

(I)

In Formula (I), A is N or $CR^1$; B, C, and D are each N or C—H, with the proviso that only one or two of A, B, C, and D can be N. $R^1$ is hydrogen, amino, OH, CN, —NHOH or $CONH_2$; $R^2$ is

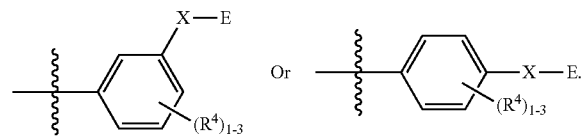

—X-E is one of the followings: (1) X is O, $OCR^aR^b$, S(O), $S(O)_2$, $CR^aR^b$, $NR^c(C=O)$, $C=ONR^c$ or a bond; and E is a hydrogen, an aryl or a heteroaryl substituted with one to three $R^5$ substituents; or a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or (2) —X-E is hydrogen, halogen, —$OR^a$, —$O(CH_2)_{1-4}R^a$, —CN, —$NO_2$. $R^4$ and $R^5$ are each independently selected from the group consisting of hydrogen, halogen, hydroxy, cyano, $OCF_3$, $OCF_2H$, $C_{1-6}$ alkyl, optionally substituted with one to five fluorines, $C_{3-6}$ cycloalkyl, optionally substituted with one to five fluorines, $C_{1-4}$ alkoxy, optionally substituted with one to five fluorines, $C_{1-4}$ alkylthio, optionally substituted with one to five fluorines, $C_{1-4}$ alkylsulfonyl, optionally substituted with one to five fluorines, carboxy, $C_{1-4}$ alkyloxycarbonyl, and $C_{1-4}$ alkylcarbonyl. $R^a$ and $R^b$ are each independently hydrogen, fluorine, or $C_{1-3}$ alkyl, optionally substituted with one to five fluorines. $R^c$ is hydrogen or $C_{1-3}$ alkyl, optionally substituted with one to five fluorines. $R^3$ is a group having a double bond.

Further described is an isomer or tautomer thereof, a pharmaceutical acceptable solvate thereof, or a pharmaceutical acceptable prodrug thereof.

In one aspect, in Formula (I), E is selected from aryl, heteroaryl, carbocyclyl, heterocyclyl, any of which is optionally substituted with one to three $R^5$ substituents.

In another aspect, in Formula (I), $R^3$ is selected from the group consisting of:

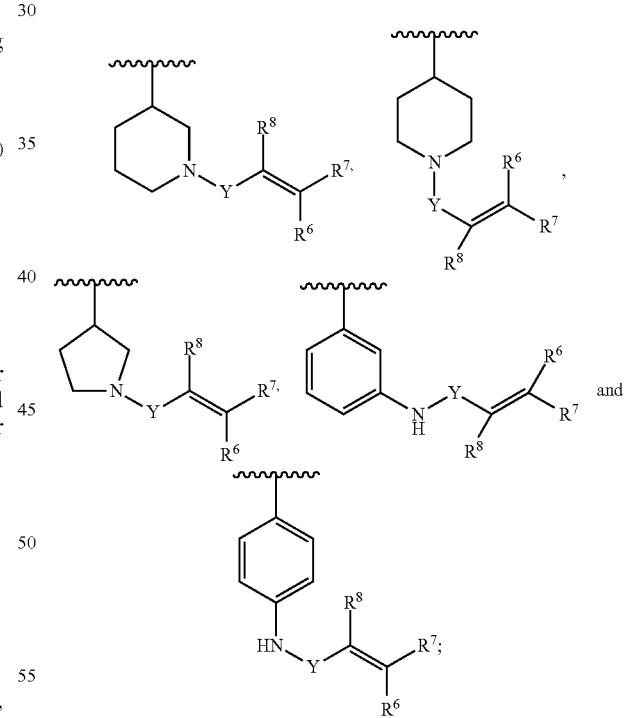

Y is C(=O); OC(=O), NHC(=O), S=O, $S(=O)_2$, or $NHS(=O)_2$; $R^6$, $R^7$, $R^8$ are each independently hydrogen, halogen, CN, $C_{1-4}$ alkyl, $C_{1-6}$ alkoxyalkyl, $C_{1-8}$ alkylaminoalkyl, or $C_{1-4}$ alkylphenyl; or $R^7$ and $R^8$ taken together form a bond.

In another aspect, in Formula (I), $R^3$ is selected from the group consisting of:

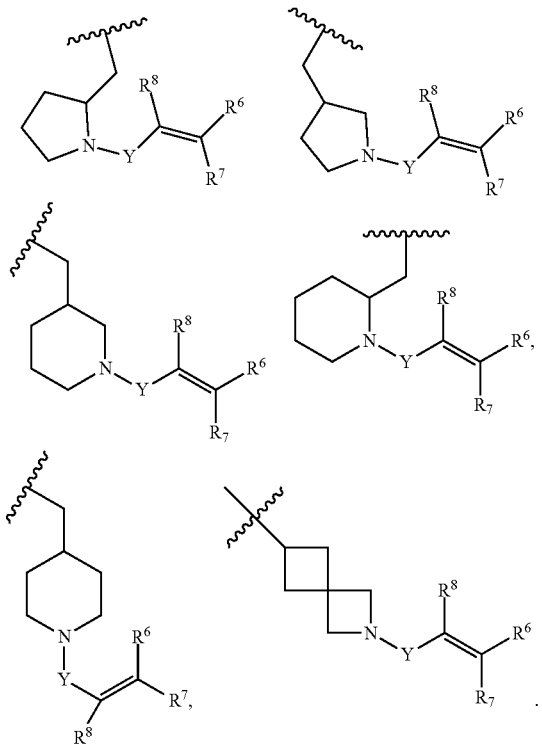

Y is C(=O); OC(=O), NHC(=O), S=O, S(=O)$_2$, or NHS(=O)$_2$; R$^6$, R$^7$, R$^8$ are each independently hydrogen, halogen, CN, C$_{1-4}$ alkyl, C$_{1-6}$ alkoxyalkyl, C$_{1-8}$ alkylaminoalkyl, or C$_{1-4}$ alkylphenyl; or R$^7$ and R$^8$ taken together form a bond.

In another aspect, in Formula (I), A is CR$^1$, and one of B, C, and D is N.

In another aspect, in Formula (I), A is CR$^1$, B is N, and C and D are CR$^1$.

In another aspect, described herein is a pharmaceutical composition including a therapeutically effective amount of the compound of Formula (I), and a pharmaceutically acceptable excipient.

In another aspect, described herein is a method for treating an autoimmune disease comprising administering to a subject in need thereof a composition containing a therapeutically effective amount of the compound of Formula (I) and other therapeutic agents.

In another aspect, the Btk inhibitors described herein are selected from the group consisting of (R)-1-(1-acryloylpyrrolidin-3-yl)-3-(4-phenoxyphenyl)-1H-imidazo[4,5-c]pyridin-2(3H)-one, (R)-1-(1-acryloylpyrrolidin-3-yl)-3-(4-(3-methoxyphenoxy)phenyl)-1H-imidazo[4,5-c]pyridin-2(3H)-one, N-(3-(2-oxo-3-(4-phenoxyphenyl)-2,3-dihydro-1H-imidazo[4,5-c]pyridin-1-yl), (R)-1-(1-acryloylpyrrolidin-3-yl)-3-(4-(m-tolyloxy)phenyl)-1H-imidazo[4,5-c]pyridin-2(3H)-one, (R)-1-(1-acryloylpyrrolidin-3-yl)-3-(3-chloro-4-phenoxyphenyl)-1H-imidazo[4,5-c] pyridin-2(3H)-one, 1-(1-acryloylpyrrolidin-3-yl)-3-(3-chloro-4-(3-(trifluoromethyl)phenoxy)phenyl)-1H-imidazo[4,5-c]pyridin-2(3H)-one, N-(3-(2-oxo-3-(3-phenoxyphenyl)-2,3-dihydro-1H-imidazo[4,5-c]pyridin-1-yl)phenyl)acrylamide, (S)-1-(1-acryloylpiperidin-3-yl)-3-(4-(2-chloro-3-methoxyphenoxy)phenyl)-1H-imidazo[4,5-c]pyridin-2(3H)-one, (R)-1-(1-acryloylpyrrolidin-3-yl)-3-(4-(3-chloro-5-methoxyphenoxy)phenyl)-1H-imidazo[4,5-c]pyridin-2(3H)-one, (R)-1-(1-acryloylpyrrolidin-3-yl)-3-(4-(3-cyclopropylphenoxy)phenyl)-1H-imidazo[4,5-c]pyridin-2(3H)-one, (R)-1-(3-(2-thioxo-3-(4-(m-tolyloxy) phenyl)-2,3-dihydro-1H-imidazo[4,5-c]pyridin-1-yl) pyrrolidin-1-yl)prop-2-en-1-one, (R)-1-(1-acryloylpiperidin-3-yl)-3-(3-fluoro-4-phenoxyphenyl)-1H-imidazo[4,5-c]pyridin-2(3H)-one, (R)-1-(1-acryloylpiperidin-3-yl)-3-(4-(m-tolyloxy)phenyl)-1H-imidazo[4,5-c]pyridin-2(3H)-one, 1-((1-acryloylpiperidin-4-yl)methyl)-3-(4-phenoxyphenyl)-1H-imidazo[4,5-c]pyridin-2(3H)-one, 1-((1-acryloylpiperidin-4-yl)methyl)-3-(4-phenoxyphenyl)-1H-imidazo[4,5-c]pyridin-2(3H)-one, (R)-1-(1-acryloylpyrrolidin-3-yl)-3-(3-(p-tolyloxy)phenyl)-1H-imidazo[4,5-c]pyridin-2(3H)-one, (R)-1-(1-acryloylpyrrolidin-3-yl)-3-(3-(4-methoxyphenoxy)phenyl)-1H-imidazo[4,5-c]pyridin-2(3H)-one, (R,E)-3-(3-chloro-4-phenoxyphenyl)-1-(1-(3-morpholinoacryloyl)pyrrolidin-3-yl)-1H-imidazo[4,5-c]pyridin-2(3H)-one, (R)-1-(1-acryloylpyrrolidin-3-yl)-3-(3-chloro-4-(m-tolyloxy) phenyl)-1H-imidazo[4,5-c]pyridin-2(3H)-one, (R)-1-(1-acryloylpiperidin-3-yl)-3-(4-phenoxyphenyl)-1H-imidazo[4,5-c]pyridin-2(3H)-one, 1-((1-acryloylpyrrolidin-2-yl)methyl)-3-(4-phenoxyphenyl)-1H-imidazo[4,5-c]pyridin-2(3H)-one, (R,E)-3-(3-chloro-4-phenoxyphenyl)-1-(1-cinnamoylpyrrolidin-3-yl)-1H-imidazo[4,5-c]pyridin-2(3H)-one, (R)-3-(3-chloro-4-phenoxyphenyl)-1-(1-(vinylsulfonyl)pyrrolidin-3-yl)-1H-imidazo[4,5-c]pyridin-2(3H)-one, (R)-1-(1-acryloylpyrrolidin-3-yl)-3-(4-(3-ethoxyphenoxy)phenyl)-1H-imidazo[4,5-c]pyridin-2(3H)-one, (R)-1-(1-acryloylpyrrolidin-3-yl)-3-(4-(3-isopropoxyphenoxy)phenyl)-1H-imidazo[4,5-c]pyridin-2(3H)-one, (R)-1-(1-acryloylpyrrolidin-3-yl)-3-(3-chloro-4-(3-chlorophenoxy)phenyl)-1H-imidazo[4,5-c]pyridin-2(3H)-one, N-(3-(3-(3-methyl-4-phenoxyphenyl)-2-oxo-2,3-dihydro-1H-imidazo[4,5-c]pyridin-1-yl)phenyl) acrylamide, (R)-1-(1-methacryloylpyrrolidin-3-yl)-3-(4-phenoxyphenyl)-1H-imidazo[4,5-c]pyridin-2(3H)-one, (R,E)-1-(1-cinnamoylpyrrolidin-3-yl)-3-(4-phenoxyphenyl)-1H-imidazo[4,5-c]pyridin-2(3H)-one, 1-(1-acryloylpiperidin-4-yl)-3-(4-phenoxyphenyl)-1H-imidazo[4,5-c]pyridin-2(3H)-one, (R)-1-(1-acryloylpyrrolidin-3-yl)-3-(4-(phenylthio)phenyl)-1H-imidazo[4,5-c]pyridin-2(3H)-one, (R)-1-(1-acetylpyrrolidin-3-yl)-3-(4-phenoxyphenyl)-1H-imidazo[4,5-c]pyridin-2(3H)-one, (R)-1-(1-acryloylpyrrolidin-3-yl)-3-(4-phenoxyphenyl)-1H-imidazo[4,5-c]pyridin-2(3H)-one, (R)-1-(1-(but-2-ynoyl)pyrrolidin-3-yl)-3-(4-phenoxyphenyl)-1H-imidazo[4,5-c]pyridin-2(3H)-one, (R)-1-(1-acryloylpyrrolidin-3-yl)-3-(4-(4-methoxyphenoxy)phenyl)-1H-imidazo[4,5-c]pyridin-2(3H)-one, (R)-1-(1-acryloylpyrrolidin-3-yl)-3-(4-(4-(trifluoromethyl)phenoxy)phenyl)-1H-imidazo[4,5-c]pyridin-2(3H)-one, (R)-1-(1-acryloylpyrrolidin-3-yl)-3-(4-(3,4-dichlorophenoxy)phenyl)-1H-imidazo[4,5-c]pyridin-2(3H)-one, (R)-1-(1-acryloylpyrrolidin-3-yl)-3-(3-chloro-4-(3,5-difluorophenoxy)phenyl)-1H-imidazo[4,5-c]pyridin-2(3H)-one, (R)-1-(1-acryloylpyrrolidin-3-yl)-3-(4-(3,4-dimethoxyphenoxy)phenyl)-1H-imidazo[4,5-c]pyridin-2(3H)-one, (R)-1-(1-acryloylpyrrolidin-3-yl)-3-(3-chloro-4-(3-fluorophenoxy)phenyl)-1H-imidazo[4,5-c]pyridin-2(3H)-one, (R)-1-(1-acryloylpyrrolidin-3-yl)-3-(3-chloro-4-(4-methoxyphenoxy)phenyl)-1H-imidazo[4,5-c]pyridin-2(3H)-one, (R)-1-(1-acryloylpyrrolidin-3-yl)-3-(3-chloro-4-(4-(trifluoromethyl)phenoxy)phenyl)-1H-imidazo[4,5-c]pyridin-2(3H)-one, (R)-1-(1-acryloylpyrrolidin-3-yl)-3-(3-chloro-4-(3,4-dichlorophenoxy)phenyl)-1H-imidazo[4,5-c]

pyridin-2(3H)-one, (R)-1-(1-acryloylpyrrolidin-3-yl)-3-(3-chloro-4-(3-methoxyphenoxy)phenyl)-1H-imidazo[4,5-c]pyridin-2(3H)-one, N-(3-(3-(4-(3-isopropoxyphenoxy)-3-methylphenyl)-2-oxo-2,3-dihydro-1H-imidazo[4,5-c]pyridin-1-yl)phenyl)acrylamide, N-(3-(3-(3-methyl-4-(m-tolyloxy)phenyl)-2-oxo-2,3-dihydro-1H-imidazo[4,5-c]pyridin-1-yl)phenyl) acrylamide, N-(3-(3-(3-fluoro-4-(3-isopropoxyphenoxy)phenyl)-2-oxo-2,3-dihydro-1H-imidazo [4,5-c]pyridin-1-yl)phenyl)acrylamide, N-(3-(3-(3-fluoro-4-(m-tolyloxy) phenyl)-2-oxo-2,3-dihydro-1H-imidazo [4,5-c]pyridin-1-yl)phenyl)acrylamide, (N-(3-(3-(4-(3-chlorophenoxy)-3-fluorophenyl)-2-oxo-2,3-dihydro-1H-imidazo[4,5-c]pyridin-1-yl)phenyl)acrylamide, (R)-1-(1-acryloylpyrrolidin-3-yl)-3-(4-(2,3-dimethylphenoxy)phenyl)-1H-imidazo[4,5-c]pyridin-2(3H)-one, (R)-1-(1-acryloylpyrrolidin-3-yl)-3-(3-fluoro-4-(3-isopropoxyphenoxy) phenyl)-1H-imidazo [4,5-c]pyridin-2(3H)-one, (R)-1-(1-acryloylpyrrolidin-3-yl)-3-(3-fluoro-4-(3-methoxyphenoxy)phenyl)-1H-imidazo[4,5-c]pyridin-2(3H)-one, (R)-1-(1-acryloylpyrrolidin-3-yl)-3-(3-fluoro-4-(3-methoxyphenoxy) phenyl)-1H-imidazo [4,5-c]pyridin-2(3H)-one, (R)-1-(1-acryloylpyrrolidin-3-yl)-3-(3-(3-fluoro-2-methylphenoxy)phenyl)-1H-imidazo[4,5-c]pyridin-2(3H)-one, (R)-1-(1-acryloylpyrrolidin-3-yl)-3-(3-(3-cyclopropoxyphenoxy)phenyl)-1H-imidazo[4,5-c]pyridin-2(3H)-one, (R)-1-(1-acryloylpiperidin-3-yl)-3-(4-(3-fluoro-2-methylphenoxy)phenyl)-1H-imidazo[4,5-c]pyridin-2(3H)-one, (R)-1-(1-acryloylpiperidin-3-yl)-3-(4-(2,3-dimethylphenoxy)phenyl)-1H-imidazo[4,5-c]pyridin-2(3H)-one, (R)-1-(1-acryloylpiperidin-3-yl)-3-(4-(3-chloro-2-fluorophenoxy)phenyl)-1H-imidazo[4,5-c]pyridin-2(3H)-one, (R)-1-(1-acryloylpyrrolidin-3-yl)-3-(4-(2,3-difluorophenoxy)phenyl)-1H-imidazo[4,5-c]pyridin-2(3H)-one, (R)-1-(1-acryloylpiperidin-3-yl)-3-(4-(2,3-difluorophenoxy)phenyl)-1H-imidazo[4,5-c]pyridin-2(3H)-one, N-(3-(3-(4-(3-methoxyphenoxy)-3-methylphenyl)-2-oxo-2,3-dihydro-1H-imidazo[4,5-c]pyridin-1-yl)phenyl)acrylamide, (R)-1-(1-acryloylpyrrolidin-3-yl)-3-(4-(3-chloro-2-methoxyphenoxy)phenyl)-1H-imidazo[4,5-c]pyridin-2(3H)-one, (R)-1-(1-acryloylpiperidin-3-yl)-3-(4-(3-chloro-2-methoxyphenoxy)phenyl)-1H-imidazo[4,5-c]pyridin-2(3H)-one, ((R)-1-(1-acryloylpyrrolidin-3-yl)-2-oxo-3-(4-phenoxyphenyl)-2,3-dihydro-1H-imidazo[4,5-c]pyridin-4-carbonitrile, (R)-1-(1-acryloylpiperidin-3-yl)-3-(4-(2-methoxy-3-methylphenoxy)phenyl)-1H-imidazo[4,5-c]pyridin-2(3H)-one, (R)-1-(1-acryloylpyrrolidin-3-yl)-3-(4-(2-methoxy-3-methylphenoxy)phenyl)-1H-imidazo[4,5-c]pyridin-2(3H)-one, (R)-1-(1-acryloylpyrrolidin-3-yl)-3-(4-(2-methoxy-3-methylphenoxy)phenyl)-1H-imidazo[4,5-c]pyridin-2(3H)-one, N-(3-(3-(4-(3-chlorophenoxy)phenyl)-2-oxo-2,3-dihydro-1H-imidazo[4,5-c]pyridin-1-yl)phenyl)acrylamide, N-(3-(2-oxo-3-(4-(3-(trifluoromethoxy)phenoxy)phenyl)-2,3-dihydro-1H-imidazo[4,5-c]pyridin-1-yl)phenyl)acrylamide, N-(3-(3-(4-(3-chloro-5-methoxyphenoxy)phenyl)-2-oxo-2,3-dihydro-1H-imidazo[4,5-c]pyridin-1-yl)phenyl)acrylamide, (R)-1-(1-acryloylpyrrolidin-3-yl)-3-(4-(3-chlorophenoxy)phenyl)-1H-imidazo[4,5-c]pyridin-2(3H)-one, N-(3-(3-(3-chloro-4-phenoxyphenyl)-2-oxo-2,3-dihydro-1H-imidazo[4,5-c]pyridin-1-yl)phenyl)acrylamide, N-(3-(3-(3-(3-chlorophenoxy)phenyl)-2-oxo-2,3-dihydro-1H-imidazo[4,5-c]pyridin-1-yl)phenyl)acrylamide, N-(3-(3-(3-(3-fluorophenoxy)phenyl)-2-oxo-2,3-dihydro-1H-imidazo[4,5-c]pyridin-1-yl)phenyl)acrylamide, N-(3-(2-oxo-3-(4-(p-tolyloxy)phenyl)-2,3-dihydro-1H-imidazo[4,5-c]pyridin-1-yl)phenyl)acrylamide, (R)-1-(1-acryloylpyrrolidin-3-yl)-3-(3-fluoro-4-(3-fluorophenoxy)phenyl)-1H-imidazo[4,5-c]pyridin-2(3H)-one, (R)-1-(1-acryloylpyrrolidin-3-yl)-3-(3-fluoro-4-(m-tolyloxy)phenyl)-1H-imidazo[4,5-c]pyridin-2(3H)-one, N-(3-(3-(4-(3-fluoro-2-methylphenoxy)phenyl)-2-oxo-2,3-dihydro-1H-imidazo[4,5-c]pyridin-1-yl)phenyl)acrylamide, N-(3-(3-(4-(4-methoxyphenoxy)phenyl)-2-oxo-2,3-dihydro-1H-imidazo[4,5-c]pyridin-1-yl)phenyl)acrylamide, (R)-1-(1-acryloylpyrrolidin-3-yl)-3-(4-(4-fluorophenoxy)phenyl)-1H-imidazo[4,5-c]pyridin-2(3H)-one, (R)-1-(1-acryloylpyrrolidin-3-yl)-3-(4-(4-chlorophenoxy)phenyl)-1H-imidazo[4,5-c]pyridin-2(3H)-one, (R)-1-(1-acryloylpyrrolidin-3-yl)-3-(4-(o-tolyloxy)phenyl)-1H-imidazo[4,5-c]pyridin-2(3H)-one, (R)-1-(1-acryloylpyrrolidin-3-yl)-3-(4-(3-fluorophenoxy)phenyl)-1H-imidazo[4,5-c]pyridin-2(3H)-one, N-(3-(3-(4-(3-isopropoxyphenoxy)phenyl)-2-oxo-2,3-dihydro-1H-imidazo[4,5-c]pyridin-1-yl)phenyl)acrylamide, N-(3-(3-(3-chloro-4-(3-methoxyphenoxy)phenyl)-2-oxo-2,3-dihydro-1H-imidazo[4,5-c]pyridin-1-yl)phenyl)acrylamide, N-(3-(3-(3-(3-methoxyphenoxy)phenyl)-2-oxo-2,3-dihydro-1H-imidazo[4,5-c]pyridin-1-yl)phenyl)acrylamide, N-(3-(2-oxo-3-(3-(o-tolyloxy)phenyl)-2,3-dihydro-1H-imidazo[4,5-c]pyridin-1-yl)phenyl)acrylamide, N-(3-(3-(3-(2-methoxyphenoxy)phenyl)-2-oxo-2,3-dihydro-1H-imidazo[4,5-c]pyridin-1-yl)phenyl)acrylamide, N-(3-(3-(3-fluoro-4-(3-fluorophenoxy)phenyl)-2-oxo-2,3-dihydro-1H-imidazo[4,5-c]pyridin-1-yl)phenyl)acrylamide, 1-(1-acryloylpyrrolidin-3-yl)-3-(3-methyl-4-phenoxyphenyl)-1,3-dihydro-2H-imidazo[4,5-c]pyridin-2-one, 1-(1-acryloylpyrrolidin-3-yl)-3-(4-(3-methoxyphenoxy)-3-methylphenyl)-1,3-dihydro-2H-imidazo[4,5-c]pyridin-2-one, N-(3-(3-(3-fluoro-4-phenoxyphenyl)-2-oxo-2,3-dihydro-1H-imidazo[4,5-c]pyridin-1-yl)phenyl)acrylamide, N-(3-(3-(3-fluoro-4-(3-methoxyphenoxy)phenyl)-2-oxo-2,3-dihydro-1H-imidazo[4,5-c]pyridin-1-yl)phenyl)acrylamide, (R)-1-(1-acryloylpyrrolidin-3-yl)-3-(3-fluoro-4-phenoxyphenyl)-1,3-dihydro-2H-imidazo[4,5-c]pyridin-2-one, N-(3-(3-(3-chloro-2-fluorophenoxy)phenyl)-2-oxo-2,3-dihydro-1H-imidazo[4,5-c]pyridin-1-yl)phenyl)acrylamide, (R)-1-(1-acryloylpyrrolidin-3-yl)-3-(3-(3-chloro-2-fluorophenoxy)phenyl)-1,3-dihydro-2H-imidazo[4,5-c]pyridin-2-one, N-(3-(3-(4-(2,3-dichlorophenoxy)phenyl)-2-oxo-2,3-dihydro-1H-imidazo[4,5-c]pyridin-1-yl)phenyl)acrylamide, (R)-1-(1-acryloylpyrrolidin-3-yl)-3-(4-(2,3-dichlorophenoxy)phenyl)-1,3-dihydro-2H-imidazo[4,5-c]pyridin-2-one, (R)-1-(1-acryloylpiperidin-3-yl)-3-(4-(2,3-dichlorophenoxy)phenyl)-1,3-dihydro-2H-imidazo[4,5-c]pyridin-2-one, (R)-1-(1-acryloylpyrrolidin-3-yl)-3-(4-(3-chloro-2-fluorophenoxy)-3-fluorophenyl)-1,3-dihydro-2H-imidazo[4,5-c]pyridin-2-one, (R)-1-(1-acryloylpyrrolidin-3-yl)-3-(4-(2-chloro-3-fluorophenoxy)phenyl)-1,3-dihydro-2H-imidazo[4,5-c]pyridin-2-one, (R)-1-(1-acryloylpiperidin-3-yl)-3-(4-(2-chloro-3-fluorophenoxy)phenyl)-1,3-dihydro-2H-imidazo[4,5-c]pyridin-2-one, (R)-1-(1-acryloylpyrrolidin-3-yl)-3-(4-(pyridin-2-yloxy)phenyl)-1,3-dihydro-2H-imidazo[4,5-c]pyridin-2-one, (R)-1-(1-acryloylpiperidin-3-yl)-3-(3-fluoro-4-(m-tolyloxy)phenyl)-1H-imidazo[4,5-c]pyridin-2(3H)-one, (R)-1-(1-acryloylpiperidin-3-yl)-3-(4-(3-chlorophenoxy)phenyl)-1H-imidazo[4,5-c]pyridin-2(3H)-one, (R)-1-(1-acryloylpiperidin-3-yl)-3-(3-chloro-4-phenoxyphenyl)-1H-imidazo[4,5-c]pyridin-2(3H)-one, (R)-1-(1-acryloylpiperidin-3-yl)-3-(3-chloro-4-(m-tolyloxy)phenyl)-1H-imidazo[4,5-c]pyridin-2(3H)-one, N-(3-(2-oxo-3-(4-phenoxyphenyl)-2,3-dihydro-1H-imidazo[4,5-c]pyridin-1-yl)phenyl)cinnamamide, N-(3-(2-oxo-3-(4-phenoxyphenyl)-2,3-dihydro-1H-imidazo[4,5-c]pyridin-1-yl)phenyl)methacrylamide, N-(3-(3-(3-chloro-4-(4-(trifluoromethyl)phenoxy)phenyl)-2-oxo-2,3-dihydro-1H- imidazo[4,5-c]pyridin-1-yl)phenyl)acrylamide, (R)-1-(1-acryloylpyrrolidin-3-yl)-3-(4-(3-(trifluoromethoxy) phenoxy)phenyl)-1H-imidazo[4,5-c]pyridin-2(3H)-one, N-(3-(3-(4-(3-ethoxyphenoxy)phenyl)-2-oxo-2,3-dihydro-1H-imidazo[4,5-c]pyridin-1-yl)phenyl)acrylamide, N-(3-(3-(4-(3-isopropylphenoxy)phenyl)-2-oxo-2,3-dihydro-1H-imidazo[4,5-c]pyridin-1-yl)phenyl)acrylamide, 4-(4-(1-(3-acrylamidophenyl)-2-oxo-1H-imidazo[4,5-c]pyridin-3(2H)-yl)phenoxy)-N-methylpicolinamide, N-(3-(2-oxo-1-(4-phenoxyphenyl)-1H-imidazo[4,5-b]pyridin-3(2H)-yl) phenyl)acrylamide, (R)-1-(1-acryloylpiperidin-3-yl)-3-(4-(3-fluorophenoxy)phenyl)-1H-imidazo[4,5-c]pyridin-2(3H)-one, (R)-1-(1-acryloylpiperidin-3-yl)-3-(4-(3-methoxyphenoxy)phenyl)-1H-imidazo[4,5-c]pyridin-2(3H)-one, N-(3-(2-oxo-3-(4-phenoxyphenyl)-2,3-dihydro-1H-imidazo[4,5-b]pyridin-1-yl)phenyl)acrylamide, (R)-3-(1-acryloylpyrrolidin-3-yl)-1-(4-phenoxyphenyl)-1H-imidazo[4,5-b]pyridin-2(3H)-one, N-(3-(2-oxo-1-(4-phenoxyphenyl)-1H-imidazo[4,5-c]pyridin-3(2H)-yl) phenyl)acrylamide, (R)-3-(1-acryloylpiperidin-3-yl)-1-(4-phenoxyphenyl)-1H-imidazo[4,5-c]pyridin-2(3H)-one, N-(3-(2-oxo-3-(4-(4-(trifluoromethyl)phenoxy)phenyl)-2,3-dihydro-1H-imidazo[4,5-c]pyridin-1-yl)phenyl)acrylamide, N-(3-(3-(4-(4-methoxyphenoxy)phenyl)-2-oxo-2,3-dihydro-1H-imidazo[4,5-c]pyridin-1-yl)phenyl)acrylamide, N-(3-(3-(4-(2,3-difluorophenoxy)phenyl)-2-oxo-2,3-dihydro-1H-imidazo[4,5-c]pyridin-1-yl)phenyl)acrylamide, N-(3-(3-(4-(3,4-difluorophenoxy)phenyl)-2-oxo-2,3-dihydro-1H-imidazo[4,5-c]pyridin-1-yl)phenyl)acrylamide, N-(3-(3-(4-(3,5-difluorophenoxy)phenyl)-2-oxo-2,3-dihydro-1H-imidazo[4,5-c]pyridin-1-yl)phenyl)acrylamide, N-(3-(3-(4-(3-chloro-2-fluorophenoxy)phenyl)-2-oxo-2,3-dihydro-1H-imidazo[4,5-c]pyridin-1-yl)phenyl)acrylamide, N-(3-(3-(4-(3-chloro-5-fluorophenoxy)phenyl)-2-oxo-2,3-dihydro-1H-imidazo[4,5-c]pyridin-1-yl)phenyl)acrylamide, N-(3-(3-(4-(3,5-dichlorophenoxy)phenyl)-2-oxo-2,3-dihydro-1H-imidazo[4,5-c]pyridin-1-yl)phenyl)acrylamide, N-(3-(3-(4-(3,4-dimethoxyphenoxy)phenyl)-2-oxo-2,3-dihydro-1H-imidazo[4,5-c]pyridin-1-yl)phenyl)acrylamide, N-(3-(3-(3-fluoro-4-phenoxyphenyl)-2-oxo-2,3-dihydro-1H-imidazo[4,5-c]pyridin-1-yl)phenyl)acrylamide, (R)-1-(1-acryloylpyrrolidin-3-yl)-3-(4-(3-chloro-2-fluorophenoxy)phenyl)-1H-imidazo[4,5-c]pyridin-2(3H)-one, (R)-1-(1-acryloylpiperidin-3-yl)-3-(4-(3-chloro-2-methylphenoxy)phenyl)-1H-imidazo[4,5-c]pyridin-2(3H)-one, (R)-1-(1-acryloylpyrrolidin-3-yl)-3-(4-(2-chloro-3-methoxyphenoxy)phenyl)-1H-imidazo[4,5-c]pyridin-2(3H)-one, N-(3-(3-(4-(3-fluoro-2-methoxyphenoxy) phenyl)-2-oxo-2,3-dihydro-1H-imidazo[4,5-c]pyridin-1-yl) phenyl)acrylamide, (R)-1-(1-acryloylpyrrolidin-3-yl)-3-(4-(3-fluoro-2-methoxyphenoxy)phenyl)-1H-imidazo[4,5-c]pyridin-2(3H)-one, (R)-1-(1-acryloylpyrrolidin-3-yl)-3-(4-(2-fluoro-3-methylphenoxy)phenyl)-1H-imidazo[4,5-c]pyridin-2(3H)-one, (R)-1-(1-acryloylpyrrolidin-3-yl)-3-(4-(3-chloro-2-methylphenoxy)phenyl)-1H-imidazo[4,5-c]pyridin-2(3H)-one, (R)-1-(1-acryloylpiperidin-3-yl)-3-(4-(3-fluoro-2-methoxyphenoxy)phenyl)-1H-imidazo[4,5-c]pyridin-2(3H)-one, (R)-1-(1-acryloylpiperidin-3-yl)-3-(4-(2-fluoro-3-methylphenoxy)phenyl)-1H-imidazo[4,5-c]pyridin-2(3H)-one, (R)-1-(1-acryloylpiperidin-3-yl)-3-(4-(3-methoxy-2-methylphenoxy)phenyl)-1H-imidazo[4,5-c]pyridin-2(3H)-one, (R)-1-(1-acryloylpyrrolidin-3-yl)-3-(4-(3-methoxy-2-methylphenoxy)phenyl)-1H-imidazo[4,5-c]pyridin-2(3H)-one, N-(3-(3-(3-chloro-4-(m-tolyloxy)phenyl)-2-oxo-2,3-dihydro-1H-imidazo[4,5-c]pyridin-1-yl)phenyl)acrylamide, N-(3-(3-chloro-4-(3-isopropoxyphenoxy)phenyl)-2-oxo-2,3-dihydro-1H-imidazo[4,5-c]pyridin-1-yl)phenyl)acrylamide, N-(3-(3-(4-(3-fluorophenoxy)-3-methylphenyl)-2-oxo-2,3-dihydro-1H-imidazo[4,5-c]pyridin-1-yl)phenyl)acrylamide, N-(3-(3-(4-(2,3-dimethylphenoxy)phenyl)-2-oxo-2,3-dihydro-1H-imidazo[4,5-c]pyridin-1-yl)phenyl)acrylamide, N-(3-(3-(3-chloro-4-(2,3-dimethylphenoxy)phenyl)-2-oxo-2,3-dihydro-1H-imidazo[4,5-c]pyridin-1-yl)phenyl)acrylamide, (R)-1-(1-acryloylpyrrolidin-3-yl)-3-(4-(3-chlorophenoxy)-3-fluorophenyl)-1H-imidazo[4,5-c]pyridin-2(3H)-one, N-(3-(3-(4-(3-chloro-2-methylphenoxy)phenyl)-2-oxo-2,3-dihydro-1H-imidazo[4,5-c]pyridin-1-yl)phenyl)acrylamide, (R)-1-(1-acryloylpyrrolidin-3-yl)-7-chloro-3-(4-phenoxyphenyl)-1H-imidazo[4,5-c]pyridin-2(3H)-one, N-(3-(2-oxo-3-(3-(m-tolyloxy)phenyl)-2,3-dihydro-1H-imidazo[4,5-c]pyridin-1-yl)phenyl)acrylamide, (R)-1-(1-acryloylpyrrolidin-3-yl)-3-(4-(3-isopropylphenoxy)phenyl)-1H-imidazo[4,5-c]pyridin-2(3H)-one, N-(3-(3-(4-(3-chlorophenoxy)-3-methylphenyl)-2-oxo-2,3-dihydro-1H-imidazo[4,5-c]pyridin-1-yl)phenyl)acrylamide, (R)-1-(1-acryloylpyrrolidin-3-yl)-3-(3-phenoxyphenyl)-1H-imidazo[4,5-c]pyridin-2(3H)-one, (R)-1-(1-methacryloylpyrrolidin-3-yl)-3-(3-phenoxyphenyl)-1H-imidazo[4,5-c]pyridin-2(3H)-one, N-(3-(2-oxo-3-(4-(phenylthio)phenyl)-2,3-dihydro-1H-imidazo[4,5-c]pyridin-1-yl)phenyl)acrylamide, N-(3-(3-(4-(3-methoxyphenoxy)phenyl)-2-oxo-2,3-dihydro-1H-imidazo[4,5-c]pyridin-1-yl)phenyl)acrylamide, N-(3-(3-(4-(3,4-dichlorophenoxy)phenyl)-2-oxo-2,3-dihydro-1H-imidazo[4,5-c]pyridin-1-yl)phenyl)acrylamide, N-(3-(3-(4-(4-chloro-3-fluorophenoxy)phenyl)-2-oxo-2,3-dihydro-1H-imidazo[4,5-c]pyridin-1-yl)phenyl)acrylamide, N-(3-(3-(4-(3-fluoro-4-methoxyphenoxy)phenyl)-2-oxo-2,3-dihydro-1H-imidazo[4,5-c]pyridin-1-yl)phenyl)acrylamide, N-(3-(3-(4-(4-cyanophenoxy)phenyl)-2-oxo-2,3-dihydro-1H-imidazo[4,5-c]pyridin-1-yl)phenyl)acrylamide, N-(3-(3-(4-(4-methoxy-3-methylphenoxy)phenyl)-2-oxo-2,3-dihydro-1H-imidazo[4,5-c]pyridin-1-yl)phenyl)acrylamide, 1-(1-acryloylpyrrolidin-3-yl)-3-(4-(pyridin-4-yloxy)phenyl)-1H-imidazo[4,5-c]pyridin-2(3H)-one, 1-(1-acryloylpyrrolidin-3-yl)-3-(4-(pyridazin-3-yloxy)phenyl)-1H-imidazo[4,5-c]pyridin-2(3H)-one, N-(3-(2-oxo-3-(4-((2,4,5-trifluorobenzyl)oxy) phenyl)-2,3-dihydro-1H-imidazo[4,5-c]pyridin-1-yl)phenyl)acrylamide, N-(3-(2-oxo-3-(4-(pyridin-2-ylmethoxy)phenyl)-2,3-dihydro-1H-imidazo[4,5-c]pyridin-1-yl)phenyl)acrylamide, (R)-1-(1-acryloylpyrrolidin-3-yl)-3-(4-(benzyloxy)-3-chlorophenyl)-1H-imidazo[4,5-c]pyridin-2(3H)-one, (R)-1-(1-acryloylpyrrolidin-3-yl)-3-(4-((3,4-dichlorobenzyl)oxy) phenyl)-1H-imidazo[4,5-c]pyridin-2(3H)-one, (R)-1-(1-acryloylpyrrolidin-3-yl)-3-(4-((2,4-difluorobenzyl)oxy) phenyl)-1H-imidazo [4,5-c]pyridin-2(3H)-one, (R)-1-(1-acryloylpyrrolidin-3-yl)-3-(3-chloro-4-((3-(trifluoromethyl) benzyl)oxy)phenyl)-1H-imidazo[4,5-c]pyridin-2(3H)-one, (R)-1-(1-acryloylpyrrolidin-3-yl)-3-(3-chloro-4-((3,4-difluorobenzyl)oxy)phenyl)-1H-imidazo[4,5-c]pyridin-2(3H)-one, (R)-1-(1-acryloylpyrrolidin-3-yl)-3-(3-chloro-4-((2,4-difluorobenzyl)oxy)phenyl)-1H-imidazo[4,5-c]pyridin-2(3H)-one, (R)-1-(1-acryloylpyrrolidin-3-yl)-3-(3-chloro-4-((2-(trifluoromethyl)benzyl)oxy)phenyl)-1H-imidazo[4,5-c]pyridin-2(3H)-one, (R)-1-(1-acryloylpyrrolidin-3-yl)-3-(3-chloro-4-(pyridin-2-ylmethoxy)phenyl)-1H-imidazo[4,5-c]pyridin-2(3H)-one, (R)-1-(1-acryloylpyrrolidin-3-yl)-3-(3-chloro-4-((4-(trifluoromethyl)benzyl)oxy)phenyl)-1H-imidazo[4,5-c]pyridin-2(3H)-one, (R)-1-(1-acryloylpyrrolidin-3-yl)-3-(3-chloro-4-((4-(trifluoromethyl) benzyl)oxy)phenyl)-1H-imidazo[4,5-c]pyridin-2(3H)-one, (R)-1-(1-acryloylpyrrolidin-3-yl)-3-(3-chloro-4-((3,5-difluorobenzyl)oxy)phenyl)-1H-imidazo[4,5-c]pyridin-2(3H)-oneone, (R)-1-(1-acryloylpyrrolidin-3-yl)-3-(3-chloro-4-((2,4-dichlorobenzyl)oxy)phenyl)-1H-imidazo[4,5-c]pyridin-2(3H)-one, (R)-1-(1-acryloylpyrrolidin-3-yl)-3-(4-((2,5-difluorobenzyl)oxy)phenyl)-1H-imidazo[4,5-c]pyridin-2(3H)-one, (R)-1-(1-acryloylpyrrolidin-3-yl)-3-(4-((2-(trifluoromethyl)benzyl)oxy)phenyl)-1H-imidazo[4,5-c]pyridin-2(3H)-one, (R)-1-(1-acryloylpyrrolidin-3-yl)-3-(4-((3-(trifluoromethyl)benzyl)oxy)phenyl)-1H-imidazo[4,5-c]pyridin-2(3H)-one, (R)-1-(1-acryloylpyrrolidin-3-yl)-3-(4-((4-(trifluoromethyl)benzyl)oxy)phenyl)-1H-imidazo[4,5-c]pyridin-2(3H)-one, (R)-1-(1-acryloylpyrrolidin-3-yl)-3-(4-(pyridin-2-ylmethoxy)phenyl)-1H-imidazo[4,5-c]pyridin-2(3H)-one, (R)-1-(1-acryloylpyrrolidin-3-yl)-3-(4-((3,4-difluorobenzyl)oxy)phenyl)-1H-imidazo[4,5-c]pyridin-2(3H)-one, (R)-1-(1-acryloylpyrrolidin-3-yl)-3-(3-chloro-4-((3,4-dichlorobenzyl)oxy)phenyl)-1H-imidazo[4,5-c]pyridin-2(3H)-one, (R)-1-(1-acryloylpyrrolidin-3-yl)-3-(4-((2-fluorobenzyl)oxy)phenyl)-1H-imidazo[4,5-c]pyridin-2(3H)-one, N-(3-(3-(3-fluoro-4-((2-fluorobenzyl)oxy)phenyl)-2-oxo-2,3-dihydro-1H-imidazo[4,5-c]pyridin-1-yl)phenyl)acrylamide, N-(3-(3-(4-((3,4-dichlorobenzyl)oxy)phenyl)-2-oxo-2,3-dihydro-1H-imidazo[4,5-c]pyridin-1-yl)phenyl)acrylamide, N-(3-(3-(4-((3,5-difluorobenzyl)oxy)phenyl)-2-oxo-2,3-dihydro-1H-imidazo[4,5-c]pyridin-1-yl)phenyl)acrylamide, N-(3-(3-(4-((2,5-difluorobenzyl)oxy)phenyl)-2-oxo-2,3-dihydro-1H-imidazo[4,5-c]pyridin-1-yl)phenyl)acrylamide, N-(3-(3-(4-((4-chlorobenzyl)oxy)phenyl)-2-oxo-2,3-dihydro-1H-imidazo[4,5-c]pyridin-1-yl)phenyl)acrylamide, N-(3-(3-(4-((3-fluorobenzyl)oxy)phenyl)-2-oxo-2,3-dihydro-1H-imidazo[4,5-c]pyridin-1-yl)phenyl)acrylamide, N-(3-(3-(3-chloro-4-((4-(trifluoromethyl)benzyl)oxy)phenyl)-2-oxo-2,3-dihydro-1H-imidazo[4,5-c]pyridin-1-yl)phenyl)acrylamide, N-(3-(3-(4-(benzyloxy)-3-chlorophenyl)-2-oxo-2,3-dihydro-1H-imidazo[4,5-c]pyridin-1-yl)phenyl)acrylamide, N-(3-(3-(4-((2-methylbenzyl)oxy)phenyl)-2-oxo-2,3-dihydro-1H-imidazo[4,5-c]pyridin-1-yl)phenyl)acrylamide, N-(3-(3-(4-((2,6-difluorobenzyl oxy)phenyl)-2-oxo-2,3-dihydro-1H-imidazo[4,5-c]pyridin-1-yl)phenyl)acrylamide, N-(3-(3-(4-((2,6-difluorobenzyl)oxy)-3-fluorophenyl)-2-oxo-2,3-dihydro-1H-imidazo[4,5-c]pyridin-1-yl)phenyl)acrylamide, N-(3-(3-(4-((2-fluorobenzyl)oxy)phenyl)-2-oxo-2,3-dihydro-1H-imidazo[4,5-c]pyridin-1-yl)phenyl)acrylamide, N-(3-(3-(4-((2,4-dichlorobenzyl)oxy)phenyl)-2-oxo-2,3-dihydro-1H-imidazo[4,5-c]pyridin-1-yl)phenyl)acrylamide, N-(3-(3-(4-((3-chlorobenzyl)oxy)phenyl)-2-oxo-2,3-dihydro-1H-imidazo[4,5-c]pyridin-1-yl)phenyl)acrylamide, N-(3-(3-(4-((2-chlorobenzyl)oxy)phenyl)-2-oxo-2,3-dihydro-1H-imidazo[4,5-c]pyridin-1-yl)phenyl)acrylamide, N-(3-(2-oxo-3-(4-((2-(trifluoromethyl)benzyl)oxy)phenyl)-2,3-dihydro-1H-imidazo[4,5-c]pyridin-1-yl)phenyl)acrylamide, N-(3-(3-(3-(benzyloxy)phenyl)-2-oxo-2,3-dihydro-1H-imidazo[4,5-c]pyridin-1-yl)phenyl)acrylamide, N-(3-(3-(4-(benzyloxy)-3-fluorophenyl)-2-oxo-2,3-dihydro-1H-imidazo[4,5-c]pyridin-1-yl)phenyl)acrylamide, N-(3-(3-(3-chloro-4-((2-fluorobenzyl)oxy)phenyl)-2-oxo-2,3-dihydro-1H-imidazo[4,5-c]pyridin-1-yl)phenyl)acrylamide, (S)-1-(1-acryloylpyrrolidin-3-yl)-3-(3-chloro-4-((2-fluorobenzyl)oxy)phenyl)-1,3-dihydro-2H-imidazo[4,5-c]pyridin-2-one, (S)-1-(1-acryloylpyrrolidin-3-yl)-3-(4-(benzyloxy)-3-fluorophenyl)-1,3-dihydro-2H-imidazo[4,5-c]pyridin-2-one, N-(3-(3-(4-((3-chloro-2-fluorobenzyl)oxy)-3-fluorophenyl)-2-oxo-2,3-dihydro-1H-imidazo[4,5-c]pyridin-1-yl)phenyl)acrylamide, (N-(3-(4-(benzyloxy)phenyl)-2-oxo-2,3-dihydro-1H-imidazo[4,5-c]pyridin-1-yl)phenyl)acrylamide, N-(3-(2-oxo-3-(4-((3-(trifluoromethyl)benzyl)oxy)phenyl)-2,3-dihydro-1H-imidazo[4,5-c]pyridin-1-yl)phenyl)acrylamide, N-(3-(3-(4-((3,4-difluorobenzyl)oxy)phenyl)-2-oxo-2,3-dihydro-1H-imidazo[4,5-c]pyridin-1-yl)phenyl)acrylamide, N-(3-(2-oxo-3-(4-((4-(trifluoromethyl)benzyl)oxy)phenyl)-2,3-dihydro-1H-imidazo[4,5-c]pyridin-1-yl)phenyl)acrylamide, N-(3-(3-(3-chloro-4-((3-(trifluoromethyl)benzyl)oxy)phenyl)-2-oxo-2,3-dihydro-1H-imidazo[4,5-c]pyridin-1-yl)phenyl)acrylamide, (R)-1-(1-acryloylpyrrolidin-3-yl)-3-(4-((4-chloro-2-fluorobenzyl)oxy)phenyl)-1H-imidazo[4,5-c]pyridin-2(3H)-one, N-(3-(3-4-((4-chloro-2-fluorobenzyl)oxy)phenyl)-2-oxo-2,3-dihydro-1H-imidazo[4,5-c]pyridin-1-yl)phenyl)acrylamide, ((R)-1-(1-acryloylpyrrolidin-3-yl)-3-(4-(benzyloxy)phenyl)-1H-imidazo[4,5-c]pyridin-2(3H)-one, N-(3-(3-(4-((4-fluorobenzyl)oxy)phenyl)-2-oxo-2,3-dihydro-1H-imidazo[4,5-c]pyridin-1-yl)phenyl)acrylamide, N-(3-(3-(4-((2,4-difluorobenzyl)oxy)phenyl)-2-oxo-2,3-dihydro-1H-imidazo[4,5-c]pyridin-1-yl)phenyl)acrylamide, 4-(1-(3-acrylamidophenyl)-2-oxo-1H-imidazo[4,5-c]pyridin-3(2H)-yl)-N-(4-fluorobenzyl)benzamide, (R)-1-(1-acryloylpyrrolidin-3-yl)-3-(4-(morpholine-4-carbonyl)phenyl)-1H-imidazo[4,5-c]pyridin-2(3H)-one, 4-(1-(3-acrylamidophenyl)-2-oxo-1H-imidazo[4,5-c]pyridin-3(2H)-yl)-N-(3-(trifluoromethyl)phenyl)benzamide, 4-(1-(3-acrylamidophenyl)-2-oxo-1H-imidazo[4,5-c]pyridin-3(2H)-yl)-N-(3-methoxybenzyl)benzamide, N-(3-(3-(4-(morpholine-4-carbonyl)phenyl)-2-oxo-2,3-dihydro-1H-imidazo[4,5-c]pyridin-1-yl)phenyl)acrylamide, 4-(1-(3-acrylamidophenyl)-2-oxo-1H-imidazo[4,5-c]pyridin-3(2H)-yl)-N-phenylbenzamide, 4-(1-(3-acrylamidophenyl)-2-oxo-1H-imidazo[4,5-c]pyridin-3(2H)-yl)-N-(m-tolyl)benzamide, (R)-4-(1-(1-acryloylpyrrolidin-3-yl)-2-oxo-1H-imidazo[4,5-c]pyridin-3(2H)-yl)-N-(3-methoxybenzyl)benzamide, N-(4-(1-(3-acrylamidophenyl)-2-oxo-1H-imidazo[4,5-c]pyridin-3(2H)-yl)phenyl)benzamide, N-(4-(1-(3-acrylamidophenyl)-2-oxo-1H-imidazo[4,5-c]pyridin-3(2H)-yl)phenyl)-2-methoxybenzamide, N-(4-(1-(3-acrylamidophenyl)-2-oxo-1H-imidazo[4,5-c]pyridin-3(2H)-yl)phenyl)-3-chlorobenzamide, N-(3-(1-(3-acrylamidophenyl)-2-oxo-1H-imidazo[4,5-c]pyridin-3(2H)-yl)phenyl)-4-(tert-butyl)benzamide, N-(4-(1-(3-acrylamidophenyl)-2-oxo-1H-imidazo[4,5-c]pyridin-3(2H)-yl)phenyl)benzamide, N-(4-(1-(3-acrylamidophenyl)-2-oxo-1,2-dihydro-3H-imidazo[4,5-c]pyridin-3-yl)phenyl)-2-(trifluoromethyl)benzamide, N-(4-(1-(3-acrylamidophenyl)-2-oxo-1,2-dihydro-3H-imidazo[4,5-c]pyridin-3-yl)phenyl)-4-(trifluoromethyl)benzamide, N-(4-(1-(3-acrylamidophenyl)-2-oxo-1H-imidazo[4,5-c]pyridin-3(2H)-yl)phenyl)-4-methoxybenzamide, N-(4-(1-(3-acrylamidophenyl)-2-oxo-1H-imidazo[4,5-c]pyridin-3(2H)-yl)phenyl)-3-fluorobenzamide, N-(4-(1-(3-acrylamidophenyl)-2-oxo-1H-imidazo[4,5-c]pyridin-3(2H)-yl)phenyl)-3-methoxybenzamide, N-(4-(1-(3-acrylamidophenyl)-2-oxo-1H-imidazo[4,5-c]pyridin-3(2H)-yl)phenyl)-3-methylbenzamide, N-(3-(3-(3'-methyl-[1,1'-biphenyl]-4-yl)-2-oxo-2,3-dihydro-1H-imidazo[4,5-c]pyridin-1-yl)phenyl)acrylamide, N-(3-(3-([1,1'-biphenyl]-4-yl)-2-oxo-2,3-dihydro-1H-imidazo[4,5-c] pyridin-1-yl)phenyl)acrylamide, N-(3-(3-(4'-methyl-[1,1'-biphenyl]-3-yl)-2-oxo-2,3-dihydro-1H-imidazo [4,5-c]pyridin-1-yl)phenyl)acrylamide, (R) 1-(1-acryloylpyrrolidin-3-yl)-3-(2'-methyl-[1,1'-biphenyl]-3-yl)-1H-imidazo[4,5-c]pyridin-2(3H)-one, (R)-1-(1-acryloylpyrrolidin-3-yl)-3-(2-fluoro-4-methoxy-[1,1'-biphenyl]-4-yl)-1H-imidazo[4,5-c]pyridin-2(3H)-one, (R)-1-(1-acryloylpiperidin-4-yl)-3-(2',4'-dichloro-[1,1'-biphenyl]-4-yl)-1H-imidazo[4,5-c]pyridin-2(3H)-one, N-(3-(3-(4'-methyl-[1,1'-biphenyl]-4-yl)-2-oxo-2,3-dihydro-1H-imidazo[4,5-c]pyridin-1-yl)phenyl)

acrylamide, (R)-3-([1,1'-biphenyl]-3-yl)-1-(1-acryloylpyrrolidin-3-yl)-1H-imidazo[4,5-c]pyridin-2(3H)-one, and N-(3-(3-(4-cyclopropylphenyl)-2-oxo-2,3-dihydro-1H-imidazo[4,5-c]pyridin-1-yl)phenyl)acrylamide, (R)-1-(1-acryloylpiperidin-3-yl)-3-(4-(2-fluoro-3-methoxyphenoxy)phenyl)-7-methoxy-1H-imidazo[4,5-c]pyridin-2(3H)-one, (R)-1-(1-acryloylpiperidin-3-yl)-7-ethoxy-3-(4-(2-fluoro-3-methoxyphenoxy)phenyl)-1H-imidazo[4,5-c]pyridin-2(3H)-one, (R)-1-(1-acryloylpiperidin-3-yl)-3-(4-(2-fluoro-3-methoxyphenoxy)phenyl)-7-methyl-1H-imidazo[4,5-c]pyridin-2(3H)-one, (R)-1-((1-(but-2-ynoyl)pyrrolidin-2-yl)methyl)-3-(4-(2-fluoro-3-methoxyphenoxy)phenyl)-7-methyl-1H-imidazo[4,5-c]pyridin-2(3H)-one, (R)-1-((1-acryloylpyrrolidin-2-yl)methyl)-3-(4-(2-fluoro-3-methoxyphenoxy)phenyl)-7-methyl-1H-imidazo[4,5-c]pyridin-2(3H)-one, (R)-1-(1-(but-2-ynoyl)piperidin-3-yl)-3-(4-(2-fluoro-3-methoxyphenoxy)phenyl)-7-methyl-1H-imidazo[4,5-c]pyridin-2(3H)-one, (R)-1-(1-acryloylpyrrolidin-3-yl)-3-(4-(2-fluoro-3-methoxyphenoxy)phenyl)-7-methyl-1H-imidazo[4,5-c]pyridin-2(3H)-one, (R)-1-(1-(but-2-ynoyl)pyrrolidin-3-yl)-3-(4-(2-fluoro-3-methoxyphenoxy)phenyl)-7-methyl-1H-imidazo[4,5-c]pyridin-2(3H)-one, (E)-N-(3-(6-amino-8-oxo-7-(4-phenoxyphenyl)-7H-purin-9(8H)-yl)phenyl)-4-(cyclopropyl(methyl)amino)-N-methylbut-2-enamide, (R)-1-(1-(but-2-ynoyl)piperidin-3-yl)-3-(4-(2-fluoro-3-methoxyphenoxy)phenyl)-1H-imidazo[4,5-c]pyridin-2(3H)-one, (R)-1-(1-acryloylpyrrolidin-3-yl)-7-methyl-3-(4-phenoxyphenyl)-1H-imidazo[4,5-c]pyridin-2(3H)-one, (S,Z)-9-(1-acryloylpyrrolidin-3-yl)-6-(hydroxyimino)-7-(4-phenoxyphenyl)-7,9-dihydro-1H-purin-8(6H)-one, 1-(1-Acryloyl-pyrrolidin-2-ylmethyl)-3-(4-phenoxy-phenyl)-1,3-dihydro-imidazo[4,5-c]pyridin-2-one, (S,Z)-1-(1-acryloylpyrrolidin-3-yl)-N'-hydroxy-2-oxo-3-(4-phenoxyphenyl)-2,3-dihydro-1H-imidazo[4,5-c]pyridine-4-carboximidamide, 4,4-Dimethyl-2-{2-[2-oxo-3-(4-phenoxy-phenyl)-2,3-dihydro-imidazo[4,5-c] pyridin-1-ylmethyl]-pyrrolidine-1-carbonyl}-pent-2-enenitrile, (R)-1-(1-acryloylpyrrolidin-3-yl)-2-oxo-3-(4-phenoxyphenyl)-2,3-dihydro-1H-imidazo[4,5-c]pyridine-7-carbonitrile. (R)-1-(1-acryloylpyrrolidin-3-yl)-4-methoxy-3-(4-phenoxyphenyl)-1H-imidazo[4,5-c]pyridin-2(3H)-one, (R)-1-(1-acryloylpyrrolidin-3-yl)-4-hydroxy-3-(4-phenoxyphenyl)-1H-imidazo[4,5-c]pyridin-2(3H)-one, (R)-1-(1-acryloylpyrrolidin-3-yl)-7-chloro-3-(4-phenoxyphenyl)-1H-imidazo[4,5-c]pyridin-2(3H)-one, (R)-1-(1-acryloylpiperidin-3-yl)-3-(4-(2-chloro-3-methoxyphenoxy)phenyl)-1H-imidazo[4,5-c]pyridin-2(3H)-one, (R)-1-(1-acryloylpiperidin-3-yl)-3-(4-(2-fluoro-3-methoxyphenoxy)phenyl)-1H-imidazo[4,5-c]pyridin-2(3H)-one, (R,E)-1-(1-(4-(cyclopropyl(methyl)amino)but-2-enoyl)pyrrolidin-3-yl)-3-(4-phenoxyphenyl)-1H-imidazo[4,5-c]pyridin-2(3H)-one, (R,E)-1-(1-(4-(cyclopropyl(methyl)amino)but-2-enoyl)piperidin-3-yl)-3-(4-phenoxyphenyl)-1H-imidazo[4,5-c]pyridin-2(3H)-one, (R)-1-(1-acryloylpyrrolidin-3-yl)-4-nitro-3-(4-phenoxyphenyl)-1H-benzo[d]imidazol-2(3H)-one, (R)-1-(1-acryloylpyrrolidin-3-yl)-4-amino-3-(4-phenoxyphenyl)-1H-benzo[d]imidazol-2(3H)-one, (R)-1-(1-acryloylpyrrolidin-3-yl)-3-(4-(2-fluoro-3-methoxyphenoxy)phenyl)-1H-imidazo[4,5-c]pyridin-2(3H)-one, 2-oxo-2-(3-(2-oxo-3-(4-phenoxyphenyl)-2,3-dihydro-1H-imidazo[4,5-c]pyridin-1-yl)piperidin-1-yl)acetic acid, 3-(2-oxo-3-(4-phenoxyphenyl)-2,3-dihydro-1H-imidazo[4,5-c]pyridin-1-yl) cyclohexanecarboxylic acid, and 2-oxo-2-(3-(2-oxo-3-(4-phenoxyphenyl)-2,3-dihydro-1H-imidazo[4,5-c] pyridin-1-yl)piperidin-1-yl)acetamide.

DETAILED DESCRIPTION OF THE INVENTION

The methods described herein include administering to a subject in need a composition containing a therapeutically effective amount of one or more Btk inhibitor compounds described herein.

Prodrugs means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds.

Tautomers mean compounds produced by the phenomenon wherein a proton of one atom of a molecule shifts to another atom. Tautomers also refer to one of two or more structural isomers that exist in equilibrium and are readily converted from one isomeric form to another. One of ordinary skill in the art would recognize that other tautomeric ring atom arrangements are possible. All such isomeric forms of these compounds are expressly included in the present disclosure.

Isomers mean compounds having identical molecular formulae but differ in the nature or sequence of bonding of their atoms or in the arrangement of their atoms in space. Isomers that differ in the arrangement of their atoms in space are termed stereoisomers. Stereoisomers that are not mirror images of one another are termed diastereomers, and those that are non-superimposable mirror images of each other are termed enantiomers. When a compound has an asymmetric center, for example, it is bonded to four different groups, a pair of enantiomers is possible. A chiral compound can exist as either individual enantiomer or as a mixture thereof. Unless otherwise indicated, the description is intended to include individual stereoisomers as well as mixtures.

Certain compounds of the present disclosure can exist in unsolvated forms as well as solvated forms, including hydrated forms. Solvates refer to a complex formed by combination of solvent molecules with the compound of Formula I. The solvent can be an organic compound, an inorganic compound, or a mixture thereof.

Pharmaceutically acceptable salts represent those salts which are, within the scope of medical judgement, suitable for use in contact for the tissues of humans and lower animals without undue toxicity, irritation, allergic response and the like, and are commensurate with a reasonable benefit/risk ratio. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Therapeutically effective amount means an amount of compound or a composition of the present invention effective in inhibiting Bruton's tyrosine kinase and thus producing the desired therapeutic effect.

As used herein, the term alkyl refers to a monovalent straight or branched chain, saturated aliphatic hydrocarbon radical having a number of carbon atoms in the specified range. For example, $C_{1-6}$ alkyl refers to any of the hexyl alkyl and pentyl alkyl isomers as well as n-, iso-, sec- and t-butyl, n- and iso-propyl, ethyl and methyl. Alkyl also includes saturated aliphatic hydrocarbon radicals wherein one or more hydrogens are replaced with deuterium, for example, $CD_3$.

The term branched alkyl refers to an alkyl group as defined above except that straight chain alkyl groups in the specified range are excluded. As defined herein, branched alkyl includes alkyl groups in which the alkyl is attached to the rest of the compound via a secondary or tertiary carbon. For example, isopropyl is a branched alkyl group.

The term cycloalkyl refers to any monocyclic ring of an alkane having a number of carbon atoms in the specified range. For example, $C_{3-6}$cycloalkyl refers to cyclopropyl, cyclobutyl, cyclopentyl, and cyclohexyl.

The term halogen refers to fluorine, chlorine, bromine and iodine (alternatively referred to as fluoro, chloro, bromo, and iodo).

The term haloalkyl refers to an alkyl group as defined above in which one or more of the hydrogen atoms have been replaced with a halogen (i.e., F, Cl, Br and/or I). For example, $C_{1-6}$ haloalkyl refers to a $C_1$ to $C_6$ linear or branched alkyl group as defined above with one or more halogen substituents. The term fluoroalkyl has an analogous meaning except that the halogen substituents are restricted to fluoro. Suitable fluoroalkyls include the series $(CH_2)_{0-4}CF_3$.

The term C(O) or CO refers to carbonyl. The terms $S(O)_2$ or $SO_2$ refers to sulfonyl. The term S(O) or SO refers to sulfinyl.

The term aryl refers to phenyl, naphthyl, tetrahydronaphthyl, idenyl, dihydroindenyl and the like. An aryl of particular interest is phenyl.

The term heteroaryl refers to (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. A class of heteroaryls of interest consists of (i) 5- and 6-membered heteroaromatic rings containing from 1 to 3 heteroatoms independently selected from N, O and S, and (ii) heterobicyclic rings selected from quinolinyl, isoquinolinyl, and quinoxalinyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Synthetic methods for preparing the compounds of the present invention are illustrated in the following Schemes, Methods, and Examples. Starting materials are commercially available or may be prepared according to procedures known in the art or as described herein. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily appreciate that known variations in the conditions and processes can be used to prepare such compounds.

Formula (I)

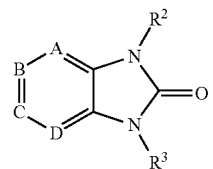

The Btk inhibitor compounds of Formula I can be prepared by methods well known in the art of organic chemistry. The starting material used for the synthesis of these compounds can be either synthesized or obtained from commercial sources, such as, but not limited to, China chemical companies or Sigma-Aldrich Chemical Co. (St. Louis, Mo.) at China. The compounds described herein, and other related compounds having different substituents are optionally synthesized using techniques and materials, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in United States Patent Application Publication No. US 2011/0130429 A1, Burgey et al. *Bioorganic & Medicinal Chemistry Letters* 10 (2006) 5052-5056. The definitions of chemistry terms used in this application may be found in these reference (if not otherwise defined herein). As a guide the following synthetic methods may be utilized.

During the synthetic sequences it may be necessary and/or desirable to protect sensitive or reactive groups on any of the molecules concerned. This is achieved by means of conventional protecting groups, such as those described in T. W Greene and P. G. M. Wutts "Protective groups in Organic Synthesis" 3rd Edition, John Wiley and Sons, 1999. The protective groups are optionally removed at a convenient subsequent stage using methods well known in the art. The products of the reactions are optionally isolated and purified.

If desired, using conventional techniques, but not limited to, filtration, distillation crystallization, chromatography and the like. Such materials are optionally characterized using conventional means, including physical constant and spectra data.

Compounds described herein may possess one or more stereocenters and each center may exist in the R or S configuration. The compounds presented herein include all diasteromeric, enantiomeric, and epimeric forms as well as the appropriate mixtures thereof.

The Btk inhibitor compounds of Formula I can be, for example, 1H-imidazo[4,5-c]pyridin-2(3H)-one derivatives. Specifically, the Btk inhibitor compounds of Formula I can be, for example, compounds F, wherein $R_1$-$R_2$ have the previously defined meanings. A non-limiting example of a synthetic approach towards the preparation of compounds F can be prepared by the general synthetic route shown in Scheme I.

Referring to Scheme I, amine (B) could be added to a range of substituted o-halonitroaromatics A, followed by nitro group reduction of the product C with Fe metal in $NH_4Cl$ in acidic methanol to deliver the o-amino anilines D. Ring closure with carbonyldiimidazole to obtain the key intermediates E, which then are derivatized by copper catalyst coupling reaction using appropriately substituted phenylboronic acid (corresponding boronic esters may also be used) directly affords the desired compounds F. In a typical procedure, a mixture of intermediates E, a copper catalyst (e.g. $Cu(OAc)_2$), base (e.g. TEA, DIPEA or the like) and an aryl boronic acid or aryl boronic ester in a suitable solvent such as DCM, or toluene to form compounds F.

Alternatively, compounds F or I may be obtained from compounds G or H, in which FG is a functional group (e.g. ester, protected anilines, protected phenols, bromide) that can be easily converted to groups defined for XAr. Non-limiting examples of suitable functional groups in compounds G are a benzyl ether, dibenzyl anime, or methyl ester, which can be treated with base or $Pd/C/H_2$ to form the key intermediates G-1a, G-2a, G-3a, then form corresponding compounds F-1, F-2, F-3, F-4 at Scheme II.

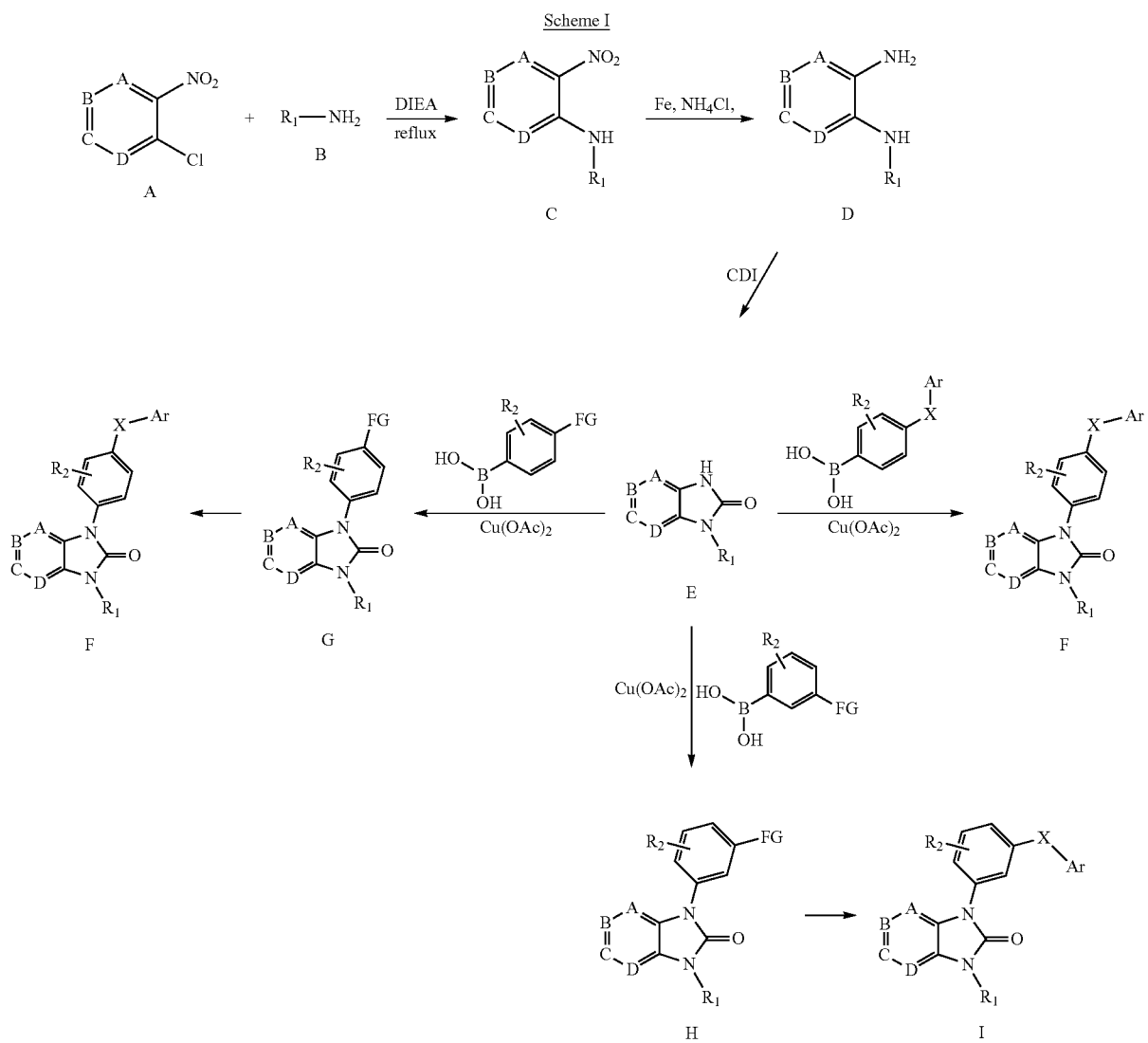

Scheme II
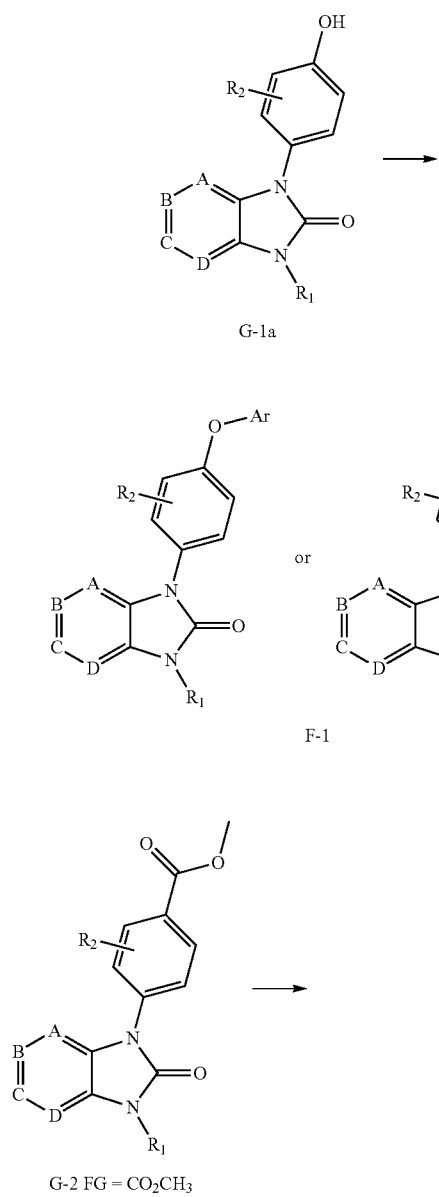
The deprotection reactions for the protective groups of compound F in Scheme III are known and can be run by the methods described below. Examples here are (a) deprotection reaction under acidic conditions for Boc protecting group and (b) deprotection reactions based on hydrogenolysis for benzyl protecting group. After deprotection with these conditions, coupling with, but not limited to, an acid chloride, such as, but not limited to, aryloyl chloride, completes the synthesis to provide compound F-b.

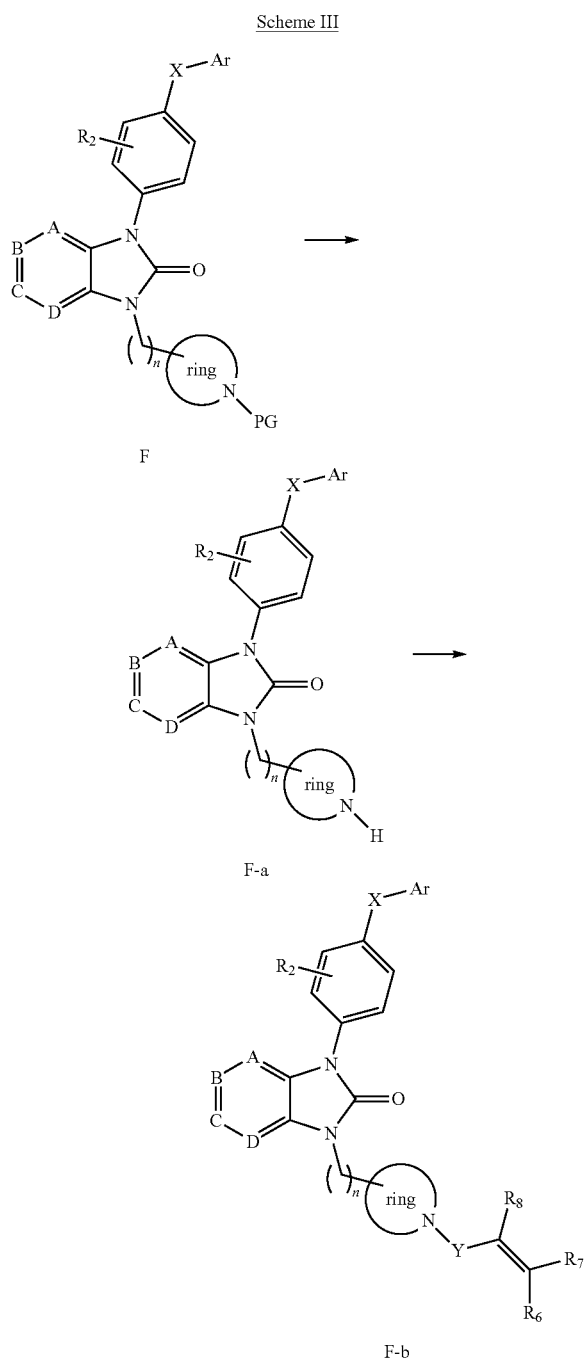

Scheme III

General experimental conditions: Preparative thin layer chromatography (PTLC) was performed on 20×20 cm plates (500 micron thick silica gel). Silica gel chromatography was performed on a Biotage Horizon flash chromatography system. 1H NMR spectra were recorded on a Bruker Ascend TM 400 spectrometer at 400 MHz at 298° K, and the chemical shifts are given in parts per million (ppm) referenced to the residual proton signal of the deuterated solvents: CHCl$_3$ at δ=7.26 ppm and CH$_3$OH or CH$_3$OD at δ=3.30 ppm. LCMS spectra were taken on an Agilent Technologies 1260 Infinity or 6120 Quadrupole spectrometer. The mobile phase for the LC was acetonitrile (A) and water (B) with 0.01% formic acid, and the eluent gradient was from 5-95% A in 6.0 min, 60-95% A in 5.0 min, 80-100% A in 5.0 min and 85-100% A in 10 min using a SBC18 50 mm×4.6 mm×2.7 μm capillary column. Mass spectra (MS) were measured by electrospray ion-mass spectroscopy (ESI). All temperatures are in degrees Celsius unless otherwise noted.

Analytical HPLC mass spectrometry conditions:
LC1: Column: SB-C18 50 mm×4.6 mm×2.7 μm
Temperature: 50° C.
Eluent: 5:95 v/v acetonitrile/water+0.01% formic acid in 6 min.
Flow Rate: 1.5 mL/min, Injection 5 μL
Detection: PDA, 200-600 nm
MS: mass range 150-750 amu; positive ion electrospray ionization
LC2: Column: SB-C18 50 mm×4.6 mm×2.7 μm
Temperature: 50° C.
Eluent: 5:95 to 95:5 v/v acetonitrile/water+0.05% TFA over 3.00 min.
Flow Rate: 1.5 mL/min, Injection 5 μL
Detection: PDA, 200-600 nm
MS: mass range 150-750 amu; positive ion electrospray ionization
LC3: Column: SB-C18 50 mm×4.6 mm×2.7 μm
Temperature: 50° C.
Eluent: 10:90 to 98:2 v/v acetonitrile/water+0.05% TFA over 3.75 min.
Flow Rate: 1.0 mL/min, Injection 10 μL
Detection: PDA, 200-600 nm
MS: mass range 150-750 amu; positive ion electrospray ionization List of Abbreviations AcOH=acetic acid
Alk=alkyl
Ar=aryl
Boc=tert-butyloxycarbonyl
bs=broad singlet
CH$_2$Cl$_2$=dichloromethane
d=doublet
dd=doublet of doublets
DBU=1,8-diazabicyclo[5.4.0]undec-7-ene
DCM=dichloromethane
DEAD=diethyl azodicarboxylate
DMF=N,N-dimethylformamide
DMSO=dimethyl sulfoxide
EA=ethyl acetate
ESI=electrospray ionization
Et=ethyl
EtOAc=ethyl acetate
EtOH=ethyl alcohol
h=hours
HOAc=acetic acid
LiOH=lithium hydroxide
m=multiplet
Me=methyl
MeCN=acetonitrile
MeOH=methyl alcohol
MgSO$_4$=magnesium sulfate
min=minutes
MS=mass spectroscopy
NaCl=sodium chloride NaOH=sodium hydroxide
Na$_2$SO$_4$=sodium sulfate
NMR=nuclear magnetic resonance spectroscopy
PE=petroleum ether
PG=protecting group
Ph=phenyl
rt=room temperature
s=singlet
t=triplet
TFA=trifluoroacetic acid
THF=tetrahydrofuran
Ts=p-toluenesulfonyl (tosyl)

The compounds of the present invention can be prepared following general methods detailed below. In certain embodiments, provided herein are methods of making the tyrosine kinase inhibitor compounds described herein. In certain embodiments, compounds described herein are synthesized using the following synthetic schemes. In other embodiments, compounds are synthesized using methodologies analogous to those described below by the use of appropriate alternative starting materials. All key intermediates were prepared according to the following methods.

Example 1

(R)-1-(1-acryloylpyrrolidin-3-yl)-3-(4-phenoxyphenyl)-1H-imidazo[4,5-c]pyridin-2(3H)-one

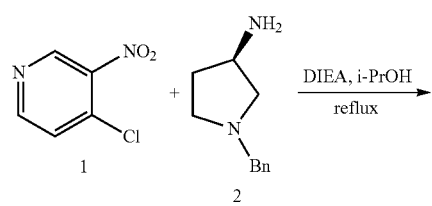

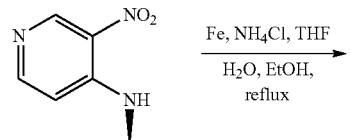

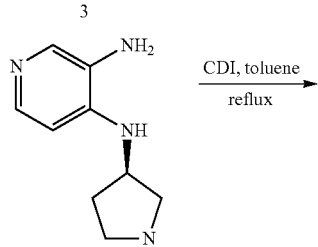

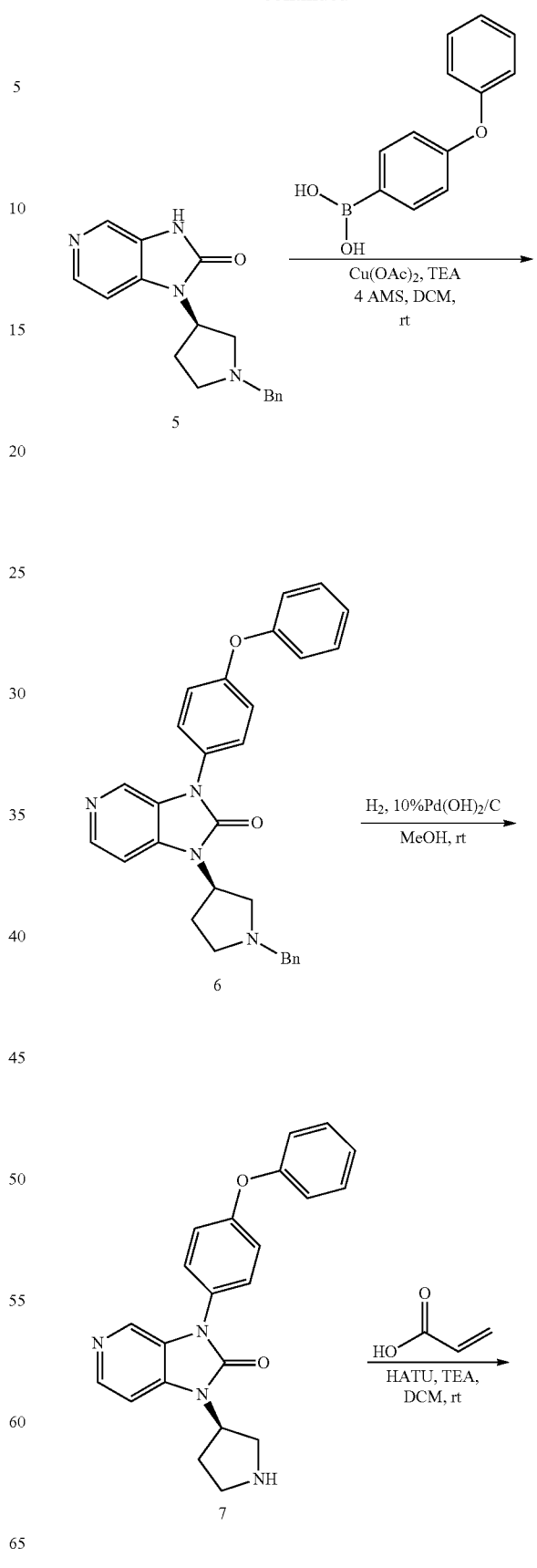

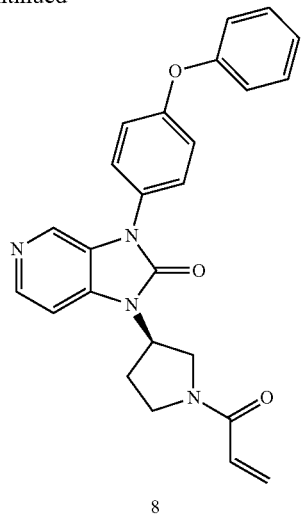

8

Step 1: (R)—N-(1-benzylpyrrolidin-3-yl)-3-nitropyridin-4-amine (3)

A mixture of 4-chloro-3-nitropyridine (12.2 g, 77.4 mmol), (R)-1-benzylpyrrolidin-3-amine (15 g, 85.2 mmol), and N,N-diisopropylethylamine (47 mL, 271.1 mmol) in 2-propanol (309 mL) was heated at reflux for 4 h. Volatile components were removed under vacuum and the residue was purified by column chromatography on silica gel (gradient: PE/EA=10/1) to provide the title product 22.1 g, yield 96%.

$^1$H NMR (400 MHz, DMSO-$d_6$): δ 9.03 (s, 1H), 8.27 (d, J=6 Hz, 1H), 8.22 (d, J=7.2 Hz, 1H), 7.34-7.26 (m, 4H), 7.25 (d, J=4 Hz, 1H), δ 7.02 (d, J=6.4 Hz, 1H), δ 4.31-4.29 (m, 1H), δ 3.65 (s, 2H), δ 2.80-2.73 (m, 2H), δ 2.65-2.61 (m, 1H), δ 2.41-2.33 (m, 2H), δ 1.74-1.73 (m, 1H).

Step 2: (R)—N4-(1-benzylpyrrolidin-3-yl)pyridine-3,4-diamine (4)

To a solution of (3) 22.1 g (74.1 mmol) in EtOH (504 mL) was added. Fe (22.55 g, 400 mmol), NH$_4$Cl (127 mL), THF (257 mL), and H$_2$O (127 mL). Then the reaction mixture was stirred at 85 degree for 2 h. The precipitate was filtered off. Solvent was removed. The reaction mixture was extracted with EA. Organic phase was purified by column chromatography on silica gel gradient: (DCM/MeOH=100/1-50/1) to give the title product 17 g, yield 85.5%.

$^1$H NMR (400 MHz, DMSO-$d_6$): δ 7.62 (s, 1H), 7.55 (d, J=5.2 Hz, 1H), 7.34-7.31 (m, 5H), 7.25-7.23 (m, 1H), 6.28 (d, J=5.2 Hz, 1H), 5.30 (d, J=6.4 Hz, 1H), 4.64 (s, 2H), 3.95-3.94 (m, 1H), 3.59 (d, J=4.4 Hz, 2H), 2.83-2.80 (m, 1H), 2.79-2.62 (m, 1H), 2.46-2.41 (m, 2H), 2.27-2.22 (m, 1H), 1.69-1.65 (m, 1H). LC-MS: m/z=268 [M+H]$^+$.

Step 3: (R)-1-(1-benzylpyrrolidin-3-yl)-1H-imidazo[4,5-c]pyridin-2(3H)-one (5)

A mixture of (4) (9.5 g, 35.4 mmol) and carbonyldiimodazole (11.48 g, 70.8 mmol) in toluene (200 mL) was reflux for 3 h. Volatile components were removed under vacuum, before being poured into H$_2$O, The reaction mixture was extracted with EA, Organic phase was purified by column chromatography on silica gel (gradient: DCM/MeOH=100/1-50/1) to give the title product (7 g, yield 67.3%).

$^1$H NMR (400 MHz, DMSO-$d_6$): δ 7.62 (s, 1H), 7.55 (d, J=5.2 Hz, 1H), 7.34-7.31 (m, 5H), 7.25-7.23 (m, 1H), 6.28 (d, J=5.2 Hz, 1H), 5.30 (d, J=6.4 Hz, 1H), 4.64 (s, 2H), 3.95-3.94 (m, 1H), 3.59 (d, J=4.4 Hz, 2H), 2.83-2.80 (m, 1H), 2.79-2.62 (m, 1H), 2.46-2.41 (m, 2H), 2.27-2.22 (m, 1H), 1.69-1.65 (m, 1H). LC-MS: m/z=295 [M+H]$^+$.

Step 4: (R)-1-(1-benzylpyrrolidin-3-yl)-3-(4-phenoxyphenyl)-1H-imidazo[4,5-c]pyridin-2(3H)-one (6)

Intermediate 5 (0.1 g, 0.34 mmol), (4-phenoxyphenyl)boronic acid (0.145 g, 0.68 mmol), TEA (68 mg, 0.68 mmol) and 4 A molecular sieves (130 mg) were added to DCM (3 mL) in a vial Copper (II) acetate (67 mg, 0.34 mmol) was added in one portion. The mixture was stirred for about 22 h at rt. Volatile components were removed under vacuum, before being poured into H$_2$O, The reaction mixture was extracted with EA, Organic phase was purified by column chromatography on silica gel (gradient: DCM/MeOH=100/1-50/1) to give the title product (63 mg, yield 40.1%).

$^1$H NMR (400 MHz, CDCl$_3$): δ 8.29 (s, 1H), 8.23 (s, 1H), 7.80 (s, 1H), 7.39-7.37 (m, 2H), 7.36-7.31 (m, 5H), 7.27 (s, 2H), 7.07-7.01 (m, 5H), 5.19 (s, 1H), 3.72 (d, J=12.8 Hz, 1H), 3.57 (d, J=12.8 Hz, 1H), 3.15 (s, 1H), 3.30-2.98 (m, 1H), 2.64-2.59 (m, 1H), 2.35-2.29 (m, 2H), 2.118 (s, 1H). LC-MS: m/z=462 [M+H]$^+$.

Step 5: (R)-3-(4-phenoxyphenyl)-1-(pyrrolidin-3-yl)-1H-imidazo[4,5-c]pyridin-2(3H)-one (7)

A suspension of 6 (50 mg, 0.1 mmol) and 10% Pd(OH)$_2$/C (20 mg) in MeOH (10 mL) was hydrogenated at 50 psi H$_2$ for 8 h. The suspension was filtered through Celite and concentrated. The residue was dried in vacuo to provide the title product (35 mg). LC-MS: m/z=373 [M+H]$^+$.

Step 6: (R)-1-(1-acryloylpyrrolidin-3-yl)-3-(4-phenoxyphenyl)-1H-imidazo[4,5-c]pyridin-2(3H)-one (8)

Intermediates 7 (35 mg, 0.094 mmol), HATU (39.3 mg, 0.10 mmol), TEA (19 mg, 0.18 mmol) and acrylic acid (7.4 mg, 0.10 mmol) were added to DCM (3 mL) was added in one portion. The mixture was stirred for about 2 h at rt. Volatile components were removed under vacuum, before being poured into H$_2$O, The reaction mixture was extracted with EA, Organic phase was purified by P-TLC to give the title product (10 mg).

$^1$H NMR (400 MHz, CDCl$_3$): δ 8.35 (s, 2H), 7.47-7.45 (m, 2H), 7.41-7.37 (m, 2H), 7.17 (d, J=8.4 Hz, 3H), 7.10 (d, J=7.6 Hz, 2H), 7.03 (d, J=8.4 Hz, 1H), 6.51-6.41 (m, 2H), 5.78-5.73 (m, 1H), 5.22-5.13 (m, 1H), 4.11-3.99 (m, 3H), 3.76-3.64 (m, 1H), 2.73-2.65 (m, 1H), 2.47-2.39 (m, 1H). LC-MS-8: m/z=427 [M+H]$^+$.

Example 2

(R)-1-(1-acryloylpyrrolidin-3-yl)-3-(4-(3-methoxyphenoxy)phenyl)-1H-imidazo[4,5-c]pyridin-2(3H)-one

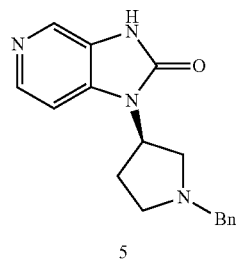
5

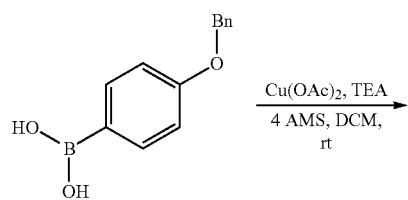

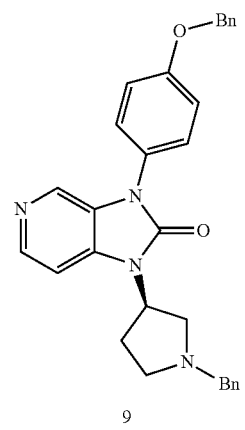

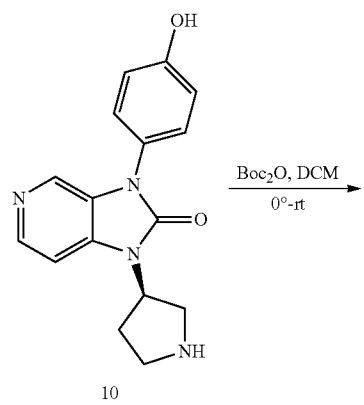

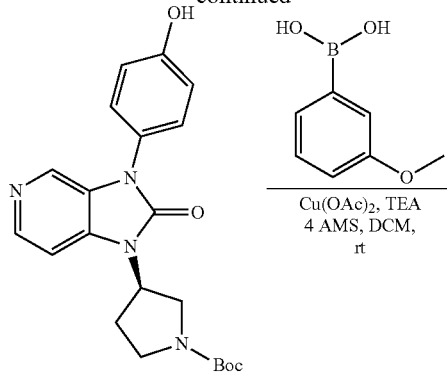

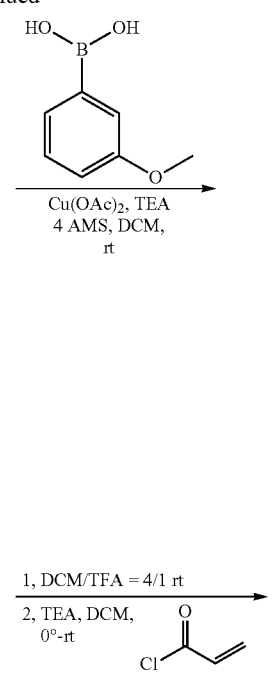

Step 1: (R)-3-(4-(benzyloxy)phenyl)-1-(1-benzylpyrrolidin-3-yl)-1H-imidazo[4,5-c]pyridin-2(3H)-one (9)

To a solution of intermediate 5 (2 g, 6.8 mmol), (4-(benzyloxy)phenyl)boronic acid (3.1 g, 13.6 mmol), TEA (1.57 g, 13.6 mmol) and 4 Å molecular sieves (3 g) were added to DCM (50 mL) in a vial Copper (II) acetate (1.23 g, 6.8 mmol) was added in one portion. The mixture was stirred for about 15 h at rt. Volatile components were removed under vacuum, before being poured into H₂O. The reaction mixture was extracted with EA, Organic phase was purified by column chromatography on silica gel (gradient: DCM/MeOH=100/1-50/1), give the title product (0.8 mg, yield 25%).

$^1$H NMR (400 MHz, CDCl$_3$): δ 8.36-8.28 (m, 2H), 7.87 (s, 1H), 7.46-7.31 (m, 12H), 7.11 (d, J=4.4 Hz, 2H), 5.26-5.23 (m, 1H), 5.09 (s, 2H), 3.78 (d, J=6.4 Hz, 1H), 3.63 (d, J=6.4 Hz, 1H), 3.23-3.19 (m, 1H), 3.06-3.03 (m, 1H), 2.69-2.64 (m, 1H), 2.44-2.36 (m, 2H), 2.17-2.14 (m, 1H). LCMS: m/z=477 [M+H]$^+$.

Step 2: (R)-3-(4-hydroxyphenyl)-1-(pyrrolidin-3-yl)-1H-imidazo[4,5-c]pyridin-2(3H)-one (10)

A suspension of 9 (0.8 g, 1.68 mmol) and 10% Pd/C (0.1 g) in MeOH (15 mL) was hydrogenated at 50 psi H$_2$ for 20 h. The suspension was filtered through Celite and concentrated. The residue was dried in vacuo to provide the title crude product 0.49 g. LCMS: m/z=297 [M+H]$^+$.

Step 3: (R)-tert-butyl 3-(3-(4-hydroxyphenyl)-2-oxo-2,3-dihydro-1H-imidazo[4,5-c]pyridin-1-yl)pyrrolidine-1-carboxylate (11)

To a suspension of 10 (0.49 g; 1.68 mmol) and TEA (0.17 g, 1.68 mmol) in CH$_2$Cl$_2$ (15 mL) at 0° C. was added di-tert-butylcarbonate (0.31 g, 1.68 mmol) The solution was then stirred to room temperature for 1 h. before being poured into H$_2$O, The reaction mixture was extracted with DCM, Organic phase was purified by column chromatography on silica gel (gradient: DCM/MeOH=100/1-50/1) to give the title product (0.58 g, yield 87.8%).

$^1$H NMR (400 MHz, CDCl$_3$) δ 9.29 (br, 1H), 8.35 (d, J=2.8 Hz 1H), 8.23 (s, 1H), 7.27 (d, J=4 Hz, 2H), 7.11 (d, J=2.8 Hz 1H), 6.96 (d, J=5.2 Hz 2H), 5.19-5.13 (m, 1H), 3.85 (br, 3H), 3.54-3.48 (m, 1H), 2.60-2.54 (m, 1H), 2.38-2.30 (m, 1H), 1.50 (s, 9H). LCMS: m/z=397 [M+H]$^+$.

Step 4: (R)-tert-butyl 3-(3-(4-(3-methoxyphenoxy)phenyl)-2-oxo-2,3-dihydro-1H-imidazo[4,5-c]pyridin-1-yl)pyrrolidine-1-carboxylate (12)

To a solution of 11 (30 mg, 0.075 mmol), (3-methoxyphenyl)boronic acid (23 mg, 0.15 mmol), TEA (15.3 mg, 0.15 mmol) and 4 A molecular sieves (0.1 g) were added to DCM (5 mL) in a vial Copper (II) acetate (13.7 mg, 0.075 mmol) was added in one portion. The mixture was stirred for about 20 h at rt. Volatile components were removed under vacuum, before being poured into H$_2$O, The reaction mixture was extracted with EA, Organic phase was purified by column chromatography on silica gel (gradient: DCM/MeOH=100/1-50/1), give the title product (32 mg, yield 86.4%).

$^1$H NMR (400 MHz, CDCl$_3$): δ 8.36 (br, 2H), 7.46 (d, J=4.4 Hz 2H), 7.30-7.26 (m, 1H), 7.16 (d, J=4.4 Hz, 2H), 7.08 (br, 1H), 6.73-6.65 (m, 3H), 5.19-5.15 (m, 1H), 3.81 (s, 3H), 3.75-3.76 (m, 3H), 3.51-3.4 (m, 1H), 2.59-2.54 (m, 1H), 2.37-2.30 (m, 1H), 1.49 (s, 9H). LCMS: m/z=503 [M+H]$^+$.

Step 5: (R)-1-(1-acryloylpyrrolidin-3-yl)-3-(4-(3-methoxyphenoxy)phenyl)-1H-imidazo[4,5-c]pyridin-2(3H)-one (13)

Intermediate 12 (32 mg, 0.063 mmol) were added to CF$_3$COOH/DCM=4/1 (5 mL) in one portion. The mixture was stirred for about 1 h at rt. Volatile components were removed under vacuum to give a crude title product, and directly used in next step without further purification. LCMS: m/z=403 [M+H]$^+$.

To a solution of Acryloyl chloride (5.7 mg, 0.068 mmol) in DCM (I mL) was added to a stirred solution of a crude product (25.3 mg, 0.063 mmol) and TEA (12.7 mg, 0.126 mmol) in DCM (5 mL) at 0° C. The reaction mixture was stirred for 1 h, poured onto brine and extracted with DCM. The organic layer was dried, concentrated and recrystallized from DCM/MeOH=100/1 to give the title product (5 mg, yield 17.4%).

$^1$H NMR (400 MHz, CDCl$_3$): δ 8.38-8.34 (m, 2H), 7.46 (d, J=3.6 Hz, 2H), 7.30-7.26 (m, 1H), 7.17 (d, J=4.2 Hz, 2H), 7.05-7.01 (m, 1H), 6.73-6.65 (m, 3H), 6.51-6.41 (m, 2H), 5.79-5.72 (m, 1H), 5.22-5.15 (m, 1H), 4.11-3.98 (m, 3H), 3.81 (s, 3H), 3.78-3.71 (m, 1H), 2.79-2.60-2.39 (m, 1H), 2.50-2.37 (m, 1H). LCMS: m/z=457 [M+H]$^+$.

Example 3

N-(3-(2-oxo-3-(4-phenoxyphenyl)-2,3-dihydro-1H-imidazo[4,5-c]pyridin-1-yl) (19)

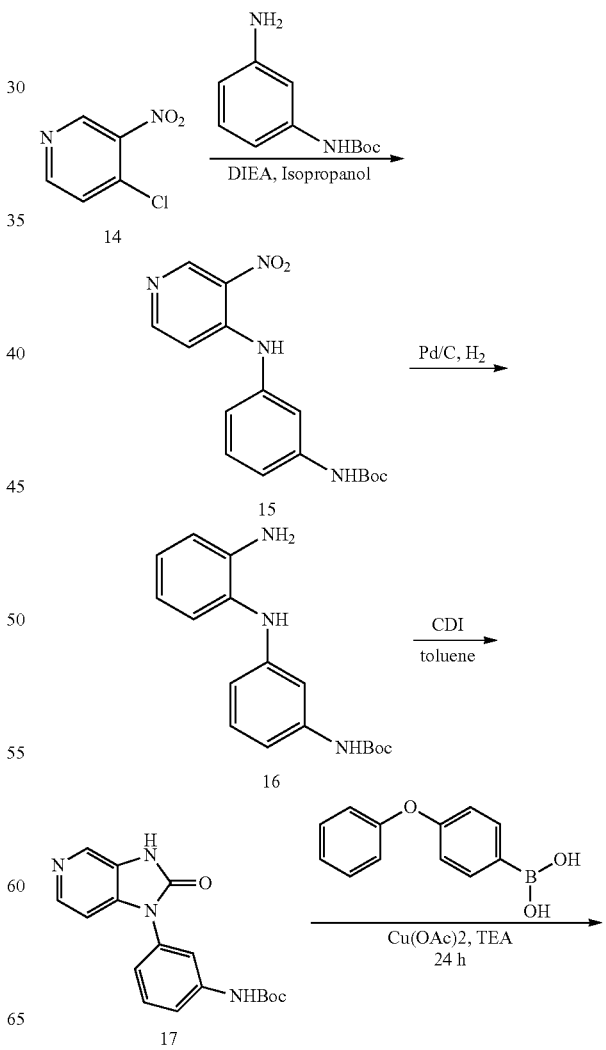

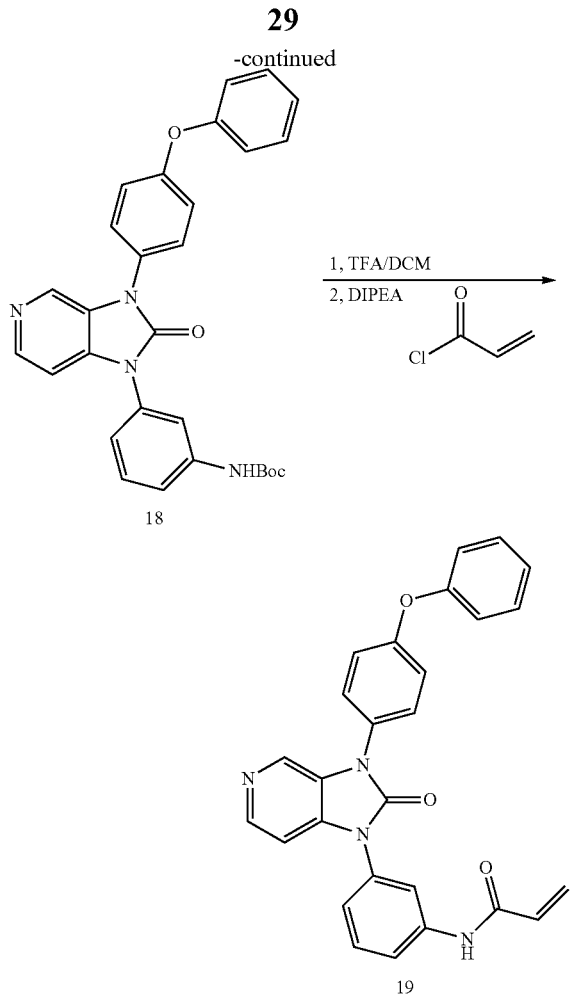

Step 1: tert-butyl (3-((3-nitropyridin-4-yl)amino) phenyl)carbamate (15)

4-chloro-3-nitropyridine (1.614 g, 10.18 mmol, 1.0 eq) was dissolved in isopropanol (30 mL), added tert-butyl (3-aminophenyl)carbamate (2.12 g, 10.18 mmol, 1.0 eq) and DIPEA (2.63 g, 20.36 mmol, 2.0 eq), the mixture solution was stirred reflux for 5 h. Then stopped and removed the solution under reduce pressure, the residue was added EA and saturated NaHCO$_3$, extracted with EA and dried with Na$_2$SO$_4$, filtered and concentrated, purified with silica column (PE:EA=5:1~2:1) to obtain the title product (2.9 g), yellow solid, Yield: 2.9 g, 86.3%. $^1$H NMR (400 MHz, CDCl$_3$): δ=9.62 (s, 1H), 9.28 (s, 1H), 8.26 (d, J=6.0 Hz, 1H), 7.57 (s, 1H), 7.38-7.34 (m, 1H), 7.15 (d, J=8.0 Hz, 1H), 7.01-6.95 (m, 2H), 6.61 (s, 1H), 1.52 (s, 9H).

Step 2: tert-butyl (3-((2-aminophenyl)amino)phenyl)carbamate (16)

Intermediate 15 (2.9 g) was dissolved in Mathanol (50.0 mL), added Pd/C (200 mg), under H$_2$ atmosphere the mixture was stirred for 3 h at RT, stopped the reaction, filtered and concentrated under reduce pressure to obtain the title product used next step without purification, tan solid, Yield: 2.6 g, 98.9%. $^1$H NMR (400 MHz, CDCl$_3$): δ=8.05 (s, 1H), 7.97 (d, J=5.6 Hz, 1H), 7.29 (s, 1H), 7.24-7.20 (m, 1H), 7.04 (d, J=5.2 Hz, 1H), 6.89 (d, J=8.0 Hz, 1H), 6.78-6.76 (m, 1H), 6.55 (s, 1H), 5.83 (s, 1H), 3.34 (s, 2H), 1.51 (s, 9H). LCMS (ESI) m/z=301[M+H]$^+$.

Step 3: tert-butyl (3-(2-oxo-2,3-dihydro-1H-imidazo [4,5-c]pyridin-1-yl)phenyl)carbamate (17)

Intermediate 16 (740 mg, 1.0 eq) was dissolved in toluene (30 mL), added CDI (800 mg, 2.0 eq), the mixture solution were stirred under reflux for 4 h. Then allowed the reaction was cooled to room temperature, added water and extracted with EA, dried with Na$_2$SO$_4$, filtered and concentrated, purified with silica column (DCM:MeOH=50:1~20:1) to obtain the title product, yellow solid, Yield: 700 mg, 86.8%. $^1$H NMR (400 MHz, DMSO-d$_6$): δ=11.41 (s, 1H), 9.58 (s, 1H), 8.30 (s, 1H), 8.20 (d, J=5.2 Hz, 1H), 7.68 (s, 1H), 7.50-7.42 (m, 2H), 7.14 (d, J=7.6 Hz, 1H), 7.04-7.01 (m, 2H), 1.48 (s, 9H). LCMS (ESI) m/z=327 [M+H]$^+$.

Step 4: tert-butyl (3-(2-oxo-3-(4-phenoxyphenyl)-2,3-dihydro-1H-imidazo [4,5-c]pyridin-1-yl)phenyl) carbamate (18)

Intermediate 17 (101 mg, 0.308 mmol, 1.0 eq) was dissolved in DCM (3.0 mL), added Cupric acetate (56 mg, 0.308 mmol, 1.0 eq), (4-phenoxyphenyl)boronic acid (132 mg, 0.617 mmol, 2.0 eq), 4 A molecular sieve (131 mg) and TEA (62 mg, 0.617 mmol, 2.0 eq), the mixture solution were stirred under for 30 h at RT. Then filtered the solution and removed the solution under reduce pressure, added water and extracted with EA, dried with Na$_2$SO$_4$, filtered and concentrated, purified with silica column (PE:EA=4:1~1:1) to obtain the title product, brown solid, Yield: 50 mg, 32.7%. $^1$H NMR (400 MHz, CDCl$_3$): δ=8.40 (s, 1H), 8.37 (d, J=5.6 Hz, 1H), 7.78 (s, 1H), 7.55 (d, J=8.8 Hz, 2H), 7.48-7.44 (m, 1H), 7.42-7.38 (m, 2H), 7.32 (d, J=8.8 Hz, 1H), 7.24 (d, J=7.6 Hz, 1H), 7.19-7.10 (m, 6H), 6.69 (s, 1H), 1.52 (s, 9H). LCMS (ESI) m/z=495 [M+H]$^+$.

Step 5: N-(3-(2-oxo-3-(4-phenoxyphenyl)-2,3-dihydro-1H-imidazo[4,5-c]pyridin-1-yl) (19)

Intermediate 18 (50 mg) was dissolved in DCM (5.0 mL), added TFA (2.0 mL), the mixture was stirred for 1 h at RT, stopped and removed the solution under reduce pressure, the residue was added saturated NaHCO$_3$, extracted with EA and dried with Na$_2$SO$_4$, filtered and concentrated, obtained crude product (tan solid, 45 mg) used next step without purification. $^1$H NMR (400 MHz, CDCl$_3$): δ=8.39 (s, 1H), 8.35 (d, J=5.2 Hz, 1H), 7.55 (d, J=8.8 Hz, 2H), 7.42-7.38 (m, 2H), 7.34-7.30 (m, 1H), 7.19-7.16 (m, 3H), 7.12-7.10 (m, 3H), 6.91-6.87 (m, 2H), 6.77-6.74 (m, 1H), 3.87 (s, 2H). LCMS (ESI) m/z=395 [M+H]$^+$.

Crude intermediate (23 mg, 0.058 mmol, 1.0 eq) and DIEA (9 mg, 0.070 mmol, 1.2 eq) were dissolved in THF (2.0 mL), added acryloyl chloride (5.6 mg, 0.061 mmol, 1.05 eq) slowed at 0° C., the mixture solution was stirred for 0.5 h at RT, followed the reaction with LCMS, stopped the reaction added water and extracted with EA, dried with Na$_2$SO$_4$, filtered and concentrated, the residue was purification with silica gel plate (PE:EA=20:80) obtain the title product (8 mg) colorless oil, Yield: 8 mg, 30.6%. $^1$H NMR (400 MHz, CDCl$_3$): δ=8.40 (s, 1H), 8.38 (d, J=5.2 Hz, 1H), 8.01 (s, 1H), 7.76 (s, 1H), 7.55 (d, J=8.8 Hz, 2H), 7.49 (d, J=5.6 Hz, 2H), 7.42-7.38 (m, 2H), 7.34-7.32 (m, 1H), 7.20-7.17 (m, 4H), 7.12 (d, J=7.6 Hz, 2H), 6.44 (d, J=16.8 Hz, 1H), 6.27-6.20 (m, 1H), 5.78 (d, J=10.4 Hz, 1H). LCMS (ESI) m/z=449 [M+H]⁺.

Example 4

(R)-1-(1-acryloylpyrrolidin-3-yl)-3-(4-(m-tolyloxy)phenyl)-1H-imidazo[4,5-c]pyridin-2(3H)-one

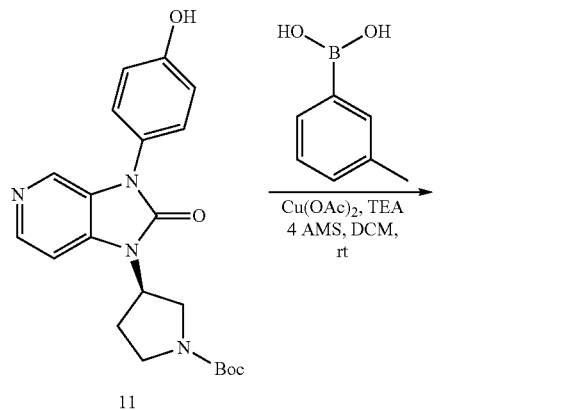

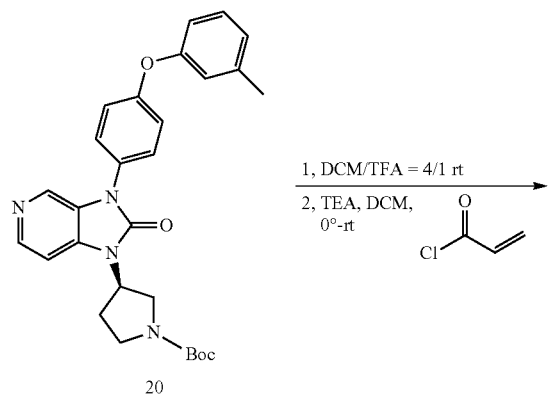

Step 1: (R)-tert-butyl 3-(2-oxo-3-(4-(m-tolyloxy)phenyl)-2,3-dihydro-1H-imidazo[4,5-c] pyridin-1-yl)pyrrolidine-1-carboxylate (20)

To a solution of intermediate 11 (100 mg, 0.25 mmol), m-tolylboronic acid (68 mg, 0.5 mmol), TEA (45 mg, 0.5 mmol) and 4 A molecular sieves (0.1 g) were added to DCM (5 mL) in a vial Copper (II) acetate (45 mg, 0.25 mmol) was added in one portion. The mixture was stirred for about 20 h at rt. Volatile components were removed under vacuum, before being poured into H₂O, The reaction mixture was extracted with EA, organic phase was purified by column chromatography on silica gel (gradient: DCM/MeOH=100/1-50/1) to give the title product (68 mg, yield 56.2%). LCMS: m/z=487 [M+H]⁺.

Step 2: (R)-1-(1-acryloylpyrrolidin-3-yl)-3-(4-(m-tolyloxy)phenyl)-1H-imidazo[4,5-c]pyridin-2(3H)-one (21)

Intermediate 20 (68 mg, 0.13 mmol) were added to CF₃COOH/DCM=4/1 (10 mL) in one portion. The mixture was stirred for about 1 h at rt. Volatile components were removed under vacuum to give a crude title product and directly used in next step without further purification. LCMS: m/z=387 [M+H]⁺.

A solution of Acryloyl chloride (11.8 mg, 0.13 mmol) in DCM (5 mL) was added to a stirred solution of crude intermediate (54 mg, 0.13 mmol) and TEA (131 mg, 1.3 mmol) in DCM (5 mL) at 0° C. The reaction mixture was stirred for 1 h, poured onto brine and extracted with DCM. The organic layer was dried, concentrated and recrystallized from DCM/MeOH=100/1 to give the title product (29 mg, yield 53.7%).

¹H NMR (400 MHz, CDCl₃): δ 8.36 (br, 2H), 7.47-7.44 (m, 2H), 7.29-7.25 (m, 1H), 7.14 (d, J=8 Hz, 2H), 7.06-6.98 (m, 2H), 6.90 (d, J=8 Hz, 2H), 6.52-6.41 (m, 2H), 5.79-5.72 (m, 1H), 5.22-5.16 (m, 1H), 4.12-4.00 (m, 3H), 3.76-3.74 (m, 1H), 2.74-2.61 (m, 1H), 2.47-2.39 (m, 1H), 2.36 (s, 3H). LCMS: m/z=441 [M+H]⁺.

Example 5

(R)-1-(1-acryloylpyrrolidin-3-yl)-3-(3-chloro-4-phenoxyphenyl)-1H-imidazo[4,5-c]pyridin-2(3H)-one

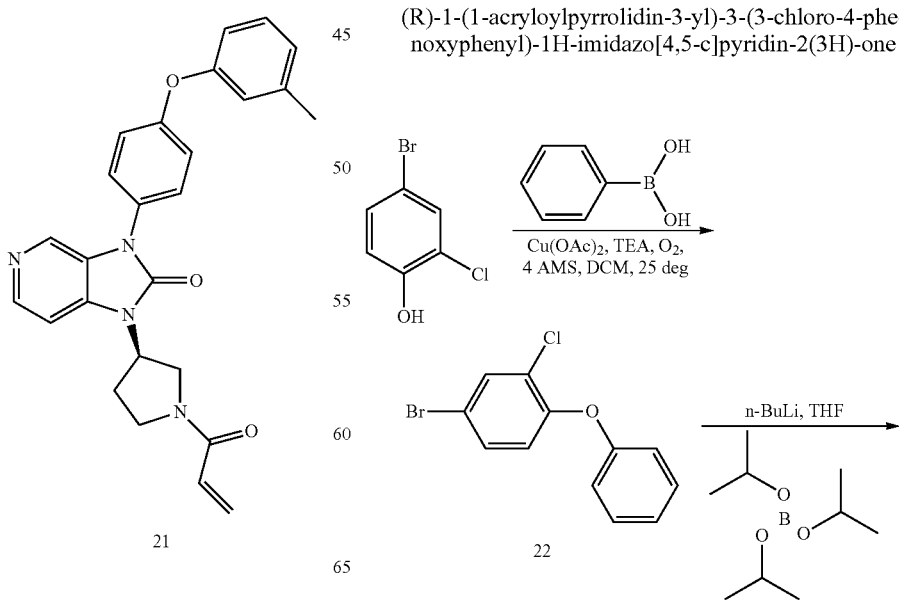

33
-continued

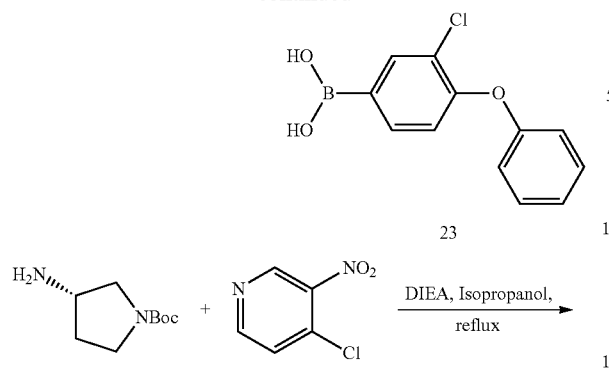

23

34
-continued

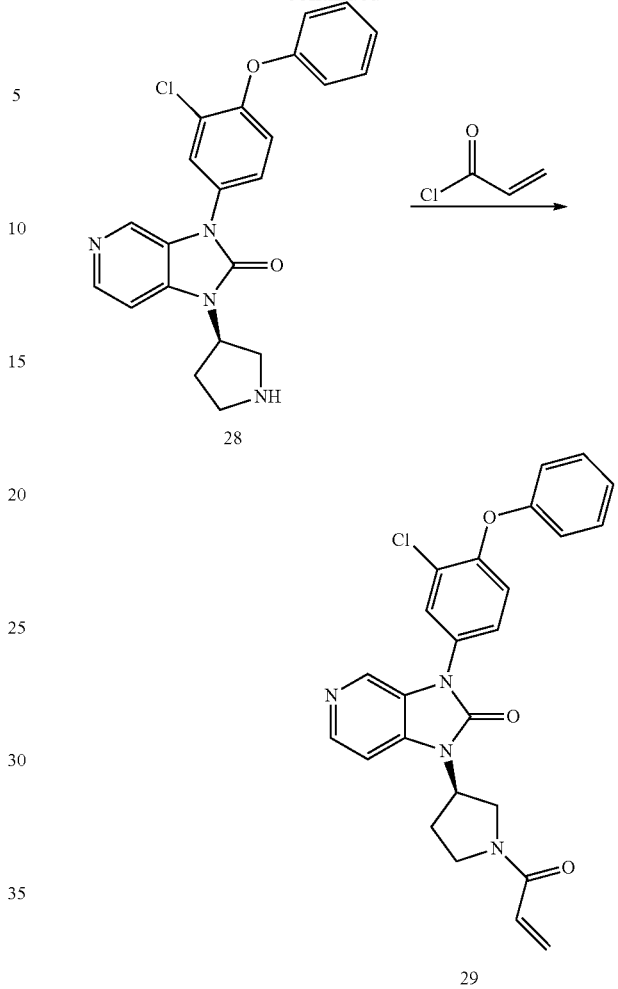

Step 1: 4-bromo-2-chloro-1-phenoxybenzene (22)

4-bromo-2-chlorophenol (10 g, 48.2 mmol, 1.0 eq) was dissolved in DCM (120.0 mL), added Cupric acetate (4.38 g, 24.1 mmol, 0.5 eq), phenylboronic acid (8.82 g, 72.3 mmol, 1.5 eq), 4 A molecular sieve (15 g) and added TEA (13.4 m, 96.4 mmol, 2.0 eq), the mixture solution was stirred for overnight at RT under Oxygen atmosphere. Then filtered the solution and removed the solution under reduce pressure, added water and extracted with EA dried with $Na_2SO_4$, filtered and concentrated, purified with silica column (PE:EA=100:1~10:1) to provide title product as colorless oil, Yield: 5.5 g, 40.2%. $^1$H NMR (400 MHz, $CDCl_3$): δ=7.61 (d, J=1.6 Hz, 1H), 7.32-7.37 (m, 3H), 7.12-7.15 (m, 1H), 6.95-7.02 (m, 2H), 6.84 (d, J=8.4 Hz, 1H).

Step 2: (3-chloro-4-phenoxyphenyl)boronic acid (23)

n-BuLi (2.45 M in hexane, 5.4 mL, 13.3 mmol) at −78° C. under nitrogen was added to a solution of 22 (2.9 g, 10.23 mmol) in THF (15 mL). After stirring for 15 min at −78° C., triisopropy borate (2.5 g, 13.3 mmol) was added in one portion. The mixture was warmed to 25° C., stirred for 30 min, and quenched with dilute HCl solution. The mixture was extracted with EtOAc (150 mL), washed with water, dried (Na$_2$SO$_4$) and evaporated to obtain a crude title product used directly for the step 6 without further purification.

Step 3: (R)-tert-butyl 3-((3-nitropyridin-4-yl)amino) pyrrolidine-1-carboxylate (24)

4-chloro-3-nitropyridine (10.145 g, 63.99 mmol, 1.0 eq) was dissolved in isopropanol (1200 mL), added (S)-tert-butyl 3-aminopyrrolidine-1-carboxylate (11.92 g, 63.99 mmol, 1.0 eq) and DIPEA (16.5 g, 127.98 mmol, 2.0 eq), the mixture solution was stirred reflux for 3.5 h. Then stopped and removed the solution under reduce pressure, added water, extracted with EA and dried with Na$_2$SO$_4$, filtered and concentrated to obtain a crude title product as yellow oil: 20 g. $^1$H NMR (400 MHz, CDCl$_3$): δ=9.24 (s, 1H), 8.35 (d, J=4.8 Hz, 1H), 8.23 (d, J=4.8 Hz, 1H), 6.73 (d, J=6.4 Hz, 1H), 4.23 (s, 1H), 3.78-3.83 (m, 1H), 3.56 (s, 2H), 3.35-3.44 (m, 1H), 2.32-2.36 (m, 1H), 2.05 (s, 1H), 1.48 (s, 9H). LCMS (ESI) m/z=309 [M+H]$^+$.

Step 4: (R)-tert-butyl 3-((3-aminopyridin-4-yl)amino)pyrrolidine-1-carboxylate (25)

Intermediate 25 (20 g, 64.94 mmol, 1.0 eq) was dissolved in MeOH (150.0 mL), added Pd/C (4.0 g), the mixture solution was stirred for 6 h at room temperature under Hydrogen atmosphere. Then filtered the solution and removed the solution under reduce pressure to obtain a crude title product as yellow solid, Yield: 17 g, 94.2%. $^1$H NMR (400 MHz, CDCl$_3$): δ=8.00 (s, 1H), 7.94 (s, 1H), 6.48 (d, J=5.2 Hz, 1H), 4.19 (s, 1H), 4.07 (s, 1H), 3.74 (s, 1H), 3.49 (s, 3H), 3.25-3.36 (m, 1H), 3.09 (s, 2H), 2.21-2.26 (m, 1H), 1.95 (s, 1H), 1.72 (s, 1H), 1.47 (s, 9H). LCMS (ESI) m/z=279 [M+H]$^+$.

Step 5: (R)-tert-butyl 3-(2-oxo-2,3-dihydro-1H-imidazo[4,5-c]pyridin-1-yl)pyrrolidine-1-carboxylate (26)

Intermediate 25 (17 g, 61.15 mmol, 1.0 eq) was dissolved in toluene (200 mL), added CDI (19.8 g, 122.3 mmol, 2.0 eq), the mixture solution were stirred under reflux for 4 h. Then allowed the reaction was cooled to room temperature, added water and extracted with EA, dried with Na$_2$SO$_4$, filtered and concentrated, purified with silica column (DCM:MeOH=200:1~50:1) to obtain the title product as canary yellow solid, Yield: 13 g, 59.4%. $^1$H NMR (400 MHz, CDCl$_3$): δ=10.35 (s, 1H), 8.43 (s, 1H), 8.33 (s, 1H), 7.03 (d, J=3.6 Hz, 1H), 5.12 (s, 1H), 3.71-3.80 (m, 3H), 3.50 (s, 1H), 2.50-2.56 (m, 1H), 2.30-2.32 (m, 1H), 1.50 (s, 9H). LCMS (ESI) m/z=305 [M+H]$^+$.

Step 6: (R)-tert-butyl 3-(3-(3-chloro-4-phenoxyphenyl)-2-oxo-2,3-dihydro-1H-imidazo[4,5-c]pyridin-1-yl)pyrrolidine-1-carboxylate (27)

Intermediate 26 (2.17 g, 7.1 mmol, 1.0 eq) was dissolved in DCM (100.0 mL), added Cupric acetate (646 mg, 3.55 mmol, 0.5 eq), Boronic acid 23 (3.53 g, 14.2 mmol, 2.0 eq), 4 A molecular sieve (3.0 g) and TEA (2.0 mL, 14.2 mmol, 2.0 eq), the mixture solution was stirred for overnight at RT under Oxygen atmosphere. Then filtered the solution and removed the solution under reduce pressure, added water and extracted with EA, dried with Na$_2$SO$_4$, filtered and concentrated, purified with silica column (DCM: MeOH=200:1~50:1) to obtain the title product 27 as gray solid, Yield: 1.7 g, 47.0%. $^1$H NMR (400 MHz, CDCl$_3$): δ=8.40 (s, 2H), 7.68 (s, 1H), 7.36-7.42 (m, 3H), 7.17-7.21 (m, 1H), 7.07-7.10 (m, 4H), 5.14-5.18 (m, 1H), 3.83 (s, 3H), 3.51 (d, J=8.4 Hz, 1H), 2.54-2.59 (m, 1H), 2.33-2.36 (m, 1H), 1.50 (s, 9H). LCMS (ESI) m/z=507 [M+H]$^+$.

Step 7: (R)-3-(3-chloro-4-phenoxyphenyl)-1-(pyrrolidin-3-yl)-1H-imidazo[4,5-c]pyridin-2(3H)-one (28)

Intermediate 27 (920 mg) was dissolved in DCM (20.0 mL), added TFA (4.0 mL), the mixture was stirred for 2.5 h at RT, and the solvent was removed under reduce pressure, the residue was added saturated NaHCO$_3$, extracted with EA and dried with Na$_2$SO$_4$, filtered and concentrated to provide a crude product 28 used next step without further purification. LCMS (ESI) m/z=407 [M+H]$^+$.

Step 8: (R)-1-(1-acryloylpyrrolidin-3-yl)-3-(3-chloro-4-phenoxyphenyl)-1H-imidazo[4,5-c]pyridin-2(3H)-one (29)

Intermediate 28 (738 mg, 1.82 mmol, 1.0 eq) was dissolved in THF (10.0 mL), added TEA (368 mg, 3.64 mmol, 2.0 eq), acryloyl chloride (197 mg, 2.18 mmol, 1.2 eq) slowly at 0° C., the mixture solution was stirred for 0.5 h at RT, followed the reaction with LCMS, water was added to the reaction mixture and extracted with EA, dried with Na$_2$SO$_4$, filtered and concentrated, the residue was purification with silica column (DCM:MeOH=200:1~30:1) to obtain the title product as canary yellow solid, Yield: 489 mg, 58.3%. $^1$H NMR (400 MHz, CDCl$_3$): δ=8.40 (s, 1H), 7.68 (s, 1H), 7.36-7.42 (m, 3H), 7.17-7.21 (m, 1H), 7.04-7.10 (m, 4H), 6.41-6.52 (m, 2H), 5.74-5.80 (m, 1H), 5.13-5.24 (m, 1H), 3.97-4.14 (m, 3H), 3.65-3.77 (m, 1H), 2.62-2.77 (m, 1H), 2.38-2.49 (m, 1H). LCMS (ESI) m/z=461 [M+H]$^+$.

Example 6

1-(1-acryloylpyrrolidin-3-yl)-3-(3-chloro-4-(3-(trifluoromethyl)phenoxy)phenyl)-1H-imidazo[4,5-c]pyridin-2(3H)-one

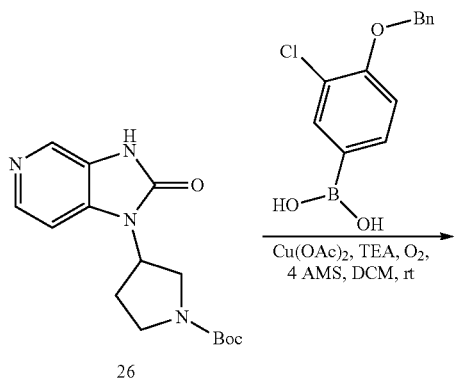

26

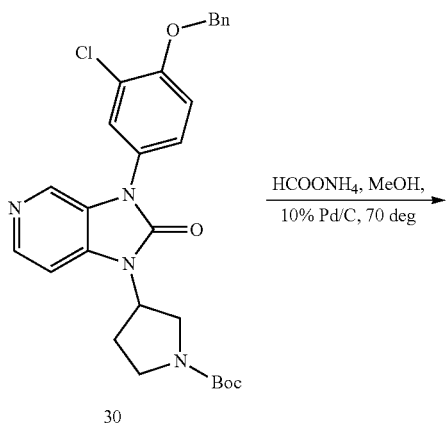

30

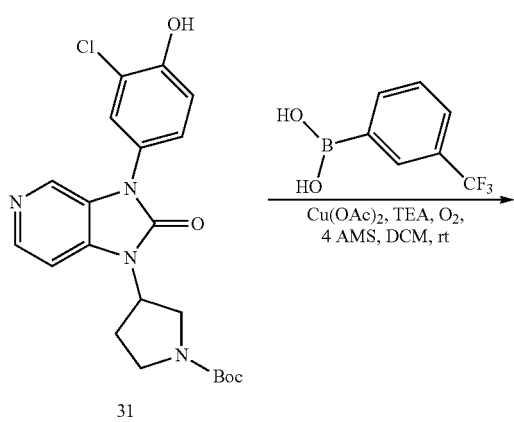

31

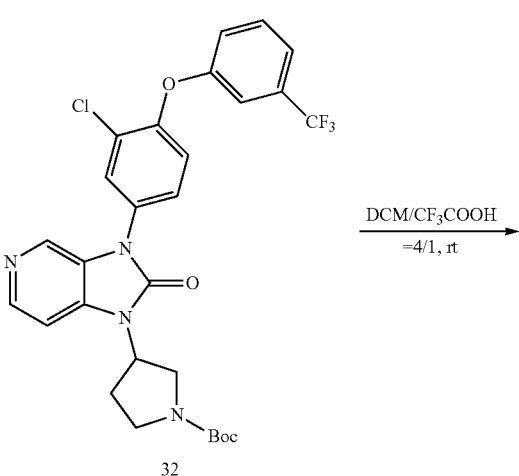

32

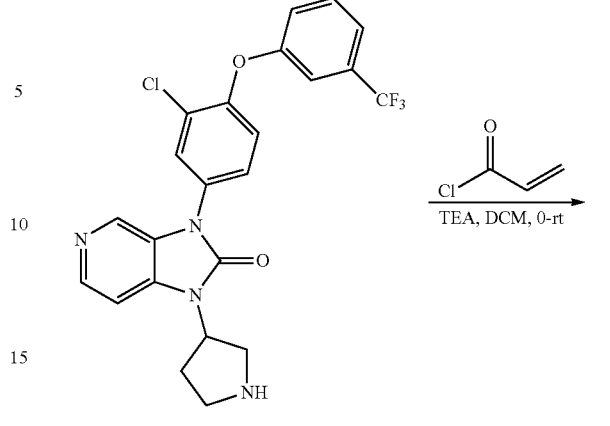

33

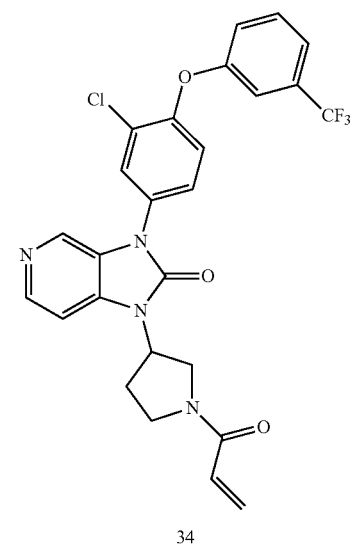

34

Step 1: tert-butyl 3-(3-(4-(benzyloxy)-3-chlorophenyl)-2-oxo-2,3-dihydro-1H-imidazo[4,5-c]pyridin-1-yl)pyrrolidine-1-carboxylate (30)

To a solution of 26 (1 g, 3.28 mmol), (4-(benzyloxy)-3-chlorophenyl)boronic acid (1.72 g, 3.57 mmol), TEA (0.66 g, 6.57 mmol) and 4 A molecular sieves (1 g) were added to DCM (30 mL) in a vial Copper (II) acetate (0.59 g, 6.57 mmol) was added in one portion. The mixture was stirred for about 21 h at rt. Volatile components were removed under vacuum, before being poured into H$_2$O, The reaction mixture was extracted with EA, Organic phase was purified by column chromatography on silica gel (gradient: DCM/MeOH=100/1-50/1) to give the title product (0.83 g, yield 48.8%).

$^1$H NMR (400 MHz, CDCl$_3$): δ 8.7 (br, 2H), 7.58 (d, J=4.0 Hz, 1H), 7.49 (d, J=4.0 Hz, 2H), 7.45-7.28 (m, 5H), 7.12-7.08 (m, 2H), 5.23 (s, 2H), 5.18-5.12 (m, 1H), 3.82-3.76 (m, 3H), 3.53-3.48 (m, 1H), 2.57-2.52 (m, 1H), 2.36-2.30 (m, 1H), 1.49 (s, 9H). LCMS: m/z 521, 523 [M+H]$^+$.

Step 2: tert-butyl 3-(3-(3-chloro-4-hydroxyphenyl)-2-oxo-2,3-dihydro-1H-imidazo[4,5-c] pyridin-1-yl)pyrrolidine-1-carboxylate (31)

To a solution of 30 (0.83 g, 1.59 mmol), HCOONH$_4$ (1 g, 15.9 mmol) and 10% Pd/C (0.35 g) in MeOH (30 mL) was added in one portion. The mixture was stirred for about 10 min at 70 deg. The suspension was filtered through Celite and concentrated. before being poured into H₂O, The reaction mixture was extracted with EA, Organic phase was purified by column chromatography on silica gel (gradient: DCM/MeOH=100/1-50/1) to give the title product (0.4 g, yield 58.8%).

¹H NMR (400 MHz, CDCl₃): δ 8.39 (br, 1H), 8.31 (br, 1H), 7.51 (s, 1H), 7.30 (d, J=8.0 Hz, 1H), 7.15 (d, J=8.0 Hz, 1H), 7.09 (br, 1H), 5.17-5.13 (m, 1H), 3.83 (br, 3H), 3.53-3.47 (m, 1H), 2.60-2.50 (m, 1H), 2.35-2.32 (m, 1H), 1.50 (s, 9H). LCMS: m/z=431, 433 [M+H]⁺.

Step 3: tert-butyl 3-(3-(3-chloro-4-(3-(trifluoromethyl)phenoxy) phenyl)-2-oxo-2,3-dihydro-1H-imidazo[4,5-c]pyridin-1-yl)pyrrolidine-1-carboxylate (32)

To a solution of 31 (30 mg, 0.069 mmol), (3-(trifluoromethyl)phenyl)boronic acid (26.5 mg, 0.139 mmol), TEA (14 mg, 0.139 mmol) and 4 A molecular sieves (0.2 g) were added to DCM (4 mL) in a vial Copper (II) acetate (12.6 mg, 0.069 mmol) was added in one portion. The mixture was stirred for about 14 h at rt. Volatile components were removed under vacuum, before being poured into H₂O. The reaction mixture was extracted with EA, Organic phase was purified by column chromatography on silica gel (gradient: DCM/MeOH=(100/1-50/1) to give the title product (20 mg, yield 50.5%).

¹H NMR (400 MHz, CDCl₃): δ 8.14 (s, 1H), 7.71 (d, J=2.0 Hz, 1H), 7.64 (d, J=8.0 Hz, 1H), 7.53-7.47 (m, 2H), 7.45-7.40 (m, 2H), 7.34 (s, 1H), 7.21-7.09 (m, 2H), 5.18-5.14 (m, 1H), 3.84-3.69 (m, 3H), 3.55-3.48 (m, 1H), 2.59-2.50 (m, 1H), 2.39-2.31 (m, 1H), 1.49 (s, 9H). LCMS: m/z=575, 576 [M+H]⁺.

Step 4: 3-(3-chloro-4-(3-(trifluoromethyl)phenoxy)phenyl)-1-(pyrrolidin-3-yl)-1H-imidazo[4,5-c]pyridin-2(3H)-one (33)

22 (20 mg, 0.034 mmol) were added to CF₃COOH/DCM=4/1 (5 mL) in one portion. The mixture was stirred for about 1 h at rt. Volatile components were removed under vacuum to give a crude title product, and directly used in next step without further purification. LCMS: m/z=475, 476 [M+H]⁺.

Step 5: 1-(1-acryloylpyrrolidin-3-yl)-3-(3-chloro-4-(3-(trifluoromethyl)phenoxy)-phenyl)-1H-imidazo[4,5-c]pyridin-2(3H)-one (34)

A solution of Acryloyl chloride (3.0 mg, 0.034 mmol) in DCM (1 mL) was added to a stirred solution of 33 (16 mg, 0.034 mmol) and TEA (13.7 mg, 0.136 mmol) in DCM (3 mL) at 0° C. The reaction mixture was stirred for 1 h, poured onto brine and extracted with DCM. The organic layer was dried, concentrated and recrystallized from DCM/MeOH=100/1 to give the title product (8 mg, yield 44.69%).

¹H NMR (400 MHz, CDCl₃): δ 8.42 (br, 2H), 7.72 (s, 1H), 7.52-7.41 (m, 3H), 7.32 (s, 1H), 7.20-7.16 (m, 2H), 7.08-7.03 (m, 1H), 6.52-6.41 (m, 2H), 5.80-5.73 (m, 1H), 5.21-5.12 (m, 1H), 4.12-3.97 (m, 3H), 3.77-3.68 (m, 1H), 2.77-2.64 (m, 1H), 2.49-2.40 (m, 1H). LCMS: m/z=529, 531 [M+H]⁺.

Example 7

N-(3-(2-oxo-3-(3-phenoxyphenyl)-2,3-dihydro-1H-imidazo[4,5-c]pyridin-1-yl)phenyl)acrylamide

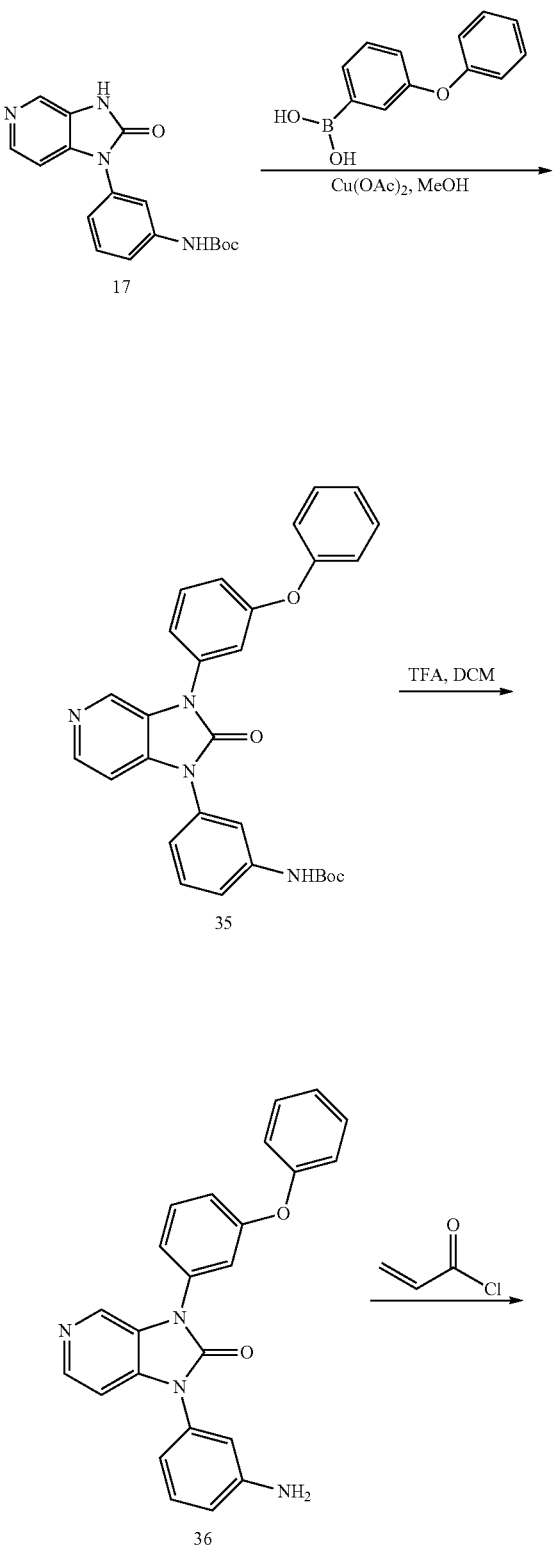

-continued

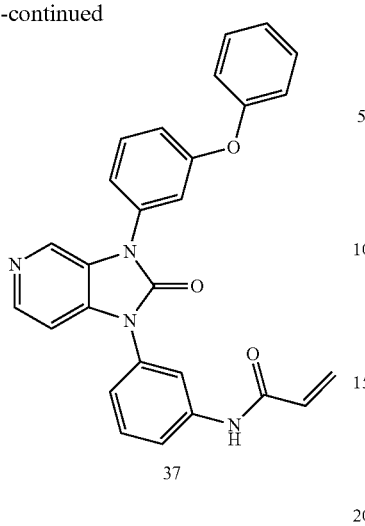

37

Step 1: tert-butyl (3-(2-oxo-3-(3-phenoxyphenyl)-2,3-dihydro-1H-imidazo[4,5-c]pyridine-1-yl)phenyl)carbamate (35)

Intermediate 17 (1.25 g, 3.83 mmol, 1.0 eq) was dissolved in MeOH (20.0 mL), added Cupric acetate (70 mg, 0.38 mmol, 0.1 eq), (3-phenoxyphenyl)boronic acid (0.9 g, 4.21 mmol, 1.1 eq), the mixture solution was stirred for 5 h under reflux. Then filtered the solution and removed the solution under reduce pressure, added water and extracted with EA, dried with $Na_2SO_4$, filtered and concentrated, purified with silica column (DCM:MeOH=100:1-50:1) to obtain the title product as gray solid, Yield: 430 mg, 22.7%. $^1$H NMR (400 MHz, $CDCl_3$, 298 K): δ=8.38-8.40 (m, 2H), 7.75 (s, 1H), 7.44-7.52 (m, 2H), 7.33-7.40 (m, 4H), 7.20-7.25 (m, 2H), 7.08-7.17 (m, 5H), 6.67 (s, 1H), 1.51 (s, 9H). LCMS (ESI) m/z=495 [M+H]$^+$.

Step 2: 1-(3-aminophenyl)-3-(3-phenoxyphenyl)-1H-imidazo[4,5-c]pyridin-2(3H)-one (36)

Intermediate 35 (420 mg) was dissolved in DCM (8.0 mL), added TFA (2.0 mL), the mixture was stirred for 1 h at RT. The solvent was removed under reduce pressure, the residue was added saturated $NaHCO_3$, extracted with EA and dried with $Na_2SO_4$, filtered and concentrated, obtained crude product 13 used next step without purification, colorless oil, Yield: 28 mg, 72.7%. $^1$H NMR (400 MHz, $CDCl_3$): δ=8.44 (s, 1H), 8.35 (s, 1H), 7.49-7.54 (m, 1H), 7.29-7.40 (m, 4H), 7.25 (s, 1H), 7.08-7.17 (m, 5H), 6.85-6.88 (m, 2H), 6.74-6.76 (m, 1H), 3.86 (s, 2H). LCMS (ESI) m/z=395 [M+H]$^+$.

Step 3: N-(3-(2-oxo-3-(3-phenoxyphenyl)-2,3-dihydro-1H-imidazo[4,5-c]pyridin-1-yl)phenyl)acrylamide (37)

Intermediate 36 (35 mg, 0.089 mmol, 1.0 eq) was dissolved in THF (4.0 mL), added acryloyl chloride (9 mg, 0.098 mmol, 1.1 eq) slowly at 0° C., the mixture solution was stirred for 0.5 h at RT, the reaction was added water and extracted with EA, dried with $Na_2SO_4$, filtered and concentrated, the residue was purification with silica gel plate (DCM:MeOH=40:1) to obtain product 14, colorless oil, Yield: 21 mg, 52.7%. $^1$H NMR (400 MHz, $CDCl_3$): δ=8.45 (s, 1H), δ=8.37 (d, J=5.2 Hz, 1H), 7.98 (s, 1H), 7.75 (s, 1H), 7.47-7.55 (m, 3H), 7.34-7.40 (m, 3H), 7.28-7.30 (m, 1H), 7.09-7.17 (m, 5H), 6.43 (d, J=16.8 Hz, 1H), 6.19-6.25 (m, 1H), 5.77 (d, J=10.4 Hz, 1H). LCMS (ESI) m/z=449 [M+H]$^+$.

Example 8

(S)-1-(1-acryloylpiperidin-3-yl)-3-(4-(2-chloro-3-methoxyphenoxy)phenyl)-1H-imidazo[4,5-c]pyridin-2(3H)-one

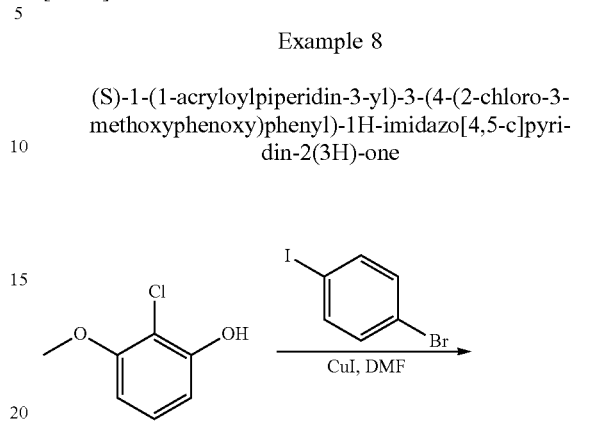

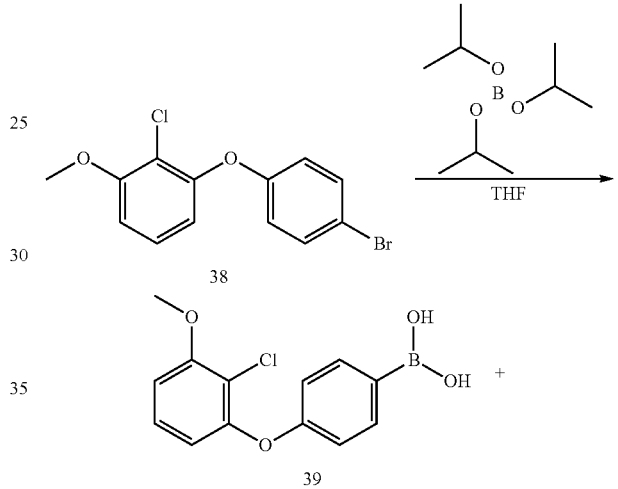

38

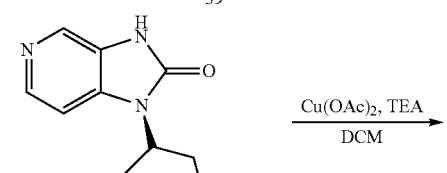

39

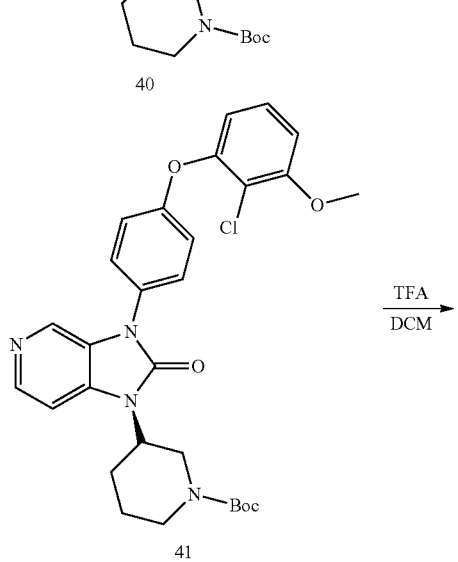

40

41

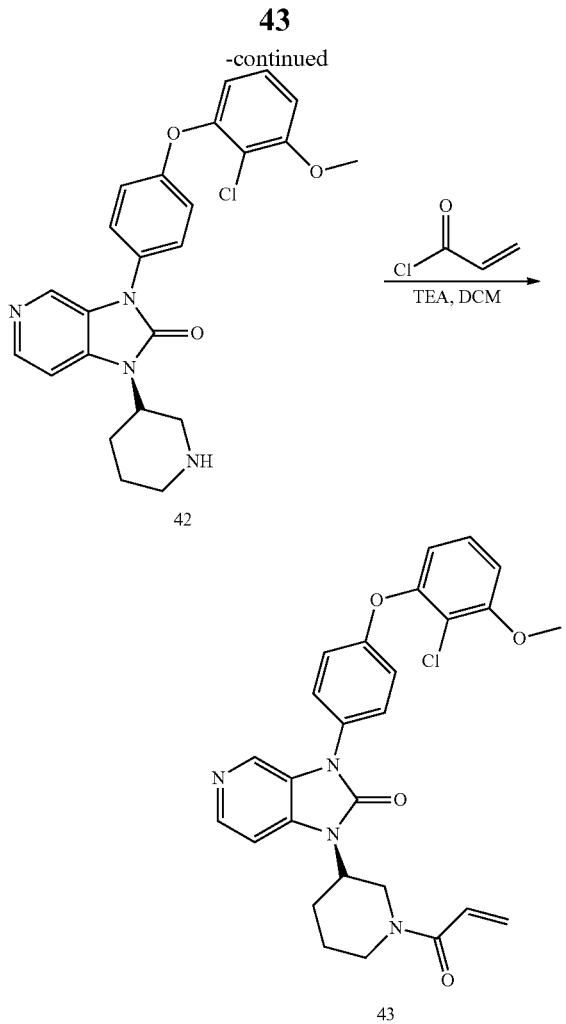

Step 1: 1-(4-bromophenoxy)-2-chloro-3-methoxybenzene (38)

To a solution of 1-bromo-4-iodobenzene (2 g, 7.04 mmol) in dioxane (30 ml), was added 2-chloro-3-methoxyphenol (1 g, 7.04 mmol), CuI (0.134 g, 0.704 mmol), Cs$_2$CO$_3$ (4.59 g, 14.08 mmol), 3-(dimethylamino)propanoic acid hydrochloride (0.294 g, 0.212 mmol). The mixture was stirred at 105° C. for 18 h, the mixture was filtered, before being poured into H$_2$O, The reaction mixture was extracted with DCM, Organic phase was purified by column chromatography on silica gel (PE) to give title product (1.2 g, yield 49.5%).

$^1$H-NMR (400 MHz, CDCl$_3$): δ 7.59 (d, J=8.0 Hz, 1H), 7.41 (d, J=8.0 Hz, 1H), 7.20-7.16 (m, 1H), 6.83 (d, J=8.0 Hz, 1H), 6.77 (d, J=8.0 Hz, 1H), 6.71 (d, J=8.0 Hz, 1H), 6.62 (d, J=8.0 Hz, 1H), 3.93 (s, 3H).

Step 2: (4-(2-chloro-3-methoxyphenoxy)phenyl)boronic acid (39)

To a solution of 1-(4-bromophenoxy)-2-chloro-3-methoxybenzene (38) (1.2 g, 3.08 mmol) in THF was cooled to −78 deg under N$_2$, n-BuLi (1.82 mL, 4.61 mmol) was added dropwise under same condition. The mixture was stirred for 30 min at −78 deg. triisopropyl borate (0.868 g, 4.61 mmol) was added dropwise at −68 deg. After 15 min, the mixture warm to 8 deg and stirred for 2 h, then 2N HCl was added to adjust to pH=3 and stirred for 30 min, was added H$_2$O (15 mL), the mixture was extracted three times with EA and dried Na$_2$SO$_4$, to give title product for crude (0.4 g).

Step 3: (S)-tert-butyl 3-(3-(4-(2-chloro-3-methoxyphenoxy)phenyl)-2-oxo-2,3-dihydro-1H-imidazo[4,5-c]pyridin-1-yl)piperidine-1-carboxylate (41)

(R)-tert-butyl 3-(2-oxo-2,3-dihydro-1H-imidazo[4,5-c]pyridin-1-yl)piperidine-1-carboxylate (40, prepared as described in Example 1, Step 1, 2 and 3), 0.1 g, 0.314 mmol), (4-(2-chloro-3-methoxyphenoxy) phenyl) boronic acid (39) (0.174 g, 0.628 mmol), TEA (63 mg, 0.628 mmol) and 4 A molecular sieves (0.1 g) were added to DCM (10 mL) in a vial Copper (II) acetate (57 mg, 0.314 mmol) was added in one portion. The mixture was stirred for about 22 h at 25 deg. Volatile components were removed under vacuum, before being poured into H$_2$O, The reaction mixture was extracted with EA, Organic phase was purified by column chromatography on silica gel (gradient: DCM/MeOH=100/1-50/1) to give the title product (25 mg, yield 14.4%). LCMS: m/z=552 [M+H]$^+$.

Step 4: (S)-3-(4-(2-chloro-3-methoxyphenoxy)phenyl)-1-(piperidin-3-yl)-1H-imidazo[4,5-c]pyridin-2(3H)-one (42)

To a solution of (R)-tert-butyl-3-(3-(4-(2-chloro-3-methoxyphenoxy)phenyl)-2-oxo-2,3-dihydro-1H-imidazo[4,5-c]pyridin-1-yl)piperidine-1-carboxylate (5) (25 mg, 0.045 mmol) were added to CF$_3$COOH/DCM=4/1 (5 mL) in one portion. The mixture was stirred for about 1 h at it. Volatile components were removed under vacuum to give the title product of crude product (20 mg), and directly used in next step without further purification. LCMS: m/z=451 [M+H]$^+$.

Step 5: (S)-1-(1-acryloylpiperidin-3-yl)-3-(4-(2-chloro-3-methoxyphenoxy)-phenyl)-1H-imidazo[4,5-c]pyridin-2(3H)-one (43)

To a solution of Acryloyl chloride (4 mg, 0.044 mmol) in DCM (1 mL) was added to a stirred solution of (R)-3-(4-(2-chloro-3-methoxyphenoxy)phenyl)-1-(piperidin-3-yl)-1H-imidazo[4,5-c]pyridin-2(3H)-one (6)(20 mg, 0.044 mmol) and TEA (9 mg, 0.88 mmol) in DCM (5 mL) at 0° C. The reaction mixture was stirred for 1 h, poured onto brine and extracted with DCM. The organic layer was dried, concentrated and recrystallized from DCM/MeOH=10)/I to give the title product (3.5 mg, yield 15.7%).

$^1$H-NMR (400 MHz, CDCl$_3$): δ 8.41 (br, 1H), 8.34 (br, 1H), 7.44 (d, J=8.0 Hz, 2H), 7.30-7.23 (m, 2H), 7.11 (d, J=8.0 Hz, 2H), 6.82 (d, J=8.0 Hz, 1H), 6.74 (d, J=8.0 Hz, 1H), 6.61-6.58 (m, 1H), 6.43-6.14 (m, 1H), 5.74 (br, 1H), 4.84 (br, 1H), 4.22-4.09 (m, 2H), 3.96 (s, 3H), 3.48 (br, 0.6H), 3.18 (br, 0.6H), 2.64-2.54 (m, 1H), 2.16-2.13 (m, 1H), 2.02-2.00 (m, 1H), 1.68 (br, 1H). LCMS: m/z=506 [M+H]$^+$.

The following additional Examples 9-165 shown in the Table below were prepared following the procedures outlined in the general methods above and detailed in Examples 1-8.

| Entry | Structure | MS (cald) [M + H]⁺/MS (found) | Name |
|---|---|---|---|
| 9 | 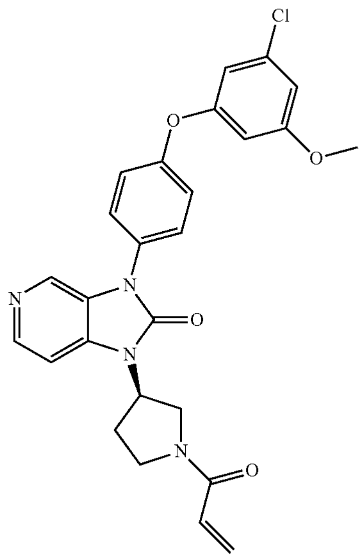 [SMILES: C=CC(=O)N1CC[C@@H](n2c(=O)n(-c3ccc(Oc4cc(Cl)cc(OC)c4)cc3)c3cnccc32)C1] | 491.14/491.1, 492.1 | (R)-1-(1-acryloylpyrrolidin-3-yl)-3-(4-(3-chloro-5-methoxyphenoxy)phenyl)-1H-imidazo[4,5-c]pyridin-2(3H)-one |
| 10 | 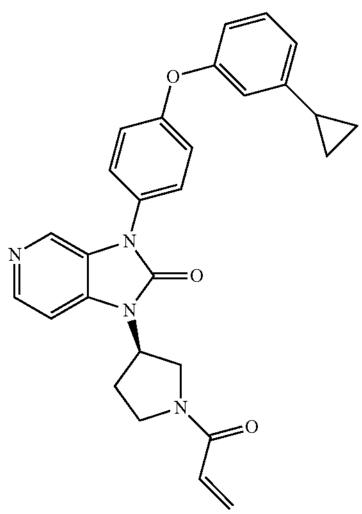 [SMILES: C=CC(=O)N1CC[C@@H](n2c(=O)n(-c3ccc(Oc4cccc(C5CC5)c4)cc3)c3cnccc32)C1] | 467.20/467.2 | (R)-1-(1-acryloylpyrrolidin-3-yl)-3-(4-(3-cyclopropylphenoxy)phenyl)-1H-imidazo[4,5-c]pyridin-2(3H)-one |
| 11 | 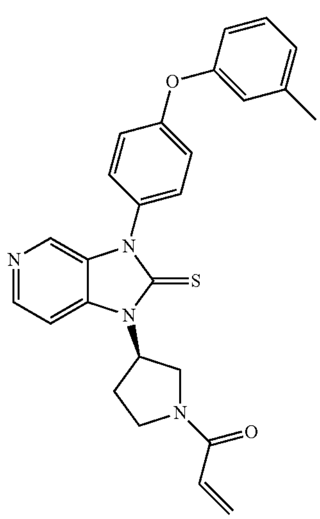 [SMILES: C=CC(=O)N1CC[C@@H](n2c(=S)n(-c3ccc(Oc4cccc(C)c4)cc3)c3cnccc32)C1] | 457.16/457.1 | (R)-1-(3-(2-thioxo-3-(4-(m-tolyloxy)phenyl)-2,3-dihydro-1H-imidazo[4,5-c]pyridin-1-yl)pyrrolidin-1-yl)prop-2-en-1-one |

-continued

| Entry | Structure | MS (calcd) [M + H]+/MS (found) | Name |
|---|---|---|---|
| 12 | 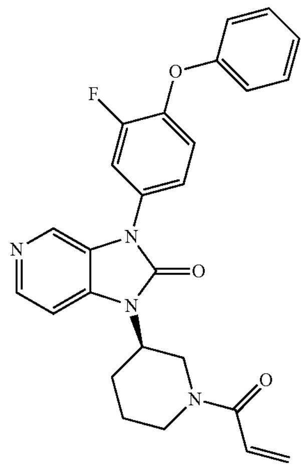 [SMILES: C=CC(=O)N1CCC[C@@H](n2c(=O)n(-c3ccc(Oc4ccccc4)c(F)c3)c3cnccc32)C1] | 459.18/459.2 | (R)-1-(1-acryloylpiperidin-3-yl)-3-(3-fluoro-4-phenoxyphenyl)-1H-imidazo[4,5-c]pyridin-2(3H)-one |
| 13 | 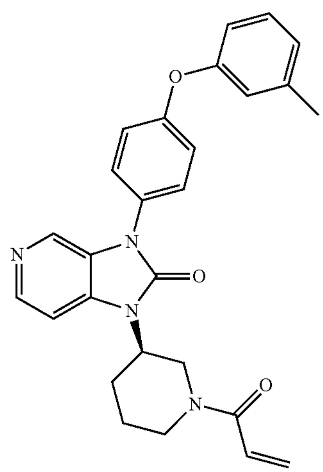 [SMILES: C=CC(=O)N1CCC[C@@H](n2c(=O)n(-c3ccc(Oc4cccc(C)c4)cc3)c3cnccc32)C1] | 455.20/455.2 | (R)-1-(1-acryloylpiperidin-3-yl)-3-(4-(m-tolyloxy)phenyl)-1H-imidazo[4,5-c]pyridin-2(3H)-one |
| 14 | 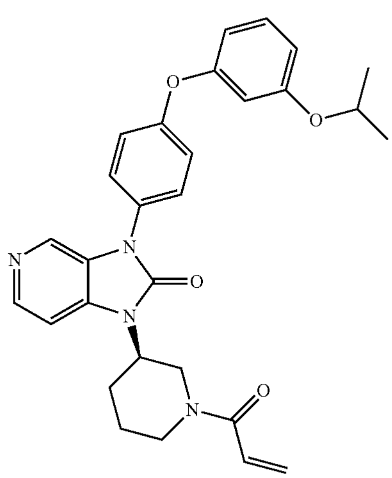 [SMILES: C=CC(=O)N1CCC[C@@H](n2c(=O)n(-c3ccc(Oc4cccc(OC(C)C)c4)cc3)c3cnccc32)C1] | 499.23/499.2 | (R)-1-(1-acryloylpiperidin-3-yl)-3-(4-(3-isopropoxyphenoxy)phenyl)-1H-imidazo[4,5-c]pyridin-2(3H)-one |

-continued

| Entry | Structure | MS (cald) [M + H]+/MS (found) | Name |
|---|---|---|---|
| 15 | 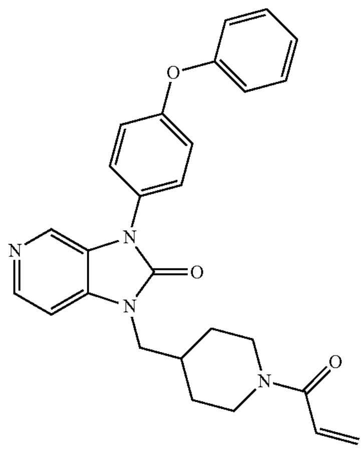 [SMILES: C=CC(=O)N1CCC(Cn2c(=O)n(-c3ccc(Oc4ccccc4)cc3)c3cnccc32)CC1] | 456.20/456.2 | 1-((1-acryloylpiperidin-4-yl)methyl)-3-(4-phenoxyphenyl)-1H-imidazo[4,5-c]pyridin-2(3H)-one |
| 16 | 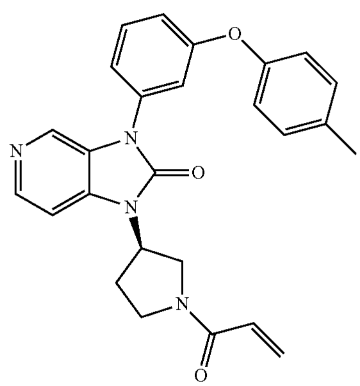 [SMILES: C=CC(=O)N1CC[C@@H](n2c(=O)n(-c3cccc(Oc4ccc(C)cc4)c3)c3cnccc32)C1] | 441.18/441.2 | (R)-1-(1-acryloylpyrrolidin-3-yl)-3-(3-(p-tolyloxy)phenyl)-1H-imidazo[4,5-c]pyridin-2(3H)-one |
| 17 | 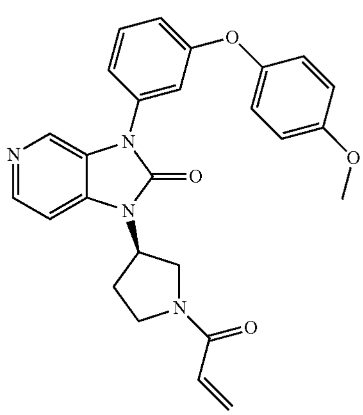 [SMILES: C=CC(=O)N1CC[C@@H](n2c(=O)n(-c3cccc(Oc4ccc(OC)cc4)c3)c3cnccc32)C1] | 457.18/457.2 | (R)-1-(1-acryloylpyrrolidin-3-yl)-3-(3-(4-methoxyphenoxy)phenyl)-1H-imidazo[4,5-c]pyridin-2(3H)-one |

| Entry | Structure | MS (cald) [M + H]⁺/MS (found) | Name |
|---|---|---|---|
| 18 | 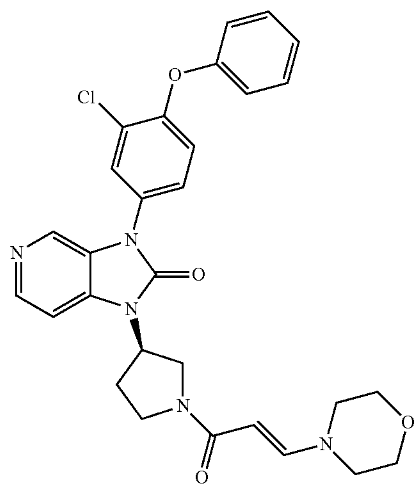 [SMILES: O=C(/C=C/N1CCOCC1)N1CC[C@@H](n2c(=O)n(-c3ccc(Oc4ccccc4)c(Cl)c3)c3cnccc32)C1] | 546.18/560.1, 561.1, 280.7, 281.4 | (R,E)-3-(3-chloro-4-phenoxyphenyl)-1-(1-(3-morpholinoacryloyl)pyrolidin-3-yl)-1H-imidazo[4,5-c]-pyridin-2(3H)-one |
| 19 | 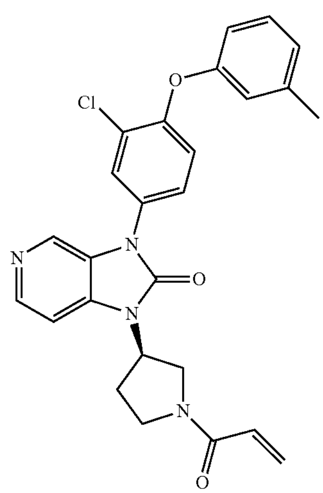 [SMILES: C=CC(=O)N1CC[C@@H](n2c(=O)n(-c3ccc(Oc4cccc(C)c4)c(Cl)c3)c3cnccc32)C1] | 475.15/475.2, 477.2 | (R)-1-(1-acryloylpyrrolidin-3-yl)-3-(3-chloro-4-(m-tolyloxy)phenyl)-1H-imidazo[4,5-c]pyridin-2(3H)-one |
| 20 | 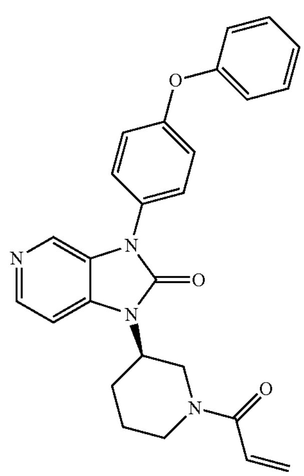 [SMILES: C=CC(=O)N1CCC[C@@H](n2c(=O)n(-c3ccc(Oc4ccccc4)cc3)c3cnccc32)C1] | 441.18/441.2 | (R)-1-(1-acryloylpiperidin-3-yl)-3-(4-phenoxyphenyl)-1H-imidazo[4,5-c]pyridin-2(3H)-one |

-continued

| Entry | Structure | MS (calcd) [M + H]+/MS (found) | Name |
|---|---|---|---|
| 21 | 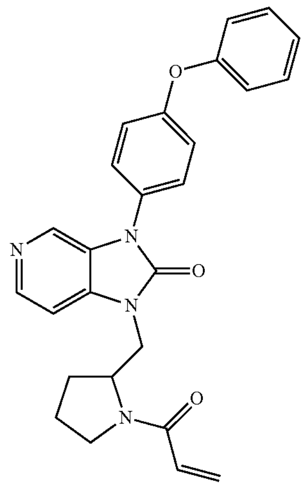 [SMILES: C=CC(=O)N1CCCC1Cn1c(=O)n(-c2ccc(Oc3ccccc3)cc2)c2cnccc21] | 441.18/441.2 | 1-((1-acryloylpyrrolidin-2-yl)methyl)-3-(4-phenoxyphenyl)-1H-imidazo[4,5-c]pyridin-2(3H)-one |
| 22 | 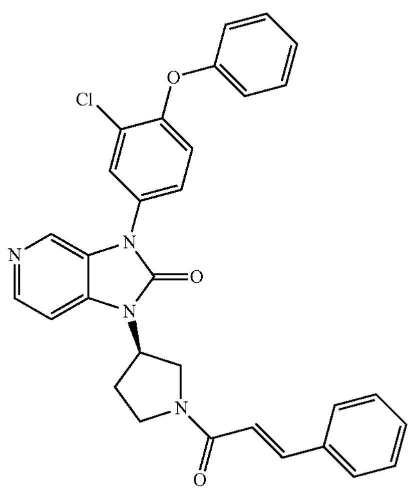 [SMILES: O=C(/C=C/c1ccccc1)N1CC[C@@H](n2c(=O)n(-c3ccc(Oc4ccccc4)c(Cl)c3)c3cnccc32)C1] | 537.16/537.1, 538.1 | (R,E)-3-(3-chloro-4-phenoxyphenyl)-1-(1-cinnamoylpyrrolidin-3-yl)-1H-imidazo[4,5-c]pyridin-2(3H)-one |
| 23 | 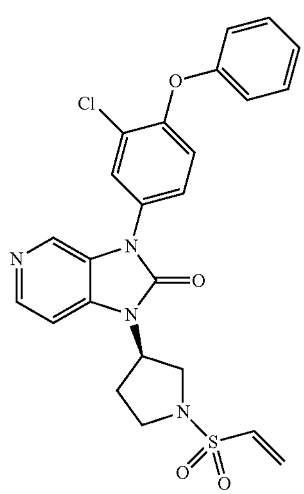 [SMILES: C=CS(=O)(=O)N1CC[C@@H](n2c(=O)n(-c3ccc(Oc4ccccc4)c(Cl)c3)c3cnccc32)C1] | 497.10/497.1, 498.1 | (R)-3-(3-chloro-4-phenoxyphenyl)-1-(1-(vinylsulfonyl)pyrrolidin-3-yl)-1H-imidazo[4,5-c]pyridin-2(3H)-one |

-continued

| Entry | Structure | MS (cald) [M + H]+/MS (found) | Name |
|---|---|---|---|
| 24 | 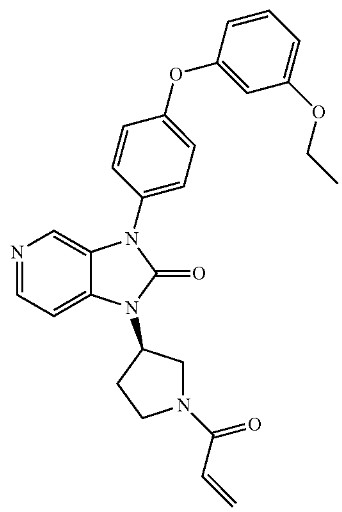 [SMILES: C=CC(=O)N1CC[C@@H](n2c(=O)n(-c3ccc(Oc4cccc(OCC)c4)cc3)c3cnccc32)C1] | 471.20/471.2 | (R)-1-(1-acryloylpyrrolidin-3-yl)-3-(4-(3-ethoxyphenoxy)phenyl)-1H-imidazo[4,5-c]pyridin-2(3H)-one |
| 25 | 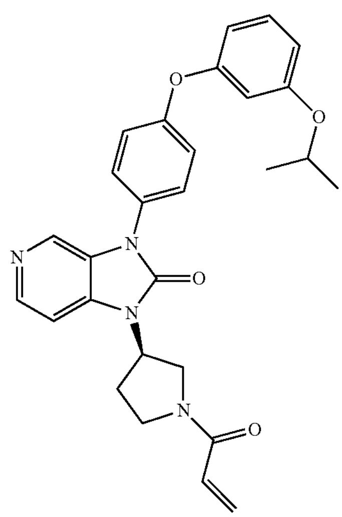 [SMILES: C=CC(=O)N1CC[C@@H](n2c(=O)n(-c3ccc(Oc4cccc(OC(C)C)c4)cc3)c3cnccc32)C1] | 485.21/485.2 | (R)-1-(1-acryloylpyrrolidin-3-yl)-3-(4-(3-isopropoxyphenoxy)phenyl)-1H-imidazo[4,5-c]pyridin-2(3H)-one |
| 26 | 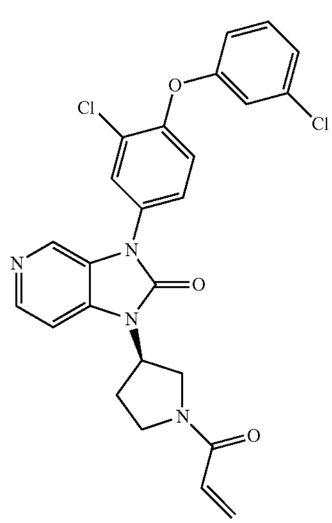 [SMILES: C=CC(=O)N1CC[C@@H](n2c(=O)n(-c3ccc(Oc4cccc(Cl)c4)c(Cl)c3)c3cnccc32)C1] | 495.09/495.0, 497.1 | (R)-1-(1-acryloylpyrrolidin-3-yl)-3-(3-chloro-4-(3-chlorophenoxy)phenyl)-1H-imidazo[4,5-c]pyridin-2(3H)-one |

-continued

| Entry | Structure | MS (cald) [M + H]+/MS (found) | Name |
|---|---|---|---|
| 27 | 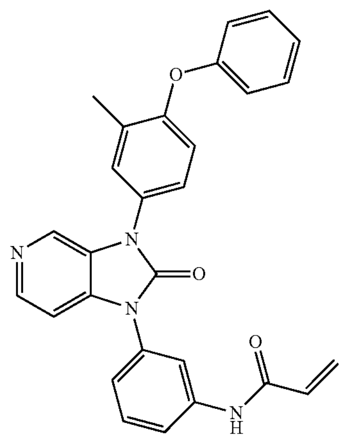 [SMILES: C=CC(=O)Nc1cccc(-n2c(=O)n(-c3ccc(Oc4ccccc4)c(C)c3)c3cnccc32)c1] | 463.17/463.2 | N-(3-(3-(3-methyl-4-phenoxyphenyl)-2-oxo-2,3-dihydro-1H-imidazo[4,5-c]pyridin-1-yl)phenyl)acrylamide |
| 28 | 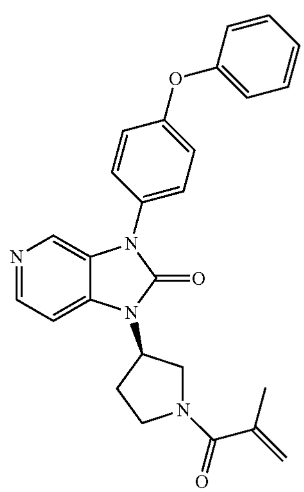 [SMILES: C=C(C)C(=O)N1CC[C@@H](n2c(=O)n(-c3ccc(Oc4ccccc4)cc3)c3cnccc32)C1] | 441.18/441.1 | (R)-1-(1-methacryloylpyrrolidin-3-yl)-3-(4-phenoxyphenyl)-1H-imidazo[4,5-c]pyridin-2(3H)-one |
| 29 | 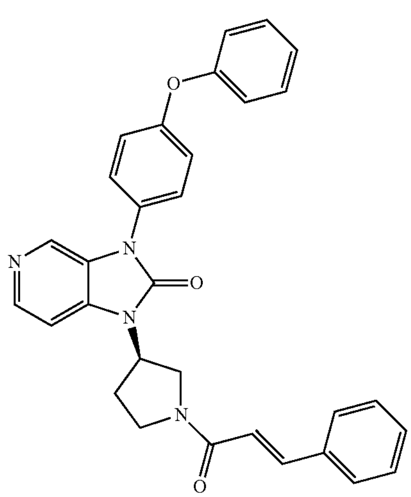 [SMILES: O=C(/C=C/c1ccccc1)N1CC[C@@H](n2c(=O)n(-c3ccc(Oc4ccccc4)cc3)c3cnccc32)C1] | 503.20/503.2 | (R,E)-1-(1-cinnamoylpyrrolidin-3-yl)-3-(4-phenoxyphenyl)-1H-imidazo[4,5-c]pyridin-2(3H)-one |

-continued

| Entry | Structure | MS (calcd) [M + H]⁺/MS (found) | Name |
|---|---|---|---|
| 30 | 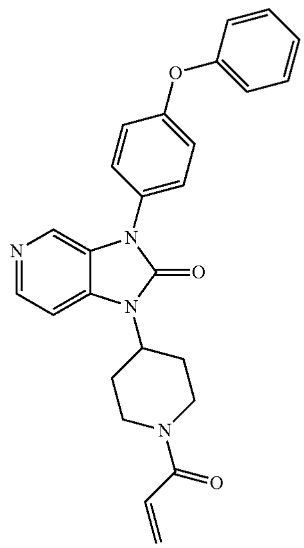 [SMILES: C=CC(=O)N1CCC(n2c(=O)n(-c3ccc(Oc4ccccc4)cc3)c3cnccc32)CC1] | 441.08/441.0 | 1-(1-acryloylpiperidin-4-yl)-3-(4-phenoxyphenyl)-1H-imidazo[4,5-c]pyridin-2(3H)-one |
| 31 | 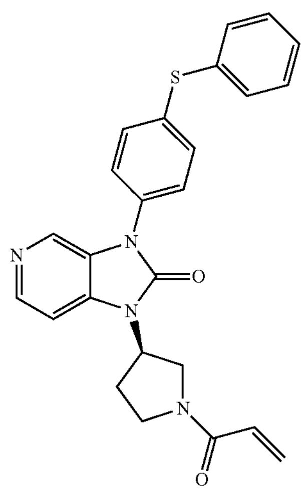 [SMILES: C=CC(=O)N1CC[C@@H](n2c(=O)n(-c3ccc(Sc4ccccc4)cc3)c3cnccc32)C1] | 442.14/442.1 | (R)-1-(1-acryloylpyrrolidin-3-yl)-3-(4-(phenylthio)phenyl)-1H-imidazo[4,5-c]pyridin-2(3H)-one |
| 32 | 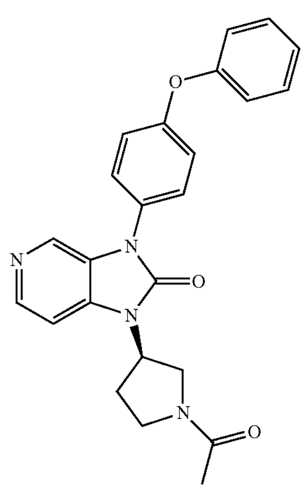 [SMILES: CC(=O)N1CC[C@@H](n2c(=O)n(-c3ccc(Oc4ccccc4)cc3)c3cnccc32)C1] | 415.17/415.1 | (R)-1-(1-acetylpyrrolidin-3-yl)-3-(4-phenoxyphenyl)-1H-imidazo[4,5-c]pyridin-2(3H)-one |

| Entry | Structure | MS (cald) [M + H]+/MS (found) | Name |
|---|---|---|---|
| 33 | 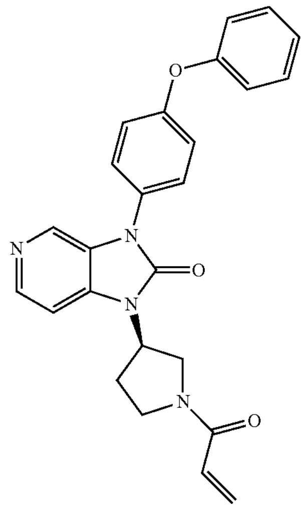 [SMILES: C=CC(=O)N1CC[C@@H](n2c(=O)n(-c3ccc(Oc4ccccc4)cc3)c3cnccc32)C1] | 427.17/427.2 | (R)-1-(1-acryloylpyrrolidin-3-yl)-3-(4-phenoxyphenyl)-1H-imidazo[4,5-c]pyridin-2(3H)-one |
| 34 | 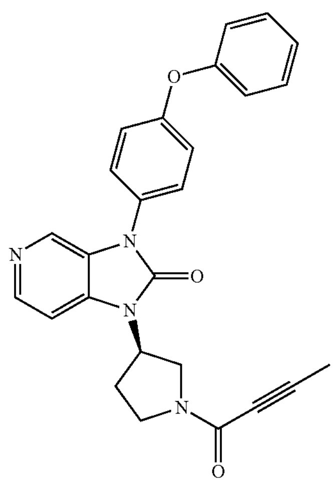 [SMILES: CC#CC(=O)N1CC[C@@H](n2c(=O)n(-c3ccc(Oc4ccccc4)cc3)c3cnccc32)C1] | 439.17/439.2 | (R)-1-(1-(but-2-ynoyl)pyrrolidin-3-yl)-3-(4-phenoxyphenyl)-1H-imidazo[4,5-c]pyridin-2(3H)-one |
| 35 | 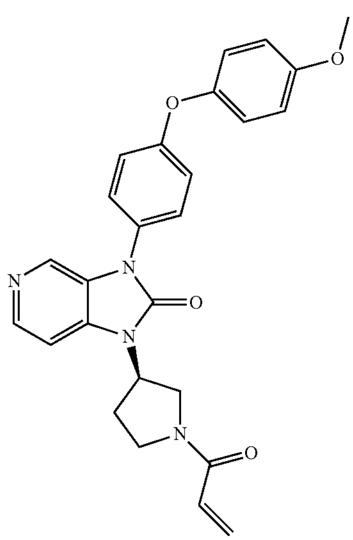 [SMILES: C=CC(=O)N1CC[C@@H](n2c(=O)n(-c3ccc(Oc4ccc(OC)cc4)cc3)c3cnccc32)C1] | 457.18/457.2 | (R)-1-(1-acryloylpyrrolidin-3-yl)-3-(4-(4-methoxyphenoxy)phenyl)-1H-imidazo[4,5-c]pyridin-2(3H)-one |

-continued

| Entry | Structure | MS (cald) [M + H]+/MS (found) | Name |
|---|---|---|---|
| 36 | 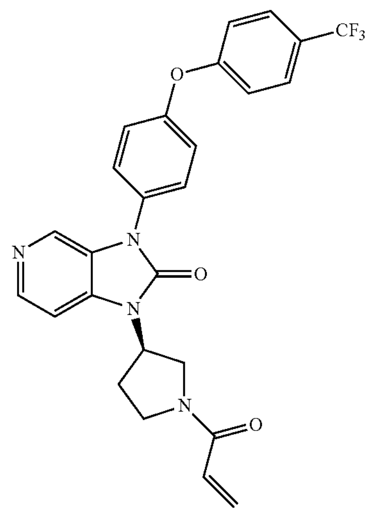 [SMILES: C=CC(=O)N1CC[C@@H](n2c(=O)n(-c3ccc(Oc4ccc(C(F)(F)F)cc4)cc3)c3cnccc32)C1] | 495.16/495.2 | (R)-1-(1-acryloylpyrrolidin-3-yl)-3-(4-(4-(trifluoromethyl)phenoxy)phenyl)-1H-imidazo[4,5-c]pyridin-2(3H)-one |
| 37 | 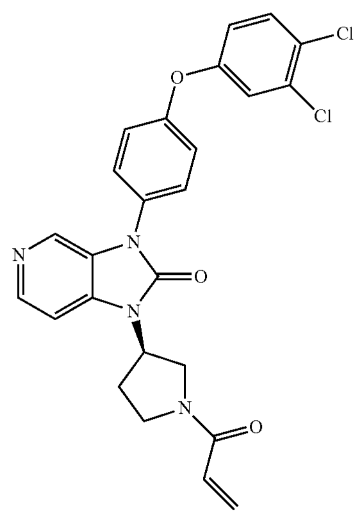 [SMILES: C=CC(=O)N1CC[C@@H](n2c(=O)n(-c3ccc(Oc4ccc(Cl)c(Cl)c4)cc3)c3cnccc32)C1] | 495.09/495.1, 496.1, 497.1, 498.1 | (R)-1-(1-acryloylpyrrolidin-3-yl)-3-(4-(3,4-dichlorophenoxy)phenyl)-1H-imidazo[4,5-c]pyridin-2(3H)-one |
| 38 | 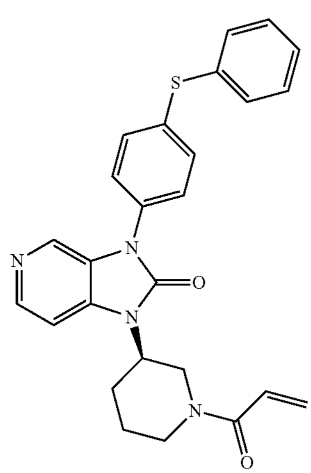 [SMILES: C=CC(=O)N1CCC[C@@H](n2c(=O)n(-c3ccc(Sc4ccccc4)cc3)c3cnccc32)C1] | 456.16 | (R)-1-(1-acryloylpiperidin-3-yl)-3-(4-(phenylthio)phenyl)-1H-imidazo[4,5-c]pyridin-2(3H)-one |

| Entry | Structure | MS (cald) [M + H]+/MS (found) | Name |
|---|---|---|---|
| 39 | 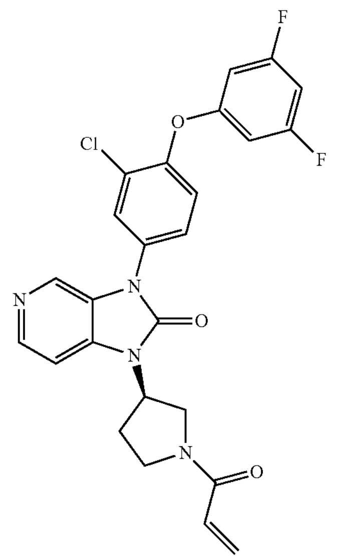 [SMILES: C=CC(=O)N1CC[C@@H](n2c(=O)n(-c3ccc(Oc4cc(F)cc(F)c4)c(Cl)c3)c3cnccc32)C1] | 497.11/497.1, 498.1 | (R)-1-(1-acryloylpyrrolidin-3-yl)-3-(3-chloro-4-(3,5-difluorophenoxy)phenyl)-1H-imidazo[4,5-c]pyridin-2(3H)-one |
| 40 | 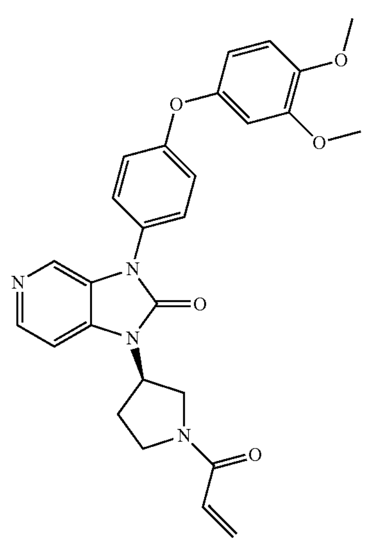 [SMILES: C=CC(=O)N1CC[C@@H](n2c(=O)n(-c3ccc(Oc4ccc(OC)c(OC)c4)cc3)c3cnccc32)C1] | 487.19/487.1 | (R)-1-(1-acryloylpyrrolidin-3-yl)-3-(4-(3,4-dimethoxyphenoxy)phenyl)-1H-imidazo[4,5-c]pyridin-2(3H)-one |

-continued

| Entry | Structure | MS (cald) [M + H]⁺/MS (found) | Name |
|---|---|---|---|
| 41 | 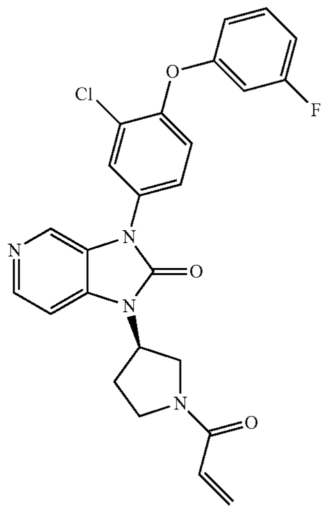 [SMILES: C=CC(=O)N1CC[C@@H](n2c(=O)n(-c3ccc(Oc4cccc(F)c4)c(Cl)c3)c3cnccc32)C1] | 479.12/479.1, 481.1 | (R)-1-(1-acryloylpyrrolidin-3-yl)-3-(3-chloro-4-(3-fluorophenoxy)phenyl)-1H-imidazo[4,5-c]pyridin-2(3H)-one |
| 42 | 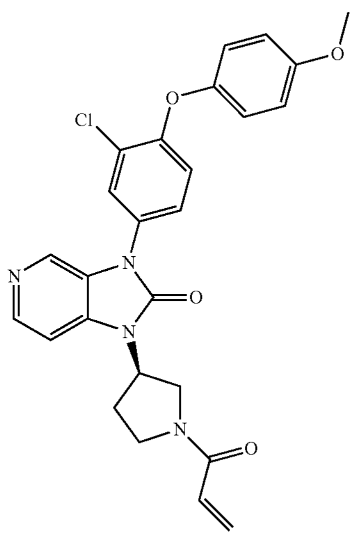 [SMILES: C=CC(=O)N1CC[C@@H](n2c(=O)n(-c3ccc(Oc4ccc(OC)cc4)c(Cl)c3)c3cnccc32)C1] | 491.14/491.1, 492.1 | (R)-1-(1-acryloylpyrrolidin-3-yl)-3-(3-chloro-4-(4-methoxyphenoxy)phenyl)-1H-imidazo[4,5-c]pyridine-2(3H)-one |
| 43 | 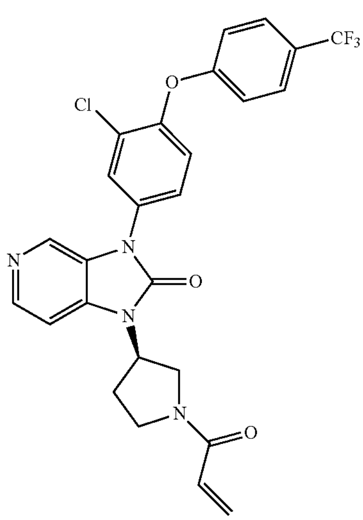 [SMILES: C=CC(=O)N1CC[C@@H](n2c(=O)n(-c3ccc(Oc4ccc(C(F)(F)F)cc4)c(Cl)c3)c3cnccc32)C1] | 529.12/529.1, 530.1 | (R)-1-(1-acryloylpyrrolidin-3-yl)-3-(3-chloro-4-(4-(trifluoromethyl)phenoxy)phenyl)-1H-imidazo[4,5-c]pyridin-2(3H)-one |

| Entry | Structure | MS (calcd) [M + H]⁺/MS (found) | Name |
|---|---|---|---|
| 44 | 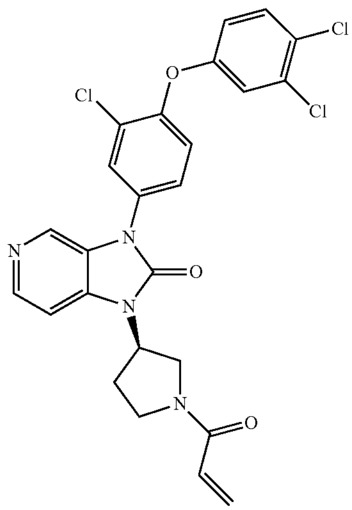 [SMILES: C=CC(=O)N1CC[C@@H](n2c(=O)n(-c3ccc(Oc4ccc(Cl)c(Cl)c4)c(Cl)c3)c3cnccc32)C1] | 529.05/529.0, 530.1, 531.0, 532.0 | (R)-1-(1-acryloylpyrrolidin-3-yl)-3-(3-chloro-4-(3,4-dichlorophenoxy)phenyl)-1H-imidazo[4,5-c]pyridin-2(3H)-one |
| 45 | 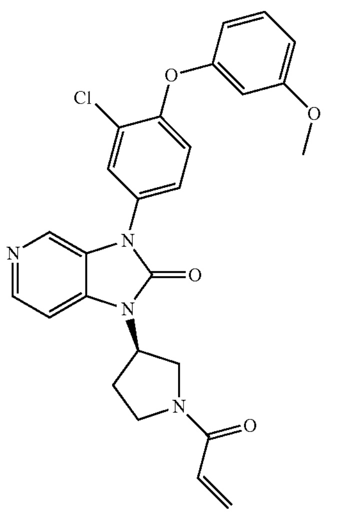 [SMILES: C=CC(=O)N1CC[C@@H](n2c(=O)n(-c3ccc(Oc4cccc(OC)c4)c(Cl)c3)c3cnccc32)C1] | 491.14/491.1, 493.1 | (R)-1-(1-acryloylpyrrolidin-3-yl)-3-(3-chloro-4-(3-methoxyphenoxy)phenyl)-1H-imidazo[4,5-c]pyridin-2(3H)-one |
| 46 | 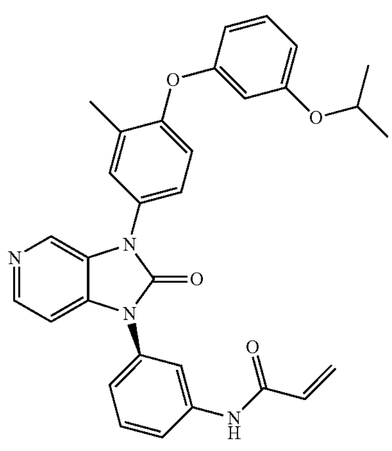 | 521.21/521.2 | N-(3-(3-(4-(3-isopropoxyphenoxy)-3-methylphenyl)-2-oxo-2,3-dihydro-1H-imidazo[4,5-c]pyridin-1-yl)phenyl)acrylamide |

-continued

| Entry | Structure | MS (cald) [M + H]+/MS (found) | Name |
|---|---|---|---|
| 47 | 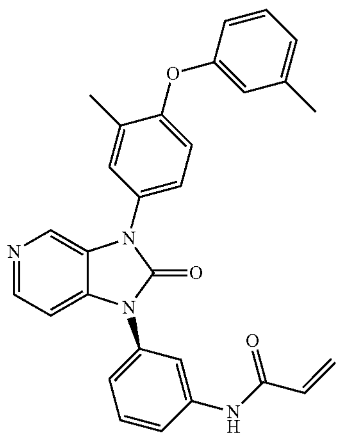 | 477.18/477.2 | N-(3-(3-(3-methyl-4-(m-tolyloxy) phenyl)-2-oxo-2,3-dihydro-1H-imidazo[4,5-c]pyridin-1-yl)phenyl) acrylamide |
| 48 | 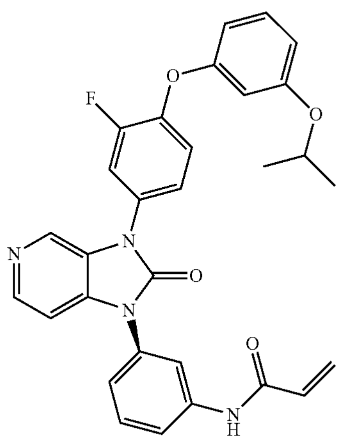 | 525.19/525.2 | N-(3-(3-(3-fluoro-4-(3-isopropoxy phenoxy)phenyl)-2-oxo-2,3-dihydro-1H-imidazo[4,5-c]pyridin-1-yl) phenyl)acrylamide |
| 49 | 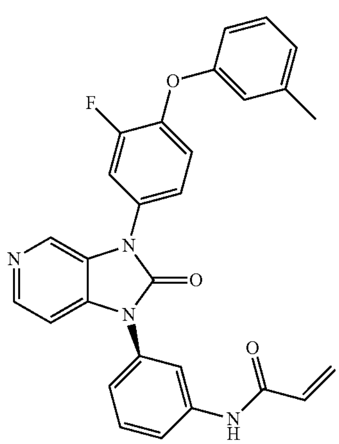 | 481.16/481.2 | N-(3-(3-(3-fluoro-4-(m-tolyloxy) phenyl)-2-oxo-2,3-dihydro-1H-imidazo[4,5-c]pyridin-1-yl) phenyl)acrylamide |

-continued

| Entry | Structure | MS (cald) [M + H]+/MS (found) | Name |
|---|---|---|---|
| 50 | 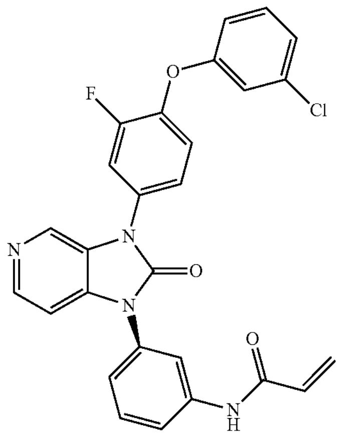 | 501.11/501.1 | (N-(3-(3-(4-(3-chlorophenoxy)-3-fluorophenyl)-2-oxo-2,3-dihydro-1H-imidazo[4,5-c]pyridin-1-yl)phenyl)acrylamide |
| 51 | 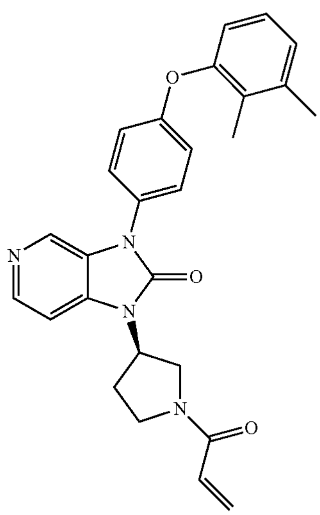 [SMILES: C=CC(=O)N1CC[C@@H](n2c(=O)n(-c3ccc(Oc4cccc(C)c4C)cc3)c3cnccc32)C1] | 455.20/455.2 | (R)-1-(1-acryloylpyrrolidin-3-yl)-3-(4-(2,3-dimethylphenoxy)phenyl)-1H-imidazo[4,5-c]pyridin-2(3H)-one |
| 52 | 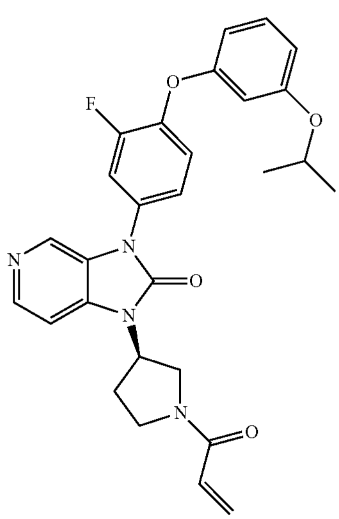 [SMILES: C=CC(=O)N1CC[C@@H](n2c(=O)n(-c3ccc(Oc4cccc(OC(C)C)c4)c(F)c3)c3cnccc32)C1] | 503.20/503.2 | (R)-1-(1-acryloylpyrrolidin-3-yl)-3-(3-fluoro-4-(3-isopropoxyphenoxy)phenyl)-1H-imidazo[4,5-c]pyridin-2(3H)-one |

-continued

| Entry | Structure | MS (cald) [M + H]+/MS (found) | Name |
|---|---|---|---|
| 53 | 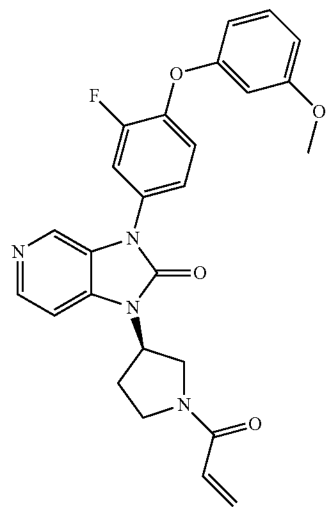 [SMILES: C=CC(=O)N1CC[C@@H](n2c(=O)n(-c3ccc(Oc4cccc(OC)c4)c(F)c3)c3cnccc32)C1] | 475.17/475.2 | (R)-1-(1-acryloylpyrrolidin-3-yl)-3-(3-fluoro-4-(3-methoxyphenoxy)phenyl)-1H-imidazo[4,5-c]pyridin-2(3H)-one |
| 54 | 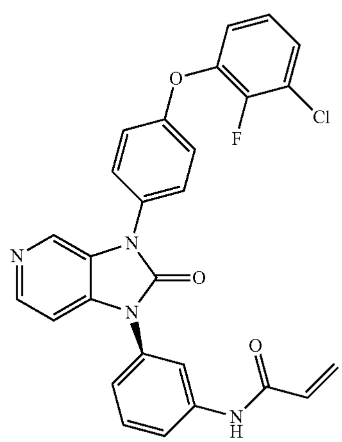 | 501.11/501.1 | N-(3-(3-(4-(3-chloro-2-fluoro phenoxy)phenyl)-2-oxo-2,3-dihydro-1H-imidazo[4,5-c]pyridin-1-yl) phenyl)acrylamide |
| 55 | 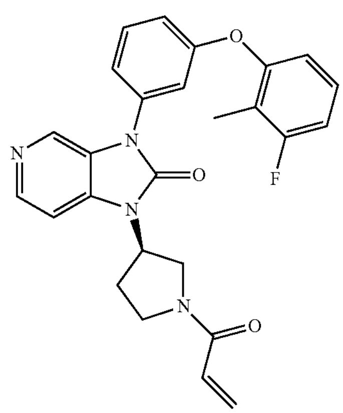 [SMILES: C=CC(=O)N1CC[C@@H](n2c(=O)n(-c3cccc(Oc4cccc(F)c4C)c3)c3cnccc32)C1] | 459.18/459.2 | (R)-1-(1-acryloylpyrrolidin-3-yl)-3-(3-(3-fluoro-2-methylphenoxy) phenyl)-1H-imidazo[4,5-c]pyridin-2(3H)-one |

| Entry | Structure | MS (cald) [M + H]⁺/MS (found) | Name |
|---|---|---|---|
| 56 | 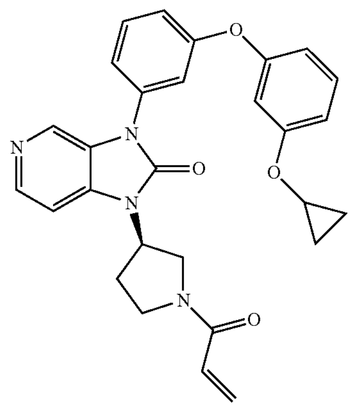 [SMILES: C=CC(=O)N1CC[C@@H](n2c(=O)n(-c3cccc(Oc4cccc(OC5CC5)c4)c3)c3cnccc32)C1] | 483.20/483.2 | (R)-1-(1-acryloylpyrrolidin-3-yl)-3-(3-(3-cyclopropoxyphenoxy)phenyl)-1H-imidazo[4,5-c]pyridin-2(3H)-one |
| 57 | 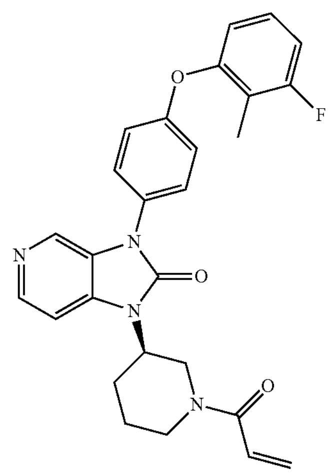 [SMILES: C=CC(=O)N1CCC[C@@H](n2c(=O)n(-c3ccc(Oc4cccc(F)c4C)cc3)c3cnccc32)C1] | 473.19/473.2 | (R)-1-(1-acryloylpiperidin-3-yl)-3-(4-(3-fluoro-2-methylphenoxy)phenyl)-1H-imidazo[4,5-c]pyridin-2(3H)-one |
| 58 | 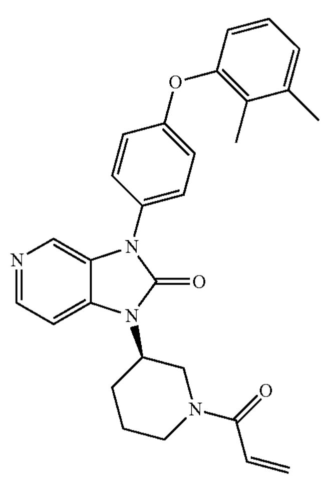 [SMILES: C=CC(=O)N1CCC[C@@H](n2c(=O)n(-c3ccc(Oc4cccc(C)c4C)cc3)c3cnccc32)C1] | 469.22/469.2 | (R)-1-(1-acryloylpiperidin-3-yl)-3-(4-(2,3-dimethylphenoxy)phenyl)-1H-imidazo[4,5-c]pyridin-2(3H)-one |

| Entry | Structure | MS (cald) [M + H]+/MS (found) | Name |
|---|---|---|---|
| 59 | 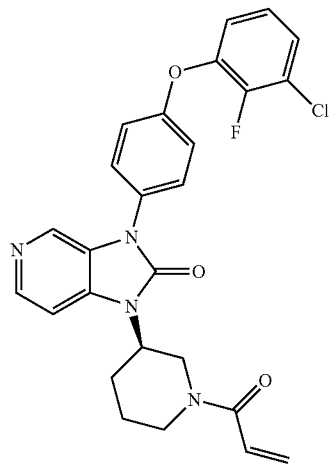 [SMILES: C=CC(=O)N1CCC[C@@H](n2c(=O)n(-c3ccc(Oc4cccc(Cl)c4F)cc3)c3cnccc32)C1] | 493.14/493.2 | (R)-1-(1-acryloylpiperidin-3-yl)-3-(4-(3-chloro-2-fluorophenoxy)phenyl)-1H-imidazo[4,5-c]pyridin-2(3H)-one |
| 60 | 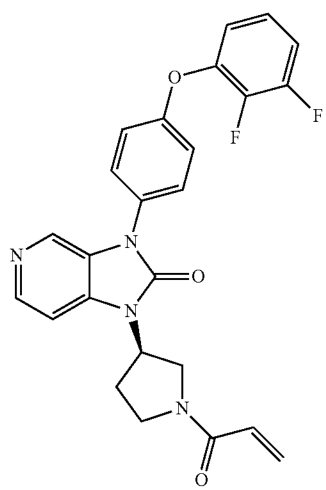 [SMILES: C=CC(=O)N1CC[C@@H](n2c(=O)n(-c3ccc(Oc4cccc(F)c4F)cc3)c3cnccc32)C1] | 463.15/463.2 | (R)-1-(1-acryloylpyrrolidin-3-yl)-3-(4-(2,3-difluorophenoxy)phenyl)-1H-imidazo[4,5-c]pyridin-2(3H)-one |
| 61 | 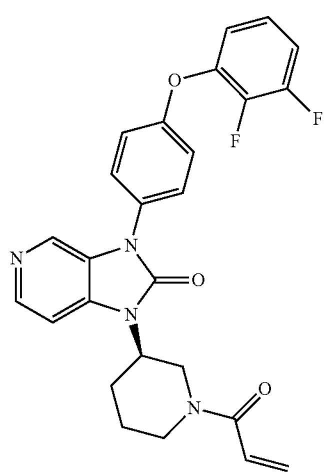 [SMILES: C=CC(=O)N1CCC[C@@H](n2c(=O)n(-c3ccc(Oc4cccc(F)c4F)cc3)c3cnccc32)C1] | 477.17/477.2 | (R)-1-(1-acryloylpiperidin-3-yl)-3-(4-(2,3-difluorophenoxy)phenyl)-1H-imidazo[4,5-c]pyridin-2(3H)-one |

-continued

| Entry | Structure | MS (cald) [M + H]+/MS (found) | Name |
|---|---|---|---|
| 62 | 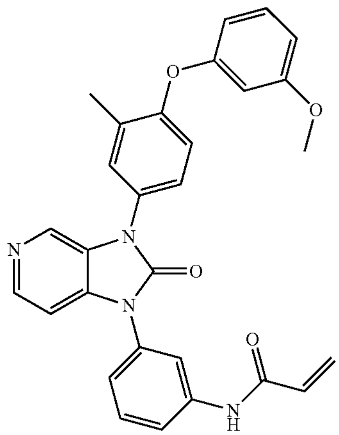 [SMILES: C=CC(=O)Nc1cccc(-n2c(=O)n(-c3ccc(Oc4cccc(OC)c4)c(C)c3)c3cnccc32)c1] | 493.18/493.2 | N-(3-(3-(4-(3-methoxyphenoxy)-3-methylphenyl)-2-oxo-2,3-dihydro-1H-imidazo[4,5-c]pyridin-1-yl)phenyl)acrylamide |
| 63 | 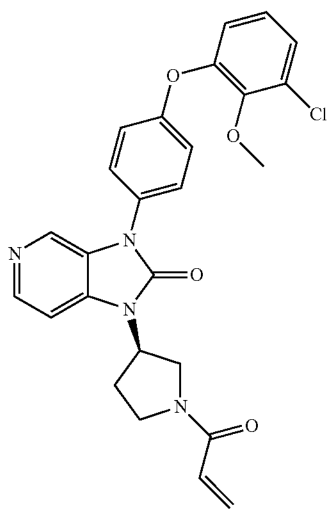 [SMILES: C=CC(=O)N1CC[C@@H](n2c(=O)n(-c3ccc(Oc4cccc(Cl)c4OC)cc3)c3cnccc32)C1] | 491.14/491.2 | (R)-1-(1-acryloylpyrrolidin-3-yl)-3-(4-(3-chloro-2-methoxyphenoxy)phenyl)-1H-imidazo[4,5-c]pyridine-2(3H)-one |
| 64 | 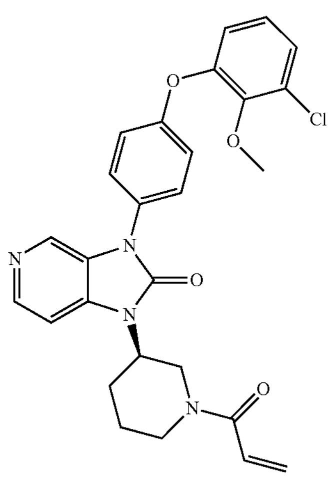 [SMILES: C=CC(=O)N1CCC[C@@H](n2c(=O)n(-c3ccc(Oc4cccc(Cl)c4OC)cc3)c3cnccc32)C1] | 505.16/505.2 | (R)-1-(1-acryloylpiperidin-3-yl)-3-(4-(3-chloro-2-methoxyphenoxy)phenyl)-1H-imidazo[4,5-c]pyridin-2(3H)-one |

-continued

| Entry | Structure | MS (calcd) [M + H]⁺/MS (found) | Name |
|---|---|---|---|
| 65 | 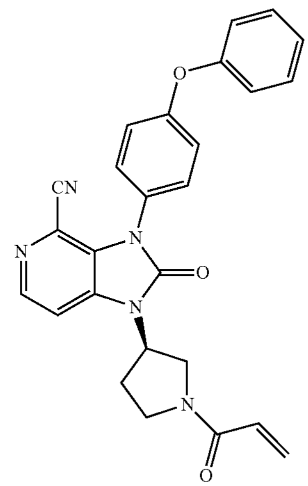 [SMILES: C=CC(=O)N1CC[C@@H](n2c(=O)n(-c3ccc(Oc4ccccc4)cc3)c3c(C#N)nccc32)C1] | 452.16/452.2 | ((R)-1-(1-acryloylpyrrolidin-3-yl)-2-oxo-3-(4-phenoxyphenyl)-2,3-dihydro-1H-imidazo[4,5-c]pyridine-4-carbonitrile |
| 66 | 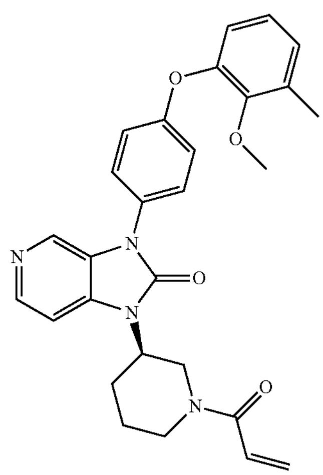 | 485.21/485.2 | (R)-1-(1-acryloylpiperidin-3-yl)-3-(4-(2-methoxy-3-methylphenoxy)phenyl)-1H-imidazo[4,5-c]pyridin-2(3H)-one |
| 67 | 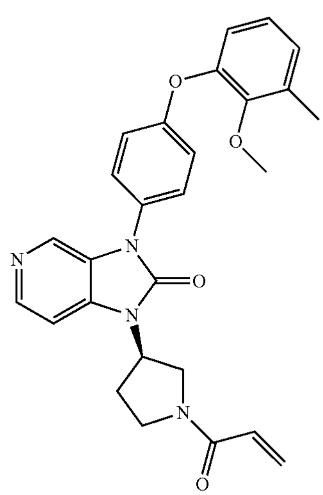 [SMILES: C=CC(=O)N1CC[C@@H](n2c(=O)n(-c3ccc(Oc4cccc(C)c4OC)cc3)c3cnccc32)C1] | 471.20/471.2 | (R)-1-(1-acryloylpyrrolidin-3-yl)-3-(4-(2-methoxy-3-methylphenoxy)phenyl)-1H-imidazo[4,5-c]pyridin-2(3H)-one |

-continued

| Entry | Structure | MS (cald) [M + H]+/MS (found) | Name |
|---|---|---|---|
| 68 | 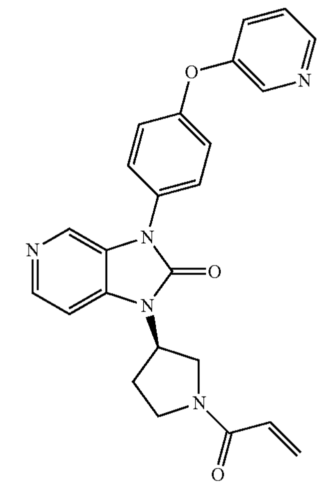 [SMILES: C=CC(=O)N1CC[C@@H](n2c(=O)n(-c3ccc(Oc4cccnc4)cc3)c3cnccc32)C1] | 428.16/428.2 | (R)-1-(1-acryloylpyrrolidin-3-yl)-3-(4-(pyridin-3-yloxy)phenyl)-1H-imidazo[4,5-c]pyridin-2(3H)-one |
| 69 | 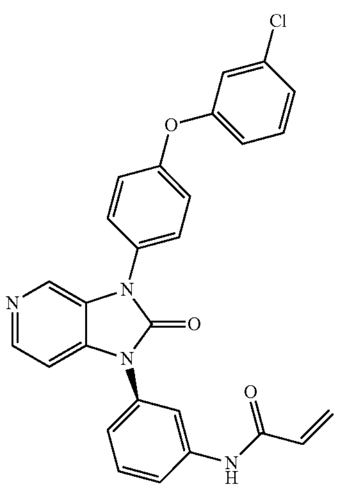 | 484.11/484.1 | N-(3-(3-(4-(3-chlorophenoxy)phenyl)-2-oxo-2,3-dihydro-1H-imidazo[4,5-c]pyridin-1-yl)phenyl)acrylamide |
| 70 | 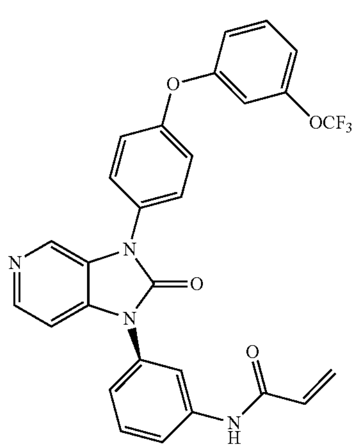 | 533.14/533.1 | N-(3-(2-oxo-3-(4-(3-(trifluoromethoxy)phenoxy)phenyl)-2,3-dihydro-1H-imidazo[4,5-c]pyridin-1-yl)phenyl)acrylamide |

| Entry | Structure | MS (cald) [M + H]⁺/MS (found) | Name |
|---|---|---|---|
| 71 | 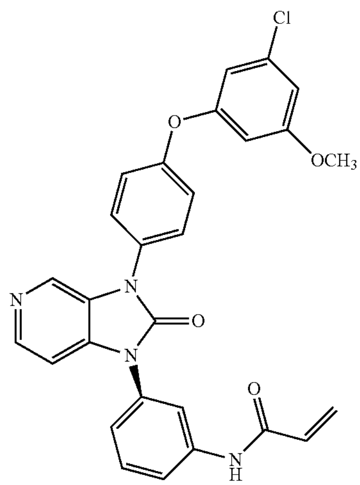 | 514.12/514.1 | N-(3-(3-(4-(3-chloro-5-methoxyphenoxy)phenyl)-2-oxo-2,3-dihydro-1H-imidazo[4,5-c]pyridin-1-yl)phenyl)acrylamide |
| 72 | 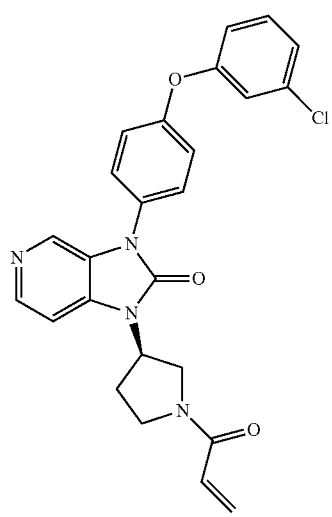 [SMILES: C=CC(=O)N1CC[C@@H](n2c(=O)n(-c3ccc(Oc4cccc(Cl)c4)cc3)c3cnccc32)C1] | 462.13/462.1 | (R)-1-(1-acryloylpyrrolidin-3-yl)-3-(4-(3-chlorophenoxy)phenyl)-1H-imidazo[4,5-c]pyridin-2(3H)-one |
| 73 | 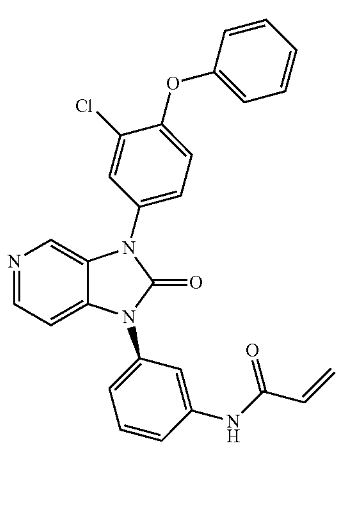 | 484.11/484.1 | N-(3-(3-(3-chloro-4-phenoxyphenyl)-2-oxo-2,3-dihydro-1H-imidazo[4,5-c]pyridin-1-yl)phenyl)acrylamide |

| Entry | Structure | MS (cald) [M + H]⁺/MS (found) | Name |
|---|---|---|---|
| 74 | 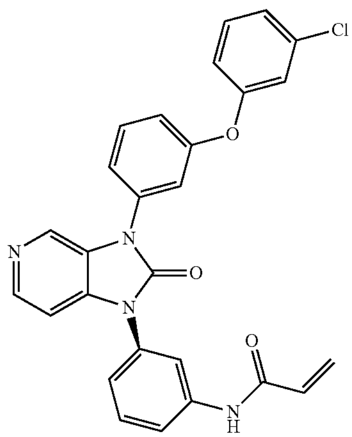 | 484.11/484.1 | N-(3-(3-(3-(3-chlorophenoxy)phenyl)-2-oxo-2,3-dihydro-1H-imidazo[4,5-c]pyridin-1-yl)phenyl)acrylamide |
| 75 | 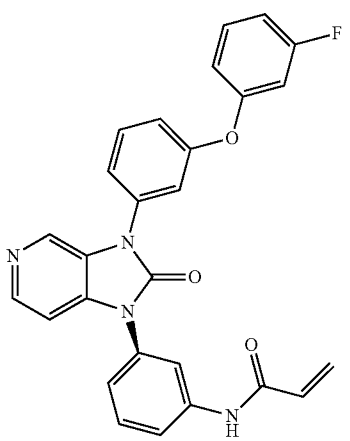 | 467.15/467.2 | N-(3-(3-(3-(3-fluorophenoxy)phenyl)-2-oxo-2,3-dihydro-1H-imidazo[4,5-c]pyridin-1-yl)phenyl)acrylamide |
| 76 | 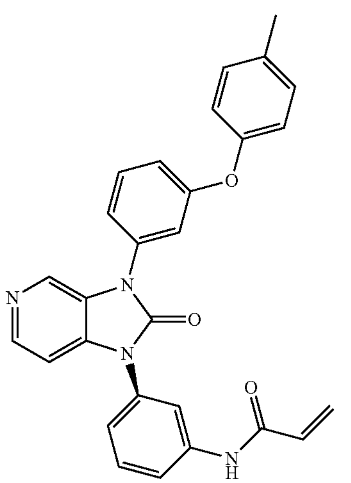 | 463.17/463.2 | N-(3-(2-oxo-3-(3-(p-tolyloxy)phenyl)-2,3-dihydro-1H-imidazo[4,5-c]pyridin-1-yl)phenyl)acrylamide |

-continued

| Entry | Structure | MS (cald) [M + H]⁺/MS (found) | Name |
|---|---|---|---|
| 77 | 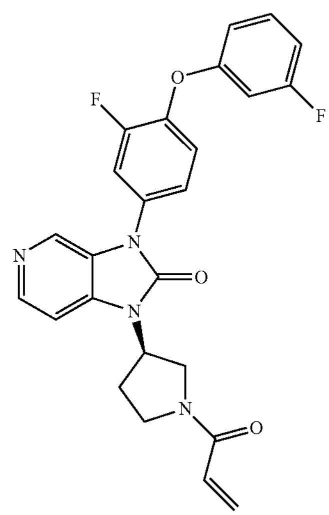 [SMILES: C=CC(=O)N1CC[C@@H](n2c(=O)n(-c3ccc(Oc4cccc(F)c4)c(F)c3)c3cnccc32)C1] | 463.15/463.2 | (R)-1-(1-acryloylpyrrolidin-3-yl)-3-(3-fluoro-4-(3-fluorophenoxy)phenyl)-1H-imidazo[4,5-c]pyridin-2(3H)-one |
| 78 | 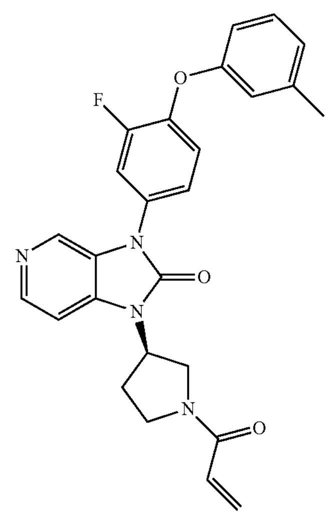 [SMILES: C=CC(=O)N1CC[C@@H](n2c(=O)n(-c3ccc(Oc4cccc(C)c4)c(F)c3)c3cnccc32)C1] | 459.18/459.2 | (R)-1-(1-acryloylpyrrolidin-3-yl)-3-(3-fluoro-4-(m-tolyloxy)phenyl)-1H-imidazo[4,5-c]pyridin-2(3H)-one |
| 79 | 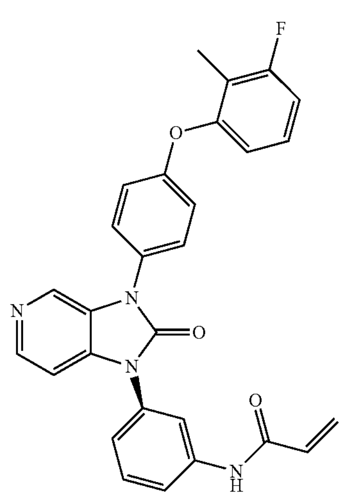 | 481.16/481.2 | N-(3-(3-(4-(3-fluoro-2-methylphenoxy)phenyl)-2-oxo-2,3-dihydro-1H-imidazo[4,5-c]pyridin-1-yl)phenyl)acrylamide |

-continued

| Entry | Structure | MS (cald) [M + H]+/MS (found) | Name |
|---|---|---|---|
| 80 | 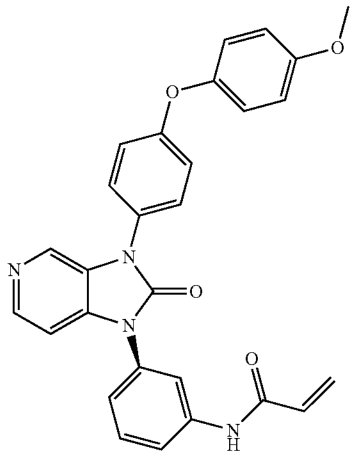 | 479.17/479.2 | N-(3-(3-(4-(4-methoxyphenoxy)phenyl)-2-oxo-2,3-dihydro-1H-imidazo[4,5-c]pyridin-1-yl)phenyl)acrylamide |
| 81 | 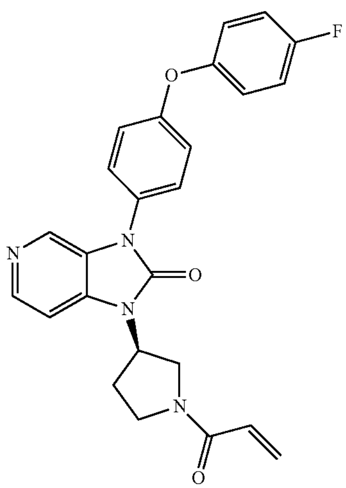 [SMILES: C=CC(=O)N1CC[C@@H](n2c(=O)n(-c3ccc(Oc4ccc(F)cc4)cc3)c3cnccc32)C1] | 445.16/445.1 | (R)-1-(1-acryloylpyrrolidin-3-yl)-3-(4-(4-fluorophenoxy)phenyl)-1H-imidazo[4,5-c]pyridin-2(3H)-one |
| 82 | 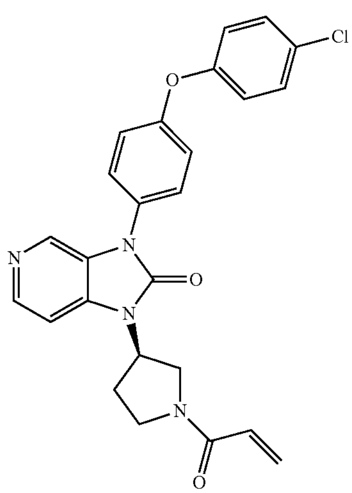 [SMILES: C=CC(=O)N1CC[C@@H](n2c(=O)n(-c3ccc(Oc4ccc(Cl)cc4)cc3)c3cnccc32)C1] | 461.13/461.1 | (R)-1-(1-acryloylpyrrolidin-3-yl)-3-(4-(4-chlorophenoxy)phenyl)-1H-imidazo[4,5-c]pyridin-2(3H)-one |

-continued

| Entry | Structure | MS (calcd) [M + H]⁺/MS (found) | Name |
|---|---|---|---|
| 83 | 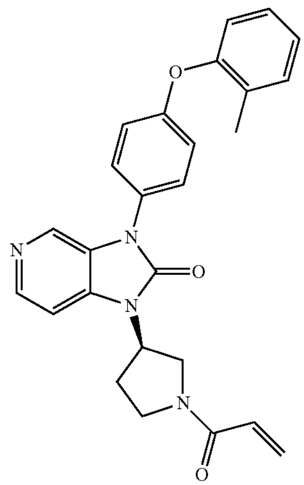 [SMILES: C=CC(=O)N1CC[C@@H](n2c(=O)n(-c3ccc(Oc4ccccc4C)cc3)c3cnccc32)C1] | 441.18/441.2 | (R)-1-(1-acryloylpyrrolidin-3-yl)-3-(4-(o-tolyloxy)phenyl)-1H-imidazo[4,5-c]pyridin-2(3H)-one |
| 84 | 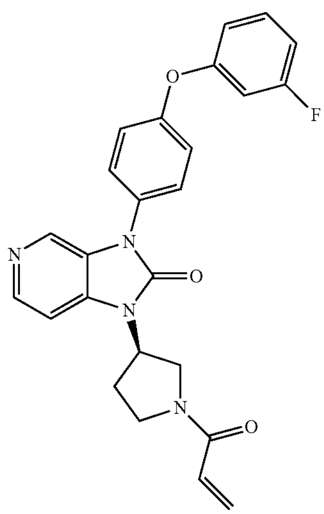 [SMILES: C=CC(=O)N1CC[C@@H](n2c(=O)n(-c3ccc(Oc4cccc(F)c4)cc3)c3cnccc32)C1] | 445.16/445.1 | (R)-1-(1-acryloylpyrrolidin-3-yl)-3-(4-(3-fluorophenoxy)phenyl)-1H-imidazo[4,5-c]pyridin-2(3H)-one |
| 85 | 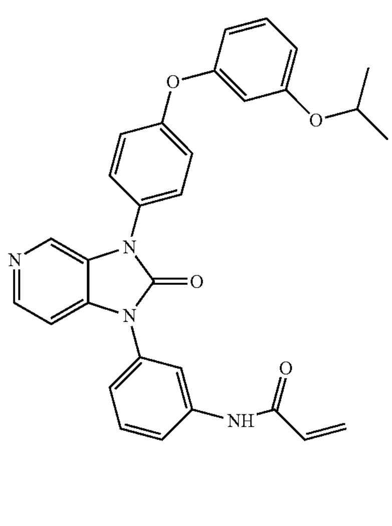 [SMILES: C=CC(=O)Nc1cccc(-n2c(=O)n(-c3ccc(Oc4cccc(OC(C)C)c4)cc3)c3cnccc32)c1] | 506.20/507.2 | N-(3-(3-(4-(3-isopropoxyphenoxy)phenyl)-2-oxo-2,3-dihydro-1H-imidazo[4,5-c]pyridin-1-yl)phenyl)acrylamide |

US 10,358,446 B2

| Entry | Structure | MS (cald) [M + H]⁺/MS (found) | Name |
|---|---|---|---|
| 86 | 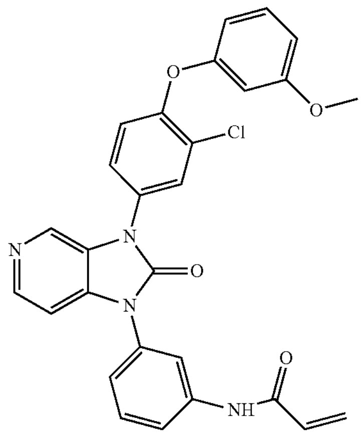 [SMILES: C=CC(=O)Nc1cccc(-n2c(=O)n(-c3ccc(Oc4cccc(OC)c4)c(Cl)c3)c3cnccc32)c1] | 512.13/513.1 | N-(3-(3-(3-chloro-4-(3-methoxyphenoxy)phenyl)-2-oxo-2,3-dihydro-1H-imidazo[4,5-c]pyridin-1-yl)phenyl)acrylamide |
| 87 | 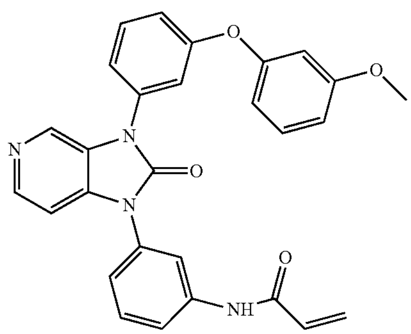 [SMILES: C=CC(=O)Nc1cccc(-n2c(=O)n(-c3cccc(Oc4cccc(OC)c4)c3)c3cnccc32)c1] | 478.16/479.2 | N-(3-(3-(3-methoxyphenoxy)phenyl)-2-oxo-2,3-dihydro-1H-imidazo[4,5-c]pyridin-1-yl)phenyl)acrylamide |
| 88 | 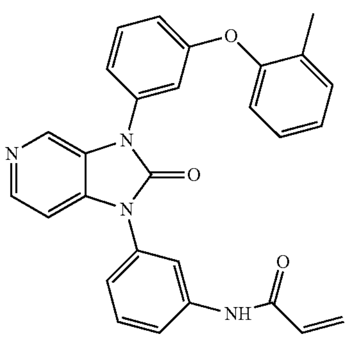 [SMILES: C=CC(=O)Nc1cccc(-n2c(=O)n(-c3cccc(Oc4ccccc4C)c3)c3cnccc32)c1] | 462.17/463.2 | N-(3-(2-oxo-3-(3-(o-tolyloxy)phenyl)-2,3-dihydro-1H-imidazo[4,5-c]pyridin-1-yl)phenyl)acrylamide |
| 89 | 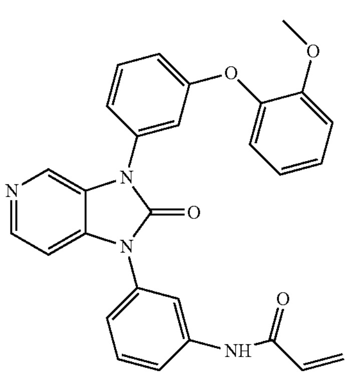 [SMILES: C=CC(=O)Nc1cccc(-n2c(=O)n(-c3cccc(Oc4ccccc4OC)c3)c3cnccc32)c1] | 478.16/479.2 | N-(3-(3-(3-(2-methoxyphenoxy)phenyl)-2-oxo-2,3-dihydro-1H-imidazo[4,5-c]pyridin-1-yl)phenyl)acrylamide |

| Entry | Structure | MS (cald) [M + H]⁺/MS (found) | Name |
|---|---|---|---|
| 90 | 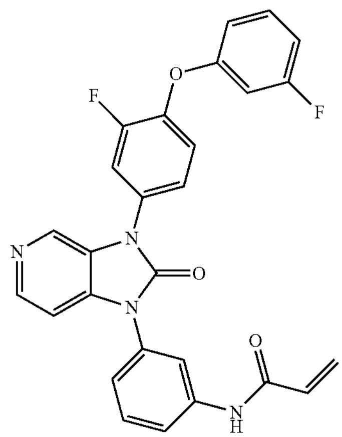 [SMILES: C=CC(=O)Nc1cccc(-n2c(=O)n(-c3ccc(Oc4cccc(F)c4)c(F)c3)c3cnccc32)c1] | 484.13/485.0 | N-(3-(3-(3-fluoro-4-(3-fluorophenoxy)phenyl)-2-oxo-2,3-dihydro-1H-imidazo[4,5-c]pyridin-1-yl)phenyl)acrylamide |
| 91 | 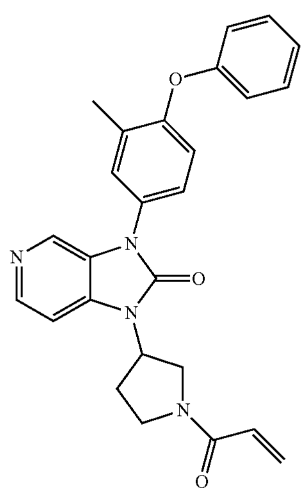 [SMILES: C=CC(=O)N1CCC(n2c(=O)n(-c3ccc(Oc4ccccc4)c(C)c3)c3cnccc32)C1] | 440.18/441.2 | 1-(1-acryloylpyrrolidin-3-yl)-3-(3-methyl-4-phenoxyphenyl)-1,3-dihydro-2H-imidazo[4,5-c]pyridin-2-one |
| 92 | 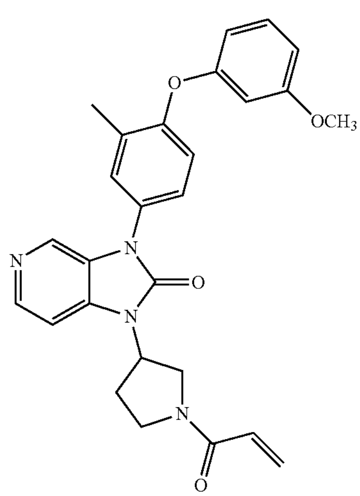 [SMILES: C=CC(=O)N1CCC(n2c(=O)n(-c3ccc(Oc4cccc(OC)c4)c(C)c3)c3cnccc32)C1] | 470.20/471.2 | 1-(1-acryloylpyrrolidin-3-yl)-3-(4-(3-methoxyphenoxy)-3-methylphenyl)-1,3-dihydro-2H-imidazo[4,5-c]pyridin-2-one |

| Entry | Structure | MS (calcd) [M + H]⁺/MS (found) | Name |
|---|---|---|---|
| 93 | 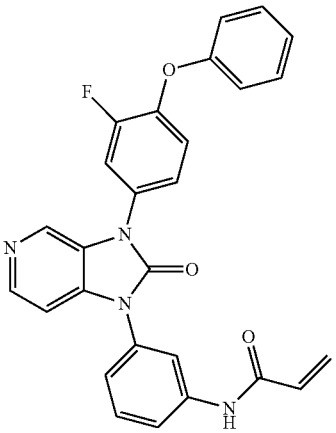 [SMILES: C=CC(=O)Nc1cccc(-n2c(=O)n(-c3ccc(Oc4ccccc4)c(F)c3)c3cnccc32)c1] | 466.14/467.1 | N-(3-(3-(3-fluoro-4-phenoxyphenyl)-2-oxo-2,3-dihydro-1H-imidazo[4,5-c]pyridin-1-yl)phenyl)acrylamide |
| 94 | 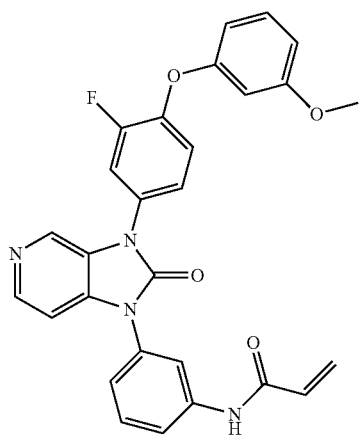 [SMILES: C=CC(=O)Nc1cccc(-n2c(=O)n(-c3ccc(Oc4cccc(OC)c4)c(F)c3)c3cnccc32)c1] | 496.15/497.2 | N-(3-(3-(3-fluoro-4-(3-methoxyphenoxy)phenyl)-2-oxo-2,3-dihydro-1H-imidazo[4,5-c]pyridin-1-yl)phenyl)acrylamide |
| 95 | 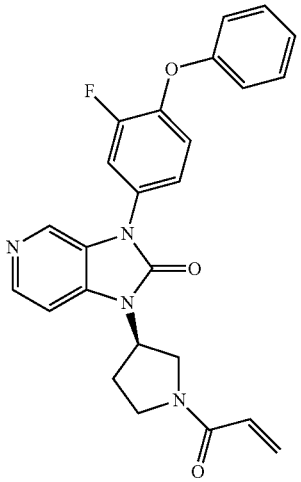 [SMILES: C=CC(=O)N1CC[C@@H](n2c(=O)n(-c3ccc(Oc4ccccc4)c(F)c3)c3cnccc32)C1] | 444.16/445.2 | (R)-1-(1-acryloylpyrrolidin-3-yl)-3-(3-fluoro-4-phenoxyphenyl)-1,3-dihydro-2H-imidazo[4,5-c]pyridin-2-one |

-continued

| Entry | Structure | MS (cald) [M + H]+/MS (found) | Name |
|---|---|---|---|
| 96 | 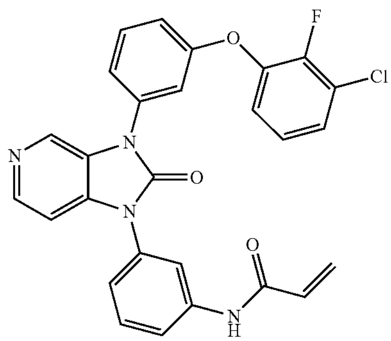 [SMILES: C=CC(=O)Nc1cccc(-n2c(=O)n(-c3cccc(Oc4cccc(Cl)c4F)c3)c3cnccc32)c1] | 500.11/501.1 | N-(3-(3-(3-(3-chloro-2-fluorophenoxy)phenyl)-2-oxo-2,3-dihydro-1H-imidazo[4,5-c]pyridin-1-yl)phenyl)acrylamide |
| 97 | 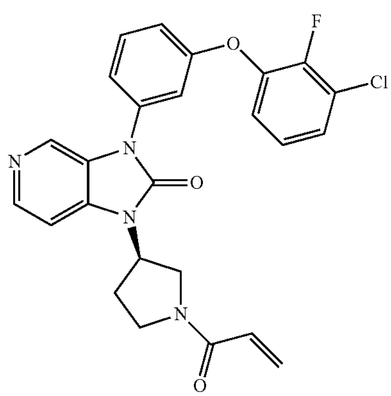 [SMILES: C=CC(=O)N1CC[C@@H](n2c(=O)n(-c3cccc(Oc4cccc(Cl)c4F)c3)c3cnccc32)C1] | 478.12/479.1 | (R)-1-(1-acryloylpyrrolidin-3-yl)-3-(3-(3-chloro-2-fluorophenoxy)phenyl)-1,3-dihydro-2H-imidazo[4,5-c]pyridin-2-one |
| 98 | 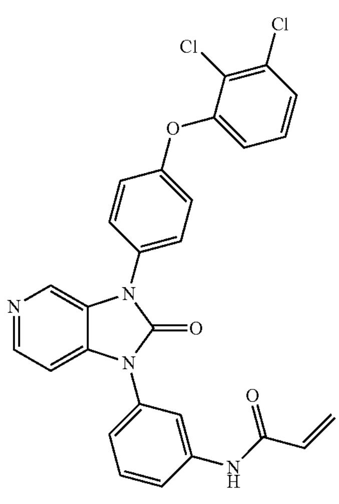 [SMILES: C=CC(=O)Nc1cccc(-n2c(=O)n(-c3ccc(Oc4cccc(Cl)c4Cl)cc3)c3cnccc32)c1] | 516.08/517.1 | N-(3-(3-(4-(2,3-dichlorophenoxy)phenyl)-2-oxo-2,3-dihydro-1H-imidazo[4,5-c]pyridin-1-yl)phenyl)acrylamide |

-continued

| Entry | Structure | MS (cald) [M + H]⁺/MS (found) | Name |
|---|---|---|---|
| 99 | 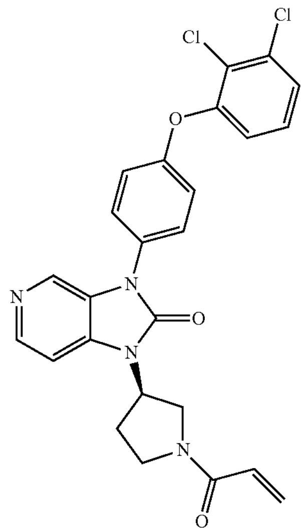 [SMILES: C=CC(=O)N1CC[C@@H](n2c(=O)n(-c3ccc(Oc4cccc(Cl)c4Cl)cc3)c3cnccc32)C1] | 494.09/495.1 | (R)-1-(1-acryloylpyrrolidin-3-yl)-3-(4-(2,3-dichlorophenoxy)phenyl)-1,3-dihydro-2H-imidazo[4,5-c]pyridin-2-one |
| 100 | 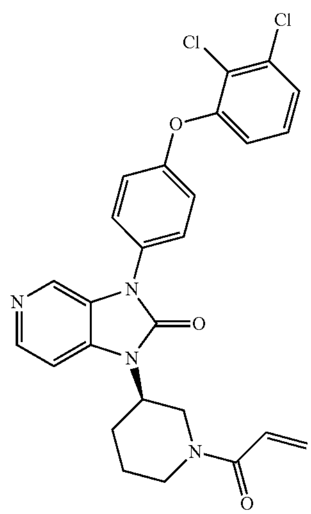 [SMILES: C=CC(=O)N1CCC[C@@H](n2c(=O)n(-c3ccc(Oc4cccc(Cl)c4Cl)cc3)c3cnccc32)C1] | 508.11/509.1 | (R)-1-(1-acryloylpiperidin-3-yl)-3-(4-(2,3-dichlorophenoxy)phenyl)-1,3-dihydro-2H-imidazo[4,5-c]pyridin-2-one |
| 101 | 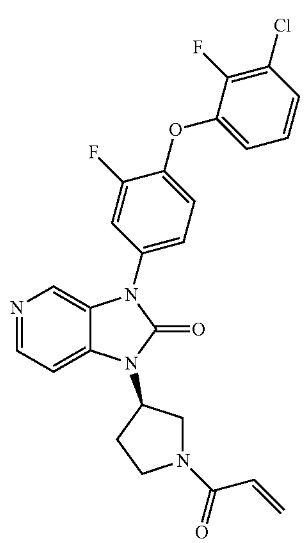 [SMILES: C=CC(=O)N1CC[C@@H](n2c(=O)n(-c3ccc(Oc4cccc(Cl)c4F)c(F)c3)c3cnccc32)C1] | 496.11/497.1 | (R)-1-(1-acryloylpyrrolidin-3-yl)-3-(4-(3-chloro-2-fluorophenoxy)-3-fluorophenyl)-1,3-dihydro-2H-imidazo[4,5-c]pyridin-2-one |

-continued
| Entry | Structure | MS (cald) [M + H]+/MS (found) | Name |
|---|---|---|---|
| 102 | 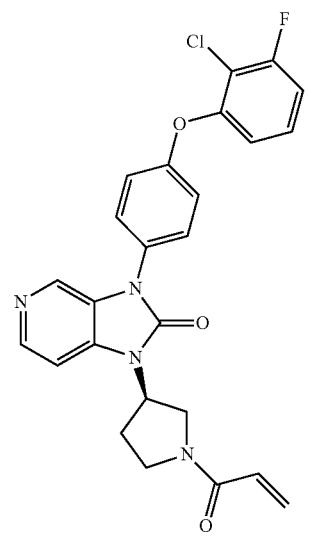 [SMILES: C=CC(=O)N1CC[C@@H](n2c(=O)n(-c3ccc(Oc4cccc(F)c4Cl)cc3)c3cnccc32)C1] | 478.12/479.1 | (R)-1-(1-acryloylpyrrolidin-3-yl)-3-(4-(2-chloro-3-fluorophenoxy)phenyl)-1,3-dihydro-2H-imidazo[4,5-c]pyridin-2-one |
| 103 | 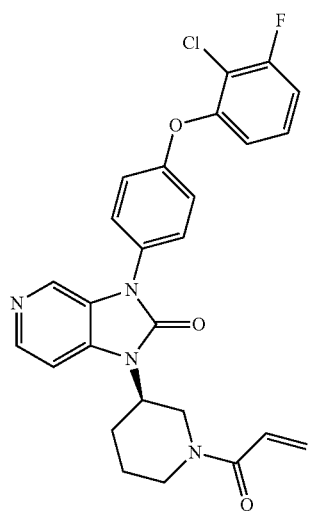 | 492.14/493.2 | (R)-1-(1-acryloylpiperidin-3-yl)-3-(4-(2-chloro-3-fluorophenoxy)phenyl)-1,3-dihydro-2H-imidazo[4,5-c]pyridin-2-one |
| 104 | 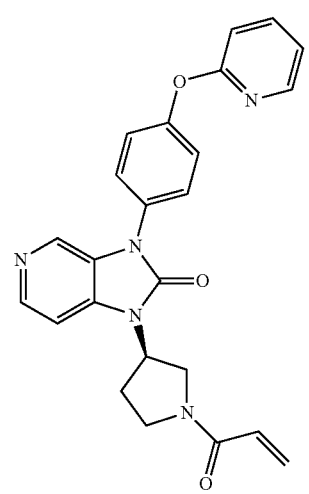 [SMILES: C=CC(=O)N1CC[C@@H](n2c(=O)n(-c3ccc(Oc4ccccn4)cc3)c3cnccc32)C1] | 427.16/428.2 | (R)-1-(1-acryloylpyrrolidin-3-yl)-3-(4-(pyridin-2-yloxy)phenyl)-1,3-dihydro-2H-imidazo[4,5-c]pyridin-2-one |

-continued

| Entry | Structure | MS (calcd) [M + H]+/MS (found) | Name |
|---|---|---|---|
| 105 | 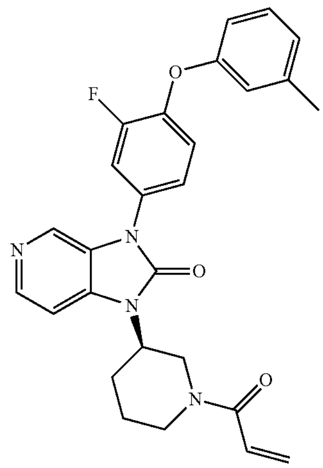 | 473.19/473.2 | (R)-1-(1-acryloylpiperidin-3-yl)-3-(3-fluoro-4-(m-tolyloxy)phenyl)-1H-imidazo[4,5-c]pyridin-2(3H)-one |
| 106 | 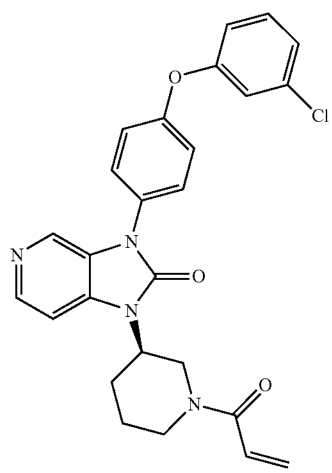 [SMILES: C=CC(=O)N1CCC[C@@H](n2c(=O)n(-c3ccc(Oc4cccc(Cl)c4)cc3)c3cnccc32)C1] | 475.15/475.2 | (R)-1-(1-acryloylpiperidin-3-yl)-3-(4-(3-chlorophenoxy)phenyl)-1H-imidazo[4,5-c]pyridin-2(3H)-one |
| 107 | 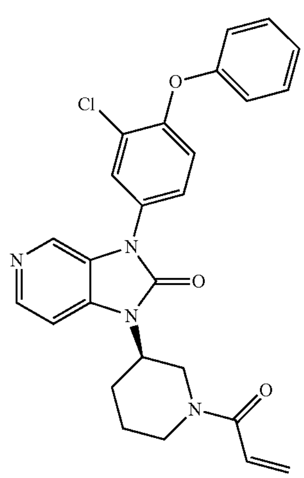 [SMILES: C=CC(=O)N1CCC[C@@H](n2c(=O)n(-c3ccc(Oc4ccccc4)c(Cl)c3)c3cnccc32)C1] | 475.15/475.2 | (R)-1-(1-acryloylpiperidin-3-yl)-3-(3-chloro-4-phenoxyphenyl)-1H-imidazo[4,5-c]pyridin-2(3H)-one |

-continued

| Entry | Structure | MS (calcd) [M + H]⁺/MS (found) | Name |
|---|---|---|---|
| 108 | 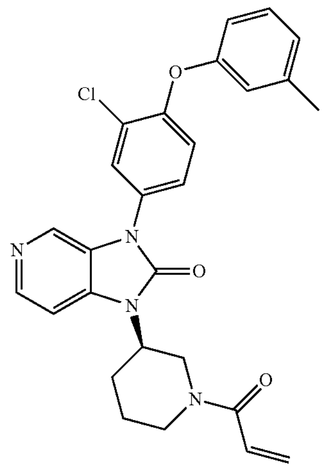 [SMILES: C=CC(=O)N1CCC[C@@H](n2c(=O)n(-c3ccc(Oc4cccc(C)c4)c(Cl)c3)c3cnccc32)C1] | 488.16/488.1 | (R)-1-(1-acryloylpiperidin-3-yl)-3-(3-chloro-4-(m-tolyloxy)phenyl)-1H-imidazo[4,5-c]pyridin-2(3H)-one |
| 109 | 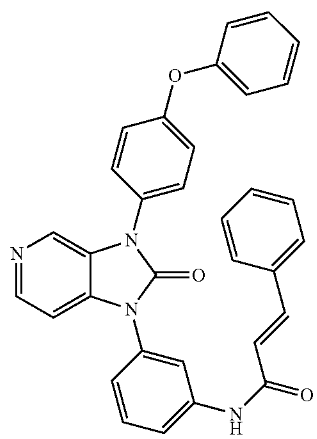 [SMILES: O=C(/C=C/c1ccccc1)Nc1cccc(-n2c(=O)n(-c3ccc(Oc4ccccc4)cc3)c3cnccc32)c1] | 525.18/525.2 | N-(3-(2-oxo-3-(4-phenoxyphenyl)-2,3-dihydro-1H-imidazo[4,5-c]pyridin-1-yl)phenyl)cinnamamide |
| 110 | 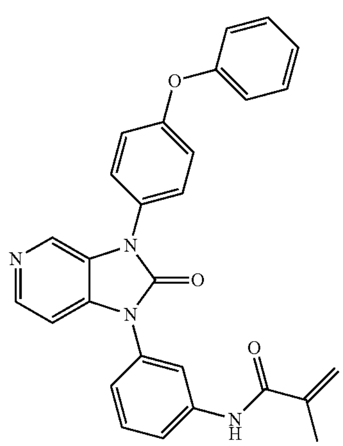 [SMILES: C=C(C)C(=O)Nc1cccc(-n2c(=O)n(-c3ccc(Oc4ccccc4)cc3)c3cnccc32)c1] | 463.17/463.2 | N-(3-(2-oxo-3-(4-phenoxyphenyl)-2,3-dihydro-1H-imidazo[4,5-c]pyridin-1-yl)phenyl)methacrylamide |

| Entry | Structure | MS (cald) [M + H]+/MS (found) | Name |
|---|---|---|---|
| 111 | 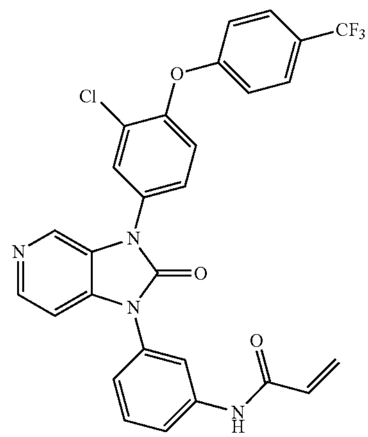 [SMILES: C=CC(=O)Nc1cccc(-n2c(=O)n(-c3ccc(Oc4ccc(C(F)(F)F)cc4)c(Cl)c3)c3cnccc32)c1] | 551.10/551.1 | N-(3-(3-(3-chloro-4-(4-(trifluoromethyl)phenoxy)phenyl)-2-oxo-2,3-dihydro-1H-imidazo[4,5-c]pyridin-1-yl)phenyl)acrylamide |
| 112 | 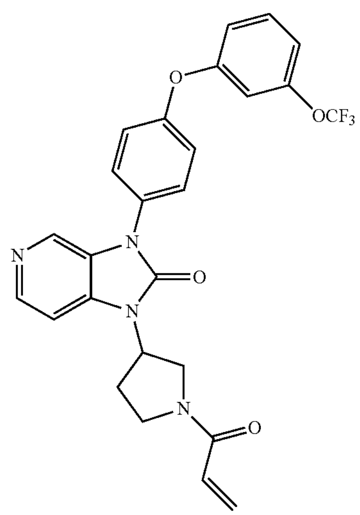 [SMILES: C=CC(=O)N1CCC(n2c(=O)n(-c3ccc(Oc4cccc(OC(F)(F)F)c4)cc3)c3cnccc32)C1] | 511.15/511.2 | 1-(1-acryloylpyrrolidin-3-yl)-3-(4-(3-(trifluoromethoxy)phenoxy)phenyl)-1H-imidazo[4,5-c]pyridin-2(3H)-one |
| 113 | 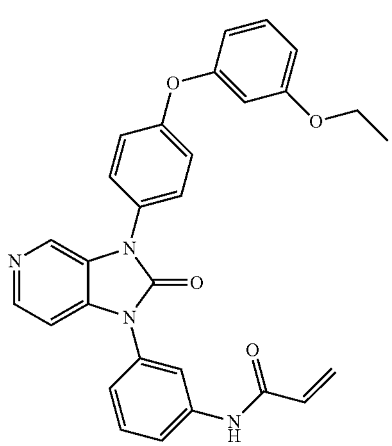 [SMILES: C=CC(=O)Nc1cccc(-n2c(=O)n(-c3ccc(Oc4cccc(OCC)c4)cc3)c3cnccc32)c1] | 493.18/493.2 | N-(3-(3-(4-(3-ethoxyphenoxy)phenyl)-2-oxo-2,3-dihydro-1H-imidazo[4,5-c]pyridin-1-yl)phenyl)acrylamide |

-continued

| Entry | Structure | MS (cald) [M + H]⁺/MS (found) | Name |
|---|---|---|---|
| 114 | 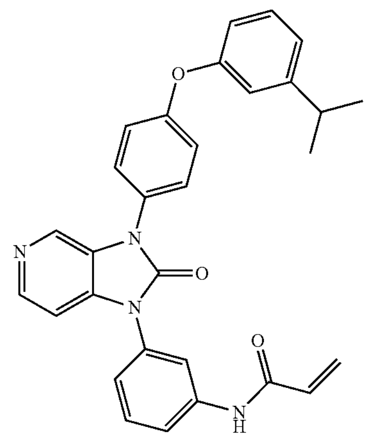 [SMILES: C=CC(=O)Nc1cccc(-n2c(=O)n(-c3ccc(Oc4cccc(C(C)C)c4)cc3)c3cnccc32)c1] | 491.20/491.2 | N-(3-(3-(4-(3-isopropylphenoxy)phenyl)-2-oxo-2,3-dihydro-1H-imidazo[4,5-c]pyridin-1-yl)phenyl)acrylamide |
| 115 | 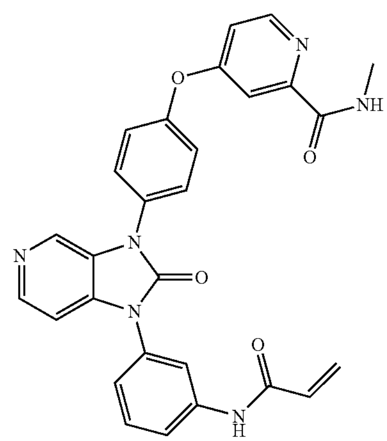 [SMILES: C=CC(=O)Nc1cccc(-n2c(=O)n(-c3ccc(Oc4ccnc(C(=O)NC)c4)cc3)c3cnccc32)c1] | 507.17/507.2 | 4-(4-(1-(3-acrylamidophenyl)-2-oxo-1H-imidazo[4,5-c]pyridin-3(2H)-yl)phenoxy)-N-methylpicolinamide |
| 116 | 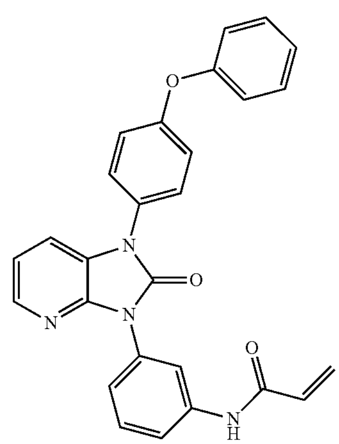 [SMILES: C=CC(=O)Nc1cccc(-n2c(=O)n(-c3ccc(Oc4ccccc4)cc3)c3cccnc32)c1] | 449.15/449.2 | N-(3-(2-oxo-1-(4-phenoxyphenyl)-1H-imidazo[4,5-b]pyridin-3(2H)-yl)phenyl)acrylamide |

-continued

| Entry | Structure | MS (calcd) [M + H]+/MS (found) | Name |
|---|---|---|---|
| 117 | 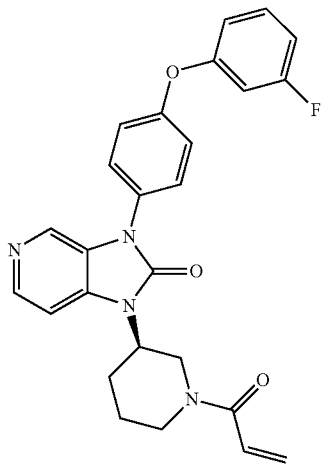 [SMILES: C=CC(=O)N1CCC[C@@H](n2c(=O)n(-c3ccc(Oc4cccc(F)c4)cc3)c3cnccc32)C1] | 459.18/459.2 | (R)-1-(1-acryloylpiperidin-3-yl)-3-(4-(3-fluorophenoxy)phenyl)-1H-imidazo[4,5-c]pyridin-2(3H)-one |
| 118 | 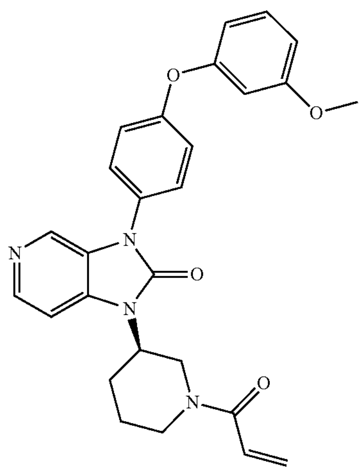 [SMILES: C=CC(=O)N1CCC[C@@H](n2c(=O)n(-c3ccc(Oc4cccc(OC)c4)cc3)c3cnccc32)C1] | 471.20/471.2 | (R)-1-(1-acryloylpiperidin-3-yl)-3-(4-(3-methoxyphenoxy)phenyl)-1H-imidazo[4,5-c]pyridin-2(3H)-one |
| 119 | 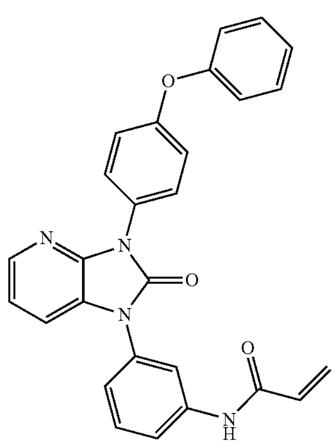 [SMILES: C=CC(=O)Nc1cccc(-n2c(=O)n(-c3ccc(Oc4ccccc4)cc3)c3ncccc32)c1] | 449.15/449.2 | N-(3-(2-oxo-3-(4-phenoxyphenyl)-2,3-dihydro-1H-imidazo[4,5-b]pyridin-1-yl)phenyl)acrylamide |

| Entry | Structure | MS (cald) [M + H]+/MS (found) | Name |
|---|---|---|---|
| 120 | 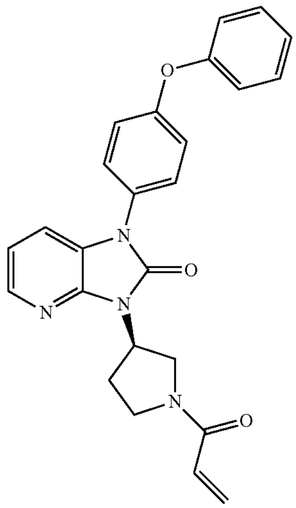 [SMILES: C=CC(=O)N1CC[C@@H](n2c(=O)n(-c3ccc(Oc4ccccc4)cc3)c3cccnc32)C1] | 427.17/427.2 | (R)-3-(1-acryloylpyrrolidin-3-yl)-1-(4-phenoxyphenyl)-1H-imidazo[4,5-b]pyridin-2(3H)-one |
| 121 | 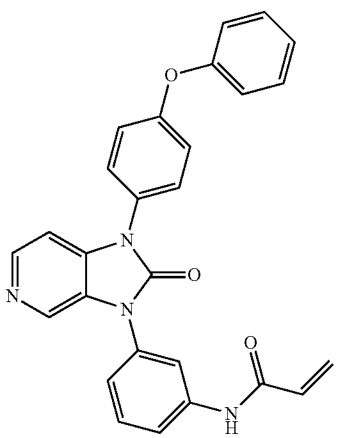 [SMILES: C=CC(=O)Nc1cccc(-n2c(=O)n(-c3ccc(Oc4ccccc4)cc3)c3ccncc32)c1] | 449.15/449.2 | N-(3-(2-oxo-1-(4-phenoxyphenyl)-1H-imidazo[4,5-c]pyridin-3(2H)-yl)phenyl)acrylamide |
| 122 | 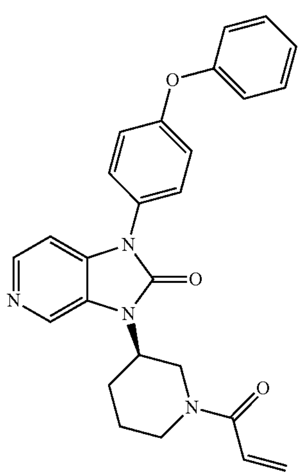 [SMILES: C=CC(=O)N1CCC[C@@H](n2c(=O)n(-c3ccc(Oc4ccccc4)cc3)c3ccncc32)C1] | 441.18/441.2 | (R)-3-(1-acryloylpiperidin-3-yl)-1-(4-phenoxyphenyl)-1H-imidazo[4,5-c]pyridin-2(3H)-one |

| Entry | Structure | MS (cald) [M + H]⁺/MS (found) | Name |
|---|---|---|---|
| 123 | 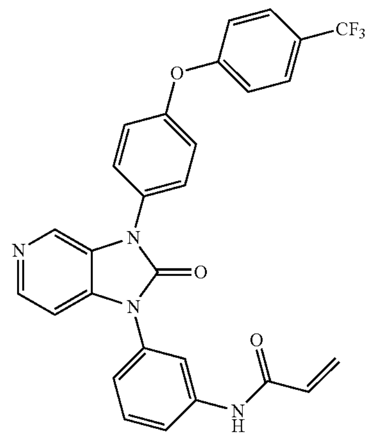 [SMILES: C=CC(=O)Nc1cccc(-n2c(=O)n(-c3ccc(Oc4ccc(C(F)(F)F)cc4)cc3)c3cnccc32)c1] | 517.14/517.1 | N-(3-(2-oxo-3-(4-(4-(trifluoromethyl)phenoxy)phenyl)-2,3-dihydro-1H-imidazo[4,5-c]pyridin-1-yl)phenyl)acrylamide |
| 124 | 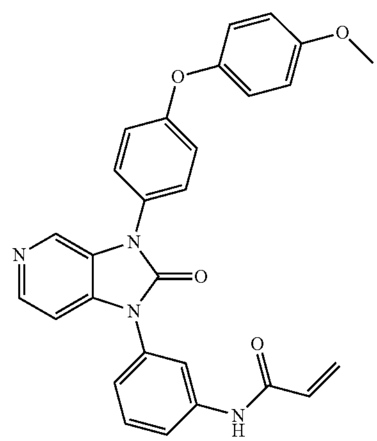 [SMILES: C=CC(=O)Nc1cccc(-n2c(=O)n(-c3ccc(Oc4ccc(OC)cc4)cc3)c3cnccc32)c1] | 479.16/479.2 | N-(3-(3-(4-(4-methoxyphenoxy)phenyl)-2-oxo-2,3-dihydro-1H-imidazo[4,5-c]pyridin-1-yl)phenyl)acrylamide |
| 125 | 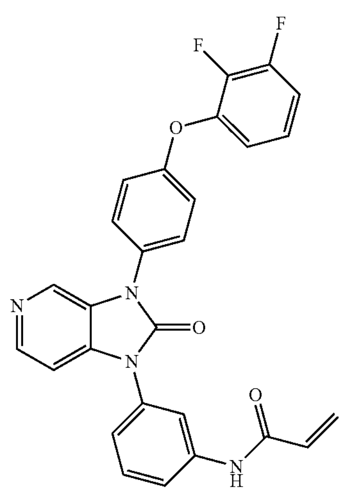 [SMILES: C=CC(=O)Nc1cccc(-n2c(=O)n(-c3ccc(Oc4cccc(F)c4F)cc3)c3cnccc32)c1] | 485.13/485.1 | N-(3-(3-(4-(2,3-difluorophenoxy)phenyl)-2-oxo-2,3-dihydro-1H-imidazo[4,5-c]pyridin-1-yl)phenyl)acrylamide |

-continued

| Entry | Structure | MS (cald) [M + H]+/MS (found) | Name |
|---|---|---|---|
| 126 | 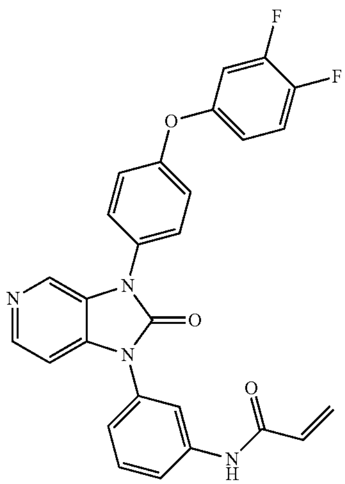 [SMILES: C=CC(=O)Nc1cccc(-n2c(=O)n(-c3ccc(Oc4ccc(F)c(F)c4)cc3)c3cnccc32)c1] | 485.13/485.1 | N-(3-(3-(4-(3,4-difluorophenoxy)phenyl)-2-oxo-2,3-dihydro-1H-imidazo[4,5-c]pyridin-1-yl)phenyl)acrylamide |
| 127 | 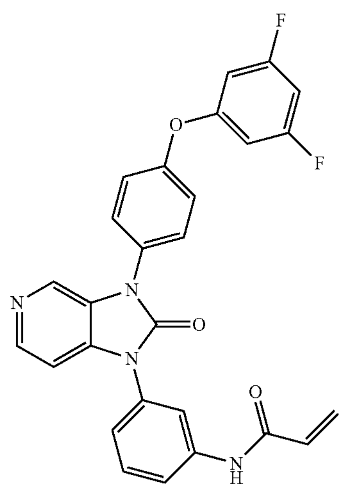 [SMILES: C=CC(=O)Nc1cccc(-n2c(=O)n(-c3ccc(Oc4cc(F)cc(F)c4)cc3)c3cnccc32)c1] | 485.13/485.1 | N-(3-(3-(4-(3,5-difluorophenoxy)phenyl)-2-oxo-2,3-dihydro-1H-imidazo[4,5-c]pyridin-1-yl)phenyl)acrylamide |
| 128 | 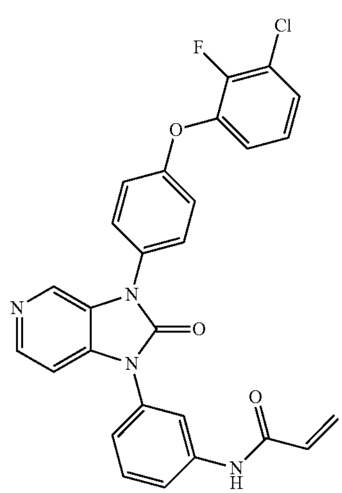 [SMILES: C=CC(=O)Nc1cccc(-n2c(=O)n(-c3ccc(Oc4cccc(Cl)c4F)cc3)c3cnccc32)c1] | 501.11/501.1 503.1 | N-(3-(3-(4-(3-chloro-2-fluorophenoxy)phenyl)-2-oxo-2,3-dihydro-1H-imidazo[4,5-c]pyridin-1-yl)phenyl)acrylamide |

| Entry | Structure | MS (cald) [M + H]+/MS (found) | Name |
|---|---|---|---|
| 129 | 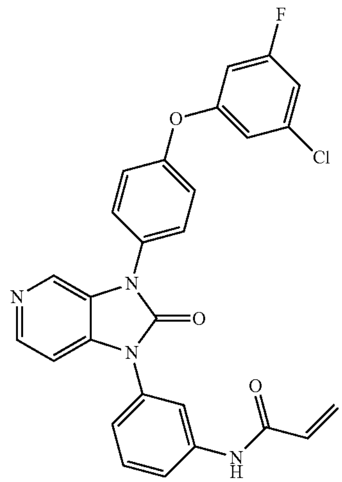 [SMILES: C=CC(=O)Nc1cccc(-n2c(=O)n(-c3ccc(Oc4cc(F)cc(Cl)c4)cc3)c3cnccc32)c1] | 501.11/501.1 503.1 | N-(3-(3-(4-(3-chloro-5-fluorophenoxy)phenyl)-2-oxo-2,3-dihydro-1H-imidazo[4,5-c]pyridin-1-yl)phenyl)acrylamide |
| 130 | 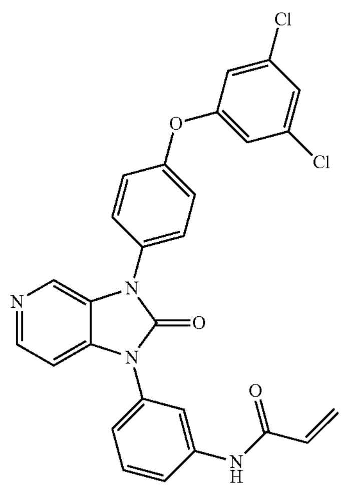 | 517.08/517.1 519.1 | N-(3-(3-(4-(3,5-dichlorophenoxy)phenyl)-2-oxo-2,3-dihydro-1H-imidazo[4,5-c]pyridin-1-yl)phenyl)acrylamide |
| 131 | 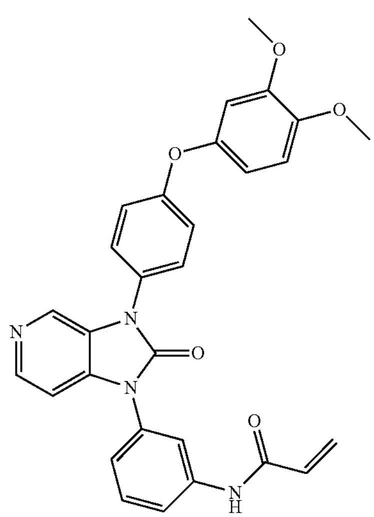 [SMILES: C=CC(=O)Nc1cccc(-n2c(=O)n(-c3ccc(Oc4ccc(OC)c(OC)c4)cc3)c3cnccc32)c1] | 509.17/509.2 | N-(3-(3-(4-(3,4-dimethoxyphenoxy)phenyl)-2-oxo-2,3-dihydro-1H-imidazo[4,5-c]pyridin-1-yl)phenyl)acrylamide |

-continued

| Entry | Structure | MS (cald) [M + H]⁺/MS (found) | Name |
|---|---|---|---|
| 132 | 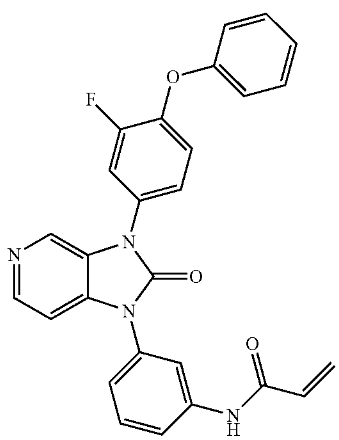 [SMILES: C=CC(=O)Nc1cccc(-n2c(=O)n(-c3ccc(Oc4ccccc4)c(F)c3)c3cnccc32)c1] | 467.14/467.1 | N-(3-(3-(3-fluoro-4-phenoxyphenyl)-2-oxo-2,3-dihydro-1H-imidazo[4,5-c]pyridin-1-yl)phenyl)acrylamide |
| 133 | 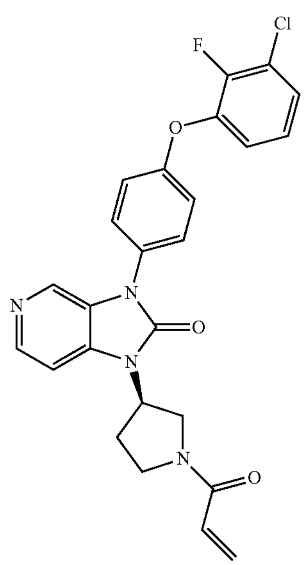 [SMILES: C=CC(=O)N1CC[C@@H](n2c(=O)n(-c3ccc(Oc4cccc(Cl)c4F)cc3)c3cnccc32)C1] | 479.12/479.1 | (R)-1-(1-acryloylpyrrolidin-3-yl)-3-(4-(3-chloro-2-fluorophenoxy)phenyl)-1H-imidazo[4,5-c]pyridin-2(3H)-one |
| 134 | 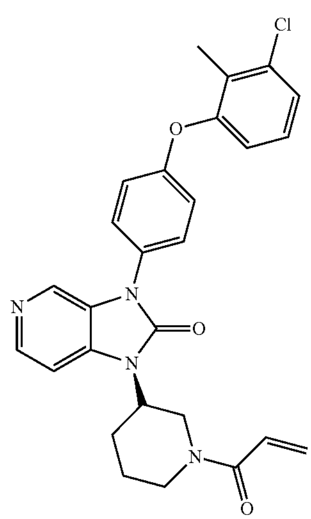 | 489.16/489.1, 490.1 | (R)-1-(1-acryloylpiperidin-3-yl)-3-(4-(3-chloro-2-methylphenoxy)phenyl)-1H-imidazo[4,5-c]pyridin-2(3H)-one |

-continued

| Entry | Structure | MS (cald) [M + H]+/MS (found) | Name |
|---|---|---|---|
| 135 | 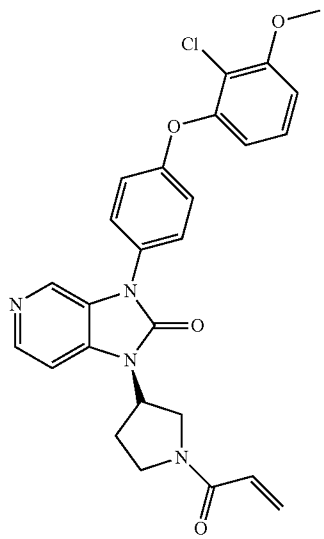 | 491.14/491.1 492.1 | (R)-1-(1-acryloylpyrrolidin-3-yl)-3-(4-(2-chloro-3-methoxyphenoxy)phenyl)-1H-imidazo[4,5-c]pyridin-2(3H)-one |
| 136 | 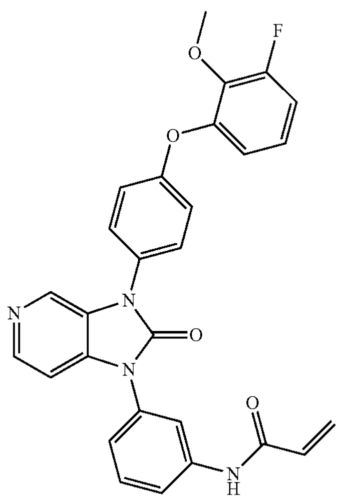 [SMILES: C=CC(=O)Nc1cccc(-n2c(=O)n(-c3ccc(Oc4cccc(F)c4OC)cc3)c3cnccc32)c1] | 497.15/497.2 | N-(3-(3-(4-(3-fluoro-2-methoxyphenoxy)phenyl)-2-oxo-2,3-dihydro-1H-imidazo[4,5-c]pyridin-1-yl)phenyl)acrylamide |
| 137 | 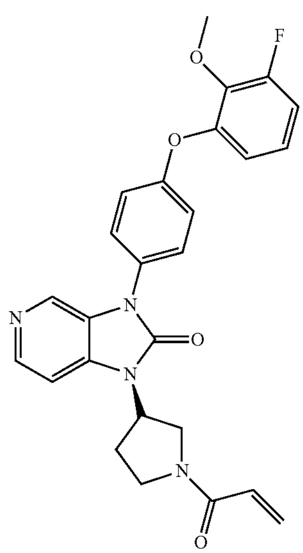 | 475.17/475.2 | (R)-1-(1-acryloylpyrrolidin-3-yl)-3-(4-(3-fluoro-2-methoxyphenoxy)phenyl)-1H-imidazo[4,5-c]pyridin-2(3H)-one |

-continued
| Entry | Structure | MS (cald) [M + H]+/MS (found) | Name |
|---|---|---|---|
| 138 | 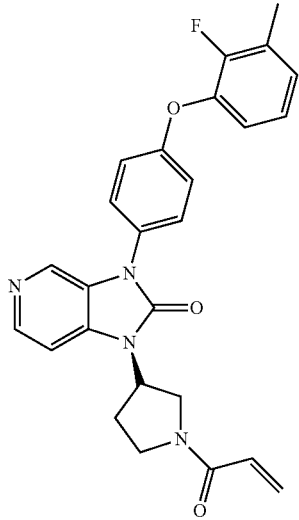 | 459.18/459.2 | (R)-1-(1-acryloylpyrrolidin-3-yl)-3-(4-(2-fluoro-3-methylphenoxy)phenyl)-1H-imidazo[4,5-c]pyridin-2(3H)-one |
| 139 | 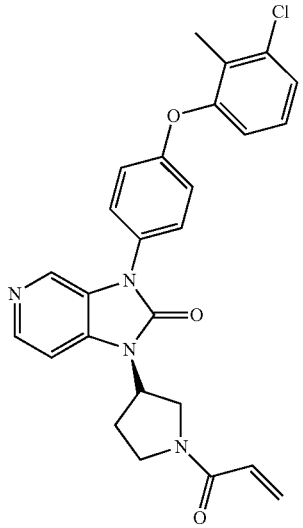 | 475.15/475.2 476.2 | (R)-1-(1-acryloylpyrrolidin-3-yl)-3-(4-(3-chloro-2-methylphenoxy)phenyl)-1H-imidazo[4,5-c]pyridin-2(3H)-one |

-continued

| Entry | Structure | MS (cald) [M + H]+/MS (found) | Name |
|---|---|---|---|
| 140 | 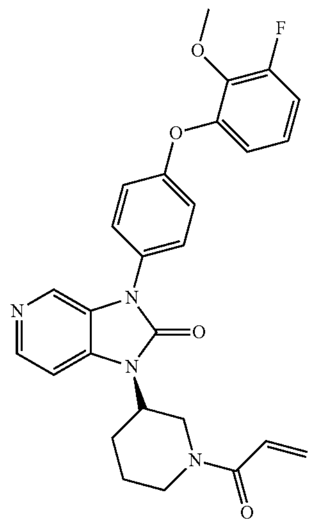 | 489.19/489.2 | (R)-1-(1-acryloylpiperidin-3-yl)-3-(4-(3-fluoro-2-methoxyphenoxy)phenyl)-1H-imidazo[4,5-c]pyridin-2(3H)-one |
| 141 | 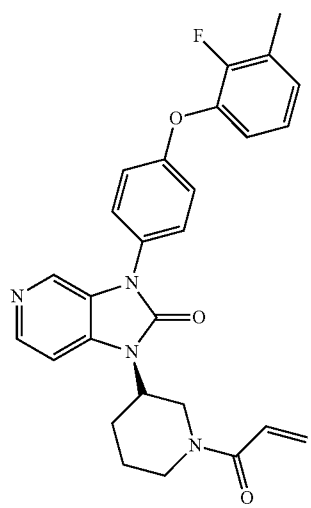 | 473.19/473.2 | (R)-1-(1-acryloylpiperidin-3-yl)-3-(4-(2-fluoro-3-methylphenoxy)phenyl)-1H-imidazo[4,5-c]pyridin-2(3H)-one |
| 142 | 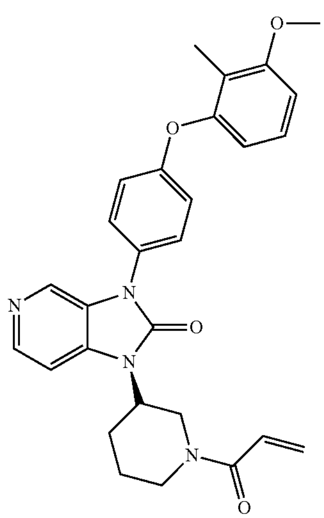 | 485.21/485.2 | (R)-1-(1-acryloylpiperidin-3-yl)-3-(4-(3-methoxy-2-methylphenoxy)phenyl)-1H-imidazo[4,5-c]pyridin-2(3H)-one |

-continued

| Entry | Structure | MS (cald) [M + H]+/MS (found) | Name |
|---|---|---|---|
| 143 | 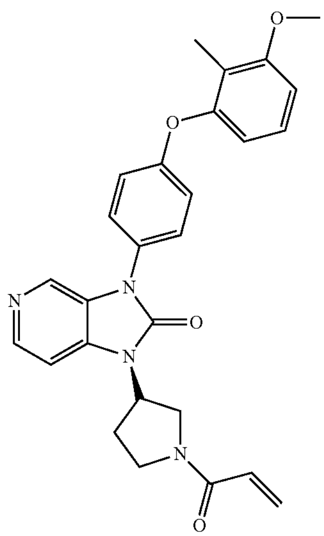 | 471.2/471.2 | (R)-1-(1-acryloylpyrrolidin-3-yl)-3-(4-(3-methoxy-2-methylphenoxy)phenyl)-1H-imidazo[4,5-c]pyridin-2(3H)-one |
| 144 | 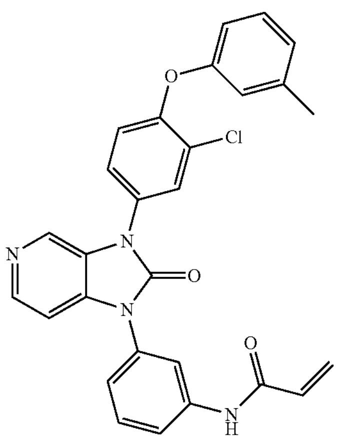 [SMILES: C=CC(=O)Nc1cccc(-n2c(=O)n(-c3ccc(Oc4cccc(C)c4)c(Cl)c3)c3cnccc32)c1] | 497.13/497.1 498.1 | N-(3-(3-(3-chloro-4-(m-tolyloxy)phenyl)-2-oxo-2,3-dihydro-1H-imidazo[4,5-c]pyridin-1-yl)phenyl)acrylamide |
| 145 | 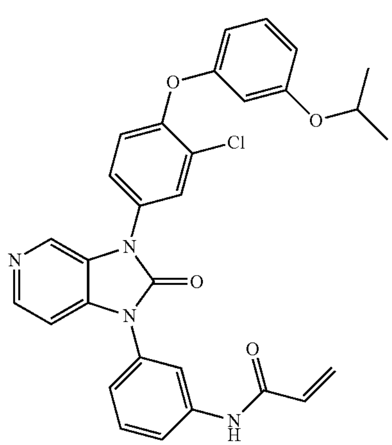 [SMILES: C=CC(=O)Nc1cccc(-n2c(=O)n(-c3ccc(Oc4cccc(OC(C)C)c4)c(Cl)c3)c3cnccc32)c1] | 541.16/541.2 542.2 | N-(3-(3-(3-chloro-4-(3-isopropoxyphenoxy)phenyl)-2-oxo-2,3-dihydro-1H-imidazo[4,5-c]pyridin-1-yl)phenyl)acrylamide |

| Entry | Structure | MS (cald) [M + H]⁺/MS (found) | Name |
|---|---|---|---|
| 146 | 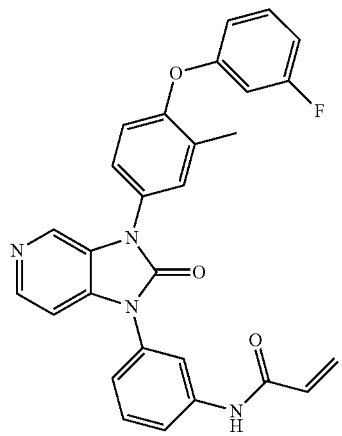 [SMILES: C=CC(=O)Nc1cccc(-n2c(=O)n(-c3ccc(Oc4cccc(F)c4)c(C)c3)c3cnccc32)c1] | 481.16/481.1 | N-(3-(3-(4-(3-fluorophenoxy)-3-methylphenyl)-2-oxo-2,3-dihydro-1H-imidazo[4,5-c]pyridin-1-yl)phenyl)acrylamide |
| 147 | 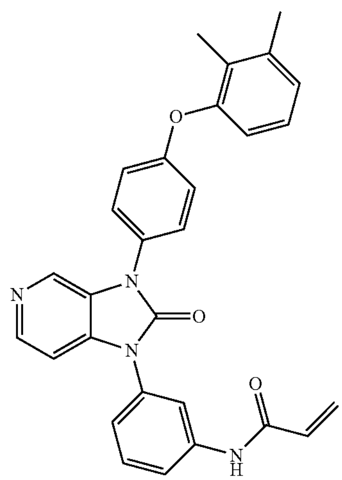 [SMILES: C=CC(=O)Nc1cccc(-n2c(=O)n(-c3ccc(Oc4cccc(C)c4C)cc3)c3cnccc32)c1] | 477.18/477.2 | N-(3-(3-(4-(2,3-dimethylphenoxy)phenyl)-2-oxo-2,3-dihydro-1H-imidazo[4,5-c]pyridin-1-yl)phenyl)acrylamide |
| 148 | 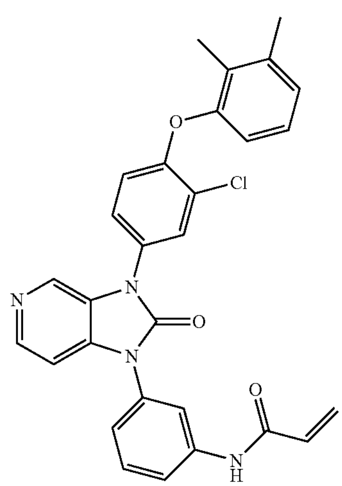 [SMILES: C=CC(=O)Nc1cccc(-n2c(=O)n(-c3ccc(Oc4cccc(C)c4C)c(Cl)c3)c3cnccc32)c1] | 511.15/511.2 | N-(3-(3-(3-chloro-4-(2,3-dimethylphenoxy)phenyl)-2-oxo-2,3-dihydro-1H-imidazo[4,5-c]pyridin-1-yl)phenyl)acrylamide |

-continued

| Entry | Structure | MS (calcd) [M + H]+/MS (found) | Name |
|---|---|---|---|
| 149 | 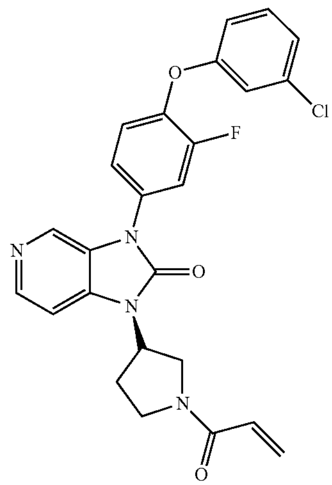 | 479.12/479.1 480.1 | (R)-1-(1-acryloylpyrrolidin-3-yl)-3-(4-(3-chlorophenoxy)-3-fluorophenyl)-1H-imidazo[4,5-c]pyridin-2(3H)-one |
| 150 | 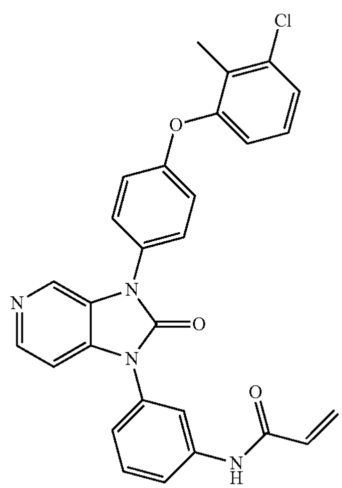 [SMILES: C=CC(=O)Nc1cccc(-n2c(=O)n(-c3ccc(Oc4cccc(Cl)c4C)cc3)c3cnccc32)c1] | 497.13/497.1 480.1 | N-(3-(3-(4-(3-chloro-2-methylphenoxy)phenyl)-2-oxo-2,3-dihydro-1H-imidazo[4,5-c]pyridin-1-yl)phenyl)acrylamide |
| 151 | 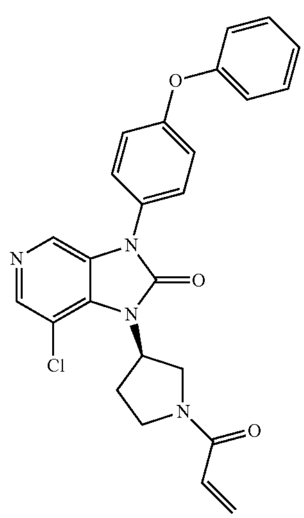 [SMILES: C=CC(=O)N1CC[C@@H](n2c(=O)n(-c3ccc(Oc4ccccc4)cc3)c3cncc(Cl)c32)C1] | 461.13/461.2 | (R)-1-(1-acryloylpyrrolidin-3-yl)-7-chloro-3-(4-phenoxyphenyl)-1H-imidazo[4,5-c]pyridin-2(3H)-one |

| Entry | Structure | MS (cald) [M + H]+/MS (found) | Name |
|---|---|---|---|
| 152 | 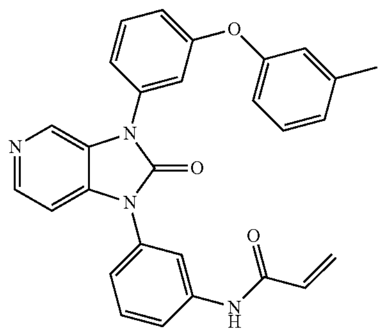 [SMILES: C=CC(=O)Nc1cccc(-n2c(=O)n(-c3cccc(Oc4cccc(C)c4)c3)c3cnccc32)c1] | 463.17/463.2 | N-(3-(2-oxo-3-(3-(m-tolyloxy)phenyl)-2,3-dihydro-1H-imidazo[4,5-c]pyridin-1-yl)phenyl)acrylamide |
| 153 | 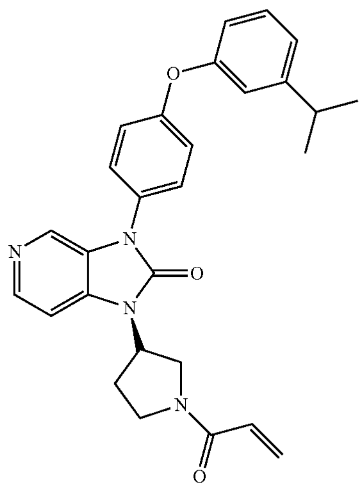 | 469.22/469.2 | (R)-1-(1-acryloylpyrrolidin-3-yl)-3-(4-(3-isopropylphenoxy)phenyl)-1H-imidazo[4,5-c]pyridin-2(3H)-one |
| 154 | 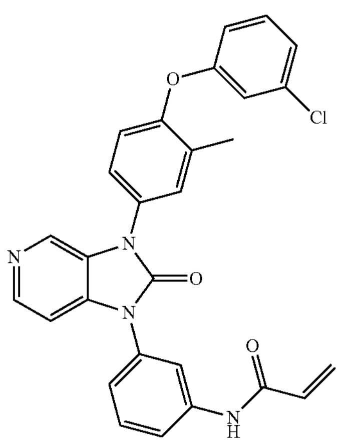 [SMILES: C=CC(=O)Nc1cccc(-n2c(=O)n(-c3ccc(Oc4cccc(Cl)c4)c(C)c3)c3cnccc32)c1] | 497.13/497.1 498.1 | N-(3-(3-(4-(3-chlorophenoxy)-3-methylphenyl)-2-oxo-2,3-dihydro-1H-imidazo[4,5-c]pyridin-1-yl)phenyl)acrylamide |

| Entry | Structure | MS (calcd) [M + H]+/MS (found) | Name |
|---|---|---|---|
| 155 | 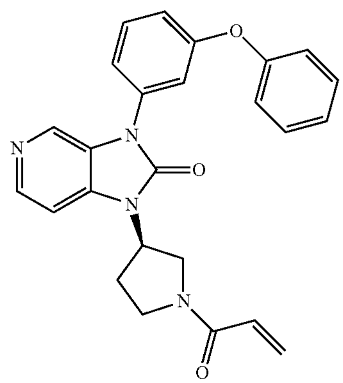 [SMILES: C=CC(=O)N1CC[C@@H](n2c(=O)n(-c3cccc(Oc4ccccc4)c3)c3cnccc32)C1] | 427.17/427.2 | (R)-1-(1-acryloylpyrrolidin-3-yl)-3-(3-phenoxyphenyl)-1H-imidazo[4,5-c]pyridin-2(3H)-one |
| 156 | 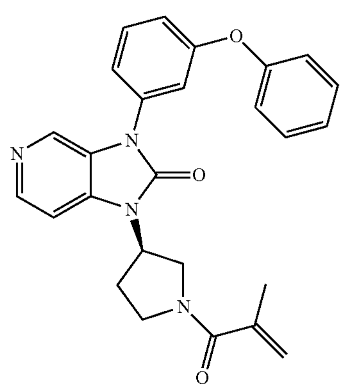 [SMILES: C=C(C)C(=O)N1CC[C@@H](n2c(=O)n(-c3cccc(Oc4ccccc4)c3)c3cnccc32)C1] | 441.18/441.2 | (R)-1-(1-methacryloylpyrrolidin-3-yl)-3-(3-phenoxyphenyl)-1H-imidazo[4,5-c]pyridin-2(3H)-one |
| 157 | 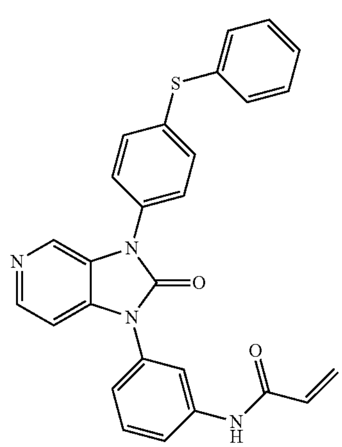 [SMILES: C=CC(=O)Nc1cccc(-n2c(=O)n(-c3ccc(Sc4ccccc4)cc3)c3cnccc32)c1] | 464.13 | N-(3-(2-oxo-3-(4-(phenylthio)phenyl)-2,3-dihydro-1H-imidazo[4,5-c]pyridin-1-yl)phenyl)acrylamide |

-continued

| Entry | Structure | MS (cald) [M + H]+/MS (found) | Name |
|---|---|---|---|
| 158 | 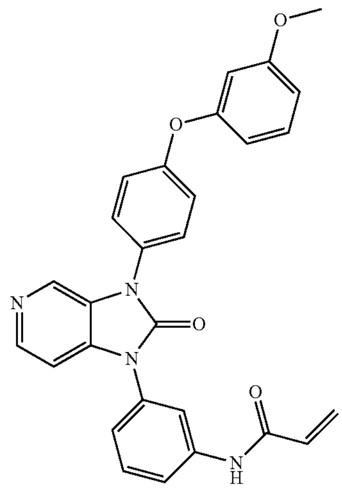 [SMILES: C=CC(=O)Nc1cccc(-n2c(=O)n(-c3ccc(Oc4cccc(OC)c4)cc3)c3cnccc32)c1] | 479.16/479.2 | N-(3-(3-(4-(3-methoxyphenoxy)phenyl)-2-oxo-2,3-dihydro-1H-imidazo[4,5-c]pyridin-1-yl)phenyl)acrylamide |
| 159 | 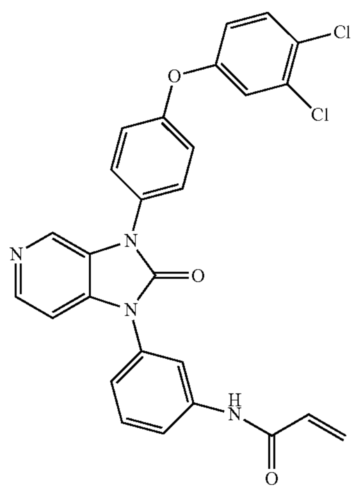 [SMILES: C=CC(=O)Nc1cccc(-n2c(=O)n(-c3ccc(Oc4ccc(Cl)c(Cl)c4)cc3)c3cnccc32)c1] | 517.08/517.1 | N-(3-(3-(4-(3,4-dichlorophenoxy)phenyl)-2-oxo-2,3-dihydro-1H-imidazo[4,5-c]pyridin-1-yl)phenyl)acrylamide |
| 160 | 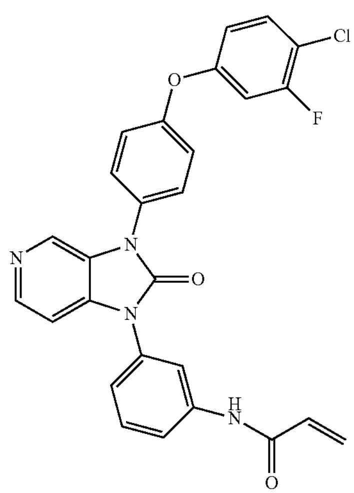 [SMILES: C=CC(=O)Nc1cccc(-n2c(=O)n(-c3ccc(Oc4ccc(Cl)c(F)c4)cc3)c3cnccc32)c1] | 501.11/501.1 | N-(3-(3-(4-(4-chloro-3-fluorophenoxy)phenyl)-2-oxo-2,3-dihydro-1H-imidazo[4,5-c]pyridin-1-yl)phenyl)acrylamide |

-continued

| Entry | Structure | MS (cald) [M + H]⁺/MS (found) | Name |
|---|---|---|---|
| 161 | 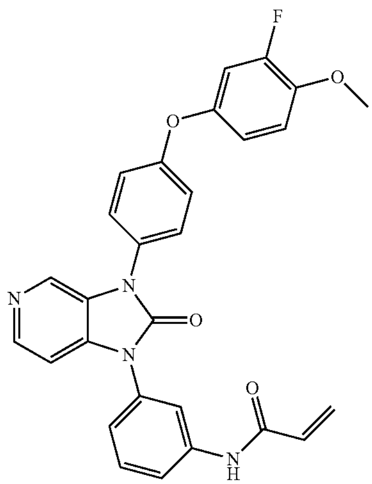 [SMILES: C=CC(=O)Nc1cccc(-n2c(=O)n(-c3ccc(Oc4ccc(OC)c(F)c4)cc3)c3cnccc32)c1] | 497.15/497.2 | N-(3-(3-(4-(3-fluoro-4-methoxyphenoxy)phenyl)-2-oxo-2,3-dihydro-1H-imidazo[4,5-c]pyridin-1-yl)phenyl)acrylamide |
| 162 | 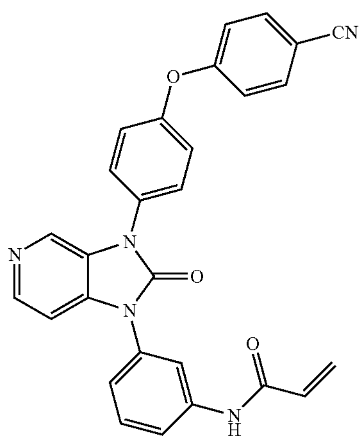 [SMILES: C=CC(=O)Nc1cccc(-n2c(=O)n(-c3ccc(Oc4ccc(C#N)cc4)cc3)c3cnccc32)c1] | 474.15/474.2 | N-(3-(3-(4-(4-cyanophenoxy)phenyl)-2-oxo-2,3-dihydro-1H-imidazo[4,5-c]pyridin-1-yl)phenyl)acrylamide |
| 163 | 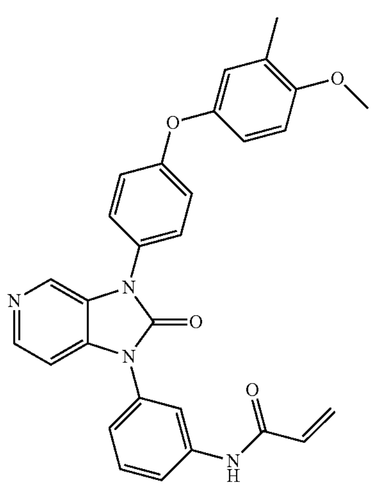 [SMILES: C=CC(=O)Nc1cccc(-n2c(=O)n(-c3ccc(Oc4ccc(OC)c(C)c4)cc3)c3cnccc32)c1] | 493.18/493.2 | N-(3-(3-(4-(4-methoxy-3-methylphenoxy)phenyl)-2-oxo-2,3-dihydro-1H-imidazo[4,5-c]pyridin-1-yl)phenyl)acrylamide |

| Entry | Structure | MS (cacld) [M + H]⁺/MS (found) | Name |
|---|---|---|---|
| 164 | 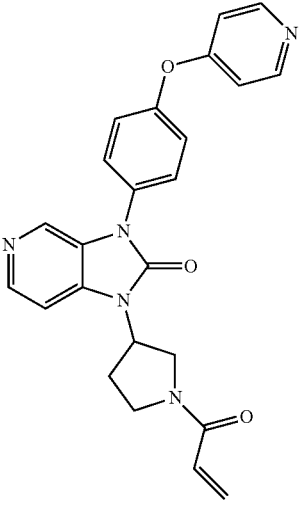 [SMILES: C=CC(=O)N1CCC(n2c(=O)n(-c3ccc(Oc4ccncc4)cc3)c3cnccc32)C1] | 427.16/428.2 | 1-(1-acryloylpyrrolidin-3-yl)-3-(4-(pyridin-4-yloxy)phenyl)-1H-imidazo[4,5-c]pyridin-2(3H)-one |
| 165 | 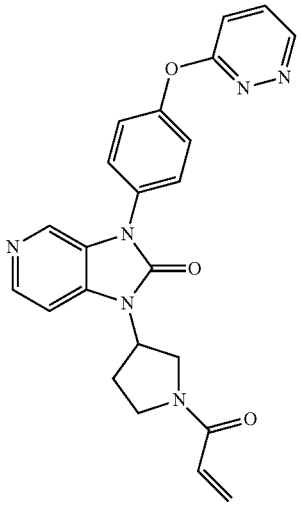 [SMILES: C=CC(=O)N1CCC(n2c(=O)n(-c3ccc(Oc4cccnn4)cc3)c3cnccc32)C1] | 428.16/429.1 | 1-(1-acryloylpyrrolidin-3-yl)-3-(4-(pyridazin-3-yloxy)phenyl)-1H-imidazo[4,5-c]pyridin-2(3H)-one |
| 166 | 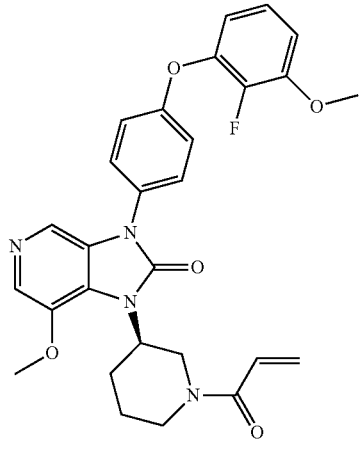 [SMILES: C=CC(=O)N1CCC[C@@H](n2c(=O)n(-c3ccc(Oc4cccc(OC)c4F)cc3)c3cncc(OC)c32)C1] | 519.20/519.2 | (R)-1-(1-acryloylpiperidin-3-yl)-3-(4-(2-fluoro-3-methoxyphenoxy)phenyl)-7-methoxy-1H-imidazo[4,5-c]pyridin-2(3H)-one |

-continued

| Entry | Structure | MS (cald) [M + H]+/MS (found) | Name |
|---|---|---|---|
| 167 | 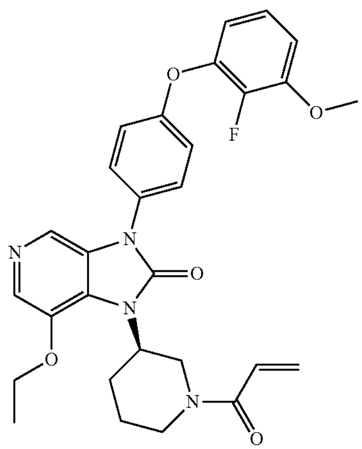 [SMILES: C=CC(=O)N1CCC[C@@H](n2c(=O)n(-c3ccc(Oc4cccc(OC)c4F)cc3)c3cncc(OCC)c32)C1] | 533.21/533.2 | (R)-1-(1-acryloylpiperidin-3-yl)-7-ethoxy-3-(4-(2-fluoro-3-methoxyphenoxy)phenyl)-1H-imidazo[4,5-c]pyridin-2(3H)-one |
| 168 | 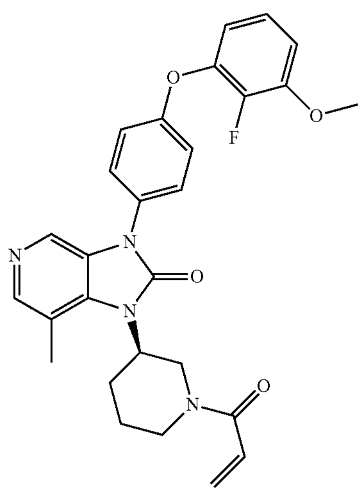 [SMILES: C=CC(=O)N1CCC[C@@H](n2c(=O)n(-c3ccc(Oc4cccc(OC)c4F)cc3)c3cncc(C)c32)C1] | 503.20/503.2 | (R)-1-(1-acryloylpiperidin-3-yl)-3-(4-(2-fluoro-3-methoxyphenoxy)phenyl)-7-methyl-1H-imidazo[4,5-c]pyridin-2(3H)-one |
| 169 | 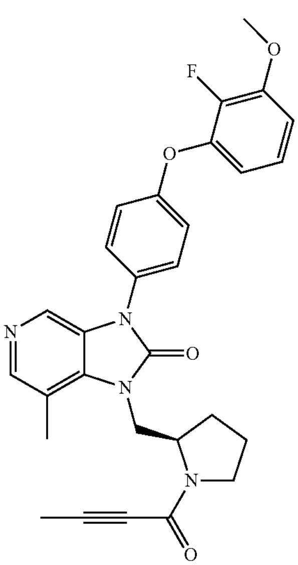 [SMILES: CC#CC(=O)N1CCC[C@@H]1Cn1c(=O)n(-c2ccc(Oc3cccc(OC)c3F)cc2)c2cncc(C)c21] | 515.20/515.2 | (R)-1-((1-(but-2-ynoyl)pyrrolidin-2-yl)methyl)-3-(4-(2-fluoro-3-methoxyphenoxy)phenyl)-7-methyl-1H-imidazo[4,5-c]pyridin-2(3H)-one |

-continued

| Entry | Structure | MS (calcd) [M + H]⁺/MS (found) | Name |
|---|---|---|---|
| 170 | 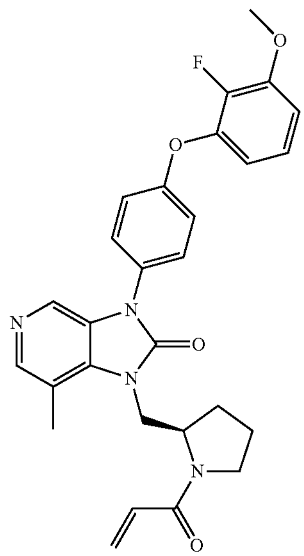 [SMILES: C=CC(=O)N1CCC[C@@H]1Cn1c(=O)n(-c2ccc(Oc3cccc(OC)c3F)cc2)c2cncc(C)c21] | 503.20/503.2 | (R)-1-((1-acryloylpyrrolidin-2-yl)methyl)-3-(4-(2-fluoro-3-methoxyphenoxy)phenyl)-7-methyl-1H-imidazo[4,5-c]pyridin-2(3H)-one |
| 171 | 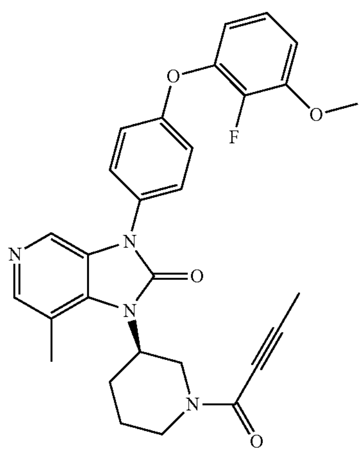 [SMILES: CC#CC(=O)N1CCC[C@@H](n2c(=O)n(-c3ccc(Oc4cccc(OC)c4F)cc3)c3cncc(C)c32)C1] | 515.20/515.2 | (R)-1-(1-(but-2-ynoyl)piperidin-3-yl)-3-(4-(2-fluoro-3-methoxyphenoxy)phenyl)-7-methyl-1H-imidazo[4,5-c]pyridin-2(3H)-one |
| 172 | 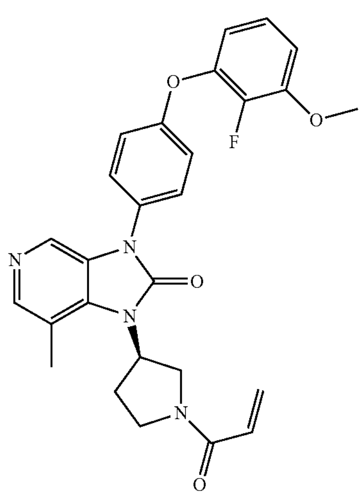 [SMILES: C=CC(=O)N1CC[C@@H](n2c(=O)n(-c3ccc(Oc4cccc(OC)c4F)cc3)c3cncc(C)c32)C1] | 489.19/489.2 | (R)-1-(1-acryloylpyrrolidin-3-yl)-3-(4-(2-fluoro-3-methoxyphenoxy)phenyl)-7-methyl-1H-imidazo[4,5-c]pyridin-2(3H)-one |

-continued

| Entry | Structure | MS (calcd) [M + H]+/MS (found) | Name |
|---|---|---|---|
| 173 | 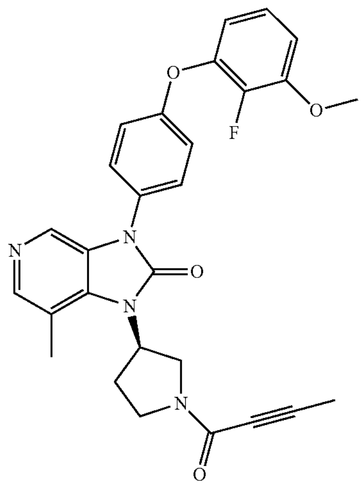 [SMILES: CC#CC(=O)N1CC[C@@H](n2c(=O)n(-c3ccc(Oc4cccc(OC)c4F)cc3)c3cncc(C)c32)C1] | 501.19/501.2 | (R)-1-(1-(but-2-ynoyl)pyrrolidin-3-yl)-3-(4-(2-fluoro-3-methoxyphenoxy)phenyl)-7-methyl-1H-imidazo[4,5-c]pyridin-2(3H)-one |
| 174 | 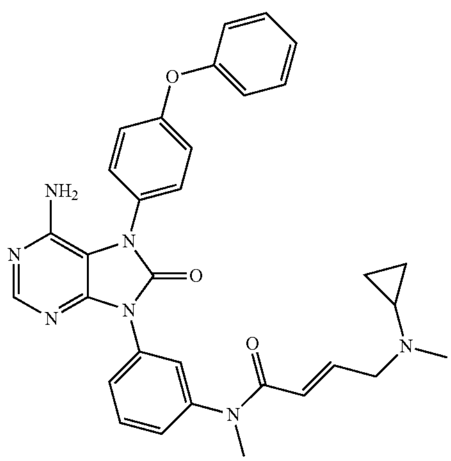 [SMILES: CN(C(=O)/C=C/CN(C)C1CC1)c1cccc(-n2c(=O)n(-c3ccc(Oc4ccccc4)cc3)c3c(N)ncnc32)c1] | 562.25/562.2 | (E)-N-(3-(6-amino-8-oxo-7-(4-phenoxyphenyl)-7H-purin-9(8H)-yl)phenyl)-4-(cyclopropyl(methyl)amino)-N-methylbut-2-enamide |
| 175 | 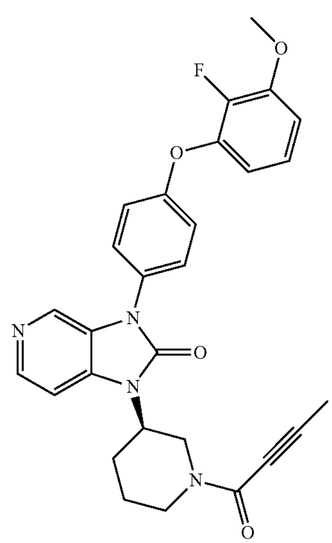 [SMILES: CC#CC(=O)N1CCC[C@@H](n2c(=O)n(-c3ccc(Oc4cccc(OC)c4F)cc3)c3cnccc32)C1] | 501.19/501.2 | (R)-1-(1-(but-2-ynoyl)piperidin-3-yl)-3-(4-(2-fluoro-3-methoxyphenoxy)phenyl)-1H-imidazo[4,5-c]pyridin-2(3H)-one |

-continued

| Entry | Structure | MS (calcd) [M + H]⁺/MS (found) | Name |
|---|---|---|---|
| 176 | 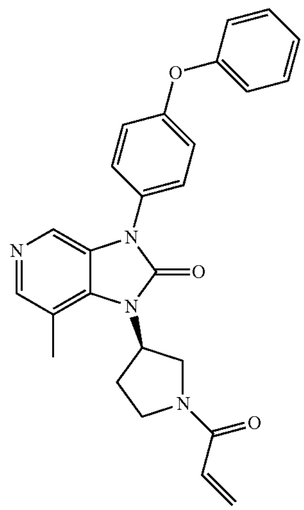 [SMILES: C=CC(=O)N1CC[C@@H](n2c(=O)n(-c3ccc(Oc4ccccc4)cc3)c3cncc(C)c32)C1] | 441.18/441.2 | (R)-1-(1-acryloylpyrrolidin-3-yl)-7-methyl-3-(4-phenoxyphenyl)-1H-imidazo[4,5-c]pyridin-2(3H)-one |
| 177 | 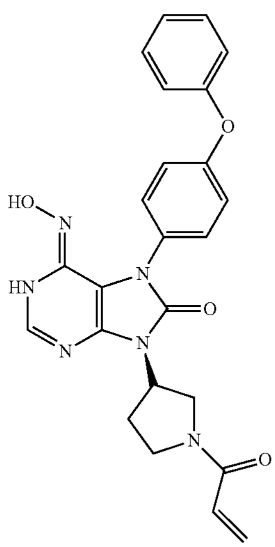 | 459.17/459.2 | (S,Z)-9-(1-acryloylpyrrolidin-3-yl)-6-(hydroxyimino)-7-(4-phenoxyphenyl)-7,9-dihydro-1H-purin-8(6H)-one |
| 178 | 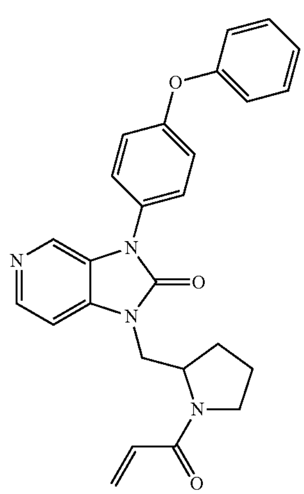 [SMILES: C=CC(=O)N1CCCC1Cn1c(=O)n(-c2ccc(Oc3ccccc3)cc2)c2cnccc21] | 440.52 440.5 | 1-(1-Acryloyl-pyrrolidin-2-ylmethyl)-3-(4-phenoxy-phenyl)-1,3-dihydro-imidazo[4,5-c]pyridin-2-one |

| Entry | Structure | MS (cald) [M + H]+/MS (found) | Name |
|---|---|---|---|
| 179 | 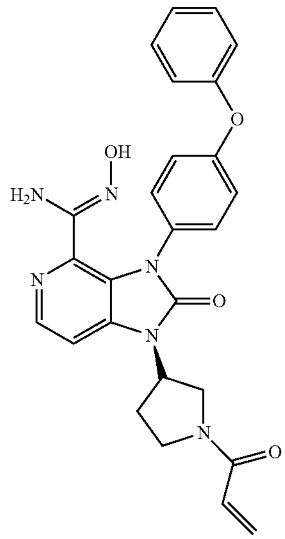 | 485.19/485.2 | (S,Z)-1-(1-acryloylpyrrolidin-3-yl)-N'-hydroxy-2-oxo-3-(4-phenoxyphenyl)-2,3-dihydro-1H-imidazo[4,5-c]pyridine-4-carboximidamide |
| 180 | 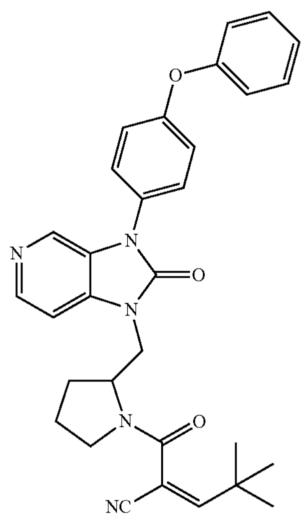 [SMILES: CC(C)(C)/C=C(/C#N)C(=O)N1CCCC1Cn1c(=O)n(-c2ccc(Oc3ccccc3)cc2)c2cnccc21] | 521.62 521.6 | 4,4-Dimethyl-2-{2-[2-oxo-3-(4-phenoxy-phenyl)-2,3-dihydro-imidazo[4,5-c]pyridin-1-ylmethyl]-pyrrolidine-1-carbonyl}-pent-2-enenitrile |
| 181 | 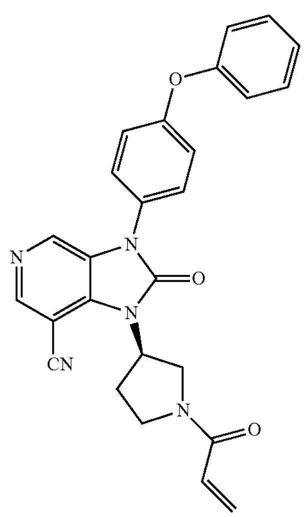 | 452.16/452.2 | (R)-1-(1-acryloylpyrrolidin-3-yl)-oxo-3-(4-phenoxyphenyl)-2,3-dihydro-1H-imidazo[4,5-c]pyridine-7-carbonitrile |

-continued

| Entry | Structure | MS (cald) [M + H]+/MS (found) | Name |
|---|---|---|---|
| 182 | 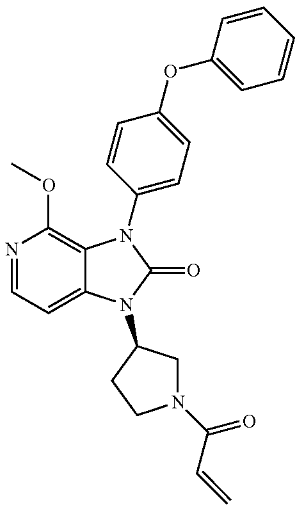 [SMILES: C=CC(=O)N1CC[C@@H](n2c(=O)n(-c3ccc(Oc4ccccc4)cc3)c3c(OC)nccc32)C1] | 457.18/457.2 | (R)-1-(1-acryloylpyrrolidin-3-yl)-4-methoxy-3-(4-phenoxyphenyl)-1H-imidazo[4,5-c]pyridin-2(3H)-one |
| 183 | 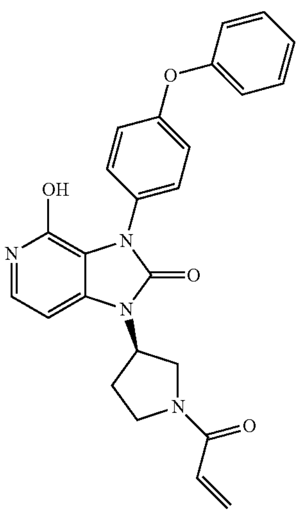 [SMILES: C=CC(=O)N1CC[C@@H](n2c(=O)n(-c3ccc(Oc4ccccc4)cc3)c3c(O)nccc32)C1] | 443.16/443.2 | (R)-1-(1-acryloylpyrrolidin-3-yl)-4-hydroxy-3-(4-phenoxyphenyl)-1H-imidazo[4,5-c]pyridin-2(3H)-one |
| 184 | 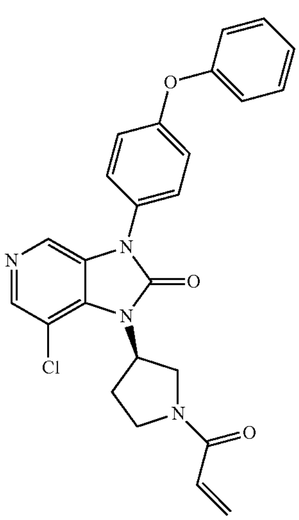 [SMILES: C=CC(=O)N1CC[C@@H](n2c(=O)n(-c3ccc(Oc4ccccc4)cc3)c3cncc(Cl)c32)C1] | 461.13/461.1 | (R)-1-(1-acryloylpyrrolidin-3-yl)-7-chloro-3-(4-phenoxyphenyl)-1H-imidazo[4,5-c]pyridin-2(3H)-one |

| Entry | Structure | MS (cald) [M + H]+/MS (found) | Name |
|---|---|---|---|
| 185 | 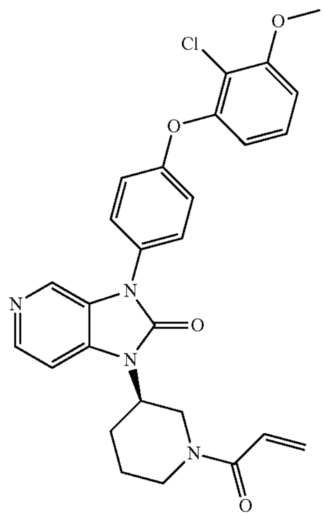 [SMILES: C=CC(=O)N1CCC[C@@H](n2c(=O)n(-c3ccc(Oc4cccc(OC)c4Cl)cc3)c3cnccc32)C1] | 505.16/505.2 | (R)-1-(1-acryloylpiperidin-3-yl)-3-(4-(2-chloro-3-methoxyphenoxy)phenyl)-1H-imidazo[4,5-c]pyridin-2(3H)-one |
| 186 | 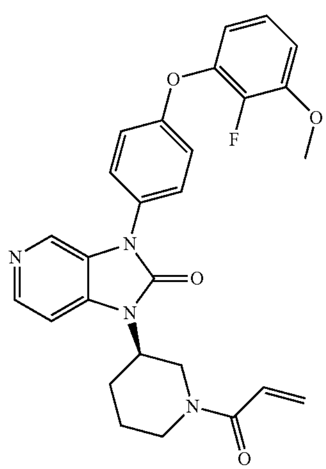 [SMILES: C=CC(=O)N1CCC[C@@H](n2c(=O)n(-c3ccc(Oc4cccc(OC)c4F)cc3)c3cnccc32)C1] | 489.19/489.2 | (R)-1-(1-acryloylpiperidin-3-yl)-3-(4-(2-fluoro-3-methoxyphenoxy)phenyl)-1H-imidazo[4,5-c]pyridin-2(3H)-one |
| 187 | 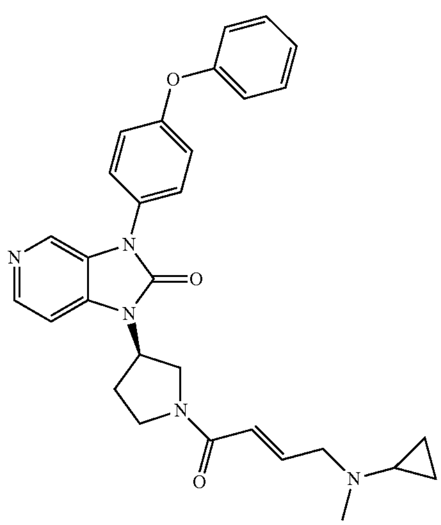 [SMILES: CN(C/C=C/C(=O)N1CC[C@@H](n2c(=O)n(-c3ccc(Oc4ccccc4)cc3)c3cnccc32)C1)C1CC1] | 510.24/501.2 | (R,E)-1-(1-(4-(cyclopropyl(methyl)amino)but-2-enoyl)pyrrolidin-3-yl)-3-(4-phenoxyphenyl)-1H-imidazo[4,5-c]pyridin-2(3H)-one |

-continued

| Entry | Structure | MS (cald) [M + H]+/MS (found) | Name |
|---|---|---|---|
| 188 | 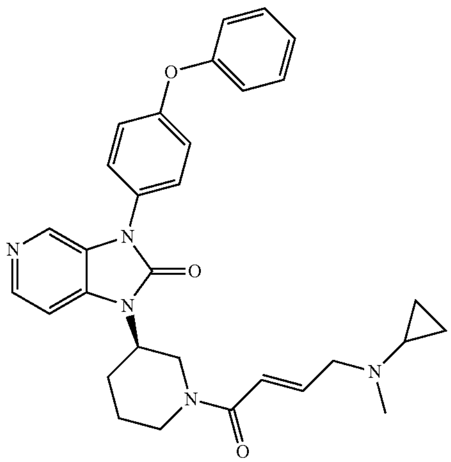 [SMILES: CN(C/C=C/C(=O)N1CCC[C@@H](n2c(=O)n(-c3ccc(Oc4ccccc4)cc3)c3cnccc32)C1)C1CC1] | 524.26/524.3 | (R,E)-1-(1-(4-(cyclopropyl(methyl)amino)but-2-enoyl)piperidin-3-yl)-3-(4-phenoxyphenyl)-1H-imidazo[4,5-c]pyridin-2(3H)-one |
| 189 | 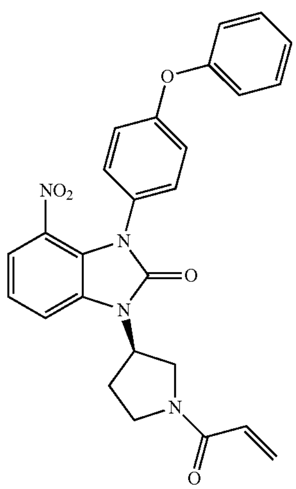 [SMILES: C=CC(=O)N1CC[C@@H](n2c(=O)n(-c3ccc(Oc4ccccc4)cc3)c3c([N+](=O)[O-])cccc32)C1] | 471.16/471.2 | (R)-1-(1-acryloylpyrrolidin-3-yl)-4-nitro-3-(4-phenoxyphenyl)-1H-benzo[d]imidazol-2(3H)-one |
| 190 | 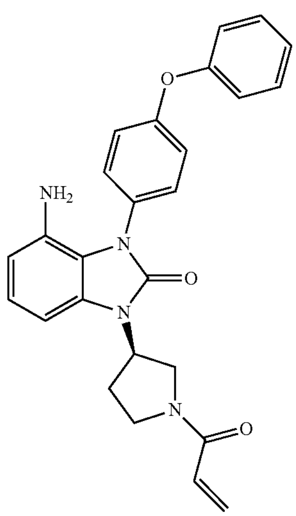 [SMILES: C=CC(=O)N1CC[C@@H](n2c(=O)n(-c3ccc(Oc4ccccc4)cc3)c3c(N)cccc32)C1] | 441.18/441.2 | (R)-1-(1-acryloylpyrrolidin-3-yl)-4-amino-3-(4-phenoxyphenyl)-1H-benzo[d]imidazol-2(3H)-one |

-continued

| Entry | Structure | MS (cald) [M + H]⁺/MS (found) | Name |
|---|---|---|---|
| 191 | 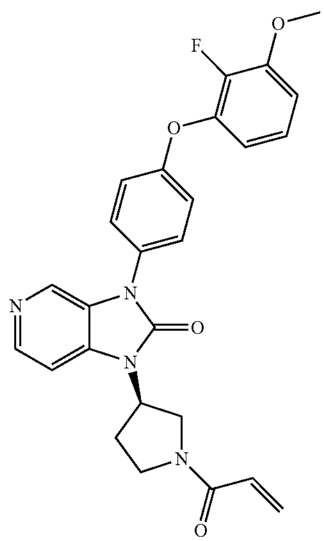 [SMILES: C=CC(=O)N1CC[C@@H](n2c(=O)n(-c3ccc(Oc4cccc(OC)c4F)cc3)c3cnccc32)C1] | 475.17/475.2 | (R)-1-(1-acryloylpyrrolidin-3-yl)-3-(4-(2-fluoro-3-methoxyphenoxy)phenyl)-1H-imidazo[4,5-c]pyridin-2(3H)-one |
| 192 | 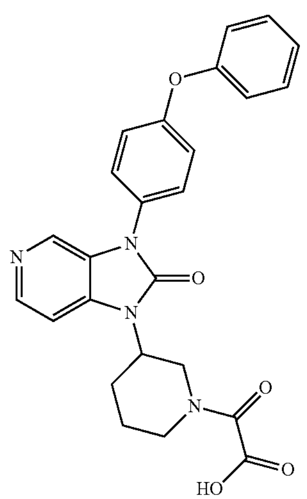 [SMILES: O=C(O)C(=O)N1CCCC(n2c(=O)n(-c3ccc(Oc4ccccc4)cc3)c3cnccc32)C1] | 459.16/459.1 | 2-oxo-2-(3-(2-oxo-3-(4-phenoxyphenyl)-2,3-dihydro-1H-imidazo[4,5-c]pyridin-1-yl)piperidin-1-yl)acetic acid |
| 193 | 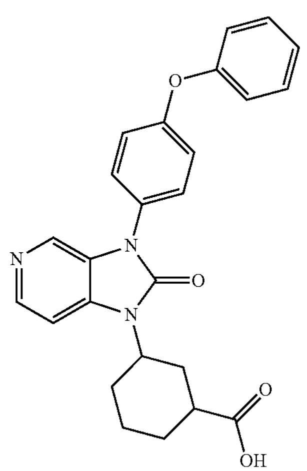 [SMILES: O=C(O)C1CCCC(n2c(=O)n(-c3ccc(Oc4ccccc4)cc3)c3cnccc32)C1] | 430.17/430.1 | 3-(2-oxo-3-(4-phenoxyphenyl)-2,3-dihydro-1H-imidazo[4,5-c]pyridin-1-yl)cyclohexanecarboxylic acid |

| Entry | Structure | MS (cald) [M + H]+/MS (found) | Name |
|---|---|---|---|
| 194 | 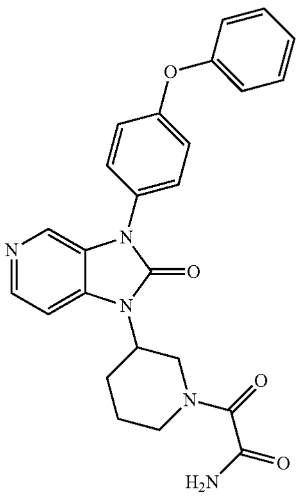 [SMILES: NC(=O)C(=O)N1CCCC(n2c(=O)n(-c3ccc(Oc4ccccc4)cc3)c3cnccc32)C1] | 458.18/458.2 | 2-oxo-2-(3-(2-oxo-3-(4-phenoxyphenyl)-2,3-dihydro-1H-imidazo[4,5-c]pyridin-1-yl)piperidin-1-yl)acetamide |
Example 195
N-(3-(2-oxo-3-(4-((2,4,5-trifluorobenzyl)oxy) phenyl)-2,3-dihydro-1H-imidazo[4,5-c]pyridin-1-yl) phenyl)acrylamide
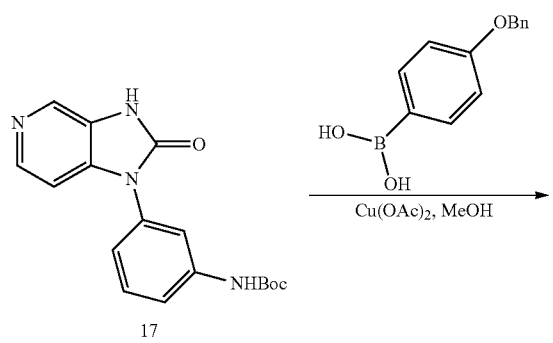
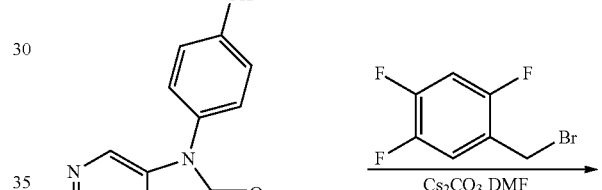
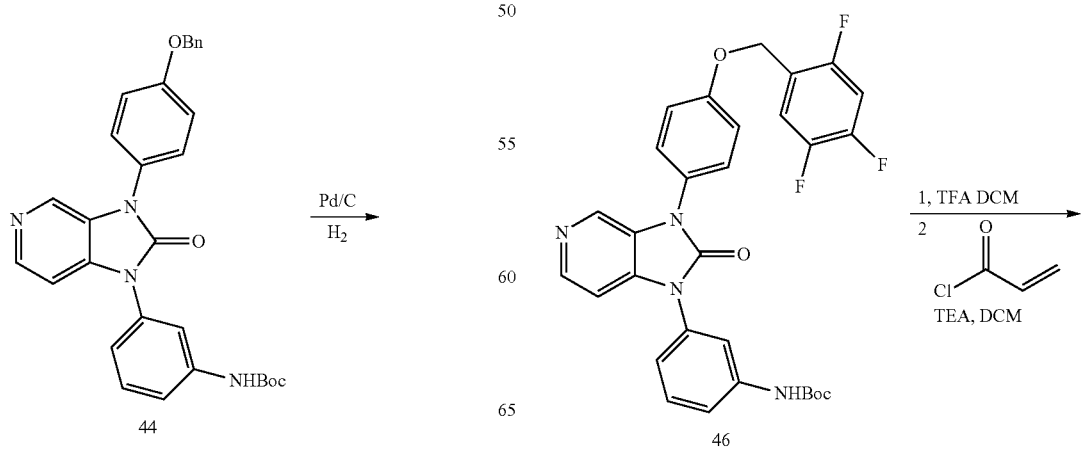

-continued

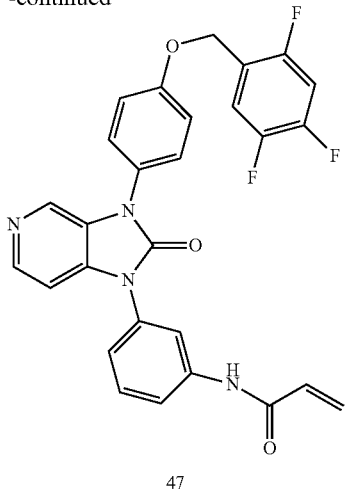

47

Step 1: tert-butyl (3-(3-(4-(benzyloxy)phenyl)-2-oxo-2,3-dihydro-1H-imidazo[4,5-c]pyridin-1-yl)phenyl)carbamate (44)

Intermediate 17 (0.914 g, 2.80 mmol, 1.0 eq) was dissolved in MeOH (20.0 mL), added Cupric acetate (59 mg, 0.28 mmol, 0.1 eq), (4-(benzyloxy)phenyl)boronic acid (0.83 g, 3.64 mmol, 1.3 eq), the mixture solution was stirred for 5 h under reflux. Then filtered the solution and removed the solution under reduce pressure, added water and extracted with EA, dried with $Na_2SO_4$, filtered and concentrated, purified with silica column (DCM:MeOH=100:1 1-50:1) to obtain the title product as gray solid, Yield: 160 mg, 11.2%. $^1$H NMR (400 MHz, $CDCl_3$): δ=8.37-8.43 (m, 1H), 7.77 (s, 1H), 7.31-7.51 (m, 10H), 7.24 (d, J=8.0 Hz, 1H), 7.15 (d, J=8.8 Hz, 2H), 6.66 (s, 1H), 5.14 (s, 2H), 1.52 (s, 9H). LCMS (ESI) m/z=509 $[M+H]^+$.

Step 2: tert-butyl (3-(3-(4-hydroxyphenyl)-2-oxo-2,3-dihydro-1H-imidazo[4,5-c]pyridin-1-yl)phenyl)carbamate (45)

Intermediate 44 (120 mg, 0.24 mmol, 1.0 eq) was dissolved in MeOH (10.0 mL), added Pd/C (40 mg), the mixture solution was stirred for 3 h under $H_2$ atmosphere. Then filtered the solution and the solvent was removed under reduce pressure to obtain the title product as gray solid, Yield: 83 mg, 84.1%. $^1$H NMR (400 MHz, $CDCl_3$): δ=8.36 (d, J=4.4 Hz, 1H), 8.30 (s, 1H), 7.79 (s, 1H), 7.45-7.49 (m, 1H), 7.37 (d, J=8.4 Hz, 2H), 7.32 (d, J=8.8 Hz, 1H), 7.23 (s, 1H), 7.16 (d, J=5.6 Hz, 1H), 6.97 (d, J=8.4 Hz, 2H), 6.71 (s, 1H), 1.52 (s, 9H). LCMS (ESI) m/z=419 $[M+H]^+$.

Step 3: tert-butyl (3-(3-(4-hydroxyphenyl)-2-oxo-2,3-dihydro-1H-imidazo[4,5-c]pyridin-1-yl)phenyl)carbamate (46)

To a solution of intermediate 45 (0.05 g, 0.12 mmol) in DMF (5 mL) was added 2,4,5-trifluorobenzyl bromide (0.027 g, 0.12 mmol) and $Cs_2CO_3$ (0.078 g, 0.24 mmol). The mixture was stirred at 25° C., after 2 hrs, the reaction mixture was partitioned between $H_2O$ and DCM, the organic layer was washed by brine, dried over $Na_2SO_4$, filtered, concentrated to give the title product as a crude product (0.04 g). LCMS (ESI) m/z=563 $[M+H]^+$.

Step 4: N-(3-(2-oxo-3-(4-((2,4,5-trifluorobenzyl)oxy)phenyl)-2,3-dihydro-1H-imidazo[4,5-c]pyridin-1-yl)phenyl)acrylamide (47)

To a solution of intermediate 46 (0.04 g, crude) in DCM (4 mL) was added TFA (1.5 mL) at 0° C., the mixture was allowed to warm to 25° C., after 1 h, the mixture was adjusted to pH=7 with $NaHCO_3$ solution, the residue was partitioned between $H_2O$ and DCM, the organic layer was washed by brine, dried over $Na_2SO_4$, filtered, concentrated to give a crude title product (0.02 g). LCMS (ESI) m/z=463 $[M+H]^+$.

To a stirred solution of crude product (0.02 g, 0.043 mmol) in DCM (10 mL) was added acryloyl chloride (0.004 g, 0.043 mmol) and TEA (0.009 g, 0.086 mmol). The mixture was stirred at 15° C., after 0.5 h, the mixture was partitioned between $H_2O$ and DCM, the organic layer was washed by brine, dried over $Na_2SO_4$, filtered, concentrated and purified by Pre-TLC to give the title product (5 mg, 22.4%).

$^1$H NMR (400 MHz, $CDCl_3$): δ 5.06 (s, 1H), 5.67-5.70 (d, 1H), 6.13-6.16 (d, 1H), 6.29-6.33 (d, 1H), 6.91-6.93 (m, 1H), 7.04-7.09 (m, 3H), 7.16-7.19 (m, 1H), 7.31-7.34 (m, 3H), 7.45-7.47 (m, 2H), 7.94 (s, 1H), 8.28-8.34 (m, 3H). LCMS (ESI) m/z=517 [M+H].

Example 196

N-(3-(2-oxo-3-(4-(pyridin-2-ylmethoxy)phenyl)-2,3-dihydro-1H-imidazo[4,5-c]pyridin-1-yl)phenyl)acrylamide

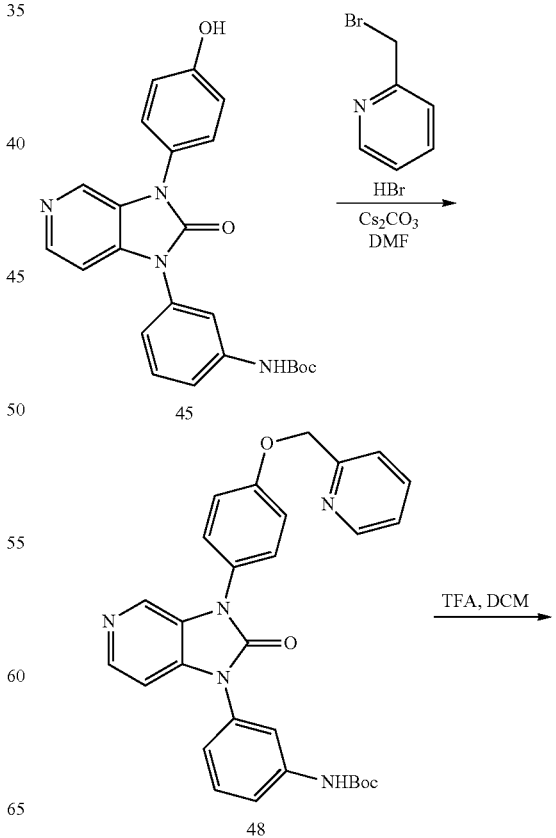

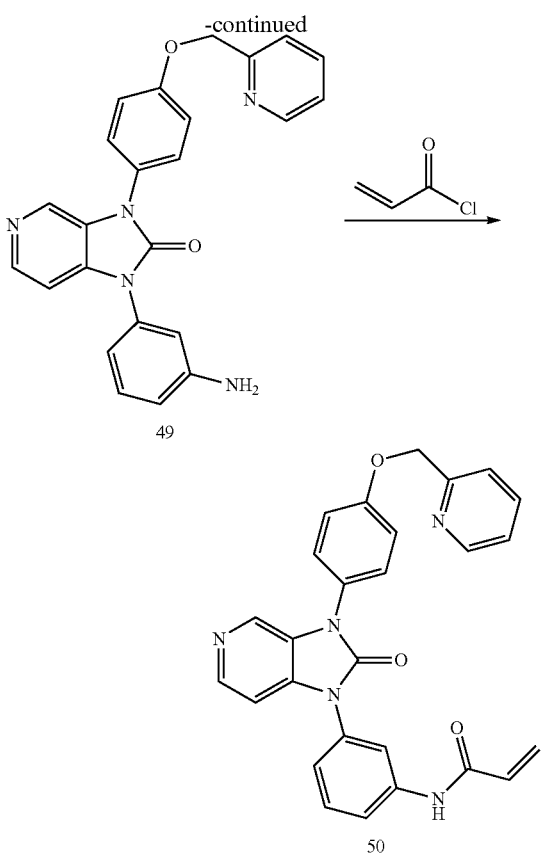

Step 1: tert-butyl (3-(2-oxo-3-(4-(pyridin-2-yl-methoxy)phenyl)-2,3-dihydro-1H-imidazo [4,5-c]pyridin-1-yl)phenyl)carbamate (48)

Intermediate 39 (76 mg, 0.183 mmol, 1.0 eq) was dissolved in DMF (2.0 mL), added Cesium carbonate (178 mg, 0.548 mmol, 3.0 eq), 2-(bromomethyl)pyridine hydrobromide salt (51 mg, 0.201 mmol, 1.1 eq), the mixture solution was stirred for 2 h at room temperature. Then added water and extracted with EA, washed with brine, dried with $Na_2SO_4$, filtered and concentrated, purified with silica column (DCM:MeOH=100:1~50:1) to obtain the title product, Yield: 48 mg, 51.9%. $^1$H NMR (400 MHz, $CDCl_3$): δ=8.63 (d, J=4.4 Hz, 1H), 8.36 (s, 1H), 8.35 (s, 1H), 7.75-7.77 (m, 2H), 7.55 (d, J=7.6 Hz, 1H), 7.50 (d, J=8.8 Hz, 2H), 7.44-7.48 (m, 1H), 7.32 (d, J=8.0 Hz, 1H), 7.23 (d, J=7.2 Hz, 1H), 7.17 (d, J=9.2 Hz, 2H), 7.13 (d, J=5.6 Hz, 1H), 6.67 (s, 1H), 5.29 (s, 2H), 1.52 (s, 9H). LCMS (ESI) m/z=510 $[M+H]^+$.

Step 2: 1-(3-aminophenyl)-3-(4-(pyridin-2-yl-methoxy)phenyl)-1H-imidazo[4,5-c]pyridin-2(3H)-one (49)

Intermediate 48 (48 mg) was dissolved in DCM (5.0 mL), added TFA (2.0 mL), the mixture was stirred for 1.5 h at RT, stopped and removed the solution under reduce pressure, the residue was added saturated $NaHCO_3$, extracted with EA and dried with $Na_2SO_4$, filtered and concentrated to obtain crude title product used next step without purification, yellow oil. $^1$H NMR (400 MHz, $CDCl_3$): δ=8.63 (d, J=4.4 Hz, 1H), 8.35 (s, 2H), 7.73-7.77 (m, 1H), 7.55 (d, J=7.6 Hz, 1H), 7.50 (d, J=9.2 Hz, 2H), 7.30-7.34 (m, 1H), 7.24 (s, 1H), 7.16 (d, J=9.2 Hz, 2H), 7.11 (d, J=4.8 Hz, 1H), 6.90 (d, J=8.0 Hz, 1H), 6.87 (s, 1H), 6.74-6.76 (m, 1H), 5.29 (s, 2H), 3.87 (s, 2H). LCMS (ESI) m/z=410 $[M+H]^+$.

Step 3: N-(3-(2-oxo-3-(4-(pyridin-2-ylmethoxy) phenyl)-2,3-dihydro-1H-imidazo[4,5-c]pyridin-1-yl) phenyl)acrylamide (50)

Crude intermediate 49 (42 mg, 0.103 mmol, 1.0 eq) was dissolved in THF (4.0 mL), added DIEA (20 mg, 0.154 mmol, 1.5 eq), acryloyl chloride (10.2 mg, 0.113 mmol, 1.1 eq) slowly at 0° C., the mixture solution was stirred for 0.5 h at RT, followed the reaction with LCMS, stopped the reaction added water and extracted with EA, dried with $Na_2SO_4$, filtered and concentrated, the residue was purification with silica gel plate (DCM:MeOH=30:1) to obtain the title product, colorless oil, Yield: 8.0 mg, 16.8%. $^1$H NMR (400 MHz, $CDCl_3$): δ=8.63 (d, J=4.4 Hz, 1H), 8.36 (s, 1H), 8.35 (s, 1H), 8.32 (s, 1H), 7.99 (s, 1H), 7.73-7.77 (m, 1H), 7.56 (d, J=7.6 Hz, 1H), 7.51 (d, J=8.8 Hz, 2H), 7.41 (d, J=7.2 Hz, 2H), 7.24-7.28 (m, 1H), 7.48 (d, J=8.8 Hz, 2H), 7.11 (d, J=5.2 Hz, 1H), 6.39 (d, J=16.4 Hz, 1H), 6.16-6.23 (m, 1H), 5.71 (d, J=10.4 Hz, 1H), 5.29 (s, 2H). LCMS (ESI) m/z=464 $[M+H]^+$.

The following additional Examples 197-248 shown in the Table below were prepared following the procedures outlined in the general methods above and detailed in Examples 195-196.

| Entry | Structure | MS(cald) $[M + H]^+$/ MS (found) | Name |
|---|---|---|---|
| 197 | 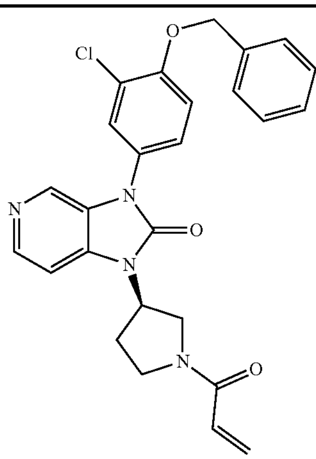 | 475.15/ 475.1, 477.1 | (R)-1-(1-acryloylpyrrolidin-3-yl)-3-(4-(benzyloxy)-3-chlorophenyl)-1H-imidazo[4,5-c]pyridin-2(3H)-one |

-continued

| Entry | Structure | MS(cald) [M + H]+/ MS (found) | Name |
|---|---|---|---|
| 198 | 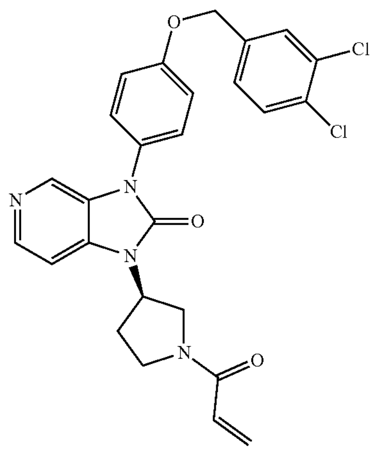 [SMILES: C=CC(=O)N1CC[C@@H](n2c(=O)n(-c3ccc(OCc4ccc(Cl)c(Cl)c4)cc3)c3cnccc32)C1] | 509.11/ 509.1, 511.1, 510.1, 513.1 | (R)-1-(1-acryloylpyrrolidin-3-yl)-3-(4-((3,4-dichlorobenzyl)oxy)phenyl)-1H-imidazo[4,5-c]pyridin-2(3H)-one |
| 199 | 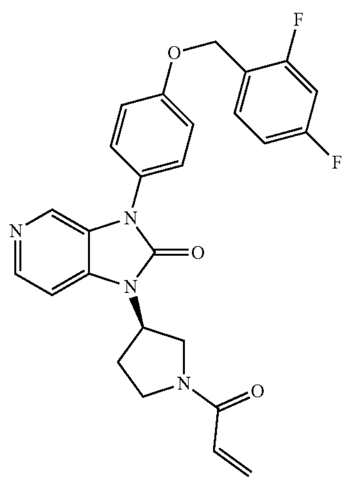 [SMILES: C=CC(=O)N1CC[C@@H](n2c(=O)n(-c3ccc(OCc4ccc(F)cc4F)cc3)c3cnccc32)C1] | 477.17/ 477.1 | (R)-1-(1-acryloylpyrrolidin-3-yl)-3-(4-((2,4-difluorobenzyl)oxy)phenyl)-1H-imidazo[4,5-c]pyridin-2(3H)-one |
| 200 | 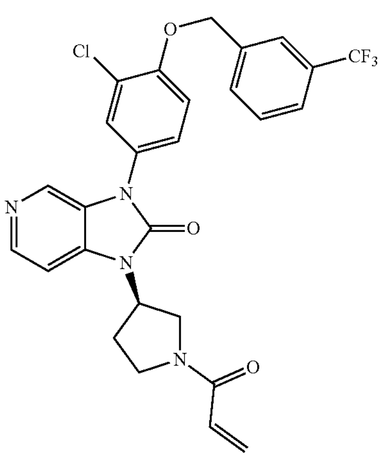 [SMILES: C=CC(=O)N1CC[C@@H](n2c(=O)n(-c3ccc(OCc4cccc(C(F)(F)F)c4)c(Cl)c3)c3cnccc32)C1] | 543.13/ 543.1, 545.1, 544.1, 546.1 | (R)-1-(1-acryloylpyrrolidin-3-yl)-3-(3-chloro-4-((3-(trifluoromethyl)benzyl)oxy)phenyl)-1H-imidazo[4,5-c]pyridine-2(3H)-one |

| Entry | Structure | MS(cald) [M + H]+/ MS (found) | Name |
|---|---|---|---|
| 201 | 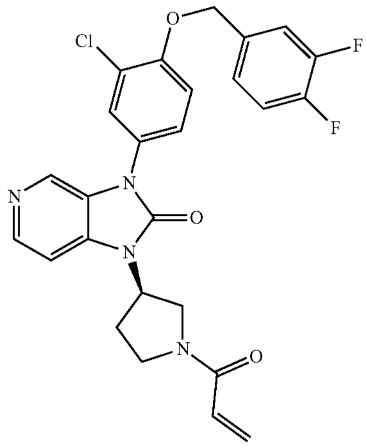 [SMILES: C=CC(=O)N1CC[C@@H](n2c(=O)n(-c3ccc(OCc4ccc(F)c(F)c4)c(Cl)c3)c3cnccc32)C1] | 511.13/ 511.1, 512.1 | (R)-1-(1-acryloylpyrrolidin-3-yl)-3-(3-chloro-4-((3,4-difluorobenzyl)oxy)phenyl)-1H-imidazo[4,5-c]pyridine-2(3H)-one |
| 202 | 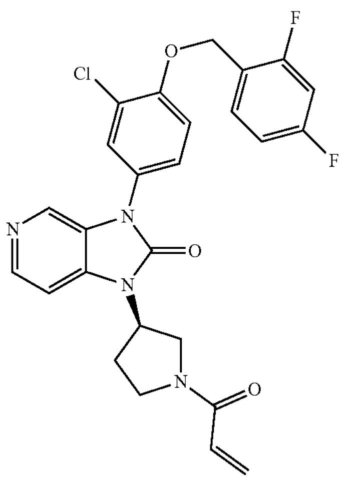 [SMILES: C=CC(=O)N1CC[C@@H](n2c(=O)n(-c3ccc(OCc4ccc(F)cc4F)c(Cl)c3)c3cnccc32)C1] | 511.13/ 511.1, 512.2 | (R)-1-(1-acryloylpyrrolidin-3-yl)-3-(3-chloro-4-((2,4-difluorobenzyl)oxy)phenyl)-1H-imidazo[4,5-c]pyridin-2(3H)-one |
| 203 | 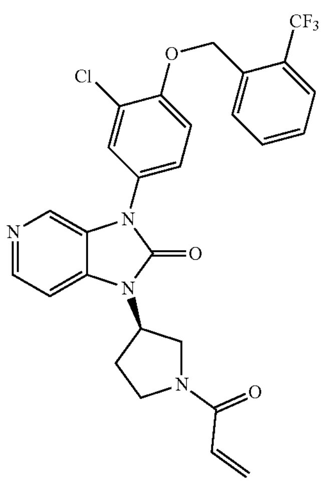 [SMILES: C=CC(=O)N1CC[C@@H](n2c(=O)n(-c3ccc(OCc4ccccc4C(F)(F)F)c(Cl)c3)c3cnccc32)C1] | 543.13/ 543.1, 544.1 | (R)-1-(1-acryloylpyrrolidin-3-yl)-3-(3-chloro-4-((2-(trifluoromethyl)benzyl)oxy)phenyl)-1H-imidazo[4,5-c]pyridin-2(3H)-one |

-continued

| Entry | Structure | MS(cald) [M + H]+/MS (found) | Name |
|---|---|---|---|
| 204 | 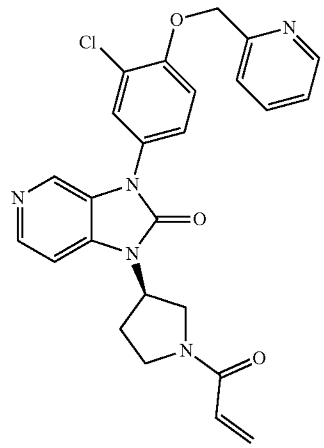 [SMILES: C=CC(=O)N1CC[C@@H](n2c(=O)n(-c3ccc(OCc4ccccn4)c(Cl)c3)c3cnccc32)C1] | 476.14/<br>476.1, 477.1, 238.6, 239.3 | (R)-1-(1-acryloylpyrrolidin-3-yl)-3-(3-chloro-4-(pyridin-2-ylmethoxy)phenyl)-1H-imidazo[4,5-c]pyridin-2(3H)-one |
| 205 | 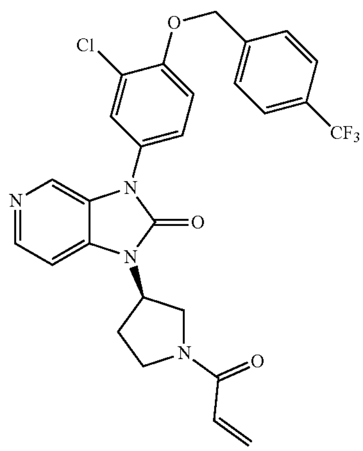 [SMILES: C=CC(=O)N1CC[C@@H](n2c(=O)n(-c3ccc(OCc4ccc(C(F)(F)F)cc4)c(Cl)c3)c3cnccc32)C1] | 543.13/<br>543.2, 544.1 | (R)-1-(1-acryloylpyrrolidin-3-yl)-3-(3-chloro-4-((4-(trifluoromethyl)benzyl)oxy)phenyl)-1H-imidazo[4,5-c]pyridin-2(3H)-one |
| 206 | 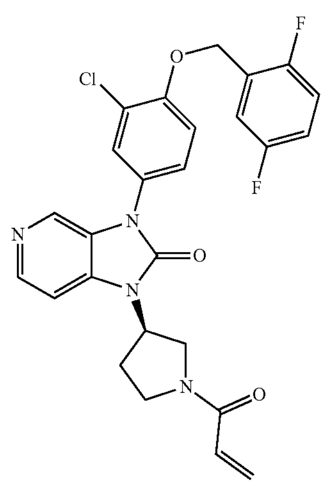 [SMILES: C=CC(=O)N1CC[C@@H](n2c(=O)n(-c3ccc(OCc4cc(F)ccc4F)c(Cl)c3)c3cnccc32)C1] | 511.13/<br>511.1, 512.2 | (R)-1-(1-acryloylpyrrolidin-3-yl)-3-(3-chloro-4-((2,5-difluorobenzyl)oxy)phenyl)-1H-imidazo[4,5-c]pyridin-2(3H)-one |

-continued

| Entry | Structure | MS(cald) [M + H]⁺/ MS (found) | Name |
|---|---|---|---|
| 207 | 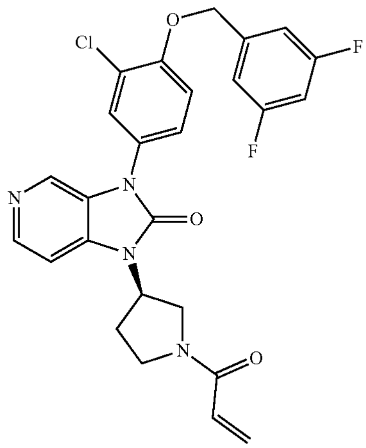 [SMILES: C=CC(=O)N1CC[C@@H](n2c(=O)n(-c3ccc(OCc4cc(F)cc(F)c4)c(Cl)c3)c3cnccc32)C1] | 511.13/ 511.1, 513.1 | (R)-1-(1-acryloylpyrrolidin-3-yl)-3-(3-chloro-4-((3,5-difluorobenzyl)oxy)phenyl)-1H-imidazo[4,5-c]pyridin-2(3H)-one |
| 208 | 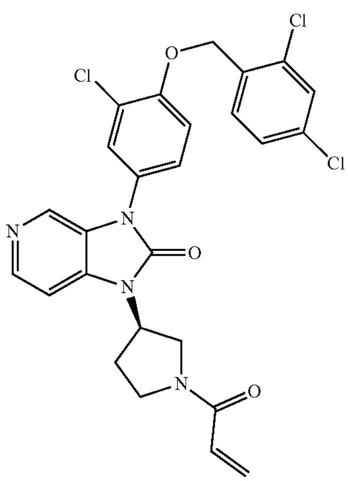 [SMILES: C=CC(=O)N1CC[C@@H](n2c(=O)n(-c3ccc(OCc4ccc(Cl)cc4Cl)c(Cl)c3)c3cnccc32)C1] | 543.07/ 543.1, 544.1 | (R)-1-(1-acryloylpyrrolidin-3-yl)-3-(3-chloro-4-((2,4-dichlorobenzyl)oxy)phenyl)-1H-imidazo[4,5-c]pyridin-2(3H)-one |
| 209 | 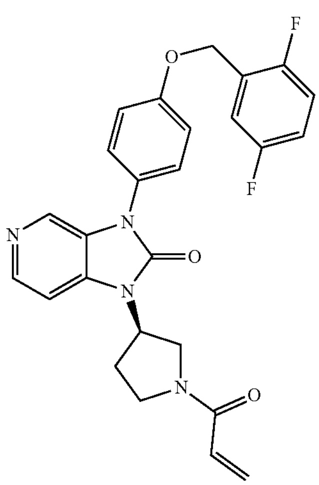 [SMILES: C=CC(=O)N1CC[C@@H](n2c(=O)n(-c3ccc(OCc4cc(F)ccc4F)cc3)c3cnccc32)C1] | 477.17/ 477.1 | (R)-1-(1-acryloylpyrrolidin-3-yl)-3-(4-((2,5-difluorobenzyl)oxy)phenyl)-1H-imidazo[4,5-c]pyridin-2(3H)-one |

-continued

| Entry | Structure | MS(cald) [M + H]+/ MS (found) | Name |
|---|---|---|---|
| 210 | 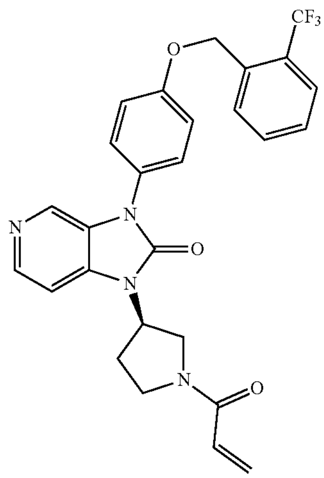 [SMILES: C=CC(=O)N1CC[C@@H](n2c(=O)n(-c3ccc(OCc4ccccc4C(F)(F)F)cc3)c3cnccc32)C1] | 509.17/ 509.1 | (R)-1-(1-acryloylpyrrolidin-3-yl)-3-(4-((2-(trifluoromethyl)benzyl)oxy)phenyl)-1H-imidazo[4,5-c]pyridine-2(3H)-one |
| 211 | 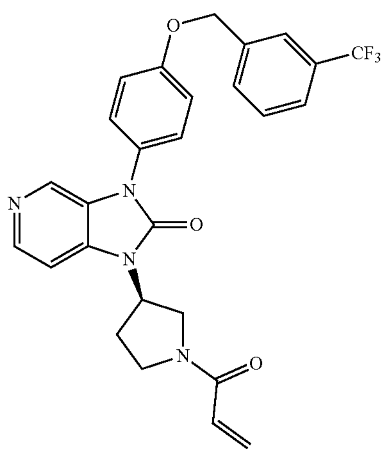 [SMILES: C=CC(=O)N1CC[C@@H](n2c(=O)n(-c3ccc(OCc4cccc(C(F)(F)F)c4)cc3)c3cnccc32)C1] | 509.17/ 509.2 | (R)-1-(1-acryloylpyrrolidin-3-yl)-3-(4-((3-(trifluoromethyl)benzyl)oxy)phenyl)-1H-imidazo[4,5-c]pyridin-2(3H)-one |
| 212 | 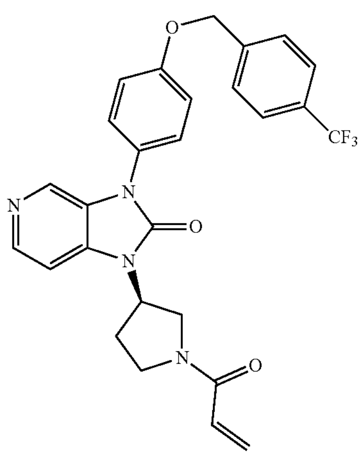 [SMILES: C=CC(=O)N1CC[C@@H](n2c(=O)n(-c3ccc(OCc4ccc(C(F)(F)F)cc4)cc3)c3cnccc32)C1] | 509.17/ 509.2 | (R)-1-(1-acryloylpyrrolidin-3-yl)-3-(4-((4-(trifluoromethyl)benzyl)oxy)phenyl)-1H-imidazo[4,5-c]pyridin-2(3H)-one |

| Entry | Structure | MS(cald) [M + H]+/ MS (found) | Name |
|---|---|---|---|
| 213 | 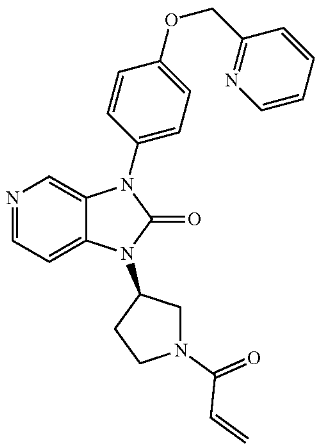 [SMILES: C=CC(=O)N1CC[C@@H](n2c(=O)n(-c3ccc(OCc4ccccn4)cc3)c3cnccc32)C1] | 442.18/ 442.2 | (R)-1-(1-acryloylpyrrolidin-3-yl)-3-(4-(pyridin-2-ylmethoxy)phenyl)-1H-imidazo[4,5-c]pyridin-2(3H)-one |
| 214 | 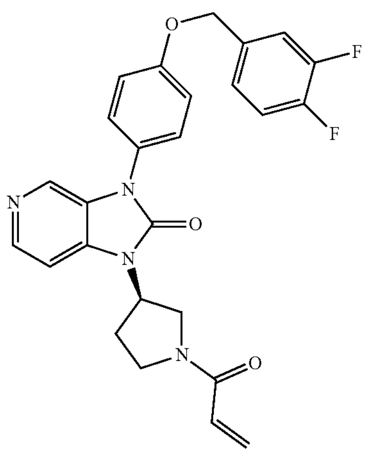 [SMILES: C=CC(=O)N1CC[C@@H](n2c(=O)n(-c3ccc(OCc4ccc(F)c(F)c4)cc3)c3cnccc32)C1] | 477.17/ 477.2 | (R)-1-(1-acryloylpyrrolidin-3-yl)-3-(4-((3,4-difluorobenzyl)oxy)phenyl)-1H-imidazo[4,5-c]pyridin-2(3H)-one |
| 215 | 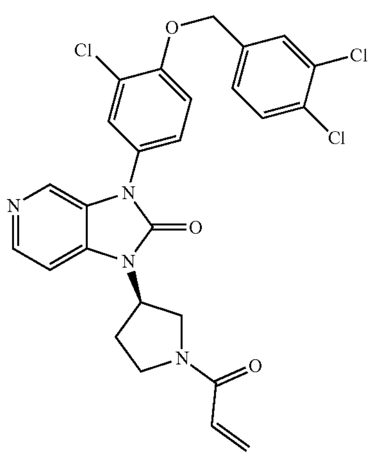 [SMILES: C=CC(=O)N1CC[C@@H](n2c(=O)n(-c3ccc(OCc4ccc(Cl)c(Cl)c4)c(Cl)c3)c3cnccc32)C1] | 543.07/ 543.1, 544.1, 545.0, 546.1 | (R)-1-(1-acryloylpyrrolidin-3-yl)-3-(3-chloro-4-((3,4-dichlorobenzyl)oxy)phenyl)-1H-imidazo[4,5-c]pyridin-2(3H)-one |

-continued

| Entry | Structure | MS(cald) [M + H]+/ MS (found) | Name |
|---|---|---|---|
| 216 | 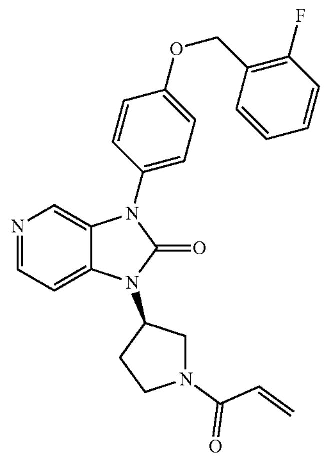 [SMILES: C=CC(=O)N1CC[C@@H](n2c(=O)n(-c3ccc(OCc4ccccc4F)cc3)c3cnccc32)C1] | 459.18/ 459.2 | (R)-1-(1-acryloylpyrrolidin-3-yl)-3-(4-((2-fluorobenzyl)oxy)phenyl)-1H-imidazo[4,5-c]pyridin-2(3H)-one |
| 217 | 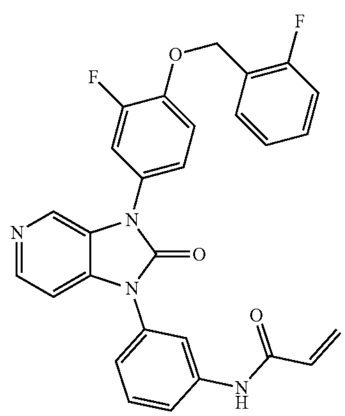 [SMILES: C=CC(=O)Nc1cccc(-n2c(=O)n(-c3ccc(OCc4ccccc4F)c(F)c3)c3cnccc32)c1] | 499.15/ 499.2 | N-(3-(3-(3-fluoro-4-((2-fluorobenzyl)oxy)phenyl)-2-oxo-2,3-dihydro-1H-imidazo[4,5-c]pyridin-1-yl)phenyl)acrylamide |
| 218 | 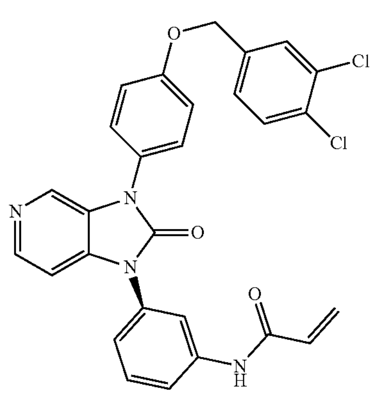 | 532.09/ 532.1 | N-(3-(3-(4-((3,4-dichlorobenzyl)oxy)phenyl)-2-oxo-2,3-dihydro-1H-imidazo[4,5-c]pyridin-1-yl)phenyl)acrylamide |

-continued

| Entry | Structure | MS(cald) [M + H]+/ MS (found) | Name |
|---|---|---|---|
| 219 | 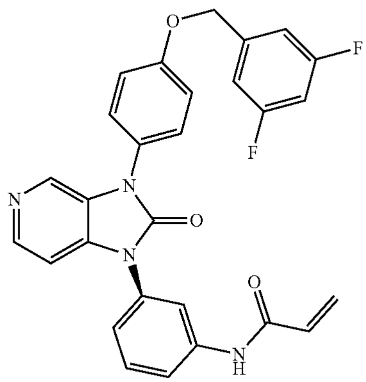 | 499.15/ 499.2 | N-(3-(3-(4-((3,5-difluorobenzyl)oxy)phenyl)-2-oxo-2,3-dihydro-1H-imidazo[4,5-c]pyridin-1-yl)phenyl)acrylamide |
| 220 | 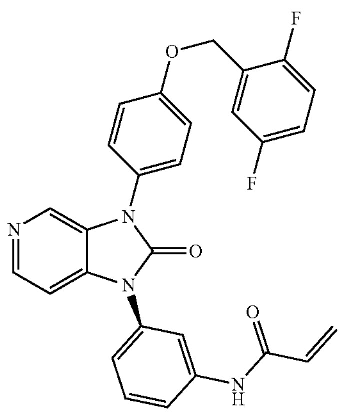 | 499.15/ 499.2 | N-(3-(3-(4-((2,5-difluorobenzyl)oxy)phenyl)-2-oxo-2,3-dihydro-1H-imidazo[4,5-c]pyridin-1-yl)phenyl)acrylamide |
| 221 | 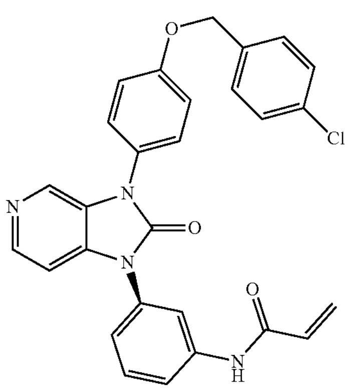 | 498.13/ 498.1 | N-(3-(3-(4-((4-chlorobenzyl)oxy)phenyl)-2-oxo-2,3-dihydro-1H-imidazo[4,5-c]pyridin-1-yl)phenyl)acrylamide |
| 222 | 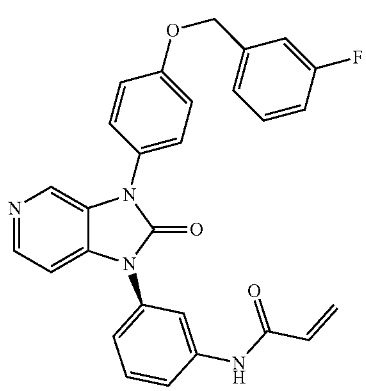 | 481.16/ 481.2 | N-(3-(3-(4-((3-fluorobenzyl)oxy)phenyl)-2-oxo-2,3-dihydro-1H-imidazo[4,5-c]pyridin-1-yl)phenyl)acrylamide |

-continued

| Entry | Structure | MS(cald) [M + H]+/ MS (found) | Name |
|---|---|---|---|
| 223 | 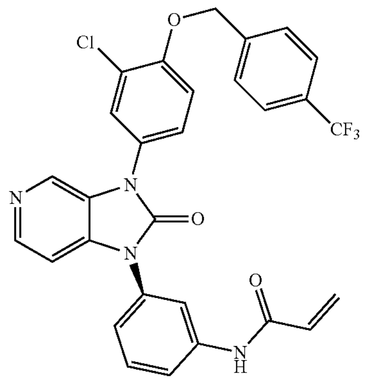 | 566.11/ 566.1 | N-(3-(3-(3-chloro-4-((4-(trifluoromethyl)benzyl)oxy)phenyl)-2-oxo-2,3-dihydro-1H-imidazo[4,5-c]pyridin-1-yl)phenyl)acrylamide |
| 224 | 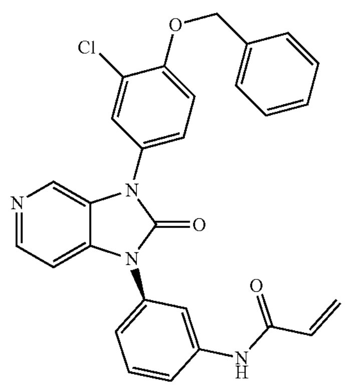 | 498.13/ 498.1 | N-(3-(3-(4-(benzyloxy)-3-chlorophenyl)-2-oxo-2,3-dihydro-1H-imidazo[4,5-c]pyridin-1-yl)phenyl)acrylamide |
| 225 | 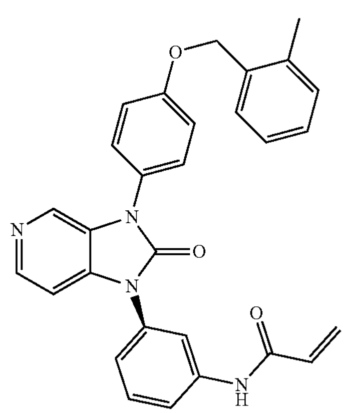 | 477.19/ 477.2 | N-(3-(3-(4-((2-methylbenzyl)oxy)phenyl)-2-oxo-2,3-dihydro-1H-imidazo[4,5-c]pyridin-1-yl)phenyl)acrylamide |

| Entry | Structure | MS(cald) [M + H]+/ MS (found) | Name |
|---|---|---|---|
| 226 | 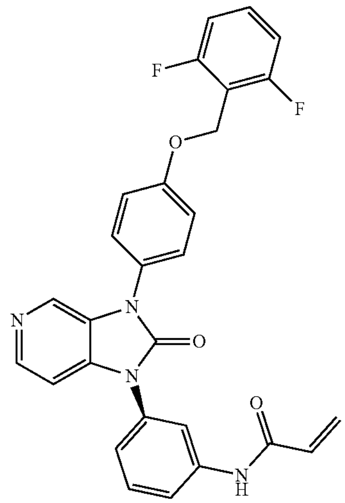 | 499.15/ 499.2 | N-(3-(3-(4-((2,6-difluorobenzyl)oxy)phenyl)-2-oxo-2,3-dihydro-1H-imidazo[4,5-c]pyridin-1-yl)phenyl)acrylamide |
| 227 | 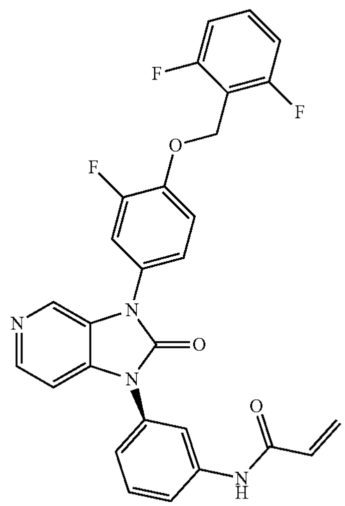 | 517.14/ 517.1 | N-(3-(3-(4-((2,6-difluorobenzyl)oxy)-3-fluorophenyl)-2-oxo-2,3-dihydro-1H-imidazo[4,5-c]pyridin-1-yl)phenyl)acrylamide |
| 228 | 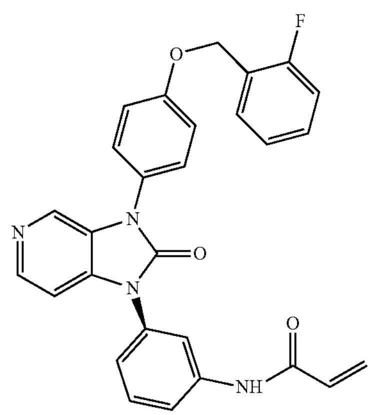 | 481.16/ 481.2 | N-(3-(3-(4-((2-fluorobenzyl)oxy)phenyl)-2-oxo-2,3-dihydro-1H-imidazo[4,5-c]pyridin-1-yl)phenyl)acrylamide |

| Entry | Structure | MS(cald) [M + H]+/ MS (found) | Name |
|---|---|---|---|
| 229 | 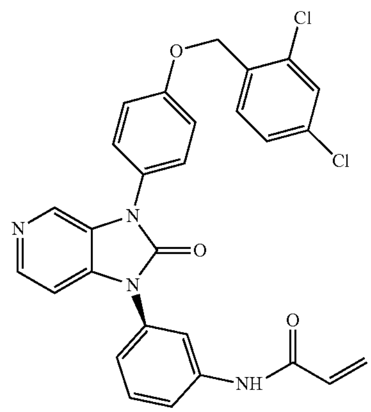 | 531.09/ 531.1 | N-(3-(3-(4-((2,4-dichlorobenzyl)oxy)phenyl)-2-oxo-2,3-dihydro-1H-imidazo[4,5-c]pyridin-1-yl)phenyl)acrylamide |
| 230 | 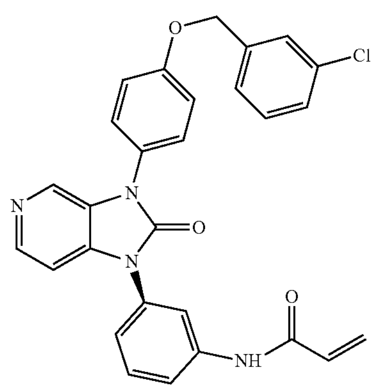 | 497.13/ 497.1 | N-(3-(3-(4-((3-chlorobenzyl)oxy)phenyl)-2-oxo-2,3-dihydro-1H-imidazo[4,5-c]pyridin-1-yl)phenyl)acrylamide |
| 231 | 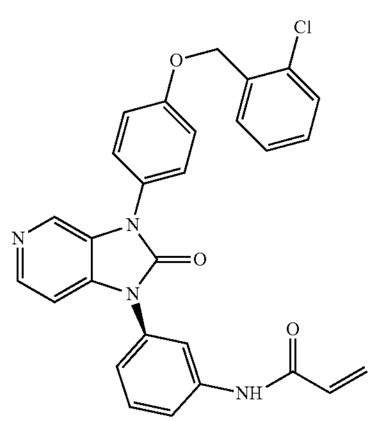 | 497.13/ 497.1 | N-(3-(3-(4-((2-chlorobenzyl)oxy)phenyl)-2-oxo-2,3-dihydro-1H-imidazo[4,5-c]pyridin-1-yl)phenyl)acrylamide |

| Entry | Structure | MS(cald) [M + H]+/ MS (found) | Name |
|---|---|---|---|
| 232 | 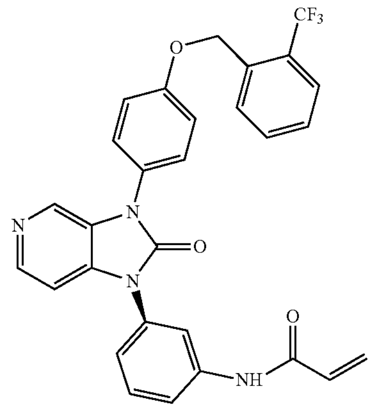 | 531.16/ 531.2 | N-(3-(2-oxo-3-(4-((2-(trifluoromethyl)benzyl)oxy)phenyl)-2,3-dihydro-1H-imidazo[4,5-c]pyridin-1-yl)phenyl)acrylamide |
| 233 | 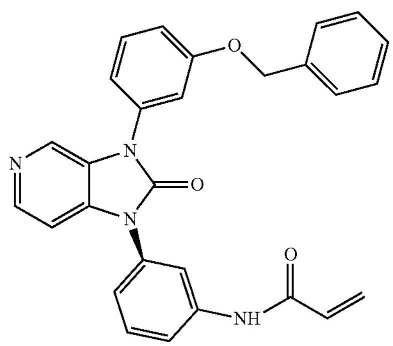 | 463.17/ 463.2 | N-(3-(3-(3-(benzyloxy)phenyl)-2-oxo-2,3-dihydro-1H-imidazo[4,5-c]pyridin-1-yl)phenyl)acrylamide |
| 234 | 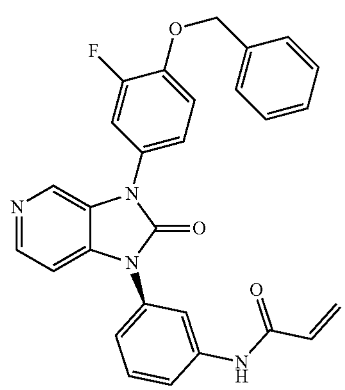 | 481.16/ 481.2 | N-(3-(3-(4-(benzyloxy)-3-fluorophenyl)-2-oxo-2,3-dihydro-1H-imidazo[4,5-c]pyridin-1-yl)phenyl)acrylamide |
| 235 | 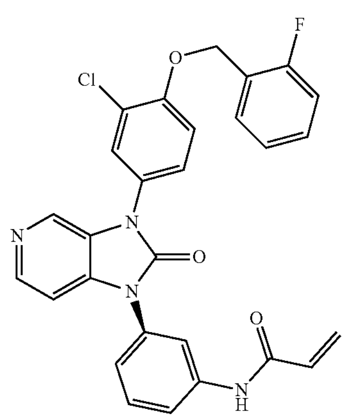 | 515.12/ 515.1 | N-(3-(3-(3-chloro-4-((2-fluorobenzyl)oxy)phenyl)-2-oxo-2,3-dihydro-1H-imidazo[4,5-c]pyridin-1-yl)phenyl)acrylamide |

-continued

| Entry | Structure | MS(calcd) [M + H]+/ MS (found) | Name |
|---|---|---|---|
| 236 | 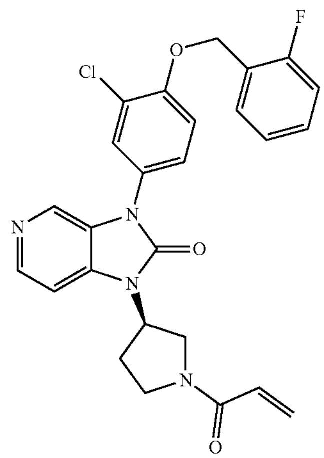 [SMILES: C=CC(=O)N1CC[C@@H](n2c(=O)n(-c3ccc(OCc4ccccc4F)c(Cl)c3)c3cnccc32)C1] | 493.14/ 493.1 | (R)-1-(1-acryloylpyrrolidin-3-yl)-3-(3-chloro-4-((2-fluorobenzyl)oxy)phenyl)-1,3-dihydro-2H-imidazo[4,5-c]pyridin-2-one |
| 237 | 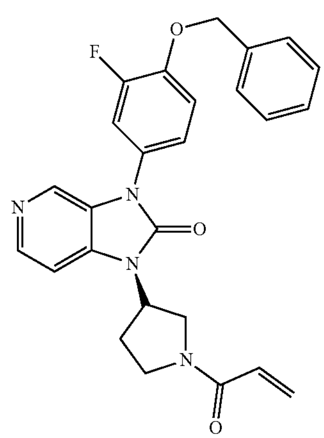 | 459.18/ 459.2 | (R)-1-(1-acryloylpyrrolidin-3-yl)-3-(4-(benzyloxy)-3-fluorophenyl)-1,3-dihydro-2H-imidazo[4,5-c]pyridin-2-one |
| 238 | 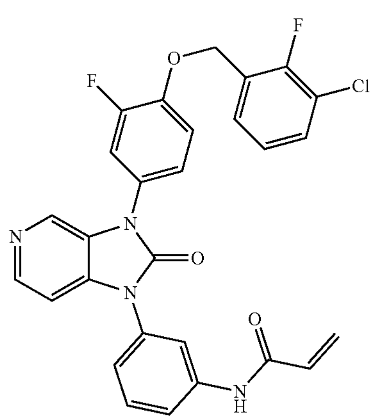 [SMILES: C=CC(=O)Nc1cccc(-n2c(=O)n(-c3ccc(OCc4cccc(Cl)c4F)c(F)c3)c3cnccc32)c1] | 533.11/ 533.1 | N-(3-(3-(4-((3-chloro-2-fluorobenzyl)oxy)-3-fluorophenyl)-2-oxo-2,3-dihydro-1H-imidazo[4,5-c]pyridin-1-yl)phenyl)acrylamide |

-continued

| Entry | Structure | MS(cald) [M + H]+/ MS (found) | Name |
|---|---|---|---|
| 239 | 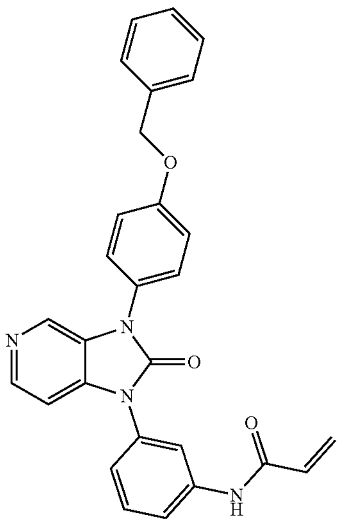 [SMILES: C=CC(=O)Nc1cccc(-n2c(=O)n(-c3ccc(OCc4ccccc4)cc3)c3cnccc32)c1] | 463.17/ 463.2 | (N-(3-(3-(4-(benzyloxy)phenyl)-2-oxo-2,3-dihydro-1H-imidazo[4,5-c]pyridin-1-yl)phenyl)acrylamide |
| 240 | 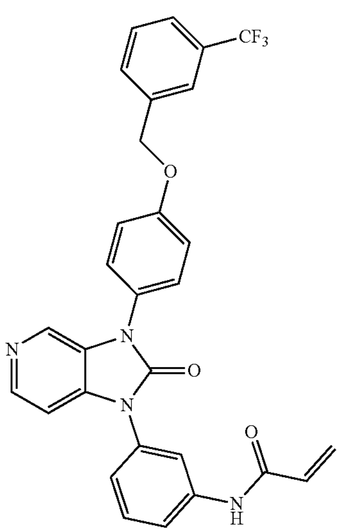 [SMILES: C=CC(=O)Nc1cccc(-n2c(=O)n(-c3ccc(OCc4cccc(C(F)(F)F)c4)cc3)c3cnccc32)c1] | 531.16/ 531.2 | N-(3-(2-oxo-3-(4-((3-(trifluoromethyl)benzyl)oxy)phenyl)-2,3-dihydro-1H-imidazo[4,5-c]pyridin-1-yl)phenyl)acrylamide |

-continued
| Entry | Structure | MS(cald) [M + H]+/ MS (found) | Name |
|---|---|---|---|
| 241 | 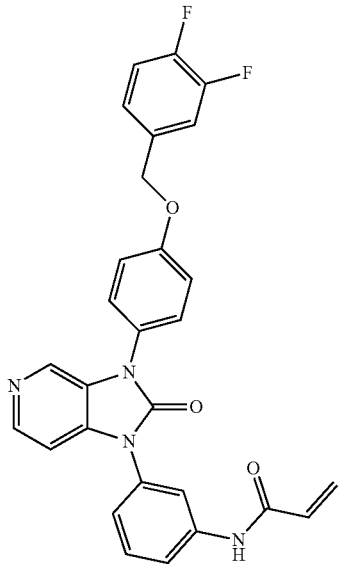 [SMILES: C=CC(=O)Nc1cccc(-n2c(=O)n(-c3ccc(OCc4ccc(F)c(F)c4)cc3)c3cnccc32)c1] | 499.15/ 499.1 | N-(3-(3-(4-((3,4-difluorobenzyl)oxy)phenyl)-2-oxo-2,3-dihydro-1H-imidazo[4,5-c]pyridin-1-yl)phenyl)acrylamide |
| 242 | 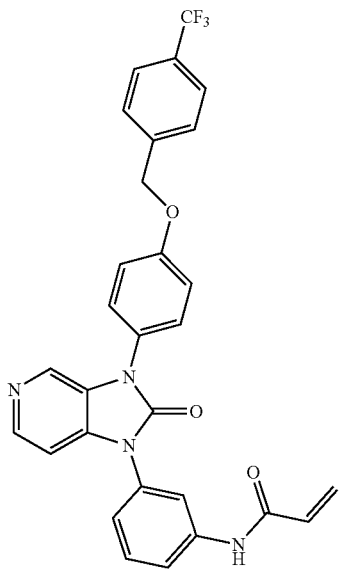 [SMILES: C=CC(=O)Nc1cccc(-n2c(=O)n(-c3ccc(OCc4ccc(C(F)(F)F)cc4)cc3)c3cnccc32)c1] | 531.16/ 531.2 | N-(3-(2-oxo-3-(4-((4-(trifluoromethyl)benzyl)oxy)phenyl)-2,3-dihydro-1H-imidazo[4,5-c]pyridin-1-yl)phenyl)acrylamide |

-continued

| Entry | Structure | MS(cald) [M + H]+/ MS (found) | Name |
|---|---|---|---|
| 243 | 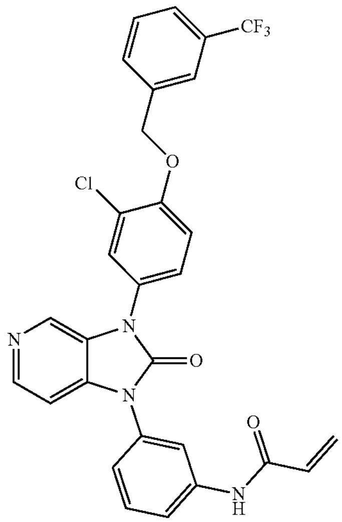 [SMILES: C=CC(=O)Nc1cccc(-n2c(=O)n(-c3ccc(OCc4cccc(C(F)(F)F)c4)c(Cl)c3)c3cnccc32)c1] | 565.12/ 565.1 | N-(3-(3-(3-chloro-4-((3-(trifluoromethyl)benzyl)oxy)phenyl)-2-oxo-2,3-dihydro-1H-imidazo[4,5-c]pyridin-1-yl)phenyl)acrylamide |
| 244 | 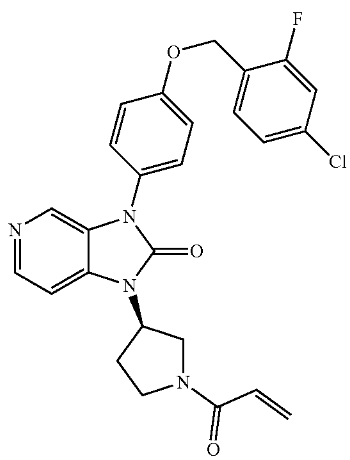 [SMILES: C=CC(=O)N1CC[C@@H](n2c(=O)n(-c3ccc(OCc4ccc(Cl)cc4F)cc3)c3cnccc32)C1] | 493.12/ 493.1 | (R)-1-(1-acryloylpyrrolidin-3-yl)-3-(4-((4-chloro-2-fluorobenzyl)oxy)phenyl)-1H-imidazo[4,5-c]pyridin-2(3H)-one |
| 245 | 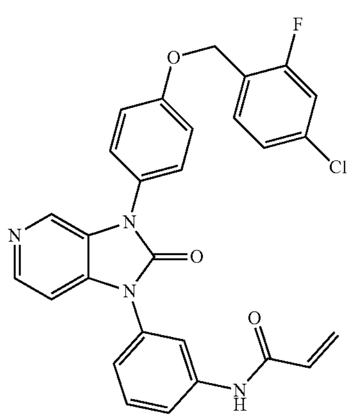 [SMILES: C=CC(=O)Nc1cccc(-n2c(=O)n(-c3ccc(OCc4ccc(Cl)cc4F)cc3)c3cnccc32)c1] | 515.14/ 515.1 | N-(3-(3-(4-((4-chloro-2-fluorobenzyl)oxy)phenyl)-2-oxo-2,3-dihydro-1H-imidazo[4,5-c]pyridin-1-yl)phenyl)acrylamide |

-continued

| Entry | Structure | MS(cald) [M + H]+/ MS (found) | Name |
|---|---|---|---|
| 246 | 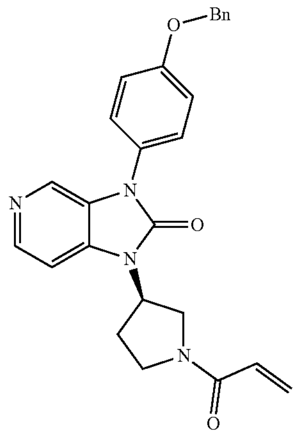 [SMILES: C=CC(=O)N1CC[C@@H](n2c(=O)n(-c3ccc(OCc4ccccc4)cc3)c3cnccc32)C1] | 441.18/ 441.2 | ((R)-1-(1-acryloylpyrrolidin-3-yl)-3-(4-(benzyloxy)phenyl)-1H-imidazo[4,5-c]pyridin-2(3H)-one |
| 247 | 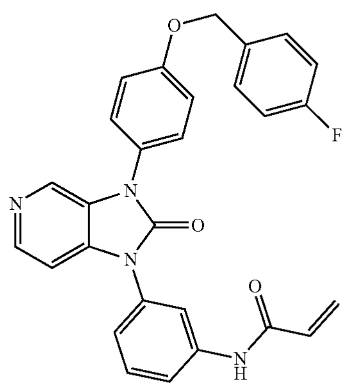 [SMILES: C=CC(=O)Nc1cccc(-n2c(=O)n(-c3ccc(OCc4ccc(F)cc4)cc3)c3cnccc32)c1] | 481.16/ 481.2 | N-(3-(3-(4-((4-fluorobenzyl)oxy)phenyl)-2-oxo-2,3-dihydro-1H-imidazo[4,5-c]pyridin-1-yl)phenyl)acrylamide |
| 248 | 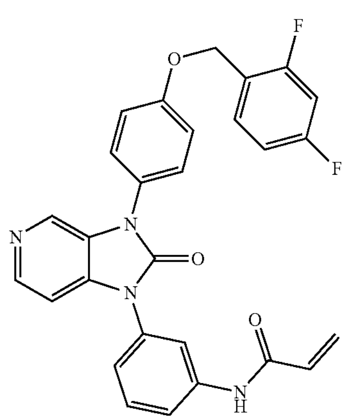 [SMILES: C=CC(=O)Nc1cccc(-n2c(=O)n(-c3ccc(OCc4ccc(F)cc4F)cc3)c3cnccc32)c1] | 499.15/ 499.2 | N-(3-(3-(4-((2,4-difluorobenzyl)oxy)phenyl)-2-oxo-2,3-dihydro-1H-imidazo[4,5-c]pyridin-1-yl)phenyl)acrylamide |

Example 249

4-(1-(3-acrylamidophenyl)-2-oxo-1H-imidazo[4,5-c]pyridin-3(2H)-yl)-N-(4-fluorobenzyl)benzamide

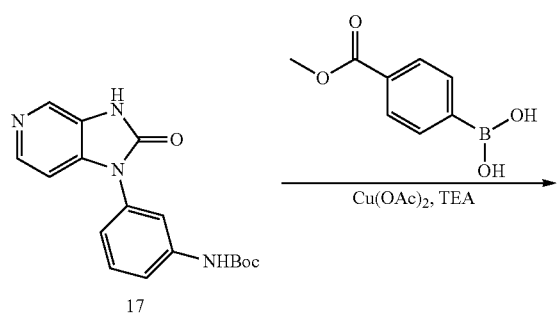

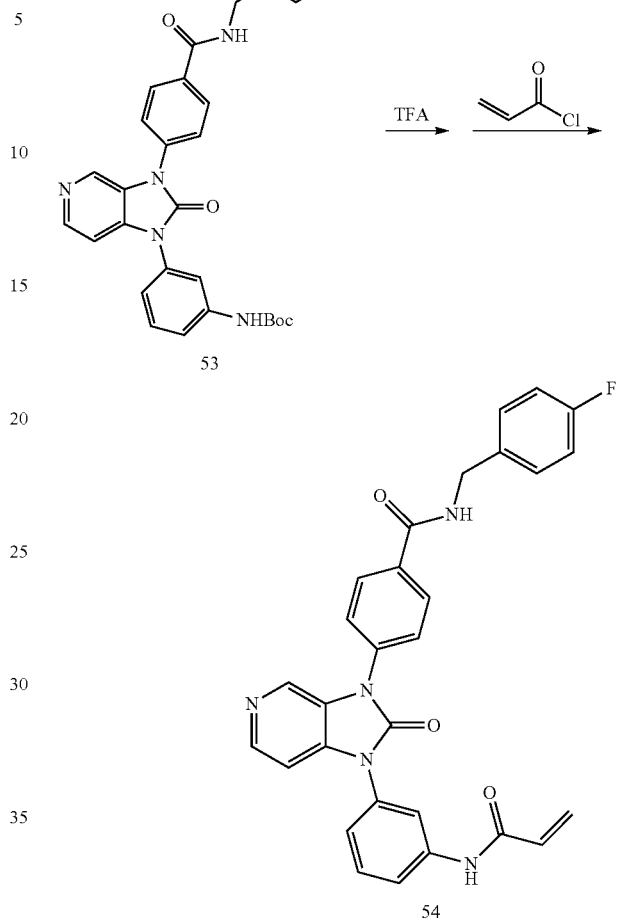

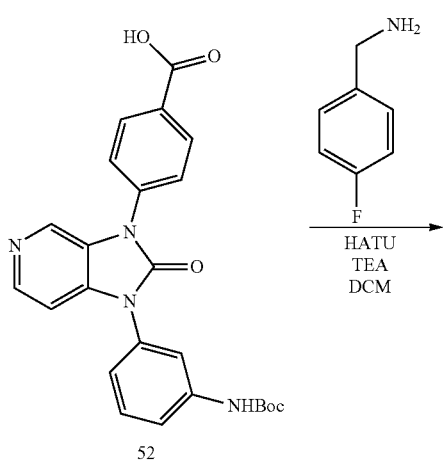

Step 1: methyl 4-(1-(3-((tert-butoxycarbonyl)amino)phenyl)-2-oxo-1H-imidazo[4,5-c]pyridin-3(2H)-yl)benzoate (51)

Intermediate 17 (0.96 g, 2.94 mmol, 1.0 eq) was dissolved in DCM (30.0 mL), added Cupric acetate (530 mg, 2.94 mmol, 1.0 eq), (4-(methoxycarbonyl)phenyl)boronic acid (1.06 g, 5.88 mmol, 2.0 eq), 4 A molecular sieve (1.3 g) and TEA (1.23 mL, 0.617 mmol, 2.0 eq), the mixture solution was stirred for 20 h at RT. Then filtered the solution and removed the solution under reduce pressure, added water and extracted with EA, dried with $Na_2SO_4$, filtered and concentrated, purified with silica column (PE:EA=4:1~1:1) to obtain the title product, brown solid, Yield: 420 mg, 33.2%. $^1$H NMR (400 MHz, $CDCl_3$): δ=8.25 (d, J=8.0 Hz, 2H), 7.80 (s, 1H), 7.85 (d, J=7.6 Hz, 2H), 7.45-7.49 (m, 1H), 7.31 (d, J=7.6 Hz, 1H), 7.22 (d, J=7.2 Hz, 2H), 6.74 (s, 1H), 3.97 (s, 3H), 1.52 (s, 9H). LCMS (ESI) m/z=461[M+H]$^+$.

Step 2: 4-(1-(3-((tert-butoxycarbonyl)amino)phenyl)-2-oxo-1H-imidazo[4,5-c]pyridine-3(2H)-yl)benzoic acid (52)

Intermediate 51 (420 mg, 1.0 eq) was dissolved in EtOH (10 mL), added lithium hydroxide (192 mg, 5.0 eq), the mixture solution were stirred for 2 h at 50° C. Then added 1 M HCl to PH=6-5, extracted with EA, dried with Na$_2$SO$_4$, filtered and concentrated to obtain product used next step without in purification, gray solid, Yield: 338 mg, 83.0%. $^1$H NMR (400 MHz, DMSO-d$_6$): δ=12.60 (s, 1H), 9.67 (s, 1H), 8.17 (d, J=8.4 Hz, 2H), 7.82-7.86 (m, 3H), 7.50 (d, J=6.0 Hz, 2H), 7.22-7.23 (m, 1H), 1.49 (s, 9H). LCMS (ESI) m/z=447 [M+H]$^+$.

Step 3: tert-butyl (3-(3-(4-((4-fluorobenzyl)carbamoyl)phenyl)-2-oxo-2,3-dihydro-1H-imidazo[4,5-c]pyridin-1-yl)phenyl)carbamate (53)

Intermediate 52 (66 mg, 0.148 mmol, 1.0 eq) was dissolved in DCM (30 mL), added (4-fluorophenyl)methanamine (22.2 mg, 0.178 mmol, 1.2 eq), TEA (45 mg, 0.444 mmol, 3.0 eq), HATU (67.5 mg, 0.178 mmol, 1.2 eq), the mixture solution were stirred for 2 h at room temperature. Then stopped and removed the solution under reduce pressure, the residue was added saturated NaHCO$_3$, extracted with EA washed with brine, dried with Na$_2$SO$_4$, filtered and concentrated, purified with silica column (DCM:MeOH=100:1~50:1) to obtain the title product as colorless oil, Yield: 47 mg, 57.4%. LCMS (ESI) m/z=554 [M+H]$^+$.

Step 4: 4-(1-(3-acrylamidophenyl)-2-oxo-1H-imidazo[4,5-c]pyridin-3(2H)-yl)-N-(4-fluorobenzyl)benzamide (54)

Intermediate 53 (47 mg) was dissolved in DCM (5.0 mL), added TFA (2.0 mL), the mixture was stirred for 1 h at RT, stopped and removed the solution under reduce pressure, the residue was added saturated NaHCO$_3$, extracted with EA and dried with Na$_2$SO$_4$, then filtered and concentrated to provide a crude product used next step without purification, colorless oil, Yield: 28 mg, 72.7%. LCMS (ESI) m/z=454 [M+H]$^+$.

Crude product (28 mg, 0.062 mmol, 1.0 eq) and DIEA (9 mg, 0.070 mmol, 1.1 eq) were dissolved in THF (2.0 mL), added acryloyl chloride (6 mg, 0.065 mmol, 1.05 eq) slowly at 0° C., the mixture solution was stirred for 0.5 h at RT, followed the reaction with LCMS, stopped the reaction added water and extracted with EA, dried with Na$_2$SO$_4$, filtered and concentrated, the residue was purification with silica gel plate (DCM:MeOH=20:1) to obtain the title product, colorless oil, Yield: 2 mg, 6.4%. $^1$H NMR (400 MHz, CD$_3$OD): δ=8.60 (s, 1H), δ=8.23 (s, 1H), 8.13 (d, J=8.0 Hz, 2H), 7.83 (d, J=8.4 Hz, 2H), 7.63-7.66 (m, 3H), 7.39-7.44 (m, 3H), 7.05-7.10 (m, 2H), 6.41-6.50 (m, 2H), 5.81-5.84 (m, 1H), 4.61 (d, J=4.4 Hz, 2H). LCMS (ESI) m/z=507 [M+H]$^+$.

The following additional Examples 250-256 shown in the Table below were prepared following the procedures outlined in the general methods above and detailed in Example 249.

| Entry | Structure | MS(cald) [M + H]$^+$/ MS (found) | Name |
| --- | --- | --- | --- |
| 250 | 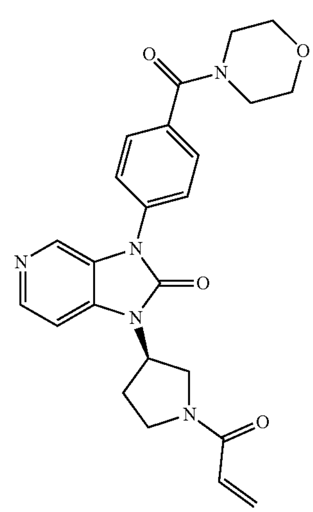 [SMILES: C=CC(=O)N1CC[C@@H](n2c(=O)n(-c3ccc(C(=O)N4CCOCC4)cc3)c3cnccc32)C1] | 448.19/ 448.2 | (R)-1-(1-acryloylpyrrolidin-3-yl)-3-(4-(morpholine-4-carbonyl)phenyl)-1H-imidazo[4,5-c]pyridin-2(3H)-one |

-continued

| Entry | Structure | MS(cald) [M + H]+/ MS (found) | Name |
|---|---|---|---|
| 251 | 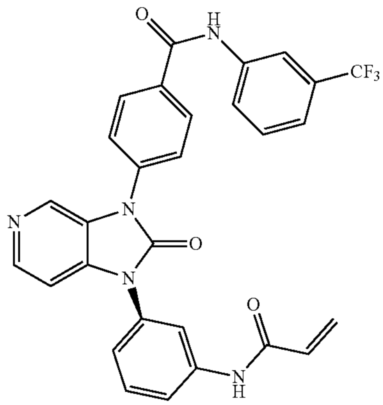 | 544.16/ 544.2 | 4-(1-(3-acrylamidophenyl)-2-oxo-1H-imidazo[4,5-c]pyridin-3(2H)-yl)-N-(3-(trifluoromethyl)phenyl)benzamide |
| 252 | 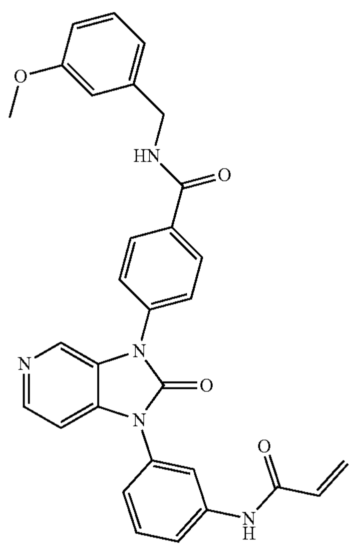 [SMILES: C=CC(=O)Nc1cccc(-n2c(=O)n(-c3ccc(C(=O)NCc4cccc(OC)c4)cc3)c3cnccc32)c1] | 520.19/ 520.2 | 4-(1-(3-acrylamidophenyl)-2-oxo-1H-imidazo[4,5-c]pyridin-3(2H)-yl)-N-(3-methoxybenzyl)benzamide |
| 253 | 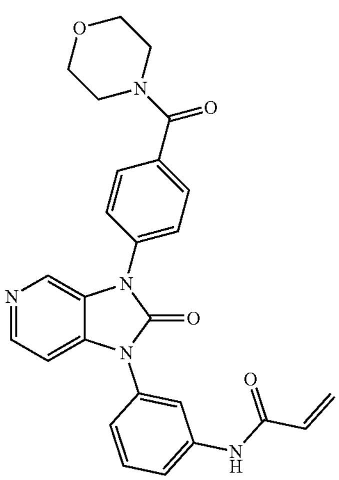 [SMILES: C=CC(=O)Nc1cccc(-n2c(=O)n(-c3ccc(C(=O)N4CCOCC4)cc3)c3cnccc32)c1] | 470.18/ 470.2 | N-(3-(3-(4-(morpholine-4-carbonyl)phenyl)-2-oxo-2,3-dihydro-1H-imidazo[4,5-c]pyridin-1-yl)phenyl)acrylamide |

| Entry | Structure | MS(cald) [M + H]+/ MS (found) | Name |
|---|---|---|---|
| 254 | 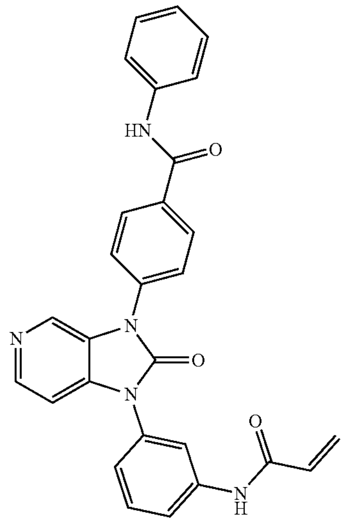 [SMILES: C=CC(=O)Nc1cccc(-n2c(=O)n(-c3ccc(C(=O)Nc4ccccc4)cc3)c3cnccc32)c1] | 476.16/ 476.2 | 4-(1-(3-acrylamidophenyl)-2-oxo-1H-imidazo[4,5-c]pyridin-3(2H)-yl)-N-phenylbenzamide |
| 255 | 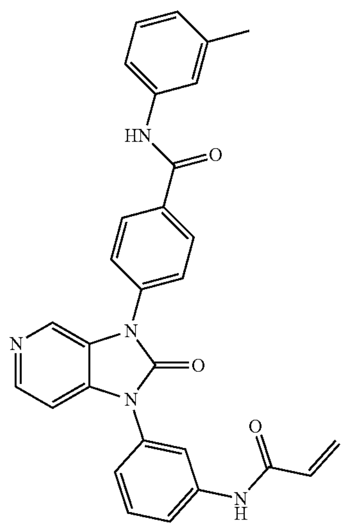 [SMILES: C=CC(=O)Nc1cccc(-n2c(=O)n(-c3ccc(C(=O)Nc4cccc(C)c4)cc3)c3cnccc32)c1] | 490.18/ 490.2 | 4-(1-(3-acrylamidophenyl)-2-oxo-1H-imidazo[4,5-c]pyridin-3(2H)-yl)-N-(m-tolyl)benzamide |
| 256 | 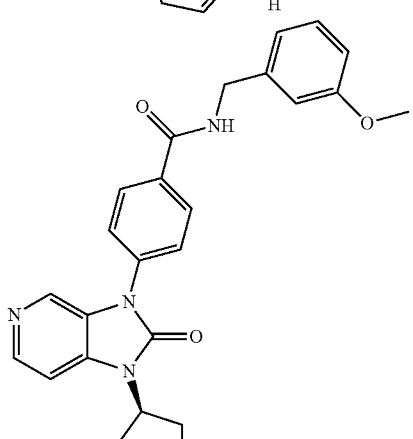 | 498.21/ 498.2 | (R)-4-(1-(1-acryloylpyrrolidin-3-yl)-2-oxo-1H-imidazo[4,5-c]pyridin-3(2H)-yl)-N-(3-methoxybenzyl)benzamide |

Example 257

N-(4-(1-(3-acrylamidophenyl)-2-oxo-1H-imidazo[4,5-c]pyridin-3(2H)-yl)phenyl)benzamide

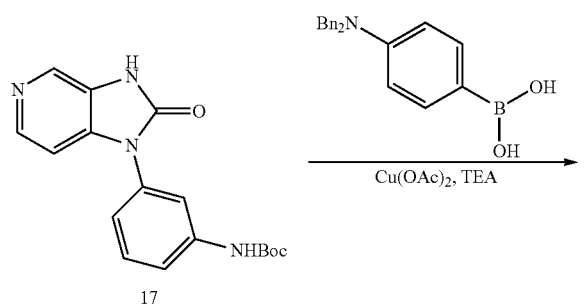

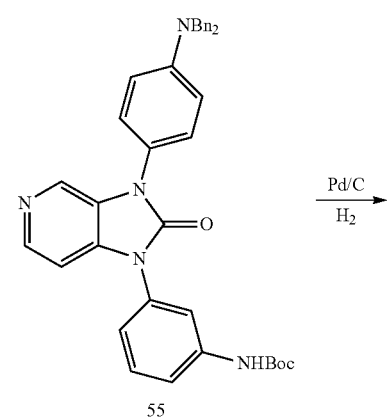

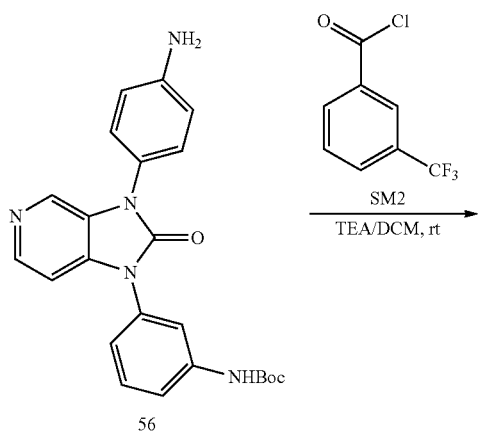

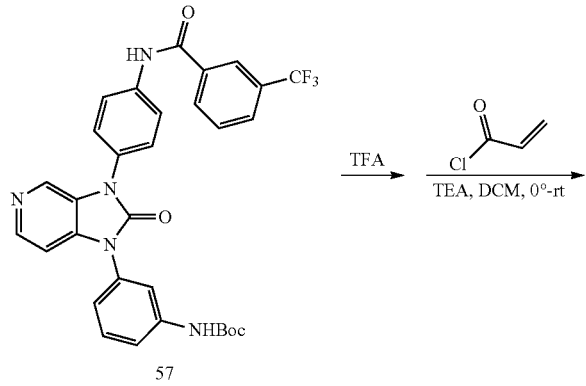

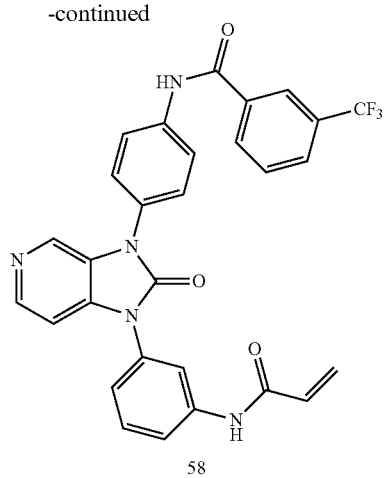

Step 1: tert-butyl (3-(3-(4-(dibenzylamino)phenyl)-2-oxo-2,3-dihydro-1H-imidazo[4,5-c]pyridin-1-yl)phenyl)carbamate (55)

The mixture of intermediate 17 (2 g, 6.1 mmol), (4-(dibenzylamino)phenyl)-boronic acid (3.8 g, 12.2 mmol), TEA (1.23 g, 12.2 mmol) and 4 A molecular sieves (1 g) were added to DCM (40 mL) in a vial Copper(II) acetate (1.1 g, 6.1 mmol) was added in one portion. The mixture was stirred for about 22 h at it. Volatile components were removed under vacuum, before being poured into H$_2$O. The reaction mixture was extracted with EA, Organic phase was purified by column chromatography on silica gel (gradient: DCM/MeOH=100/1-50/1), give the title product (1.2 g, yield 33.3%).

$^1$HNMR (400 MHz, CD$_3$OD): δ 8.33 (br, 2H), 7.73 (s, 1H), 7.46-7.11 (m, 16H), 6.85 (d, J=8.0 Hz, 2H), 6.67 (s, 1H), 4.72 (s, 4H), 1.50 (s, 9H). LCMS: m/z=598 [M+H]$^+$.

Step 2: tert-butyl (3-(3-(4-aminophenyl)-2-oxo-2,3-dihydro-1H-imidazo[4,5-c]pyridin-1-yl)phenyl)carbamate (56)

A suspension of 55 (1.2 g, 1.68 mmol) and 10% Pd/C (0.3 g) in MeOH (20 mL) was hydrogenated at 50 psi H$_2$ for 20 h. The suspension was filtered through Celite and concentrated. The residue was dried in vacuo to provide the title product (0.2 g crude).
LCMS: m/z=372 [M+H]$^+$.

Step 3: tert-butyl (3-(2-oxo-3-(4-(3-(trifluoromethyl)benzamido)phenyl)-2,3-dihydro-1H-imidazo[4,5-c]pyridin-1-yl)phenyl)carbamate (57)

To a stirred solution of 56 (60 mg, 0.14 mmol) in DCM (6 mL) was added SM2 (33 mg, 0.16 mmol) and TEA (17.4 mg, 0.17 mmol). The mixture was stirred at 15° C., after 1.0 h, the mixture was washed with H$_2$O, extracted with DCM, dried over Na$_2$SO$_4$, filtered, concentrated to give a crude title product which was used for the next step without further purification. LCMS (ESI) m/z=590 [M+H]$^+$.

Step 4: N-(4-(1-(3-acrylamidophenyl)-2-oxo-1H-imidazo[4,5-c]pyridin-3(2H)-yl)phenyl)benzamide (58)

To a stirred solution of 57 in DCM (4 mL) was added CF$_3$COOH (1 mL), The mixture was stirred at 15° C., after 1.0 h, the mixture was added NaHCO₃ to adjust the Ph=8, extracted with DCM, dried over Na₂SO₄, filtered, concentrated and purified by Pre-TLC to give the product (42 mg). LCMS (ESI) m/z=490 [M+H]⁺.

To a stirred solution of de-Boc intermediate (42 mg, 0.086 mmol) in DCM (6 mL) was added acryloyl chloride (8.5 mg, 0.09 mmol) and TEA (17.3 mg, 0.17 mmol). The mixture was stirred at 15° C., after 1.0 h, the mixture was washed with H₂O, extracted with DCM, dried over Na₂SO₄, filtered, concentrated and purified by Pre-TLC to give the title product (21 mg, 51.4%).

$^1$HNMR (CD₃OD, 400 MHz) 5.79-5.82 (d, 1H), 6.41-6.45 (m, 2H), 7.39-7.41 (d, 1H), 7.56-7.58 (q, 1H), 7.70-7.73 (m, 2H), 7.74-7.76 (m, 2H), 7.77-7.79 (m, 2H), 7.90-7.92 (d, 1H), 7.92-8.01 (m, 3H), 8.03 (s, 1H), 8.08-8.11 (d, 1H), 8.24 (s, 1H). LCMS (ESI) m/z=544 [M+H]⁺.

The following additional Examples 258-269 shown in the Table below were prepared following the procedures outlined in the general methods above and detailed in Example 257.

| Entry | Structure | MS(cald) [M + H]⁺/ MS (found) | Name |
|---|---|---|---|
| 258 | 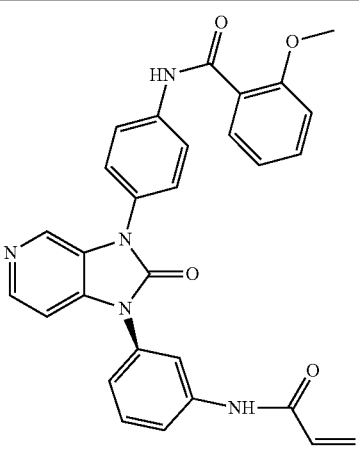 | 506.18/ 506.2 | N-(4-(1-(3-acrylamidophenyl)-2-oxo-1H-imidazo[4,5-c]pyridin-3(2H)-yl)phenyl)-2-methoxybenzamide |
| 259 | 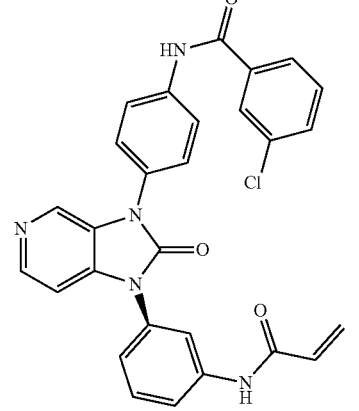 | 510.13/ 510.1 | N-(4-(1-(3-acrylamidophenyl)-2-oxo-1H-imidazo[4,5-c]pyridin-3(2H)-yl)phenyl)-3-chlorobenzamide |
| 260 | 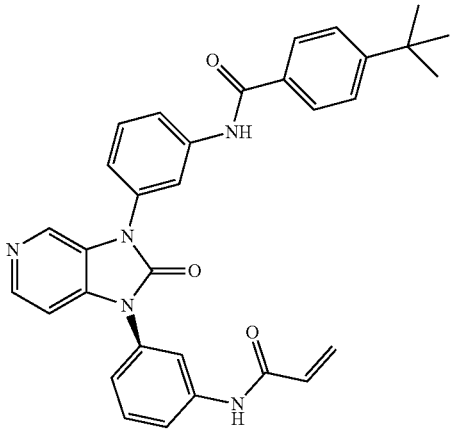 | 532.23/ 532.2 | N-(3-(1-(3-acrylamidophenyl)-2-oxo-1H-imidazo[4,5-c]pyridin-3(2H)-yl)phenyl)-4-(tert-butyl)benzamide |

-continued

| Entry | Structure | MS(cald) [M + H]+/ MS (found) | Name |
|---|---|---|---|
| 261 | 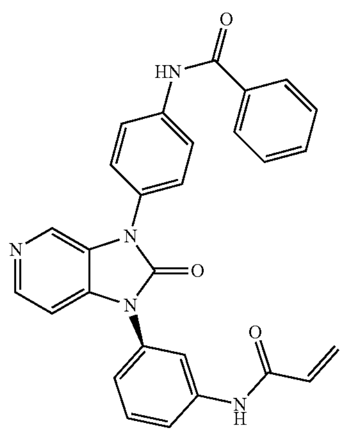 | 576.17/ 576.2 | N-(4-(1-(3-acrylamidophenyl)-2-oxo-1H-imidazo[4,5-c]pyridin-3(2H)-yl)phenyl)benzamide |
| 262 | 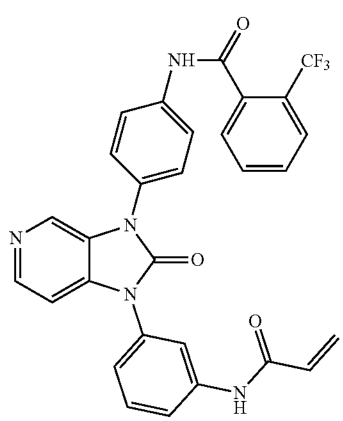 [SMILES: C=CC(=O)Nc1cccc(-n2c(=O)n(-c3ccc(NC(=O)c4ccccc4C(F)(F)F)cc3)c3cnccc32)c1] | 544.15/ 544.2 | N-(4-(1-(3-acrylamidophenyl)-2-oxo-1,2-dihydro-3H-imidazo[4,5-c]pyridin-3-yl)phenyl)-2-(trifluoromethyl)benzamide |
| 263 | 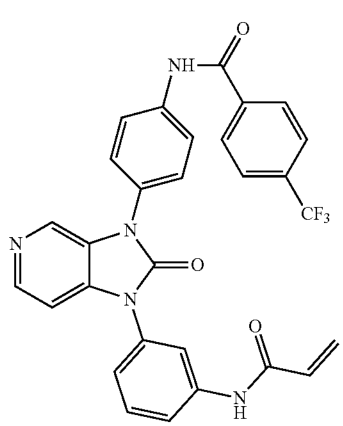 [SMILES: C=CC(=O)Nc1cccc(-n2c(=O)n(-c3ccc(NC(=O)c4ccc(C(F)(F)F)cc4)cc3)c3cnccc32)c1] | 544.15/ 544.2 | N-(4-(1-(3-acrylamidophenyl)-2-oxo-1,2-dihydro-3H-imidazo[4,5-c]pyridin-3-yl)phenyl)-4-(trifluoromethyl)benzamide |

-continued

| Entry | Structure | MS(calcd) [M + H]+/ MS (found) | Name |
|---|---|---|---|
| 264 | 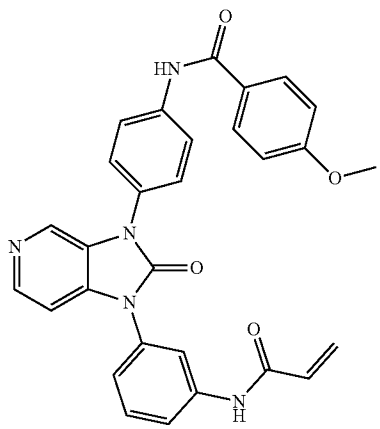 [SMILES: C=CC(=O)Nc1cccc(-n2c(=O)n(-c3ccc(NC(=O)c4ccc(OC)cc4)cc3)c3cnccc32)c1] | 506.18/ 506.2 | N-(4-(1-(3-acrylamidophenyl)-2-oxo-1H-imidazo[4,5-c]pyridin-3(2H)-yl)phenyl)-4-methoxybenzamidee |
| 265 | 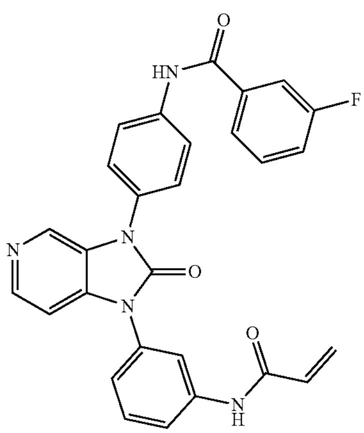 [SMILES: C=CC(=O)Nc1cccc(-n2c(=O)n(-c3ccc(NC(=O)c4cccc(F)c4)cc3)c3cnccc32)c1] | 494.16/ 494.2 | N-(4-(1-(3-acrylamidophenyl)-2-oxo-1H-imidazo[4,5-c]pyridin-3(2H)-yl)phenyl)-3-fluorobenzamide |
| 266 | 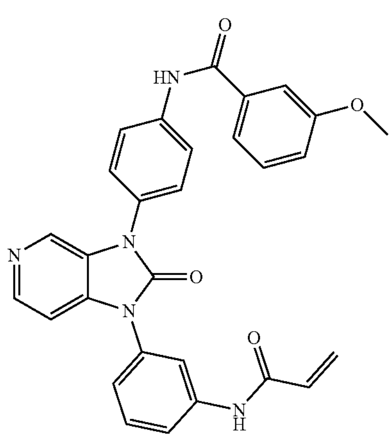 [SMILES: C=CC(=O)Nc1cccc(-n2c(=O)n(-c3ccc(NC(=O)c4cccc(OC)c4)cc3)c3cnccc32)c1] | 506.18/ 506.2 | N-(4-(1-(3-acrylamidophenyl)-2-oxo-1H-imidazo[4,5-c]pyridin-3(2H)-yl)phenyl)-3-methoxybenzamide |

-continued

| Entry | Structure | MS(cald) [M + H]+/ MS (found) | Name |
|---|---|---|---|
| 267 | 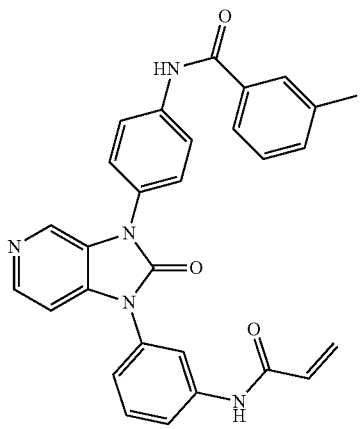 [SMILES: C=CC(=O)Nc1cccc(-n2c(=O)n(-c3ccc(NC(=O)c4cccc(C)c4)cc3)c3cnccc32)c1] | 490.18/ 490.2 | N-(4-(1-(3-acrylamidophenyl)-2-oxo-1H-imidazo[4,5-c]pyridin-3(2H)-yl)phenyl)-3-methylbenzamide |
| 268 | 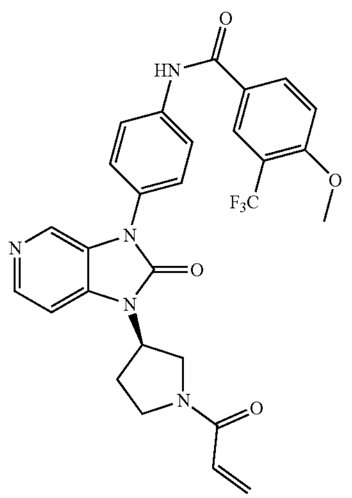 [SMILES: C=CC(=O)N1CC[C@@H](n2c(=O)n(-c3ccc(NC(=O)c4ccc(OC)c(C(F)(F)F)c4)cc3)c3cnccc32)C1] | 552.18/ 552.2 | (R)-N-(4-(1-(1-acryloylpyrrolidin-3-yl)-2-oxo-1H-imidazo[4,5-c]pyridin-3(2H)-yl)phenyl)-4-methoxy-3-(trifluoromethyl)benzamide |
| 269 | 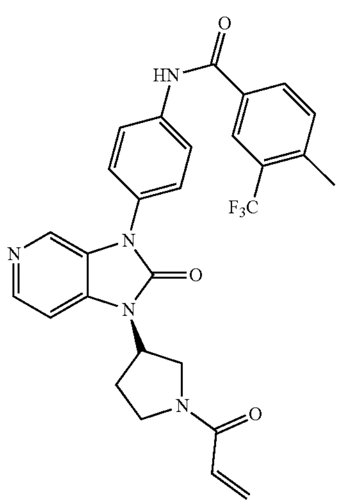 | 536.18/ 536.2 | (S)-N-(4-(1-(1-acryloylpyrrolidin-3-yl)-2-oxo-1H-imidazo[4,5-c]pyridin-3(2H)-yl)phenyl)-4-methyl-3-(trifluoromethyl)benzamide |

Example 270

Step 1: tert-butyl (3-(3-(4-bromophenyl)-2-oxo-2,3-dihydro-1H-imidazo[4,5-c]pyridin-1-yl)phenyl)carbamate (59)

Intermediate 17 (0.5 g, 1.53 mmol), (4-bromophenyl) boronic acid (0.61 g, 3.0 mmol), TEA (0.3 g, 3.0 mmol) and 4 A molecular sieves (0.1 g) were added to DCM (15 mL) in a vial Copper (II) acetate (0.27 g, 1.53 mmol) was added in one portion. The mixture was stirred for about 22 h at rt. Volatile components were removed under vacuum, before being poured into H$_2$O. The reaction mixture was extracted with EA, Organic phase was purified by column chromatography on silica gel (gradient: DCM/MeOH=100/1-50/1) to give the title product (0.26 g, yield=33.3%).

$^1$H NMR (400 MHz, CDCl$_3$): δ=7.83-7.80 (m, 2H), 7.71 (d, J=8.0 Hz, 2H), 7.51-7.44 (m, 3H), 7.30-7.26 (m, 1H), 7.21 (d, J=8.0 Hz, 1H), 6.68 (s, 1H), 1.51 (s, 9H). LCMS: m/z=481.1, 483.1 [M+H]$^+$.

Step 2: tert-butyl (3-(3-(3'-methyl-[1,1'-biphenyl]-4-yl)-2-oxo-2,3-dihydro-1H-imidazo[4,5-c]pyridin-1-yl)phenyl)carbamate (60)

To a solution of 59 (50 mg, 0.1 mmol) and m-tolylboronic acid (28 mg, 0.2 mmol) in dioxane (5 mL) and water 1 mL) was added K$_2$CO$_3$ (28 mg, 0.2 mmol) followed by (Ph$_3$P)$_4$Pd (10 mg, 0.05 mmol) under N$_2$ with stirring. The mixture was refluxed for 8 h until the material was disappeared. The reaction mixture was cooled to room temperature. The dioxane was removed by rotary evaporation. The residue was poured into water and extracted with EA. The organic layer was dried over Na$_2$SO$_4$, filtered and the solvent was removed by rotary evaporation. The product was isolated by flash chromatography on silica gel using 100:1-50:1 DCM:MeOH to give the title product (20 mg, yield 39.1%). LCMS: m/z=493[M+H]$^+$.

Step 3: 1-(3-aminophenyl)-3-(3'-methyl-[1,1'-biphenyl]-4-yl)-1H-imidazo[4,5-c]pyridin-2(3H)-one (61)

Intermediate 60 (20 mg, 0.040 mmol) were added to CF$_3$COOH/DCM=4/1 (5 mL) in one portion. The mixture was stirred for about 1 h at rt. Volatile components were removed under vacuum, give a crude title product, and directly used in next step without further purification. LCMS: m/z=393[M+H]$^+$.

Step 4: N-(3-(3-(3'-methyl-[1,1'-biphenyl]-4-yl)-2-oxo-2,3-dihydro-1H-imidazo[4,5-c]pyridin-1-yl)phenyl)acrylamide (62)

To a solution of Acryloyl chloride (3.6 mg, 0.04 mmol) in DCM (1 mL) was added to a stirred solution of 61 (16 mg, 0.04 mmol) and TEA (41 mg, 0.4 mmol) in DCM (5 mL) at 0° C. The reaction mixture was stirred for 1 h, poured onto brine and extracted with DCM. The organic layer was dried, concentrated and recrystallized from DCM/MeOH=100/1 to give the title product (3 mg, yield 6.5%).

$^1$H NMR (400 MHz, CDCl$_3$): δ=8.45 (br, 1H), 8.37 (br, 1H), 7.98 (br, 1H), 7.81 (br, 1H), 7.54-7.45 (m, 3H), 7.34-7.23 (m, 3H), 7.13 (d, J=4.0 Hz, 1H), 7.10 (d, J=4.0 Hz, 1H), 6.97-6.90 (m, 3H), 6.45-6.40 (m, 1H), 6.24-6.18 (m, 1H), 5.77-5.75 (m, 1H), 2.35 (s, 3H). LCMS: m/z=447 [M+H]$^+$.

The following additional Examples 271-278 shown in the Table below were prepared following the procedures in Examples 270.

| Entry | Structure | MS(cald) [M + H]$^+$/ MS (found) | Name |
|---|---|---|---|
| 271 | 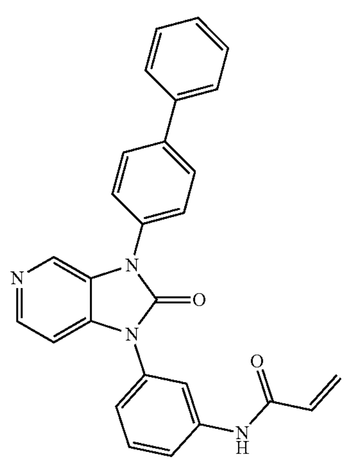 [SMILES: C=CC(=O)Nc1cccc(-n2c(=O)n(-c3ccc(-c4ccccc4)cc3)c3cnccc32)c1] | 433.16/ 433.1 | N-(3-(3-([1,1'-biphenyl]-4-yl)-2-oxo-2,3-dihydro-1H-imidazo[4,5-c]pyridin-1-yl)phenyl)acrylamide |

-continued

| Entry | Structure | MS(cald) [M + H]+/ MS (found) | Name |
|---|---|---|---|
| 272 | 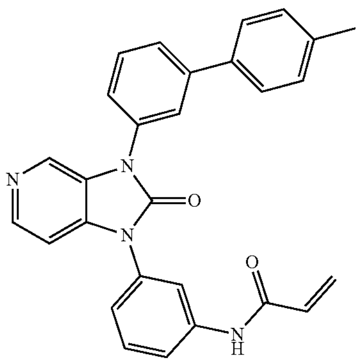 [SMILES: C=CC(=O)Nc1cccc(-n2c(=O)n(-c3cccc(-c4ccc(C)cc4)c3)c3cnccc32)c1] | 447.17/ 447.2 | N-(3-(3-(4'-methyl-[1,1'-biphenyl]-3-yl)-2-oxo-2,3-dihydro-1H-imidazo[4,5-c]pyridin-1-yl)phenyl)acrylamide |
| 273 | 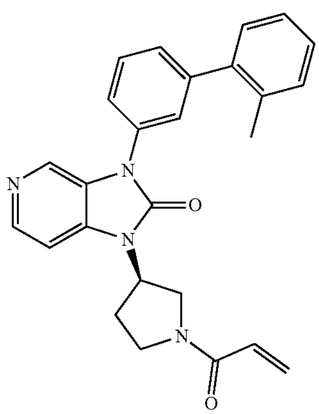 [SMILES: C=CC(=O)N1CC[C@@H](n2c(=O)n(-c3cccc(-c4ccccc4C)c3)c3cnccc32)C1] | 425.19/ 425.2 | (R)-1-(1-acryloylpyrrolidin-3-yl)-3-(2'-methyl-[1,1'-biphenyl]-3-yl)-1H-imidazo[4,5-c]pyridin-2(3H)-one |
| 274 | 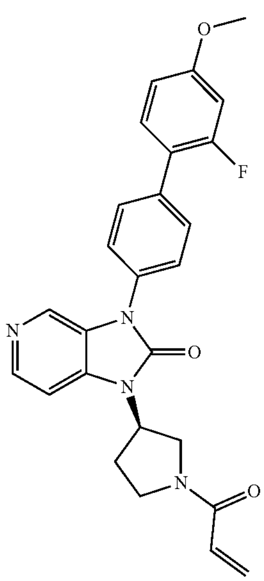 [SMILES: C=CC(=O)N1CC[C@@H](n2c(=O)n(-c3ccc(-c4ccc(OC)cc4F)cc3)c3cnccc32)C1] | 459.18/ 459.2 | (R)-1-(1-acryloylpiperidin-4-yl)-3-(2'-fluoro-4'-methoxy-[1,1'-biphenyl]-4-yl)-1H-imidazo[4,5-c]pyridin-2(3H)-one |

| Entry | Structure | MS(cald) [M + H]+/ MS (found) | Name |
|---|---|---|---|
| 275 | 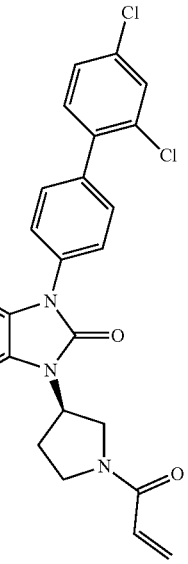 | 479.10/ 479.1, 480.2, 481.1, 483.1 | (R)-1-(1-acryloylpiperidin-4-yl)-3-(2',4'-dichloro-[1,1'-biphenyl]-4-yl)-1H-imidazo[4,5-c]pyridin-2(3H)-one |
| 276 | 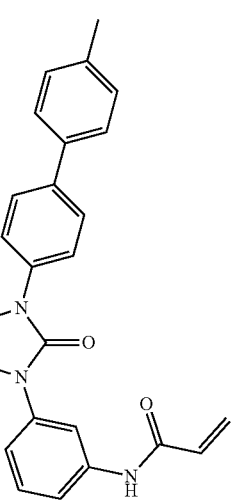 | 447.17/ 447.2 | N-(3-(3-(4'-methyl-[1,1'-biphenyl]-4-yl)-2-oxo-2,3-dihydro-1H-imidazo[4,5-c]pyridin-1-yl)phenyl)acrylamide |
| 277 | 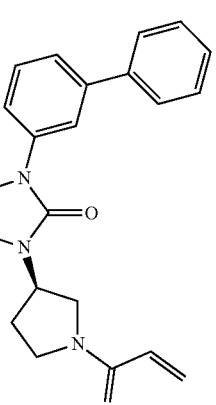 | 411.17/ 411.2 | (R)-3-([1,1'-biphenyl]-3-yl)-1-(1-acryloylpyrrolidin-3-yl)-1H-imidazo[4,5-c]pyridin-2(3H)-one |

-continued

| Entry | Structure | MS(cald) [M + H]+/ MS (found) | Name |
|---|---|---|---|
| 278 | 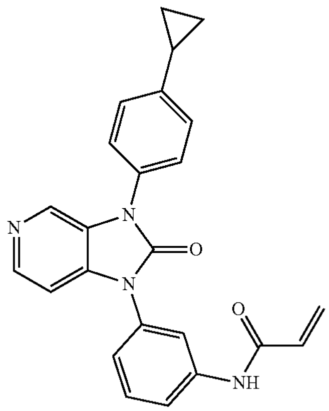 [SMILES: C=CC(=O)Nc1cccc(-n2c(=O)n(-c3ccc(C4CC4)cc3)c3cnccc32)c1] | 397/397 | N-(3-(3-(4-cyclopropylphenyl)-2-oxo-2,3-dihydro-1H-imidazo[4,5-c]pyridin-1-yl)phenyl)acrylamide |

Btk Kinase Assay and Other Kinases Assay

Btk kinase activity was determined using a homogenous time resolved fluorescence (HTRF) methodology. Measurements were performed in a reaction volume of 15 μL using 384-well assay plates. Kinase enzyme, inhibitor, ATP and 1 μM peptide substrate were incubated in a reaction buffer compose of Hepes 50 mM (pH7.0), $NaN_3$ 0.02%, BSA 0.01%, Orthocanadate 0.1 mM. After one hour, the kinase reaction was quenched by the addition of Eμ-labeled antibody and XL-665 in 1× Detection buffer containing 60 mM EDTA (Cisbio), and the mixture was allowed to incubate for one hour. The HTRF signal was measured on a multimode plate reader (EnVision® Multilabel Reader, Perkin Elmer) with an excitation wavelength ($\lambda_{Ex}$) of 330 nm and detection wavelengths ($\lambda_{Em}$) of 615 and 665 nrm. Activity was determined by the ratio of the fluorescence at 665 nm to that at 615 nm. For each compound, enzyme activity as measured at various concentrations of compound, Negative control reactions were performed in the absence of inhibitor in two replicates and eight no enzyme controls were used to determine baseline fluorescence levels. $IC_{50}$s were obtained according to the equation:

$Y=100/(1+10\hat{}((Log\ IC50-X)*HillSlope))$.

For BTK assay, [ATP]=80 μM, BTK=3.4 nM.

For LYN assay, [ATP]=20 μM, LYN=0.12 n M. For LCK assay, [ATP]=20 μM, LCK=0.2 nM. For BLK assay, [ATP]=20 μM, BLK=0.6 n M.

Example 279

The following Table shows the activity of selected compounds of this invention in the BTK inhibition assay. The compound numbers correspond to the compound numbers in previous Tables. Compounds having an activity designated as "A" provided an $IC_{50}\leq10$ nM; Compounds having an activity designated as "B" provided an $IC_{50}$ 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50}\geq10000$ nM.

| BTK Inhibition Data | | | | | | | |
|---|---|---|---|---|---|---|---|
| Compound # | BTK Inhibition | Compound # | BTK Inhibition | Compound # | BTK Inhibition | Compound # | BTK Inhibition |
| 1 | B | 2 | A | 3 | B | 4 | A |
| 5 | A | 6 | B | 7 | B | 8 | A |
| 9 | B | 10 | C | 11 | C | 12 | B |
| 13 | B | 14 | B | 15 | C | 16 | B |
| 17 | C | 18 | C | 19 | B | 20 | B |
| 21 | B | 22 | E | 23 | B | 24 | B |
| 25 | A | 26 | A | 27 | D | 28 | D |
| 29 | E | 30 | E | 31 | A | 32 | E |
| 33 | B | 34 | E | 35 | B | 36 | C |
| 37 | C | 38 | A | 39 | B | 40 | B |
| 41 | A | 42 | B | 43 | C | 44 | B |
| 45 | B | 46 | D | 47 | D | 48 | B |
| 49 | B | 50 | C | 51 | A | 52 | C |
| 53 | B | 54 | B | 55 | B | 56 | B |
| 57 | B | 58 | B | 59 | B | 60 | A |
| 61 | B | 62 | B | 63 | B | 64 | C |
| 65 | D | 66 | B | 67 | B | 68 | C |
| 69 | B | 70 | D | 71 | C | 72 | B |
| 73 | B | 74 | B | 75 | B | 76 | B |
| 77 | B | 78 | B | 79 | B | 80 | C |
| 81 | C | 82 | C | 83 | B | 84 | B |

BTK Inhibition Data

| Compound # | BTK Inhibition | Compound # | BTK Inhibition | Compound # | BTK Inhibition | Compound # | BTK Inhibition |
|---|---|---|---|---|---|---|---|
| 85 | B | 86 | C | 87 | B | 88 | B |
| 89 | B | 90 | B | 91 | B | 92 | B |
| 93 | A | 94 | B | 95 | B | 96 | B |
| 97 | B | 98 | B | 99 | B | 100 | B |
| 101 | B | 102 | B | 103 | B | 104 | C |
| 105 | B | 106 | B | 107 | B | 108 | B |
| 109 | E | 110 | C | 111 | D | 112 | B |
| 113 | B | 114 | B | 115 | C | 116 | C |
| 117 | B | 118 | B | 119 | D | 120 | D |
| 121 | C | 122 | D | 123 | E | 124 | C |
| 125 | B | 126 | C | 127 | C | 128 | A |
| 129 | C | 130 | C | 131 | B | 132 | A |
| 133 | A | 134 | B | 135 | B | 136 | B |
| 137 | C | 138 | B | 139 | B | 140 | C |
| 141 | B | 142 | B | 143 | B | 144 | B |
| 145 | C | 146 | B | 147 | B | 148 | B |
| 149 | B | 150 | B | 151 | A | 152 | B |
| 153 | B | 154 | D | 155 | B | 156 | D |
| 157 | A | 158 | B | 159 | B | 160 | C |
| 161 | C | 162 | C | 163 | C | 164 | D |
| 165 | C | 166 | A | 167 | A | 168 | A |
| 169 | C | 170 | C | 171 | C | 172 | A |
| 173 | B | 174 | B | 175 | C | 176 | A |
| 177 | C | 178 | B | 179 | E | 180 | C |
| 181 | B | 182 | E | 183 | E | 184 | A |
| 185 | A | 186 | A | 187 | C | 188 | C |
| 189 | E | 190 | C | 191 | A | 192 | D |
| 193 | D | 194 | E | 195 | B | 196 | C |
| 197 | C | 198 | C | 199 | C | 200 | C |
| 201 | B | 202 | C | 203 | C | 204 | C |
| 205 | C | 206 | C | 207 | C | 208 | C |
| 209 | C | 210 | B | 211 | C | 212 | C |
| 213 | D | 214 | D | 215 | D | 216 | C |
| 217 | C | 218 | C | 219 | C | 220 | C |
| 221 | B | 222 | B | 223 | C | 224 | C |
| 225 | C | 226 | C | 227 | C | 228 | C |
| 229 | B | 230 | B | 231 | B | 232 | B |
| 233 | B | 234 | C | 235 | B | 236 | C |
| 237 | B | 238 | C | 239 | C | 240 | B |
| 241 | C | 242 | C | 243 | C | 244 | C |
| 245 | C | 246 | C | 247 | B | 248 | C |
| 249 | B | 250 | D | 251 | D | 252 | C |
| 253 | D | 254 | D | 255 | D | 256 | D |
| 257 | D | 258 | B | 259 | C | 260 | B |
| 261 | C | 262 | C | 263 | C | 264 | C |
| 265 | C | 266 | C | 267 | E | 268 | C |
| 269 | C | 270 | E | 271 | B | 272 | C |
| 273 | C | 274 | C | 275 | E | 276 | D |
| 277 | C | 278 | B | | | | |

Example 280

The following Table shows the activity of selected compounds of this invention in the BTK, BLK, LYN, LCK inhibition assay. The compound numbers correspond to the compound numbers in previous Tables. Compounds having an activity designated as "A" provided an $IC_{50} \leq 10$ nM; Compounds having an activity designated as "B" provided an IC so 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50} \geq 10000$ nM; N/A is not available.

TABLE 2

| Compound | BTK $IC_{50}$ | BLK $IC_{50}$ | LYN $IC_{50}$ | LCK $IC_{50}$ |
|---|---|---|---|---|
| 1 | B | B | E | E |
| 2 | A | B | E | E |
| 3 | B | C | E | N/A |
| 4 | A | B | D | D |
| 5 | A | B | E | E |
| 8 | A | C | D | E |
| 20 | B | B | E | D |
| 26 | A | C | D | E |
| 31 | A | C | D | E |
| 38 | A | B | E | E |
| 51 | A | B | E | E |
| 60 | A | B | E | E |
| 103 | B | C | D | E |
| 128 | B | C | E | E |
| 132 | A | C | E | E |
| 133 | A | B | E | E |
| 138 | B | C | E | E |

Calcium FluxAssay

Calcium flux fluorescence-based assays were performed in aFDSS7000EX (Hamamatsu Photonics) fluorometric imaging plate reader according to manufacturer instructions. Compounds to be assayed were dissolved in DMSO, diluted to appropriate concentrations in $Ca^{2+}$ buffer ranging from 0 to 10 μM (at a dilution factor of 0.1), added 5 μl (6×) to each well (the final DMSO concentration was 0.1% in each well). Then 12.5 μL 2× dye loading solution (Fluo-4 NW Calcium Assay Kits, Invitrogen) was added per well of a 384-well plate. Afterwards, actively growing Ramos cells (ATCC) in RPM1640 medium supplemented with 10% FBS (Invitrogen) were washed and re-plated in assay buffer (from Fluo-4 NW Calcium Assay Kits, Invitrogen) to approximately 6.4× $10^6$/ml (80000 cells/12.5 μL in 384-well plates). The plates were incubated at 37° C. for 30 minutes, then at room temperature for an additional 30 minutes. The plates were now ready to be used in an experiment Immediately after the transfer and a 10-s recording of baseline fluorescence, the compound treated cells were stimulated with a goat anti-human IgM antibody (10 μg/ml; Jackson Immuno Research) and read in a FDSS for 240 seconds. Difference between the signal and that at baseline, designated adjusted relative fluorescence unit, was calculated by using a custom Excel (Microsoft, Redmond, Wash.) template to determine IgM-induced calcium influx and its inhibition by compounds. The table belows show the result. Compounds having an activity designated as "A" provided an $IC_{50} \leq 10$ nM; Compounds having an activity designated as "B" provided an $IC_{50}$ 10-100 nM; Compounds having an activity designated as "C" provided an $IC_{50}$ 100-1000 nM.

TABLE 3

| Cmpd. | Ramos Ca Flux (nM) |
|---|---|
| Example 4 | B |
| Example 5 | B |

Btk Occupancy in Cellular Assays

For PCI-33380 labeling of human B cells, $10^6$ Jeko-1 cells were pre-incubated with compound for 1.5 h before labeling. Then cells were treated with PCI-33380 at 5 μM for 1 h. Washed, lysed in Ripa buffer containing sample reducing agent, and analyzed by SDS/PAGE and fluorescent gel scanning using a Typhoon scanner 9500 (GE Healthcare) (Ex, 532 nm; Em, 555 nm). The gel was then blotted and total Btk levels detected by standard Western blot with Btk antibody (CST).

By using the fluorescently tagged derivative PCI-33380, we found that 100 nM of Compound 4 and 5 were sufficient to fully occupy the active site of Btk in human mantle cell lymphoma cell lines Jeko-1 cells in culture.

Btk Occupancy In Vivo

For analysis of Btk occupancy in Babc/L mice following oral dosing of compounds after 4 hours. Isolating peripheral blood mononuclear cells (PBMCs) with mouse peripheral blood separation kit (Hao Yang Biological Manufacture CO., LTD, Tianjin) were collected from Babc/L mice (1 ml blood from two mice). Spleens were processed to splenocytes followed by 5 min incubation in red blood cell lysing buffer (from mouse peripheral blood separation kit). PBMCs or splenocytes were then PCI-33380-labeled and lysates analyzed by fluorescent gel scanning as described in cellular assays. Compound 5 was achieved full occupancy at 25 mg/kg single oral dose in all Babc/L mice.

What is claimed is:

1. A compound of Formula (I) having the following structure:

Formula (I)

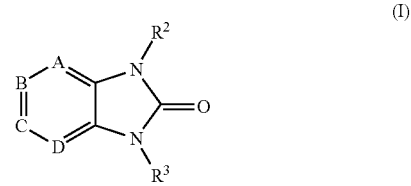

wherein:
A is $CR^1$;
B is N;
C and D are $CR^1$;
$R^1$ is hydrogen, OH, CN, NHOH or $CONH_2$;
$R^2$ is

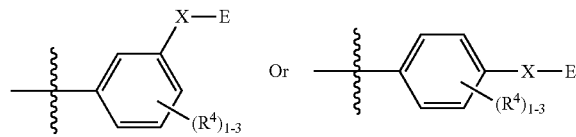

—X-E is one of the followings:
(1) X is O, $OCR^aR^b$, S(O), $S(O)_2$, $CR^aR^b$, $NR^c$ (C=O), C=$ONR^c$ or a bond; and E is a hydrogen, an aryl or a heteroaryl substituted with one to three $R^5$ substituents; or a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or
(2) —X-E is hydrogen, halogen, —$OR^a$, —$O(CH_2)_{1-4}R^a$, —CN, or —$NO_2$;
$R^4$ and $R^5$ are each independently selected from the group consisting of hydrogen, halogen, hydroxy, cyano, $OCF_3$, $OCF_2H$, $C_{1-6}$ alkyl, optionally substituted with one to five fluorines, $C_{3-6}$ cycloalkyl, optionally substituted with one to five fluorines, $C_{1-4}$ alkoxy, optionally substituted with one to five fluorines, $C_{1-4}$ alkylthio, optionally substituted with one to five fluorines, $C_{1-4}$ alkylsulfonyl, optionally substituted with one to five fluorines, carboxy, $C_{1-4}$ alkyloxycarbonyl, and $C_{1-4}$ alkylcarbonyl;
$R^a$ and $R^b$ are each independently hydrogen, fluorine, or $C_{1-3}$ alkyl, optionally substituted with one to five fluorines;
$R^c$ is hydrogen or $C_{1-3}$ alkyl, optionally substituted with one to five fluorines;
$R^3$ is a group having a double bond, a tautomer thereof, or a pharmaceutical acceptable solvate thereof.

2. The compound of claim 1, wherein $R^3$ is selected from the group consisting of:

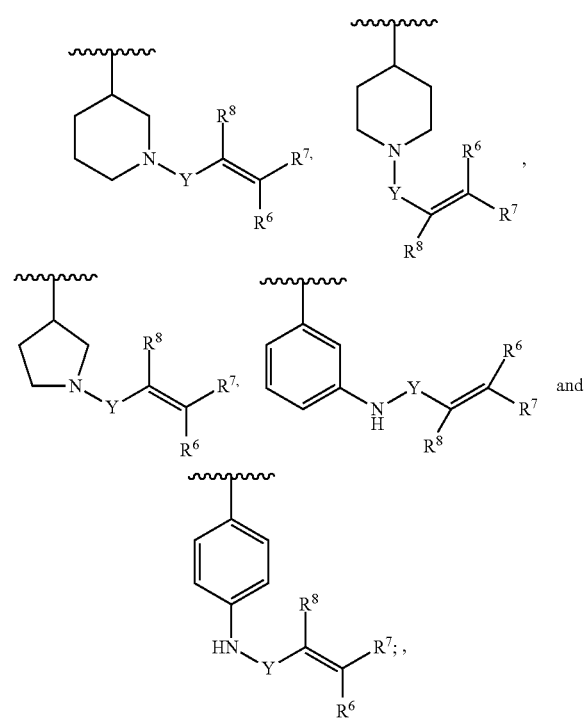

Y is C(=O); OC(=O), NHC(=O), S=O, S(=O)$_2$, or NHS(=O)$_2$;

$R^6$, $R^7$, and $R^8$ are each independently selected from the group consisting of hydrogen, halogen, CN, $C_{1-4}$ alkyl, $C_{1-6}$ alkoxyalkyl, $C_{1-8}$ alkylaminoalkyl, and $C_{1-4}$ alkylphenyl;

or $R^7$ and $R^8$ taken together form a bond.

3. The compound of claim 1, wherein $R^3$ is selected from the group consisting of:

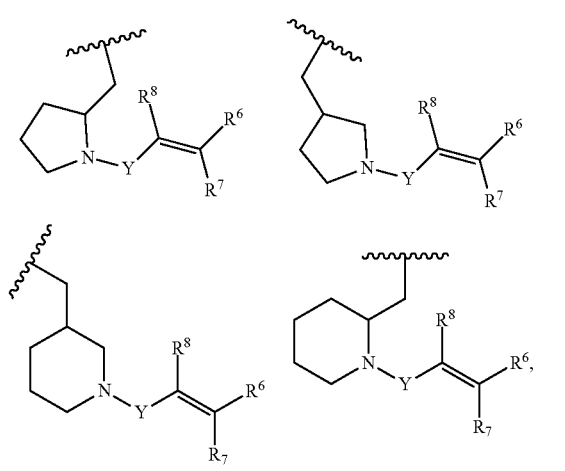

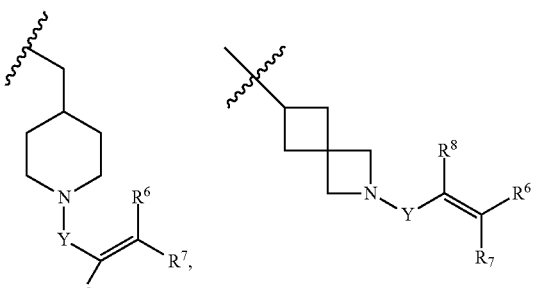

Y is C(=O); OC(=O), NHC(=O), S=O, S(=O)$_2$, or NHS(=O)$_2$;

$R^6$, $R^7$, and $R^8$ are each independently selected from the group consisting of hydrogen, halogen, CN, $C_{1-4}$ alkyl, $C_{1-6}$ alkoxyalkyl, $C_{1-8}$ alkylaminoalkyl, and $C_{1-4}$ alkylphenyl.

4. A pharmaceutical composition comprising a therapeutically effective amount of the compound of claim 1, and a pharmaceutically acceptable excipient.

5. A compound selected from the group consisting of

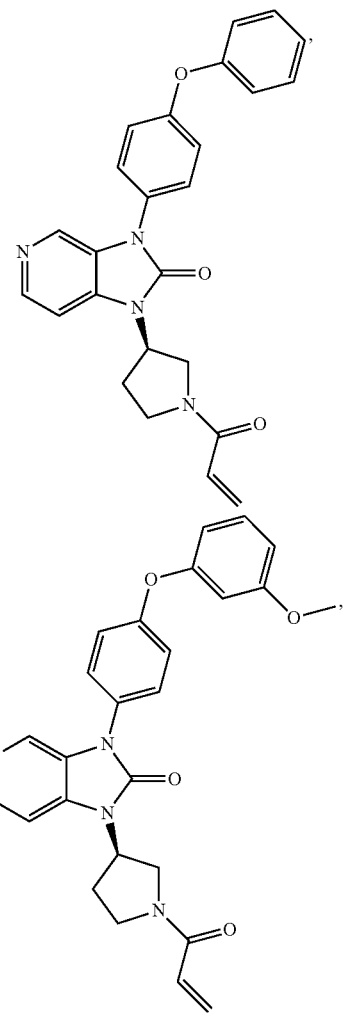

241
-continued
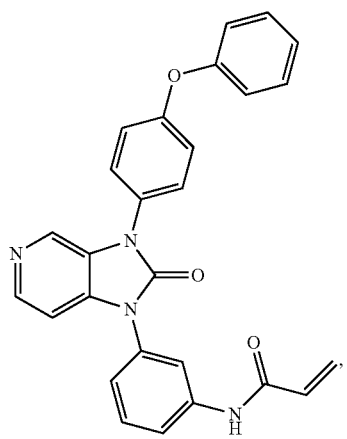
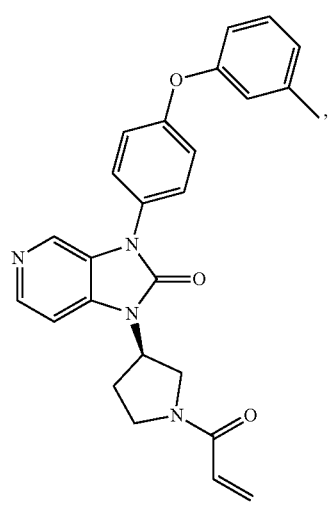
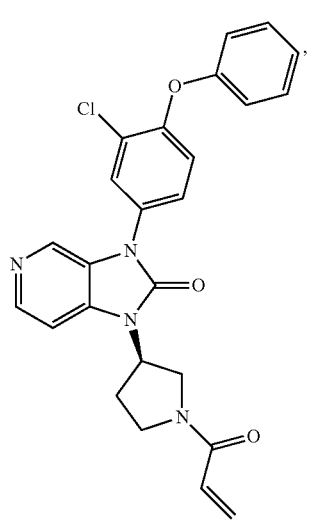
242
-continued
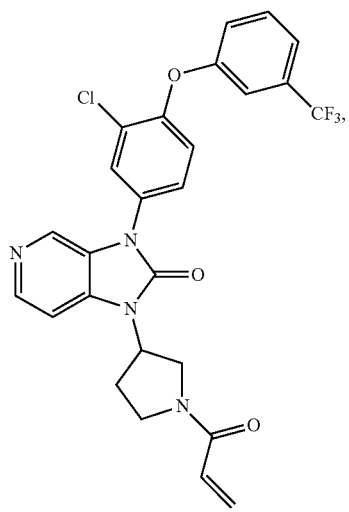
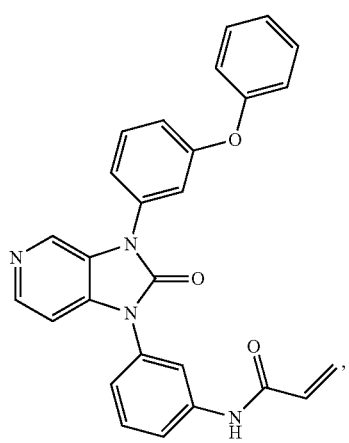
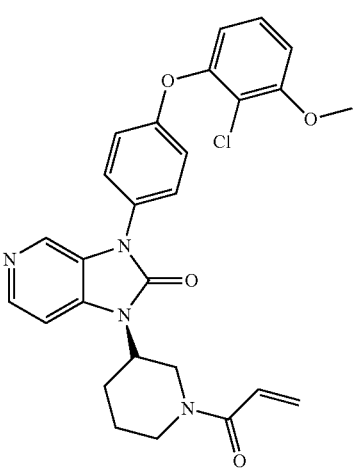

243
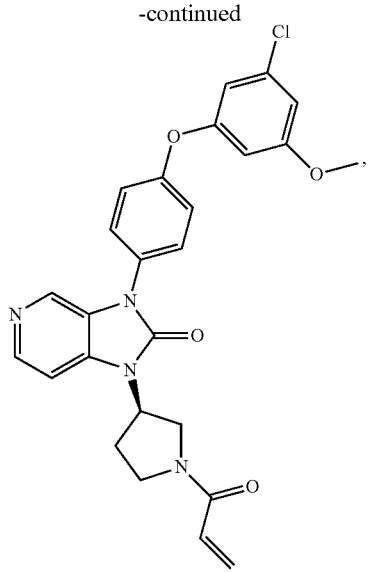
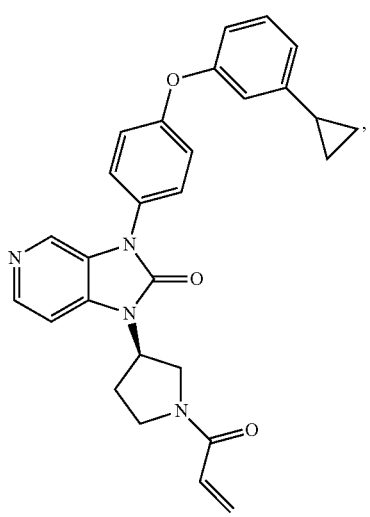
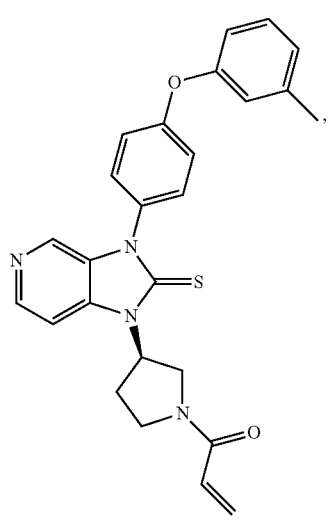
244
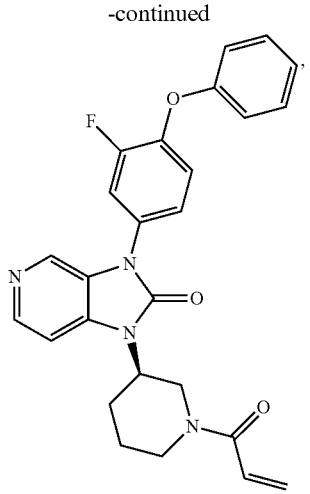
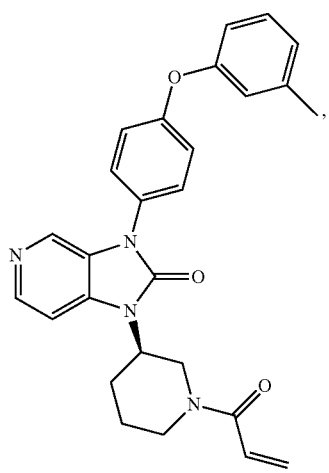
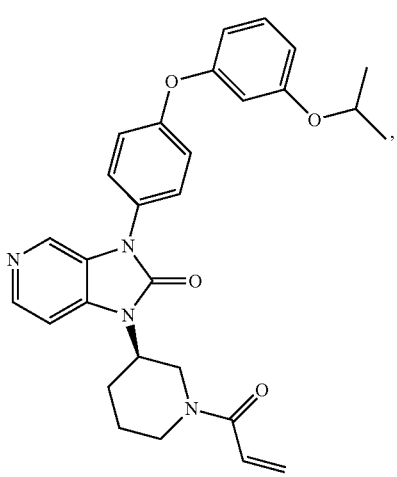

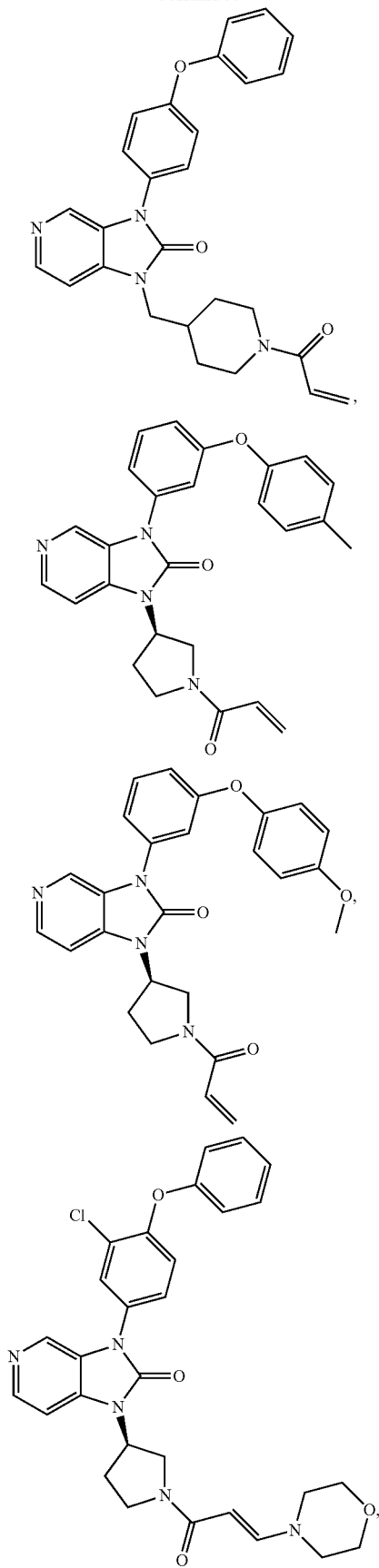
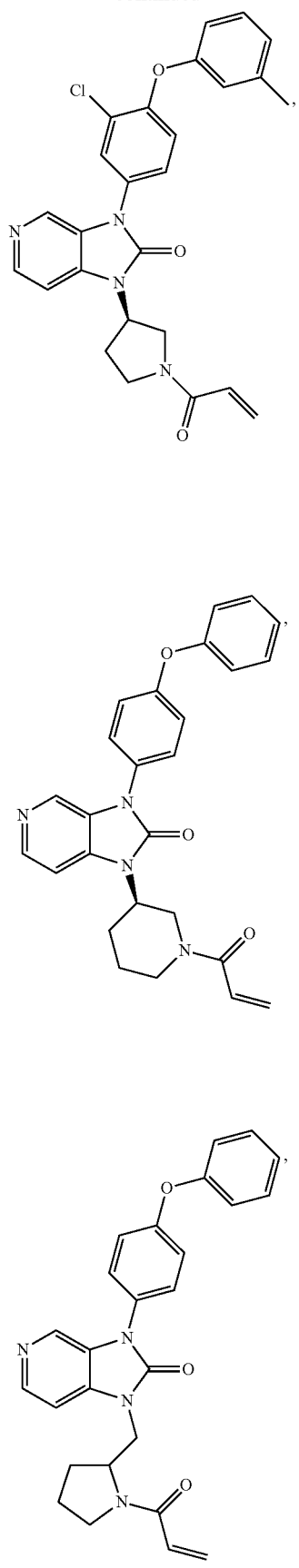

247
-continued
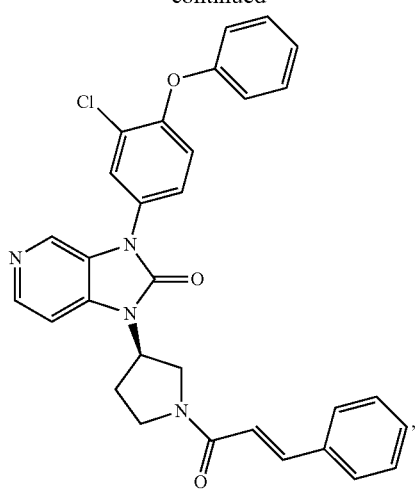
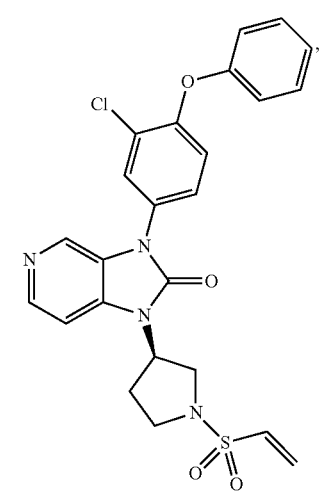
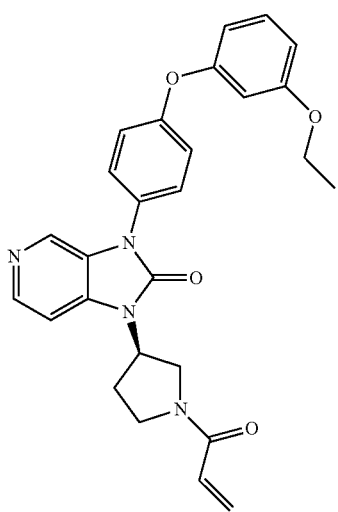
248
-continued
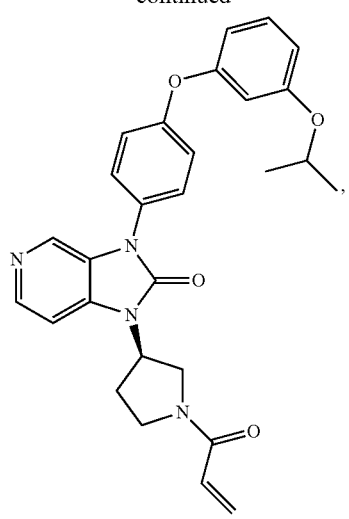
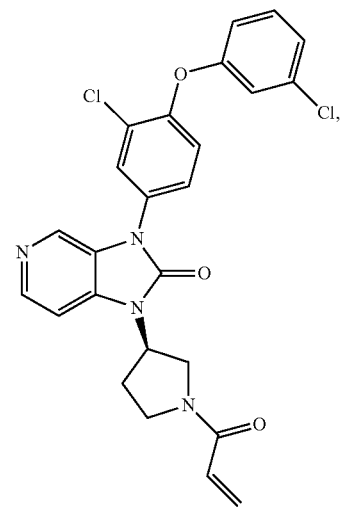
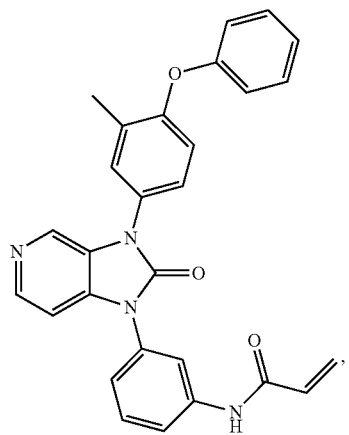

249
-continued
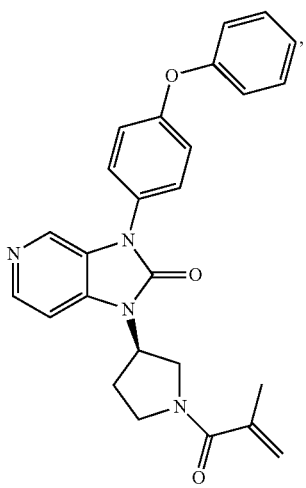
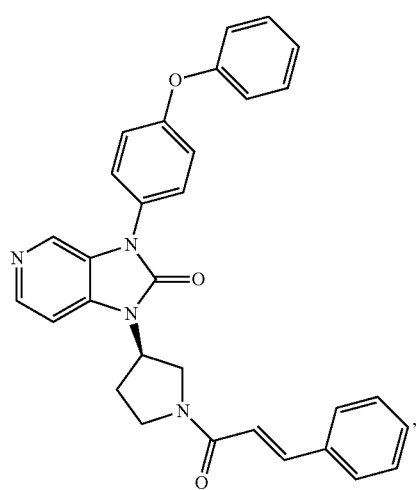
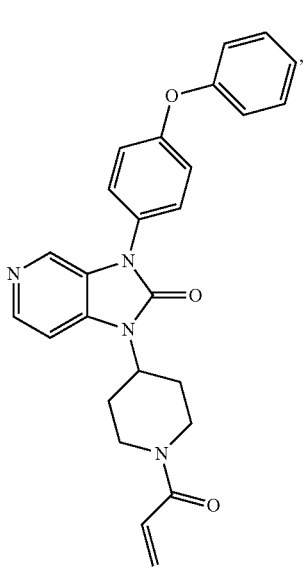
250
-continued
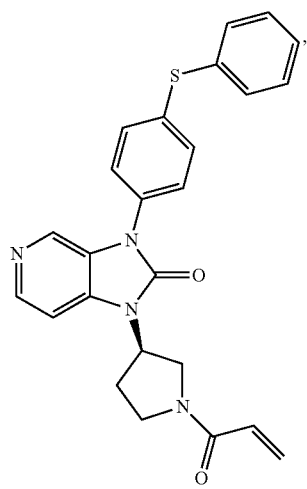
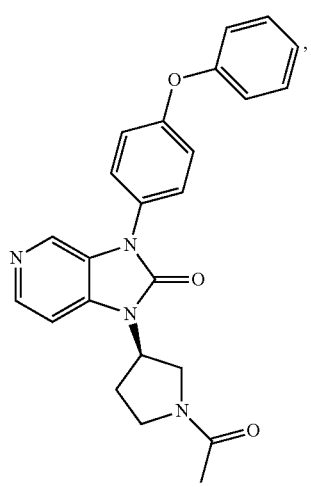
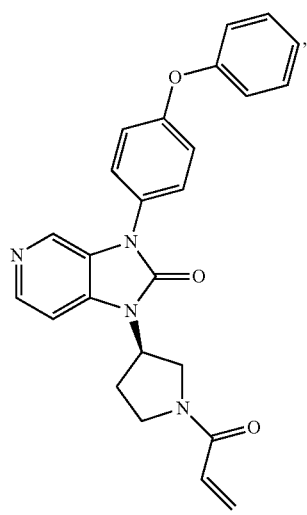

251
-continued
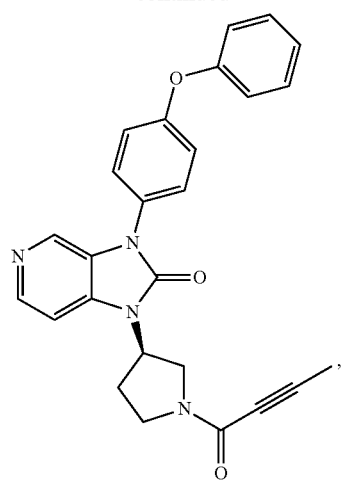
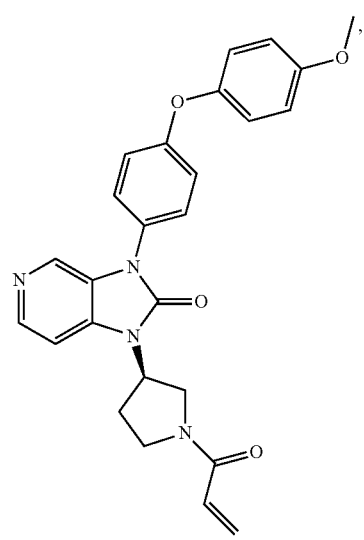
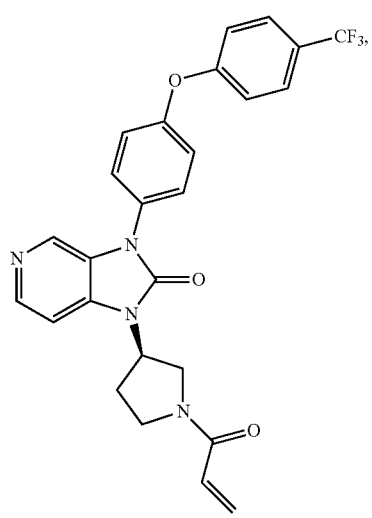
252
-continued
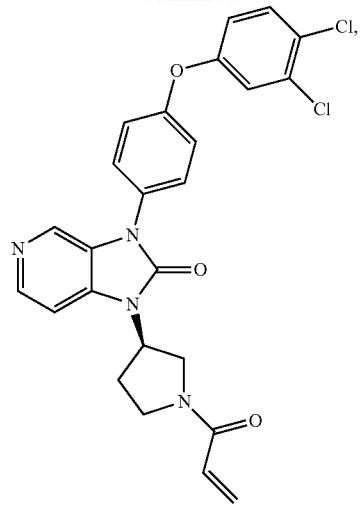
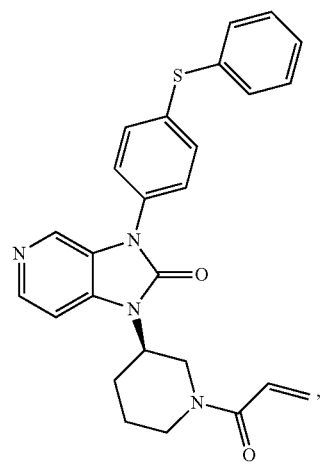
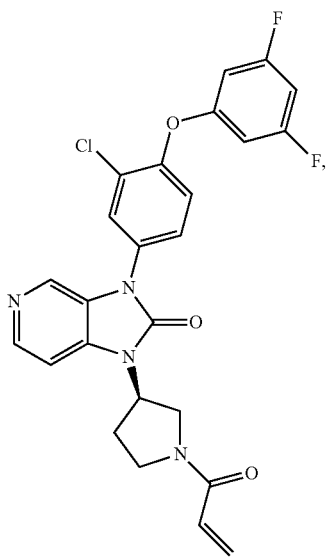

253
-continued
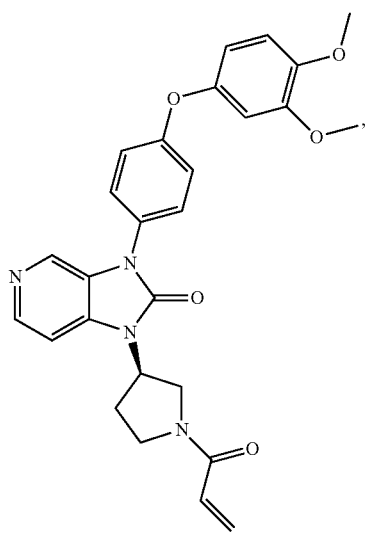
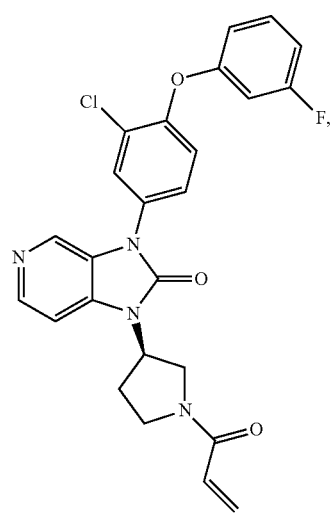
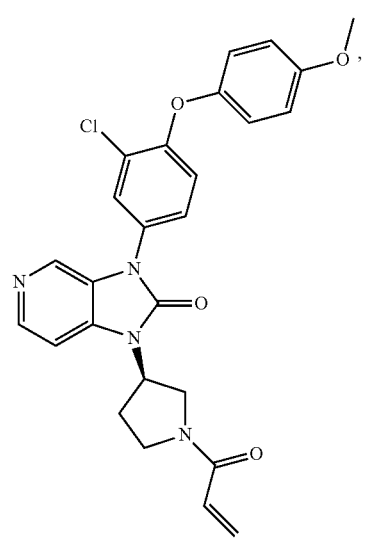
254
-continued
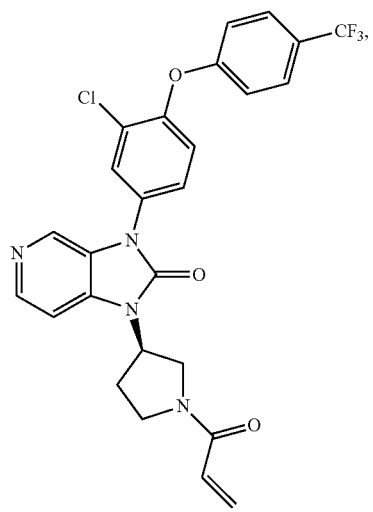
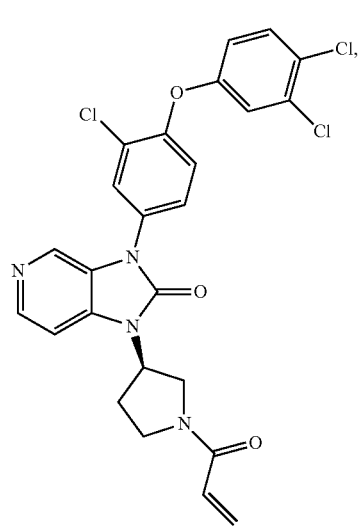
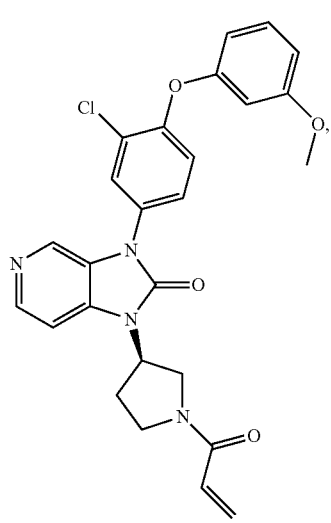

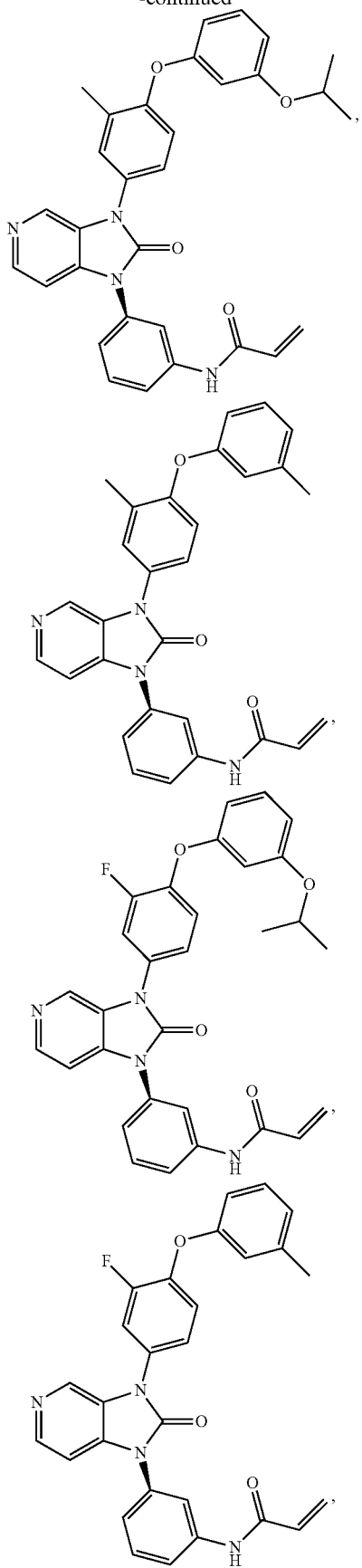
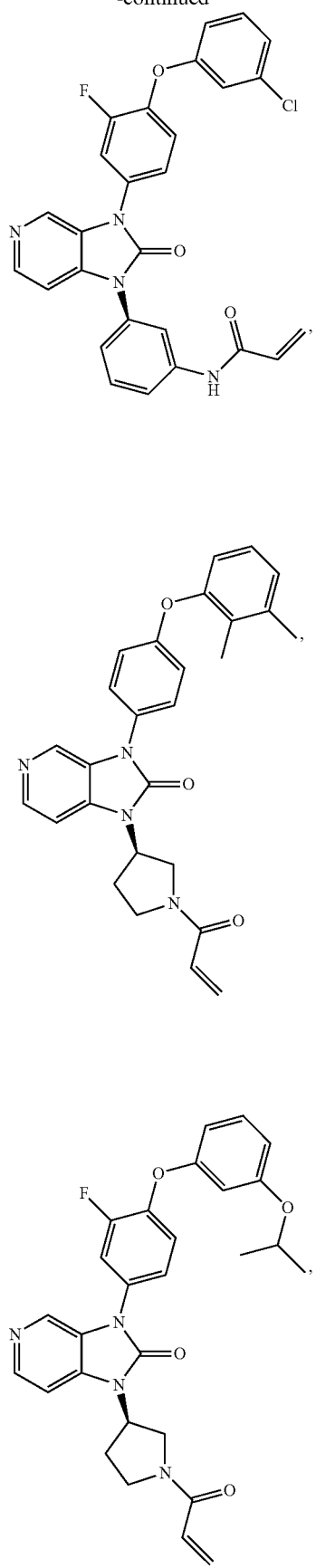

257
-continued
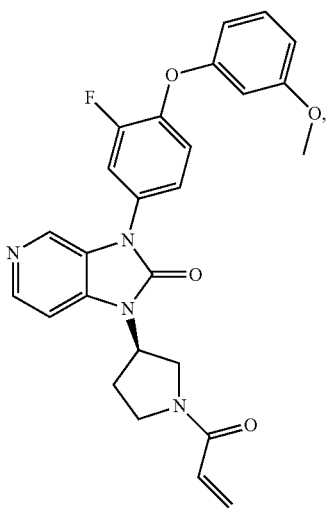
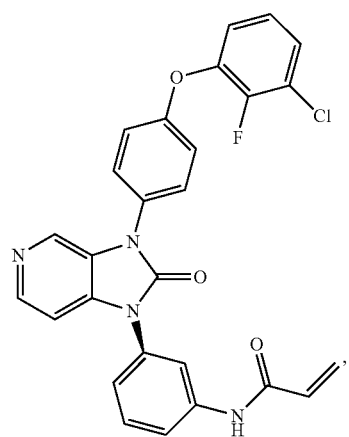
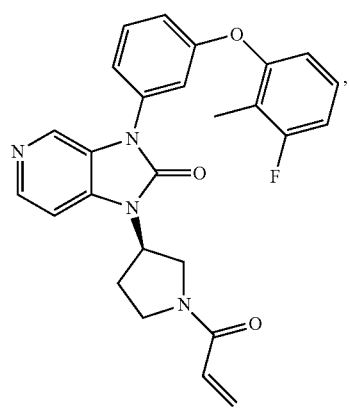
258
-continued
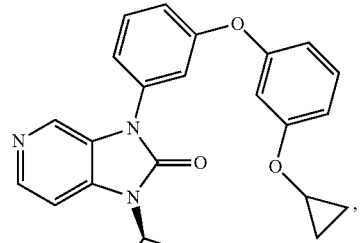
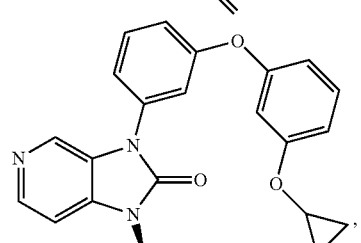
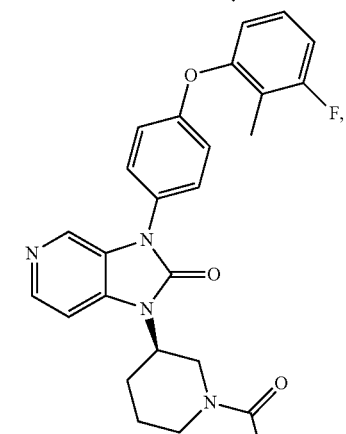
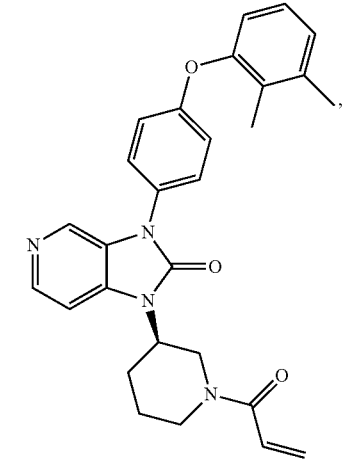

259
-continued
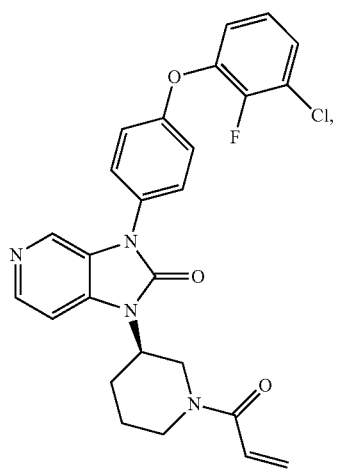
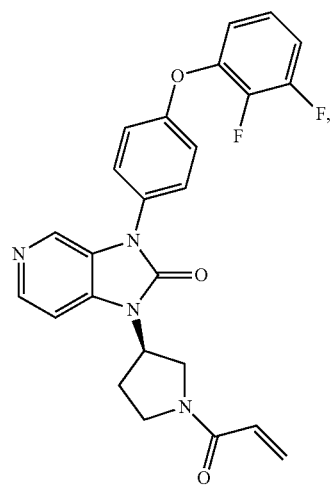
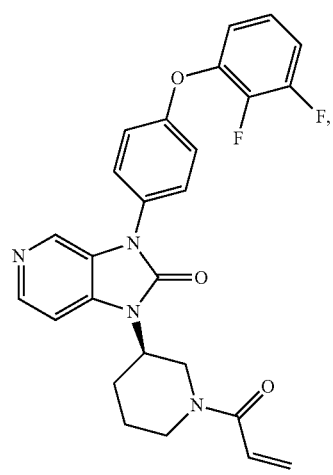
260
-continued
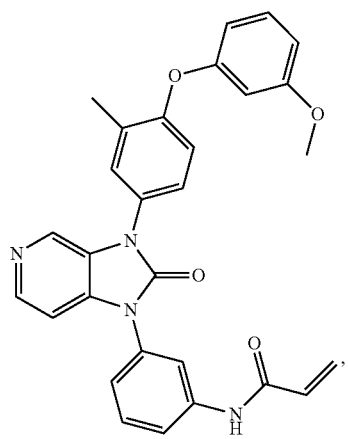
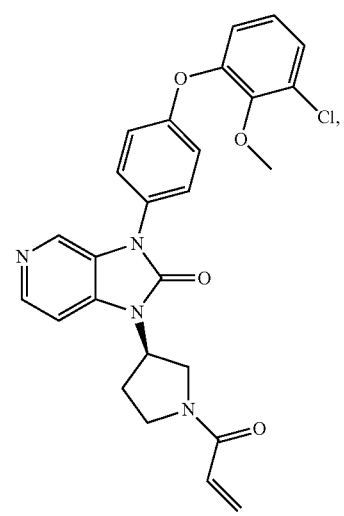
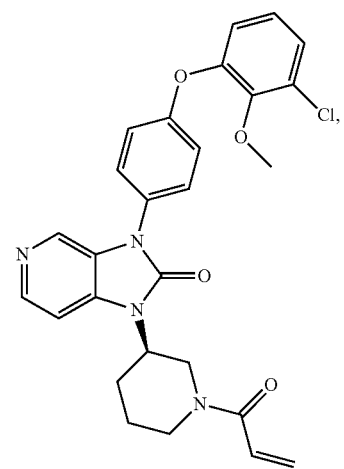

261
-continued
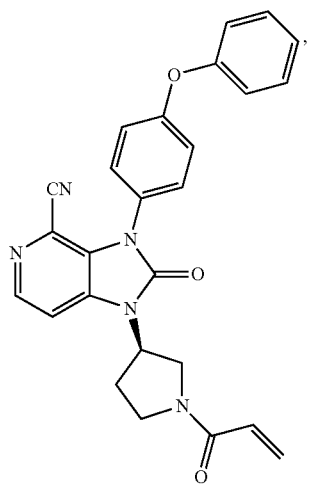
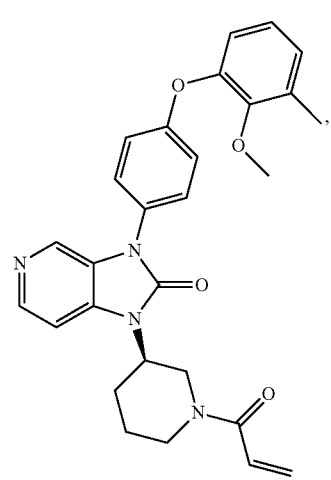
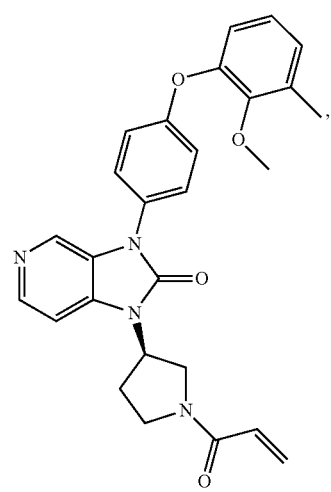
262
-continued
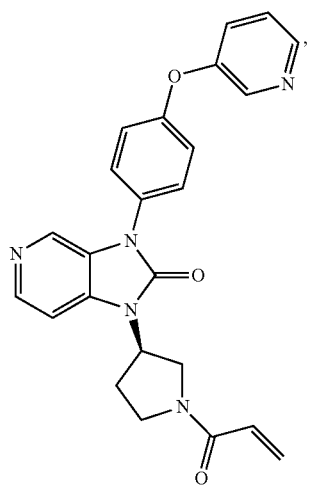
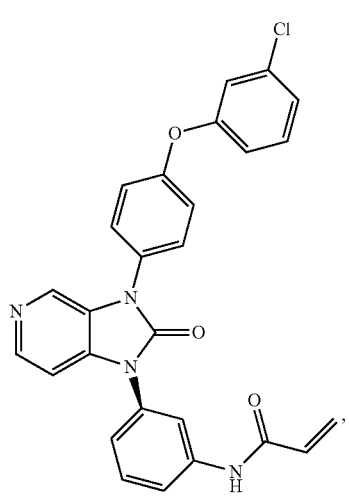
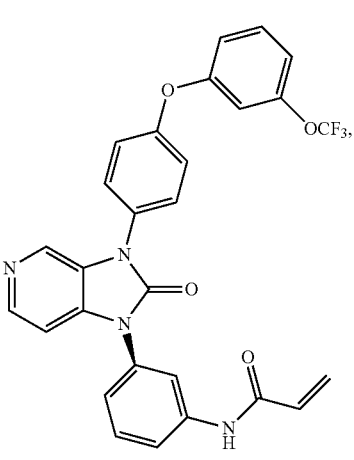

263
-continued
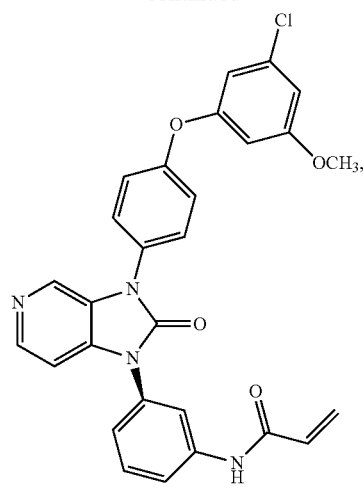
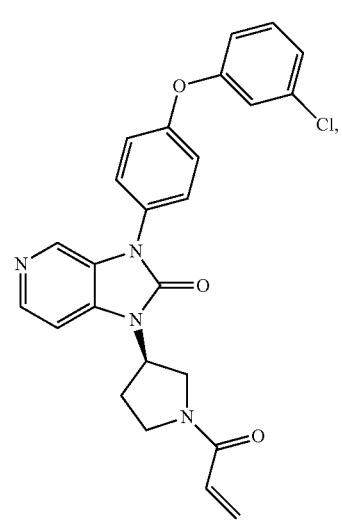
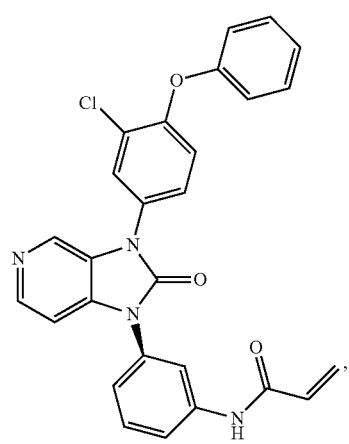
264
-continued
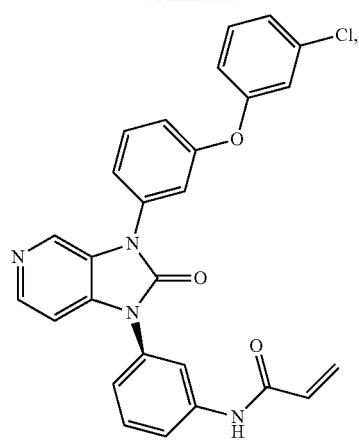
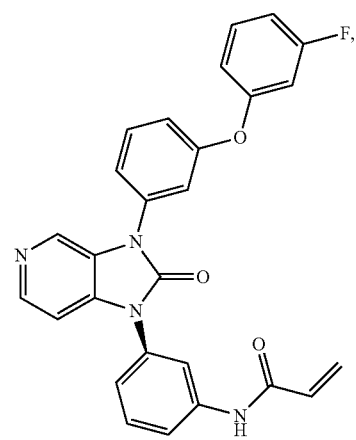
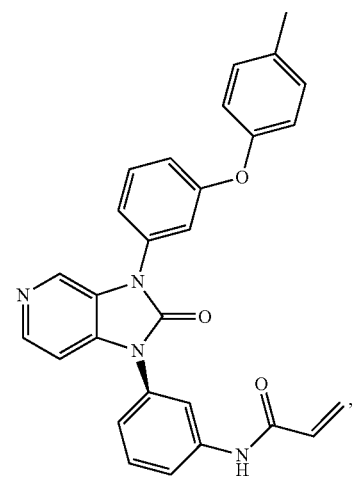

265
-continued
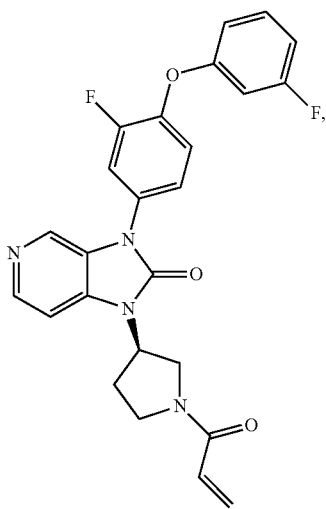
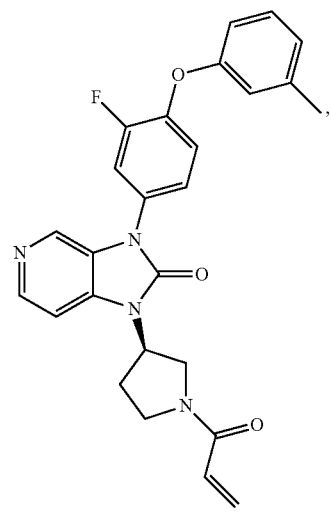
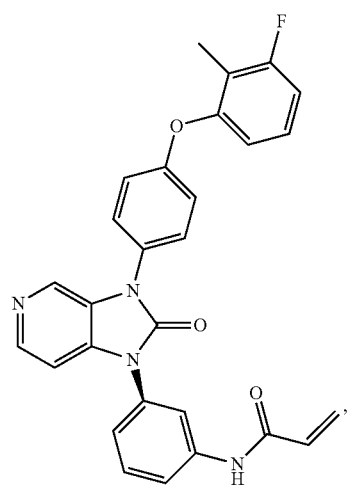
266
-continued
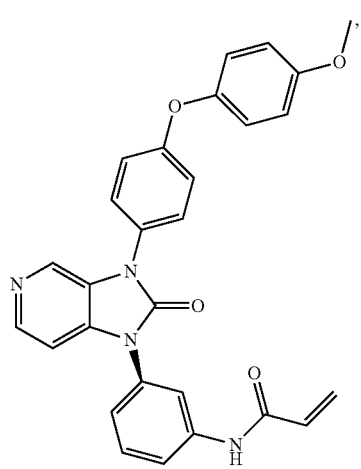
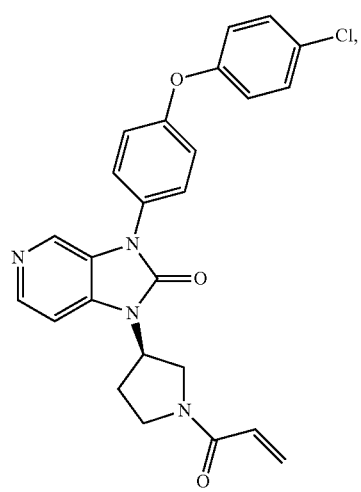

267
-continued
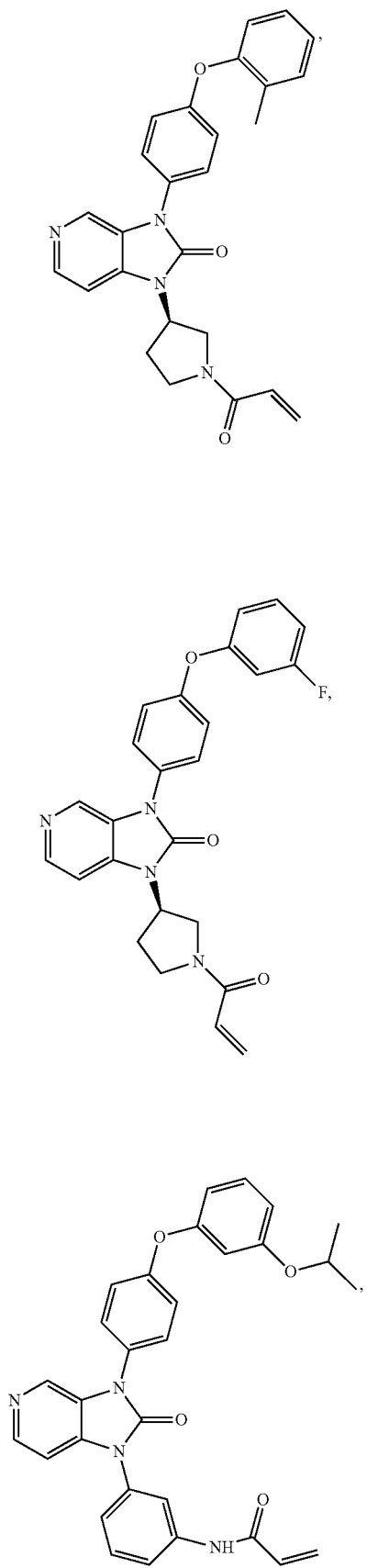
268
-continued
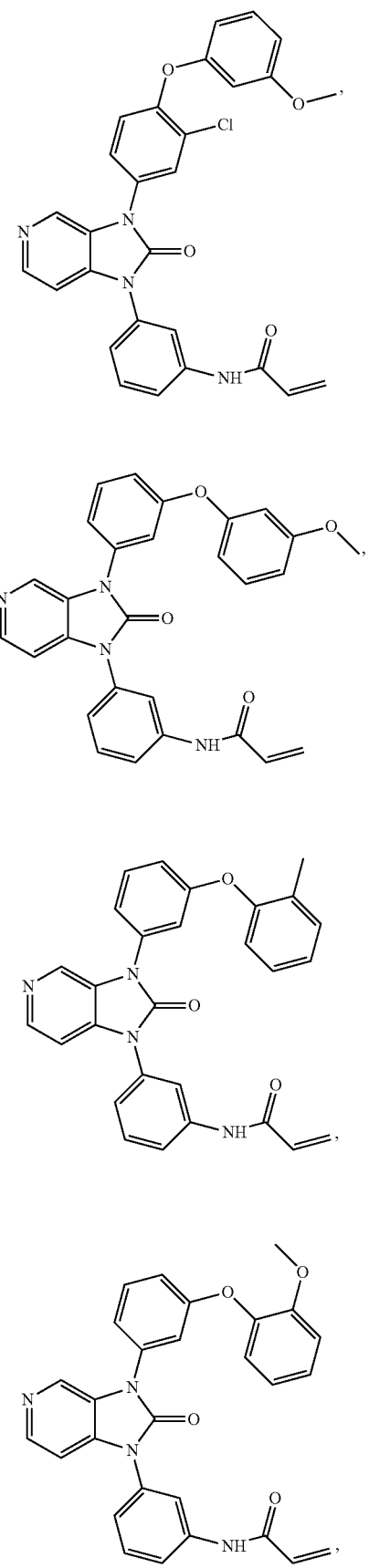

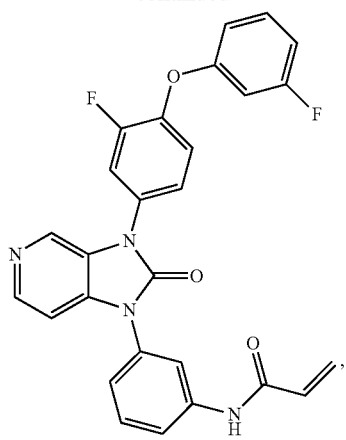
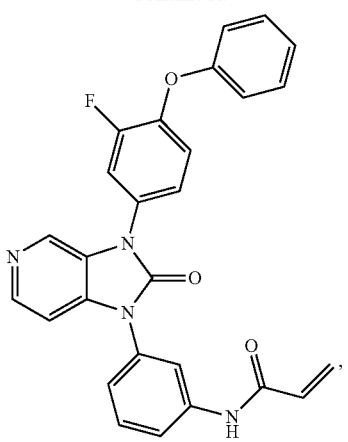

271
-continued

272
-continued

273
-continued
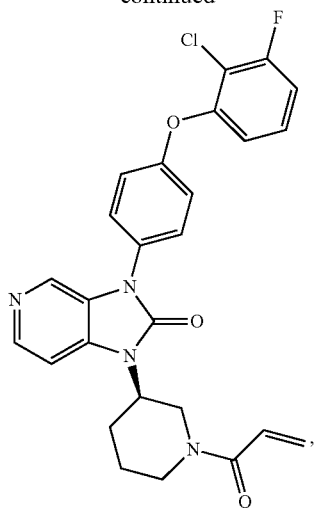
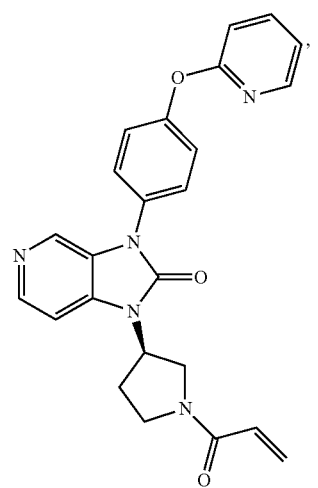
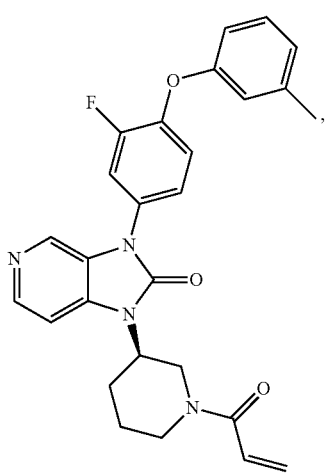
274
-continued
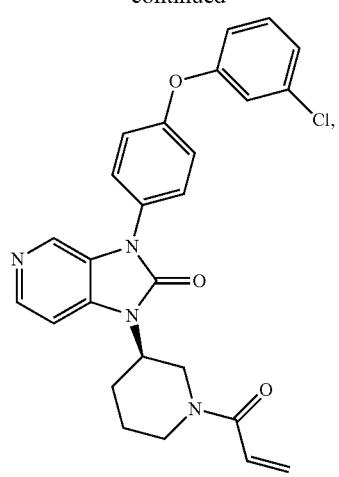
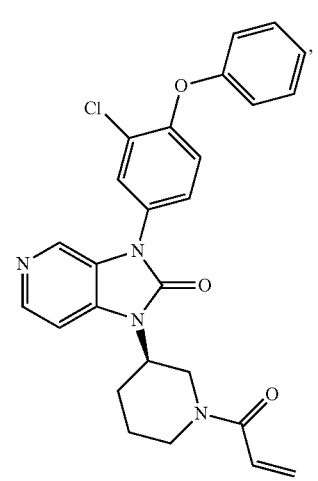
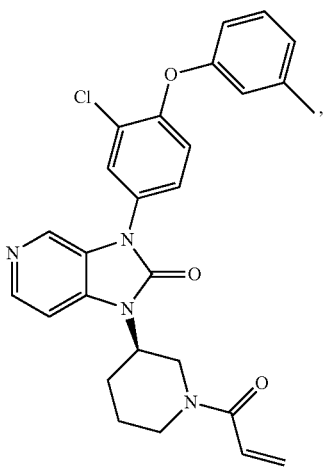

275
-continued
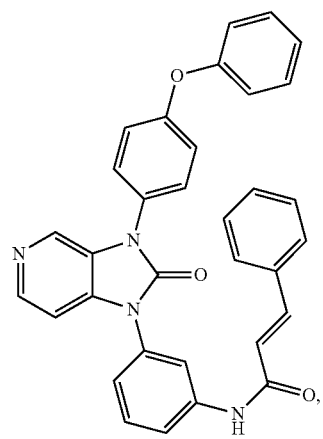
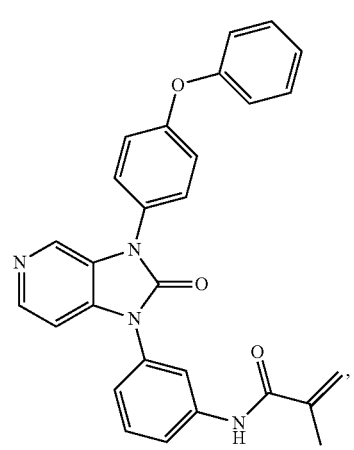
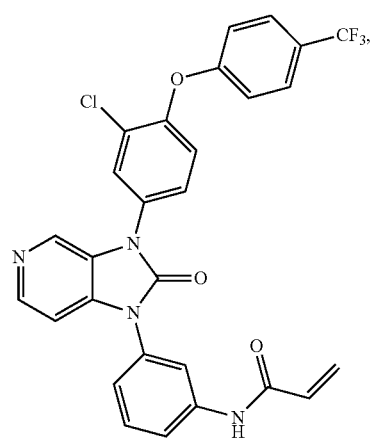
276
-continued
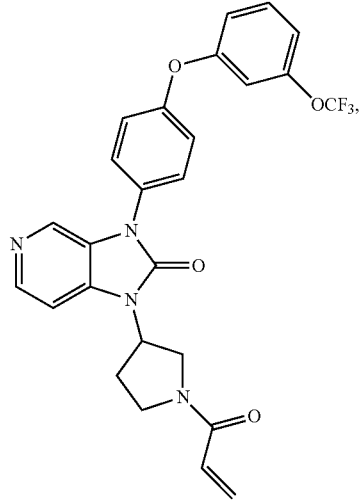
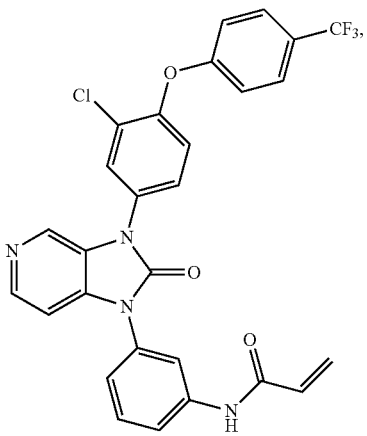
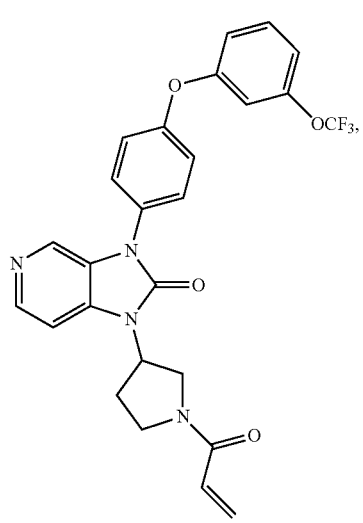

277
-continued
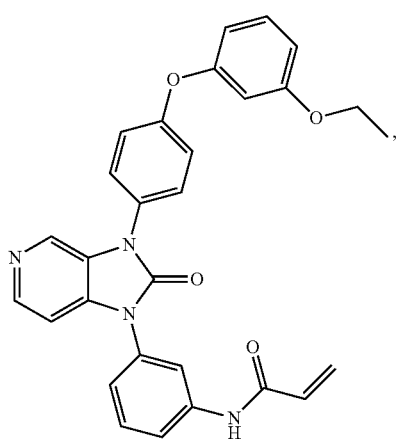
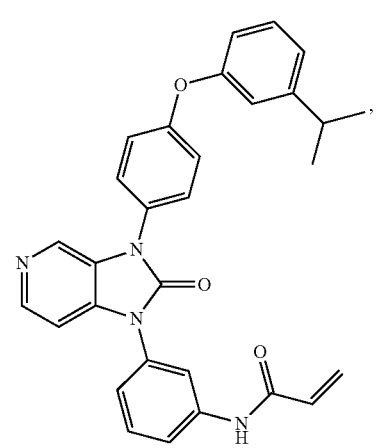
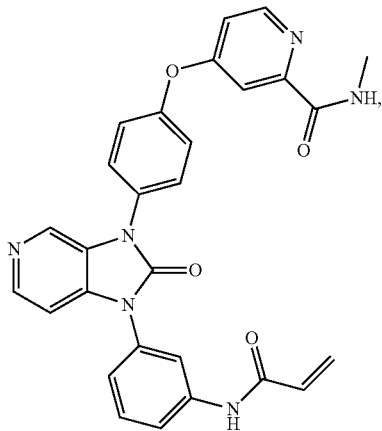
278
-continued
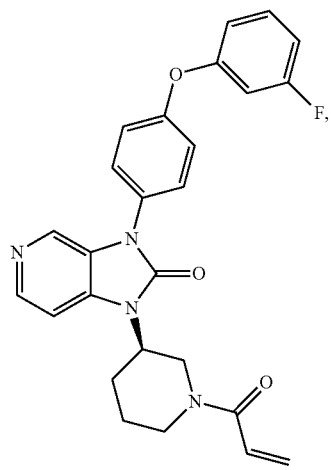
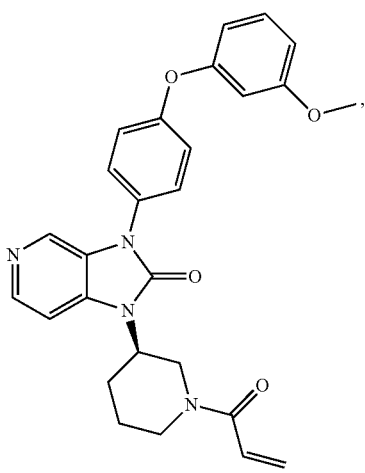
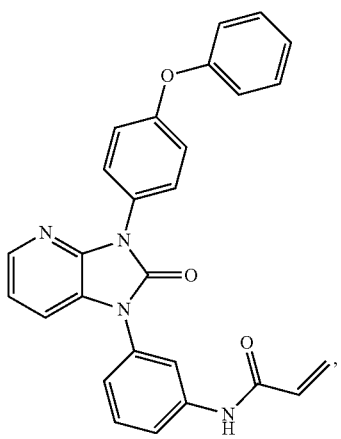

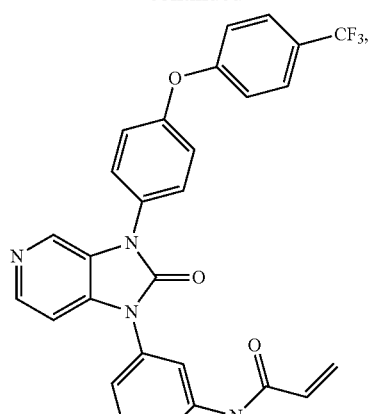
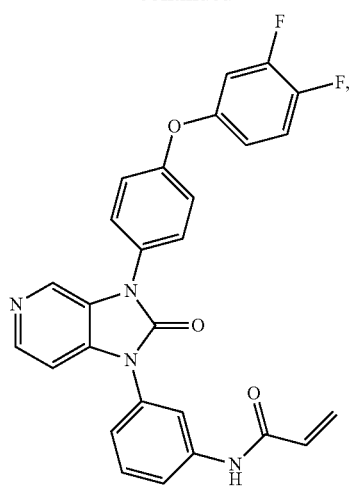
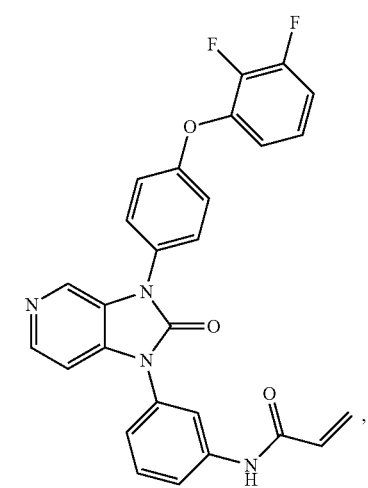
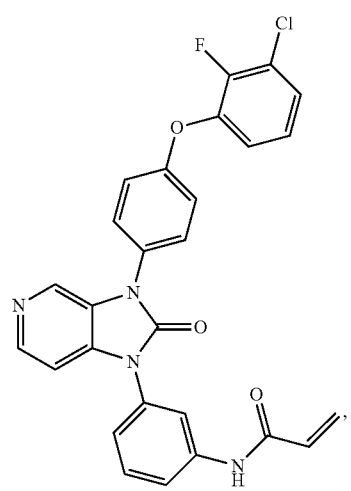

281
-continued
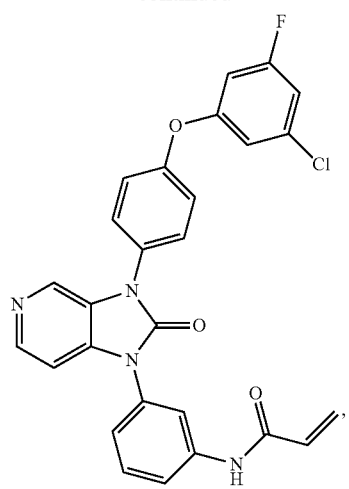
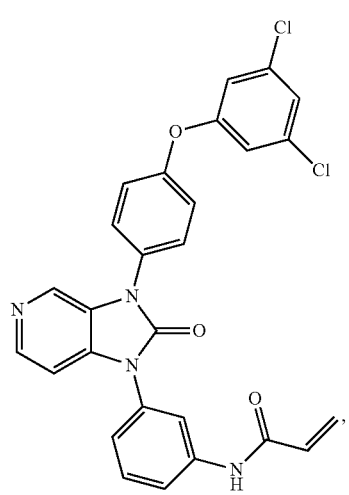
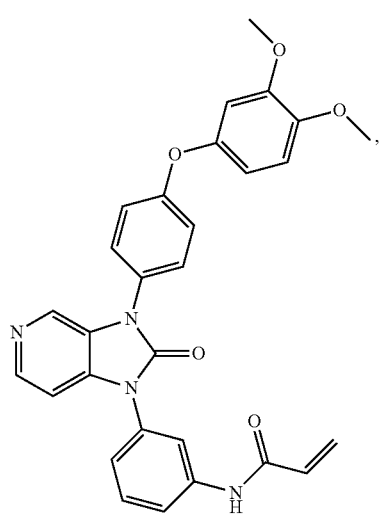
282
-continued
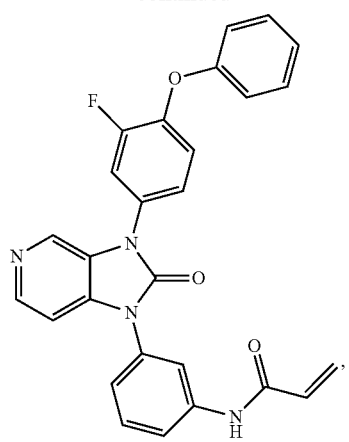
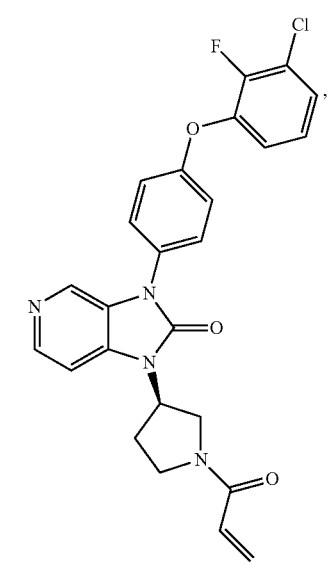
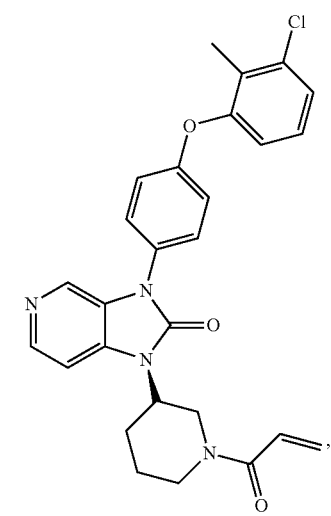

283
-continued
284
-continued
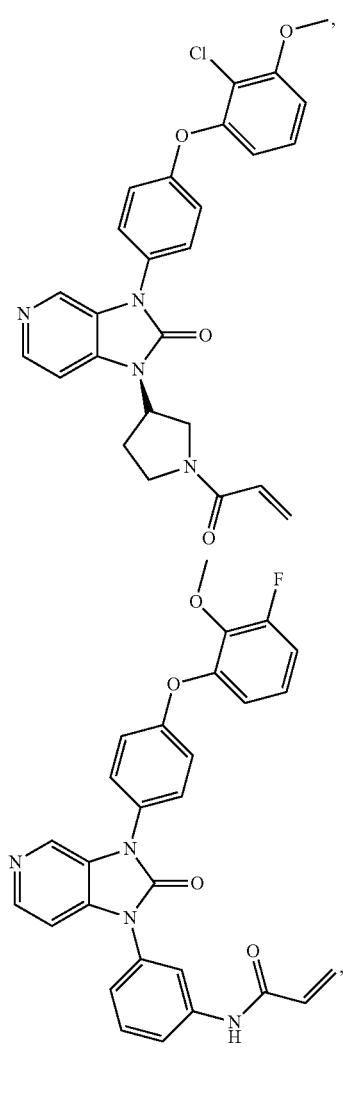
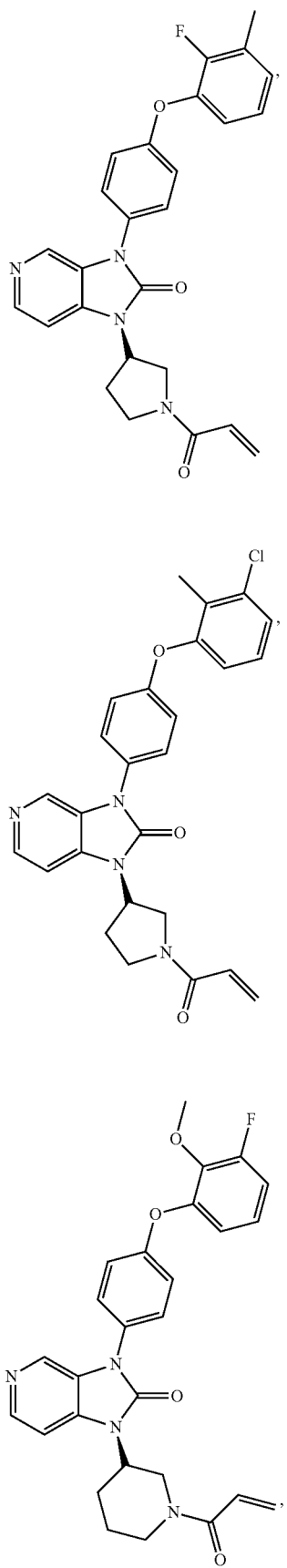

285
-continued
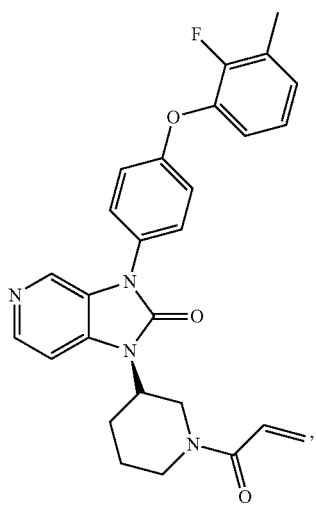
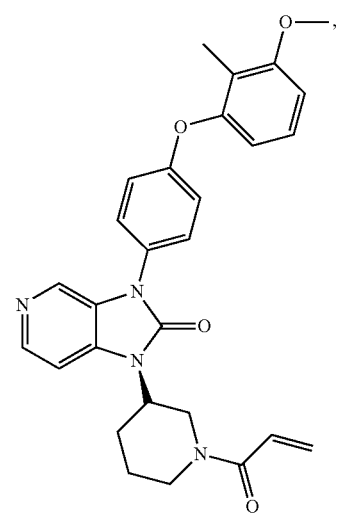
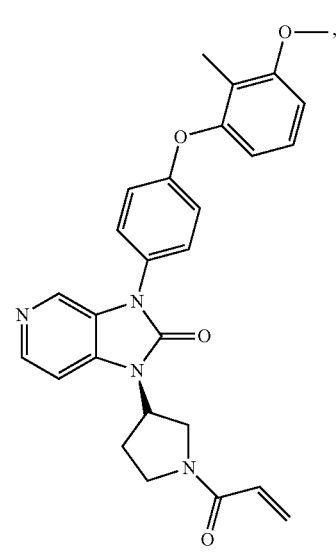
286
-continued
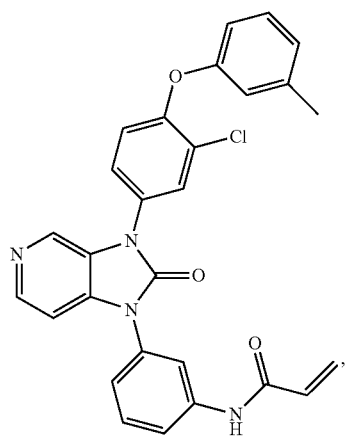
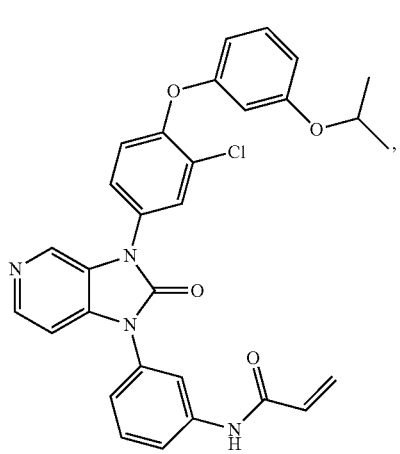
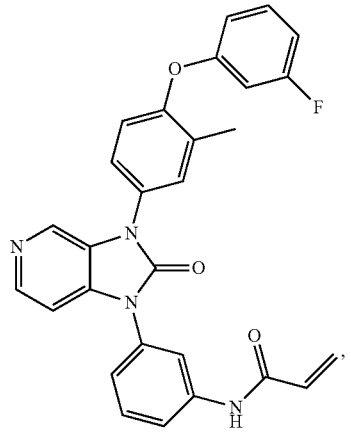

287
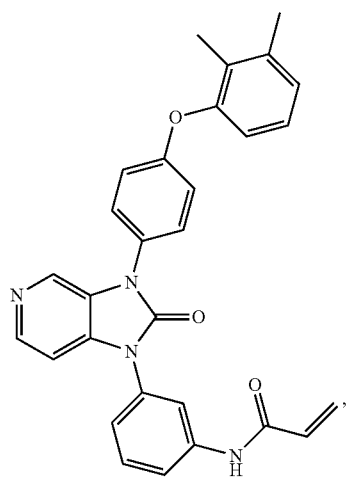
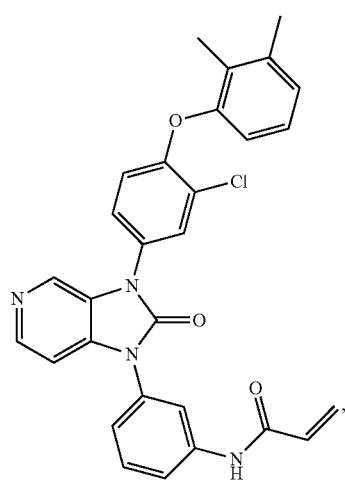
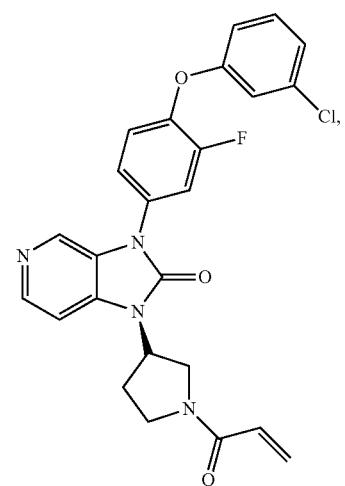
288
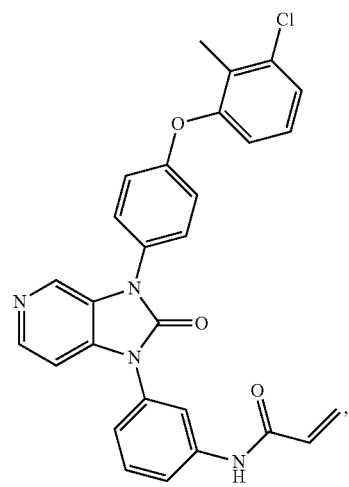
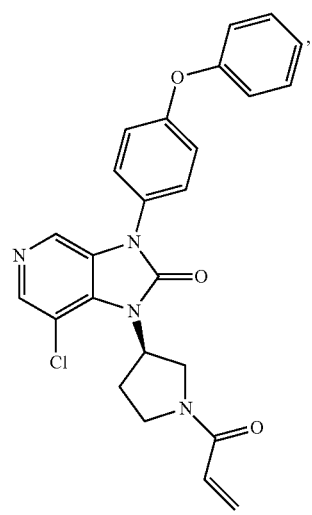
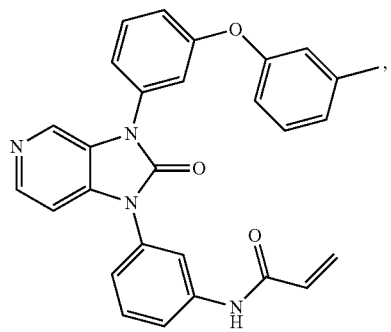

289
-continued
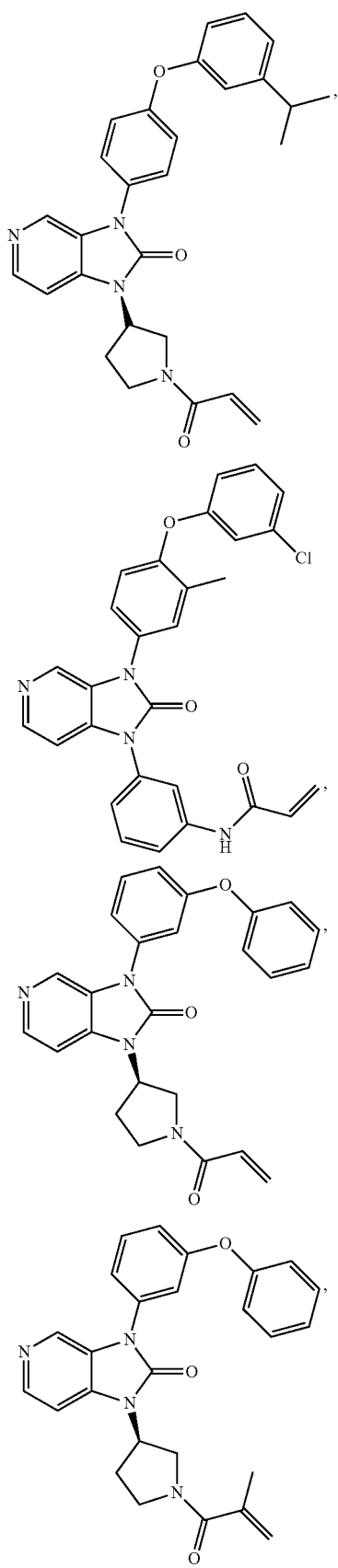
290
-continued
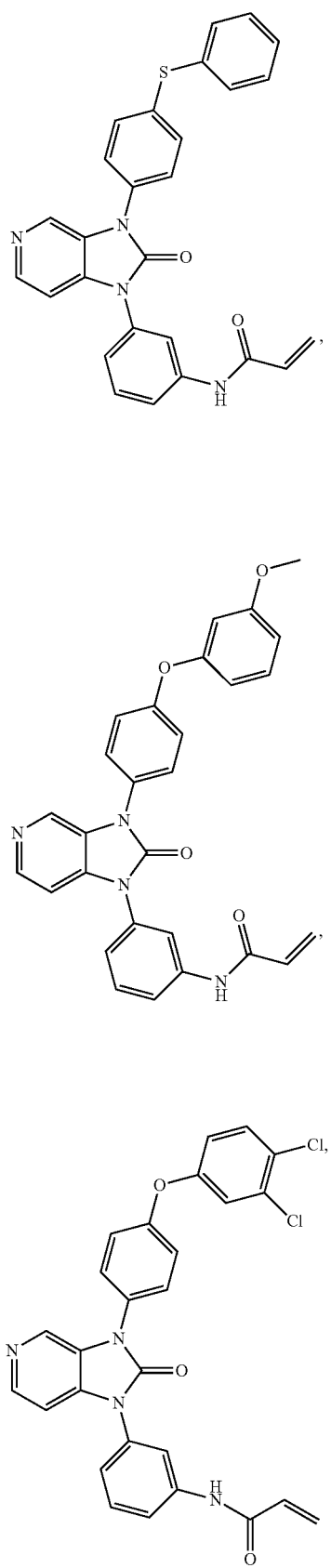

291
-continued
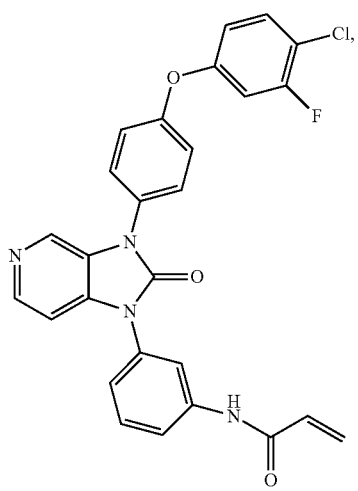
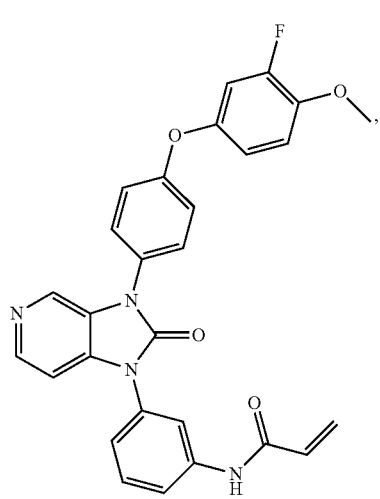
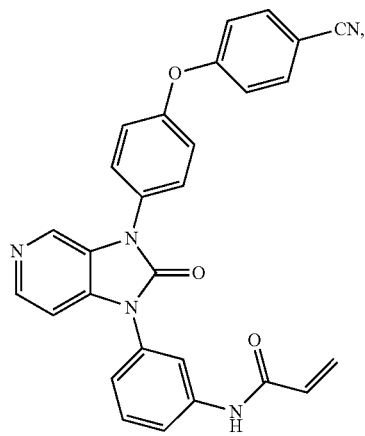
292
-continued
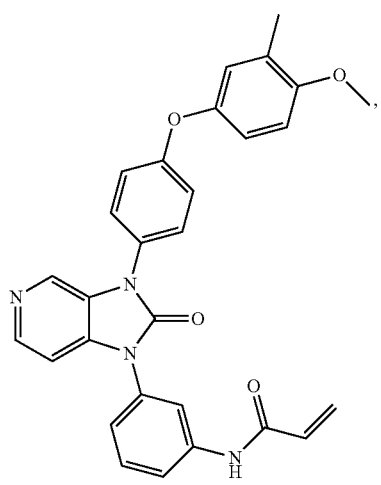
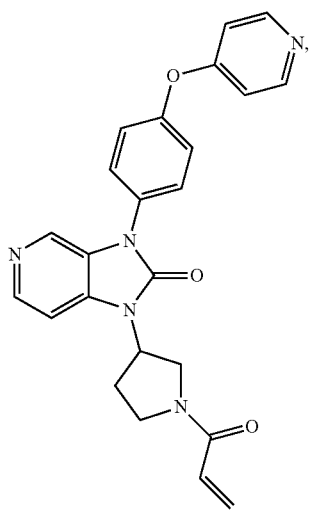
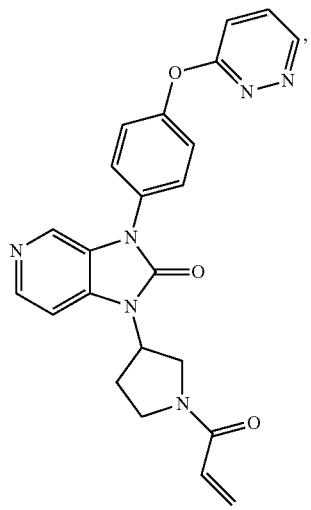

293
-continued
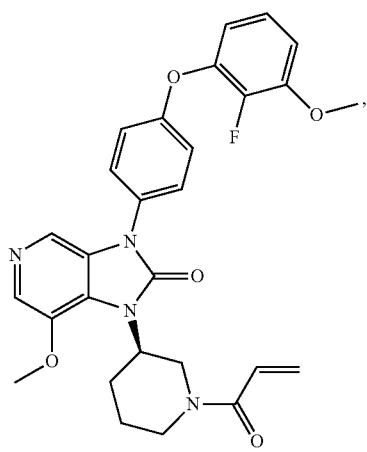
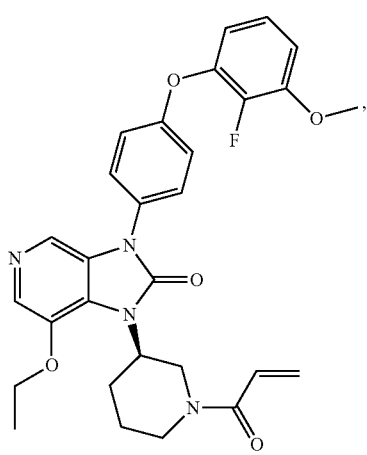
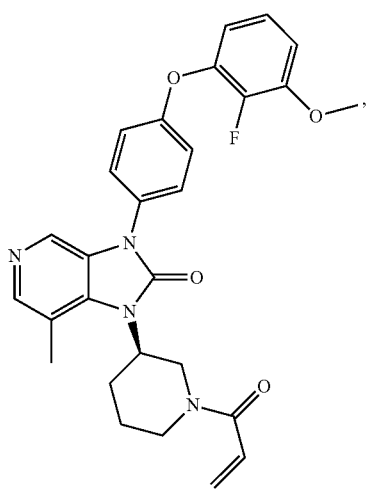
294
-continued
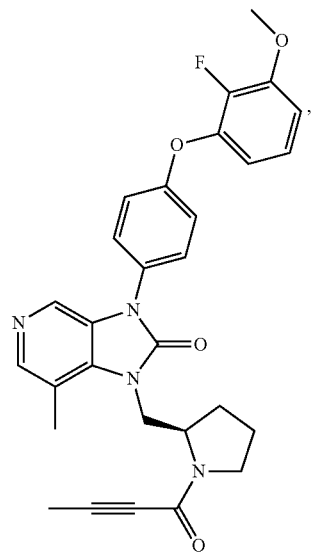
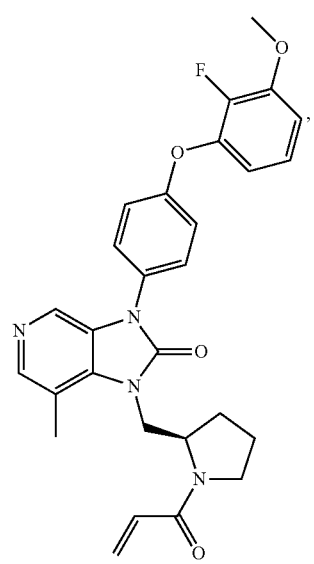
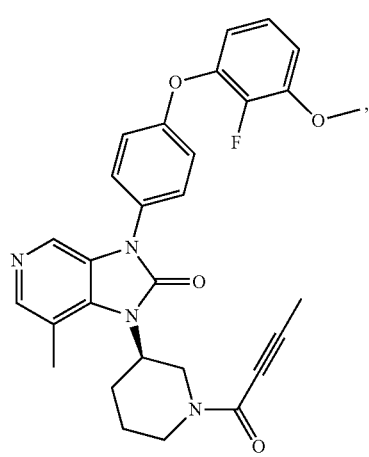

295
-continued
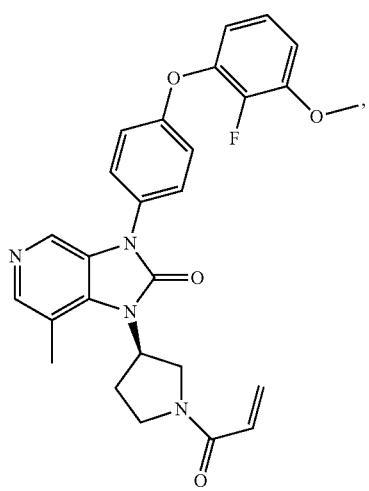
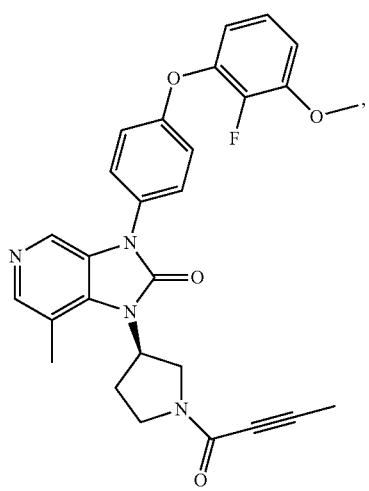
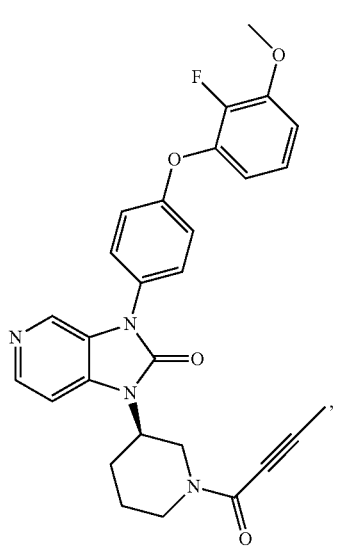
296
-continued
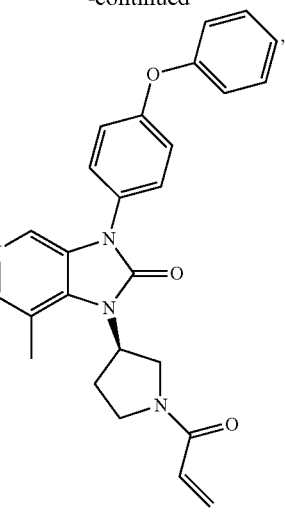
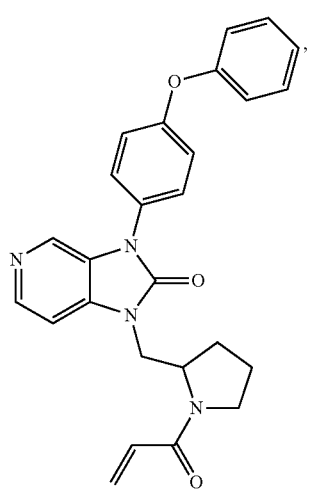
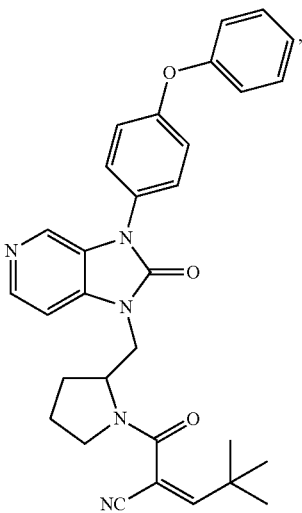

297
-continued
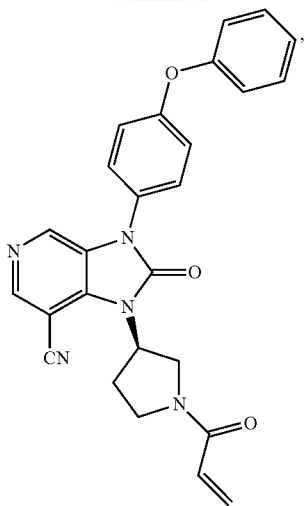
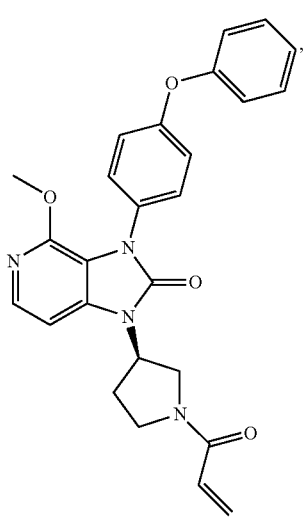
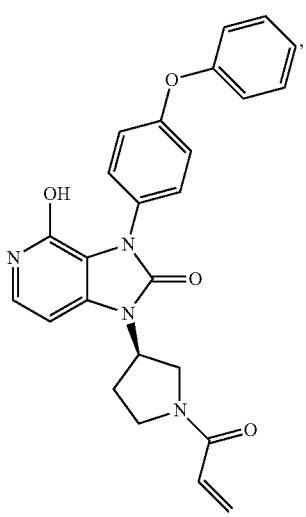
298
-continued
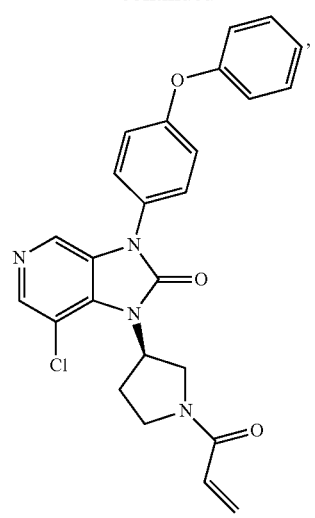
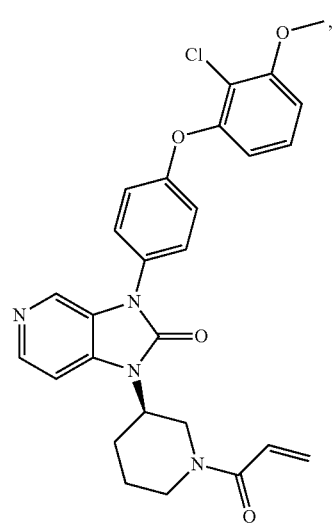
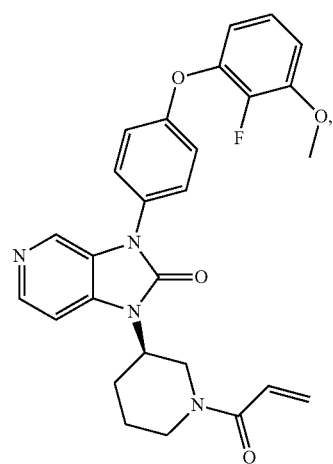

299
-continued
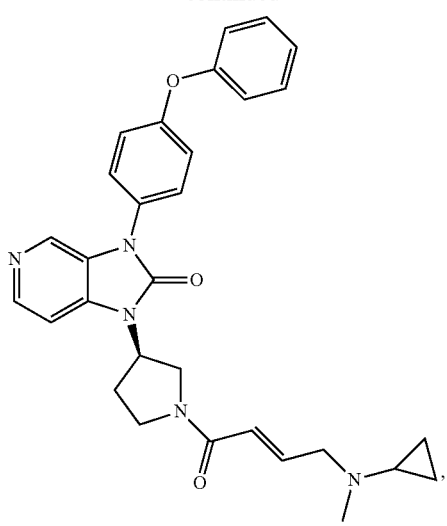
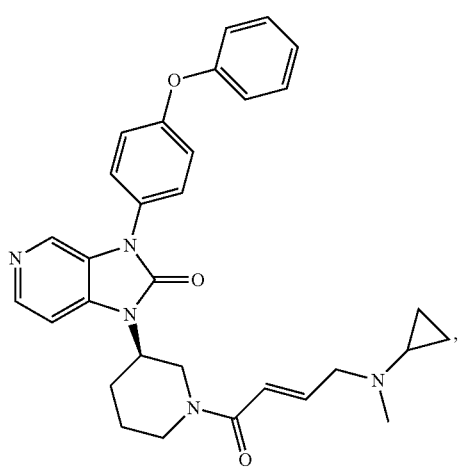
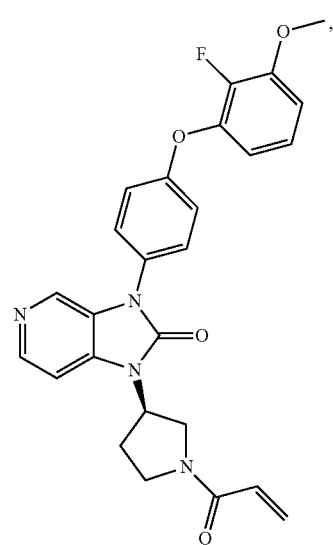
300
-continued
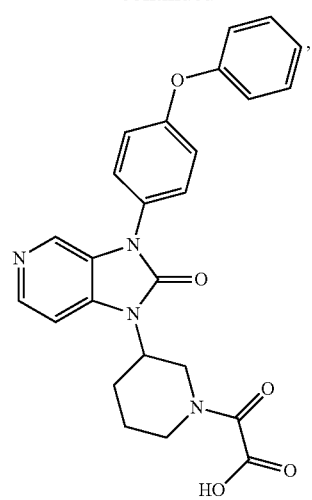
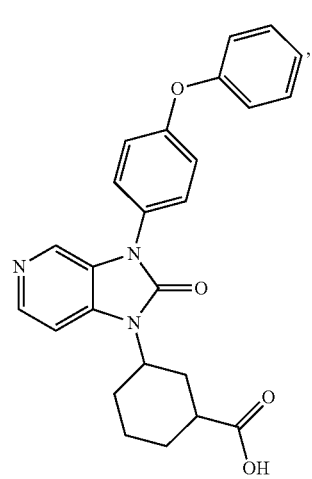
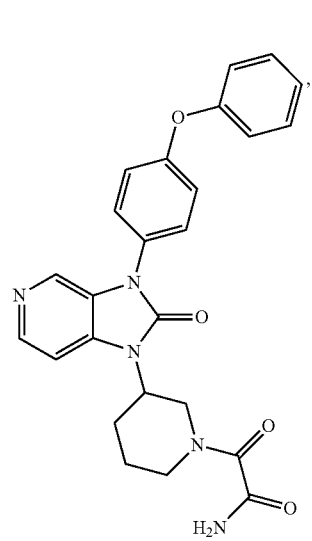

301
-continued
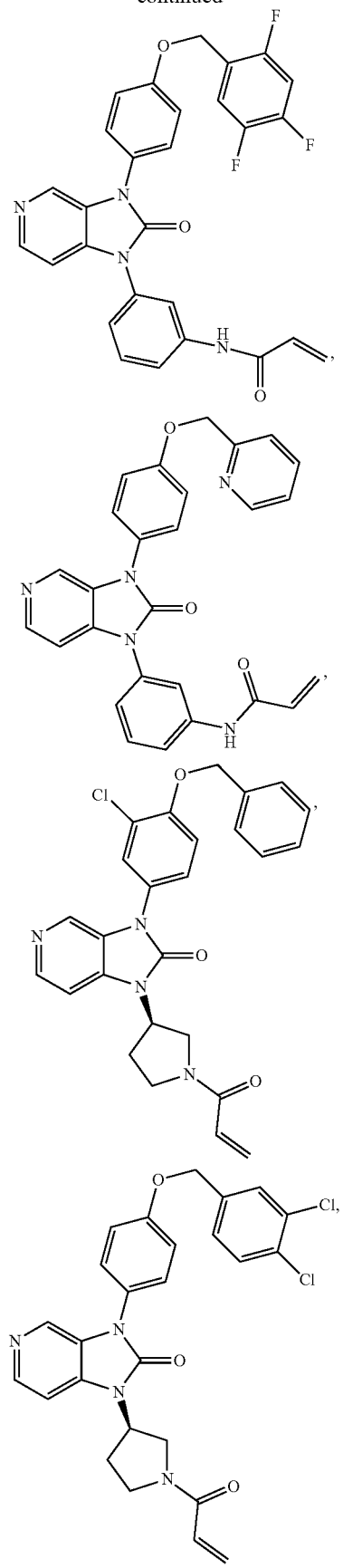
302
-continued
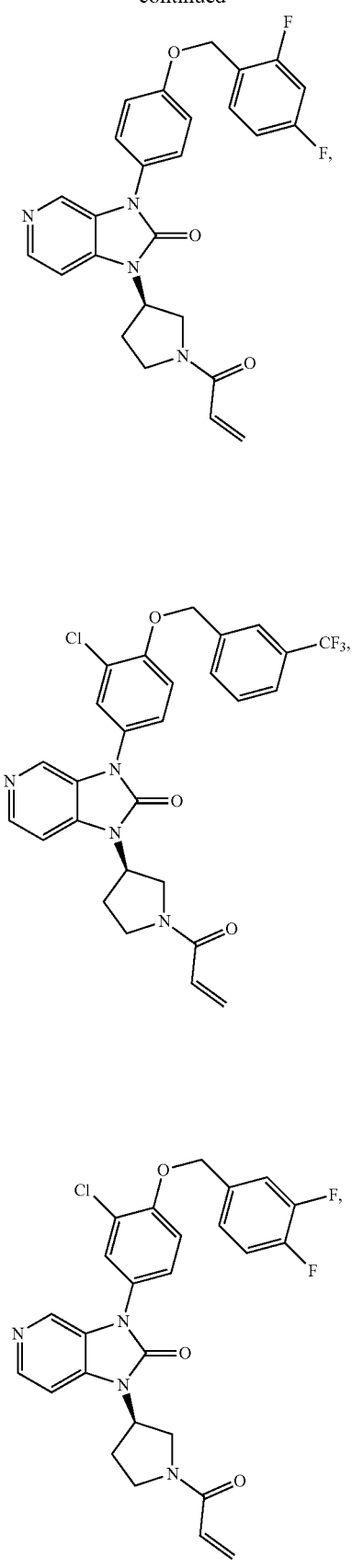

303
-continued
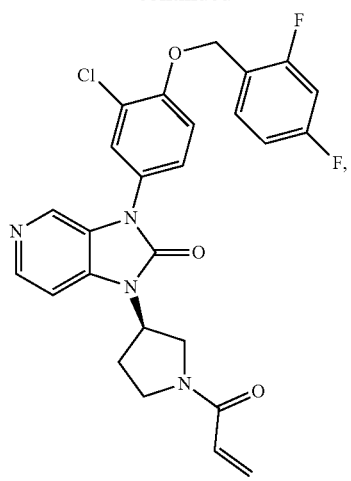
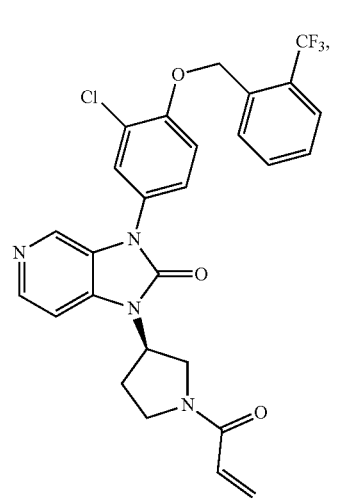
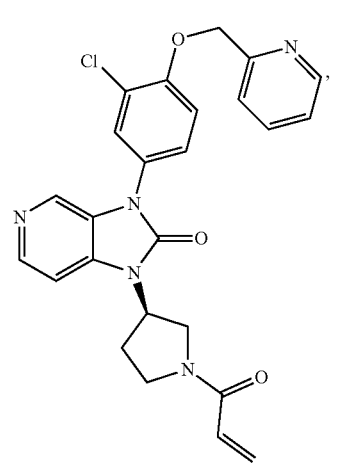
304
-continued
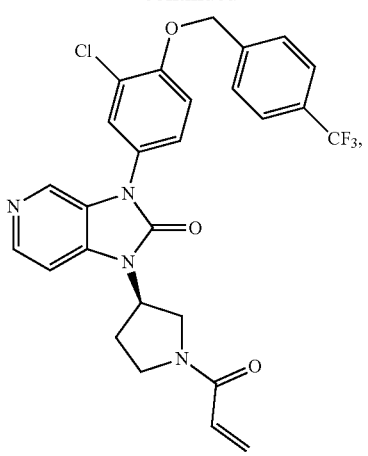
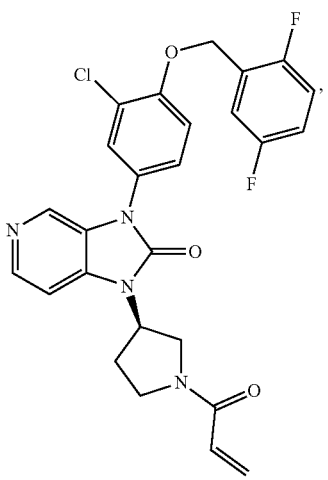
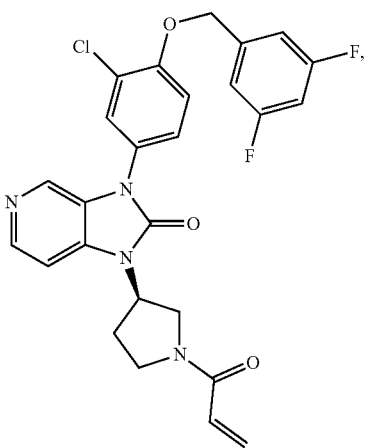

305
-continued
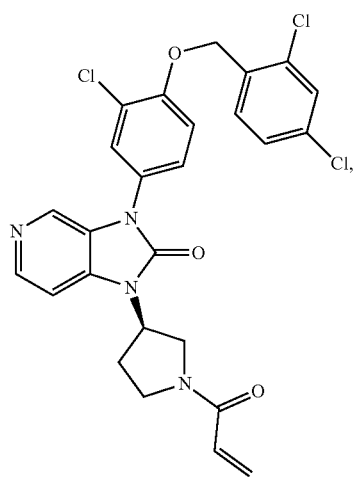
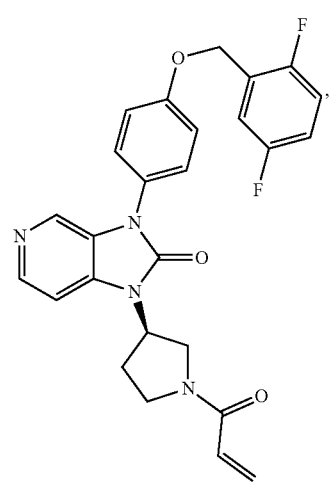
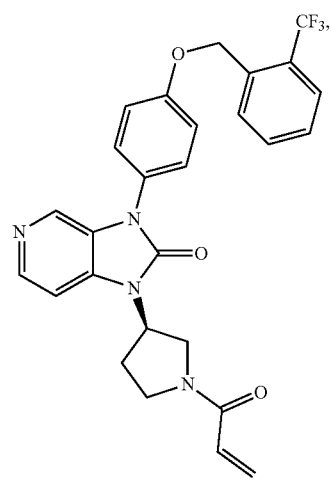
306
-continued
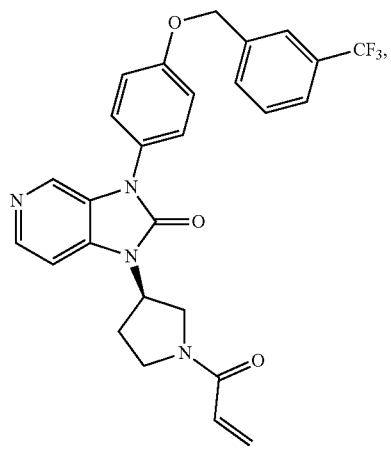
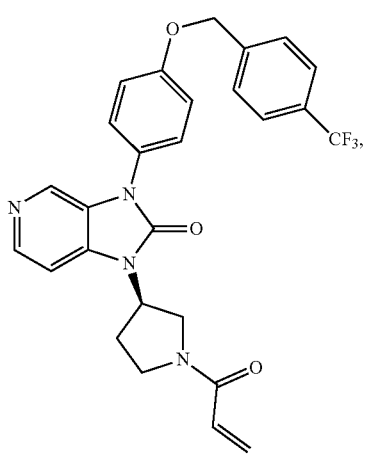
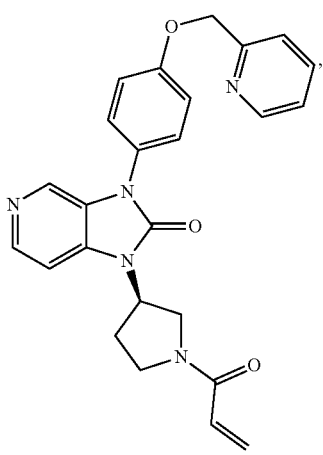

307
-continued
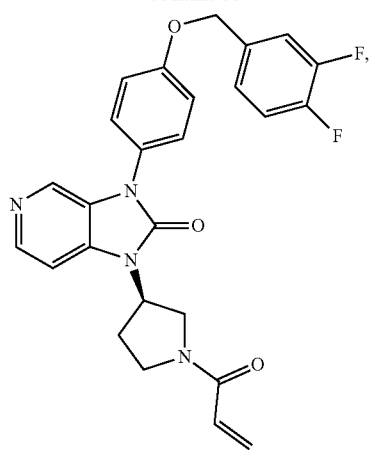
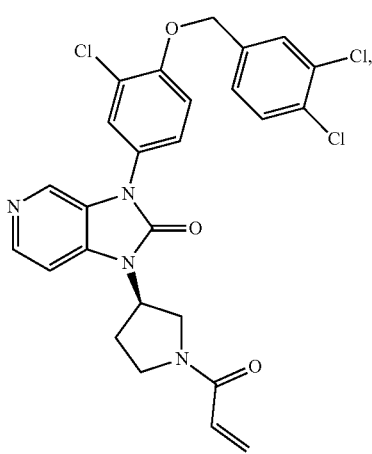
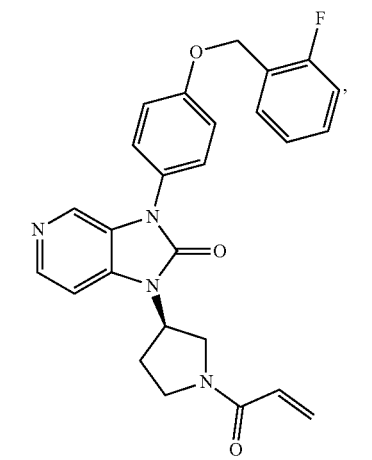
308
-continued
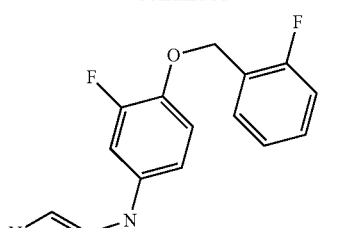
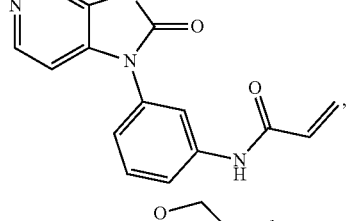
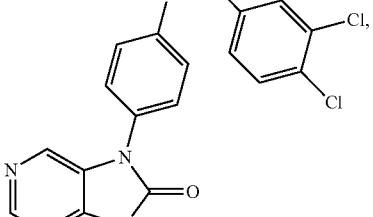
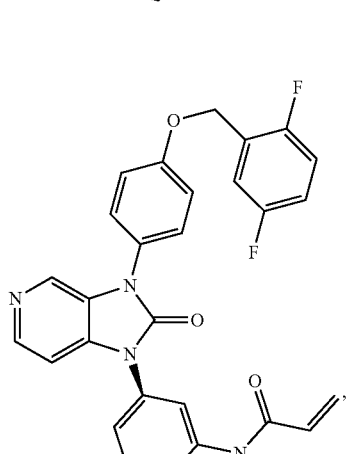

309
-continued
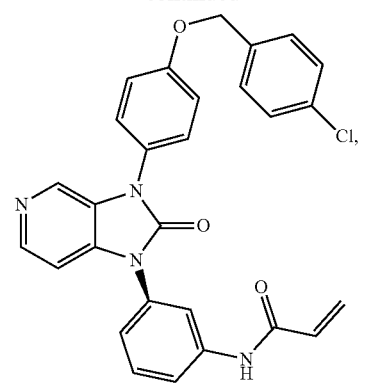
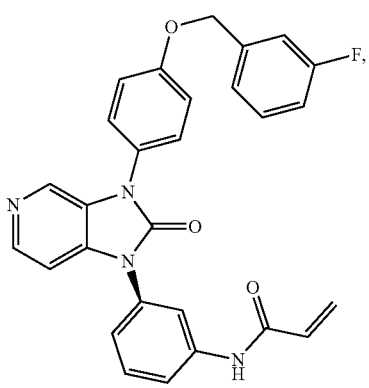
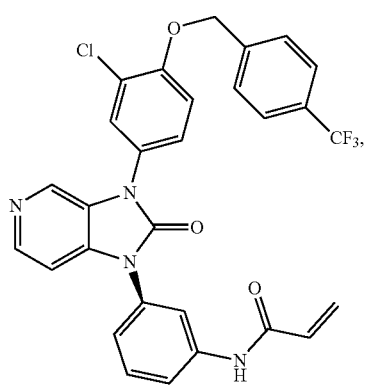
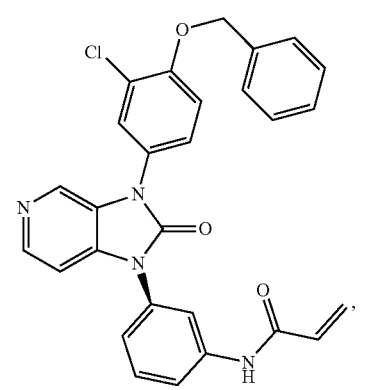
310
-continued
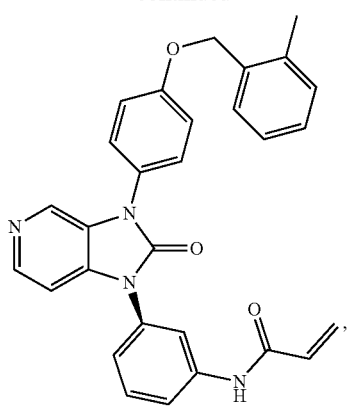
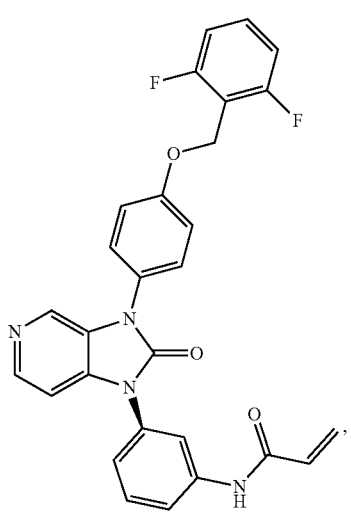
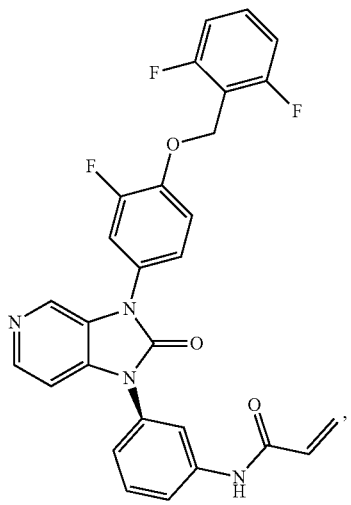

311
-continued
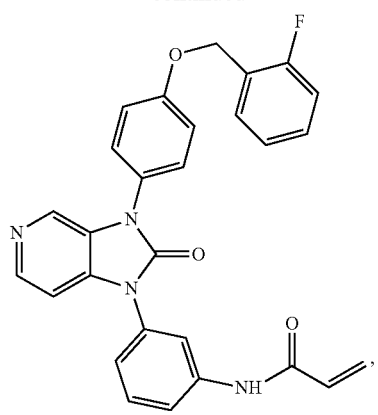
312
-continued
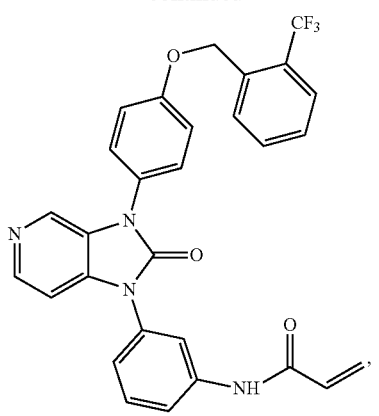
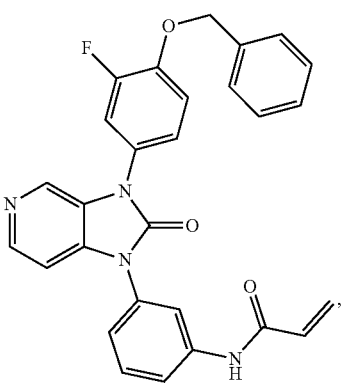
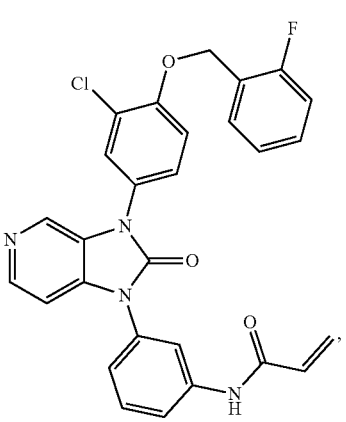

313
-continued
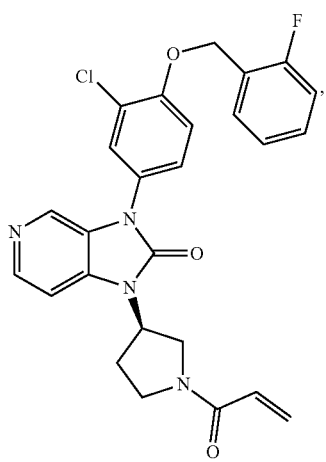
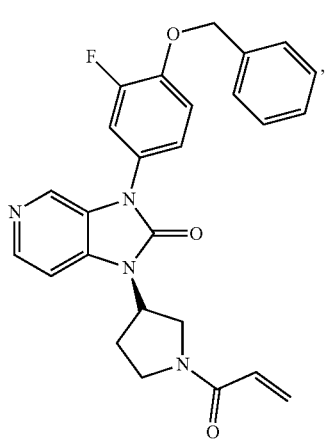
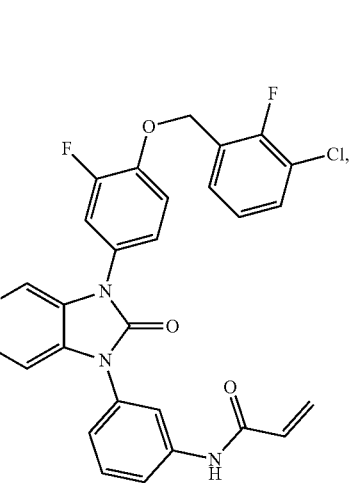
314
-continued
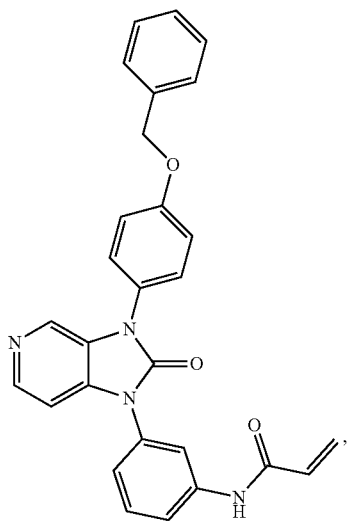
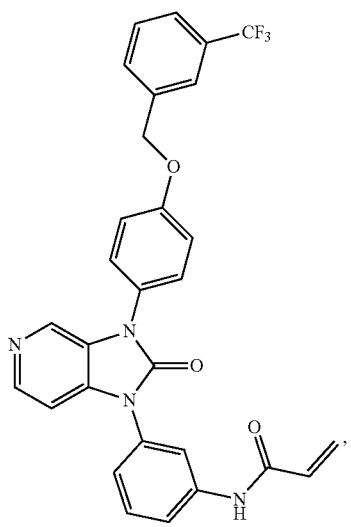
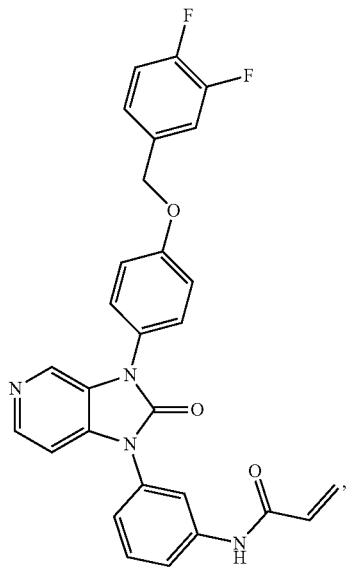

315
-continued
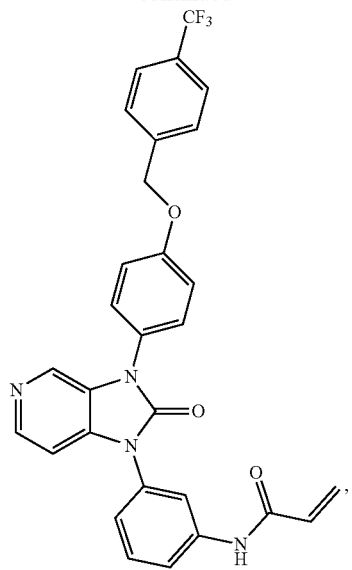
316
-continued
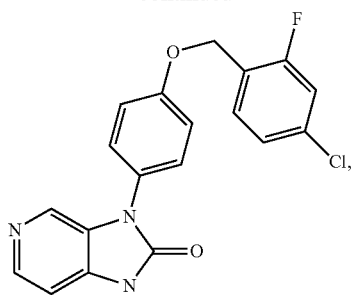
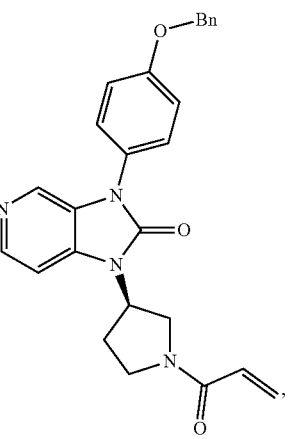
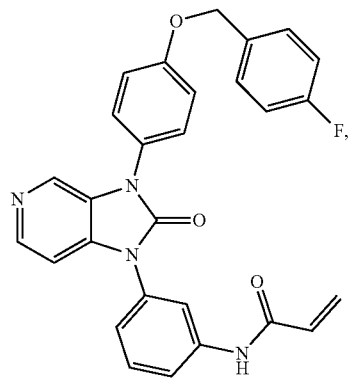
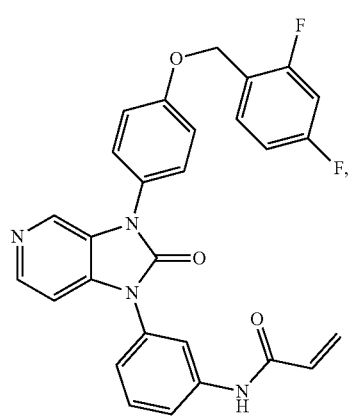

317
-continued
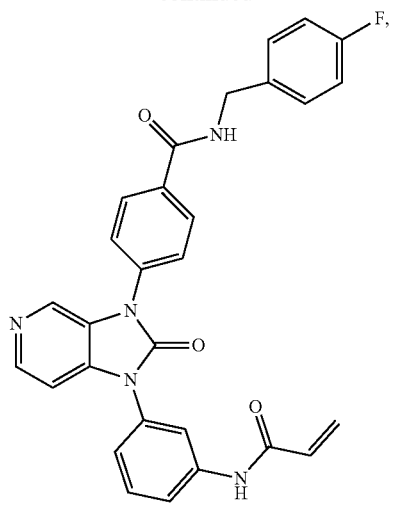
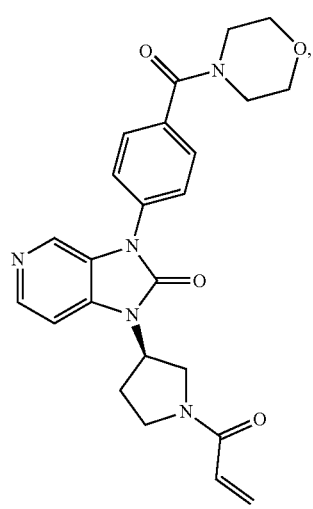
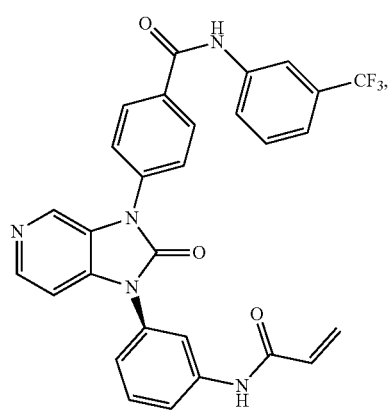
318
-continued
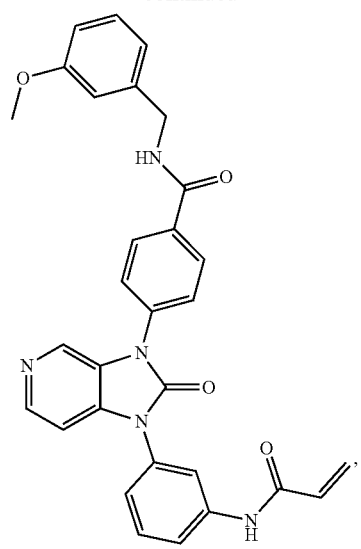
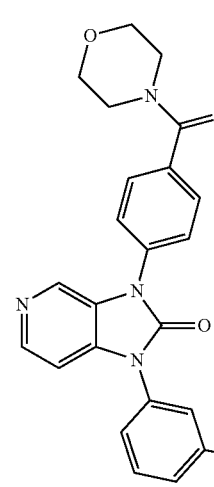
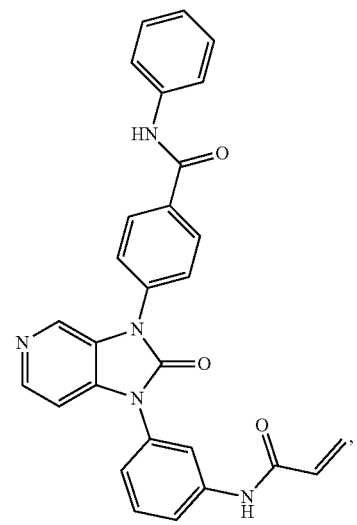

319
-continued
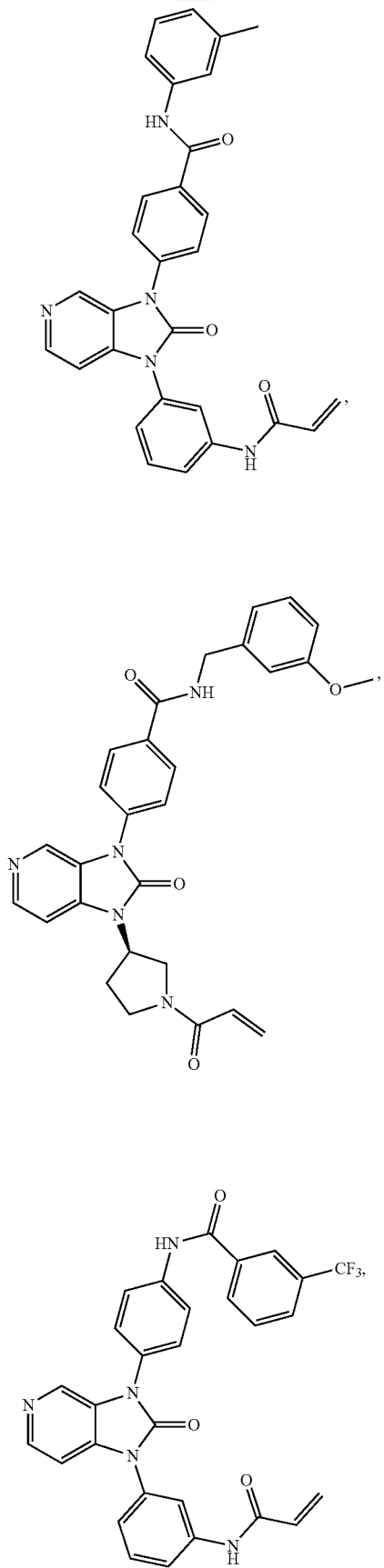
320
-continued
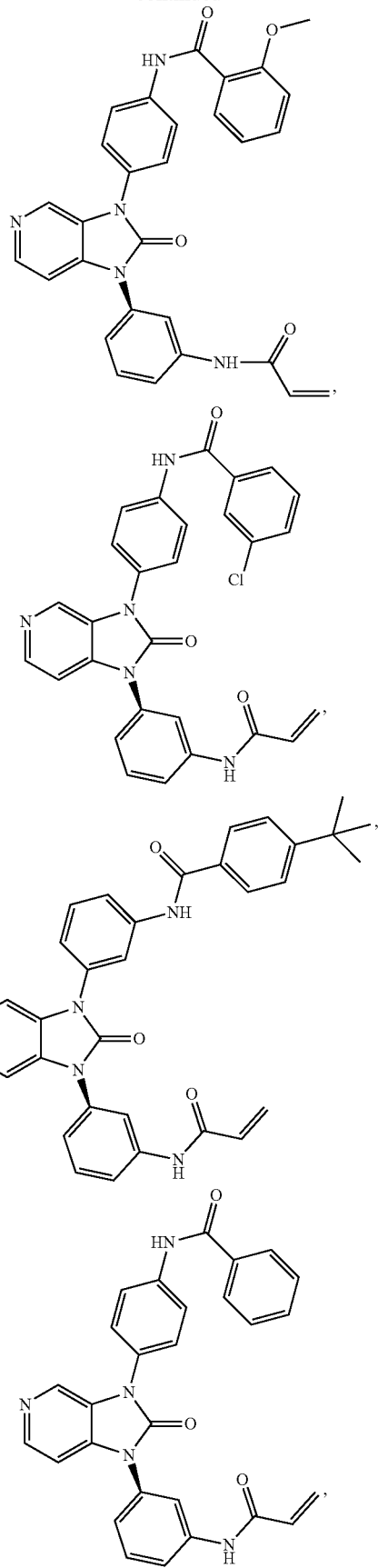

321
-continued
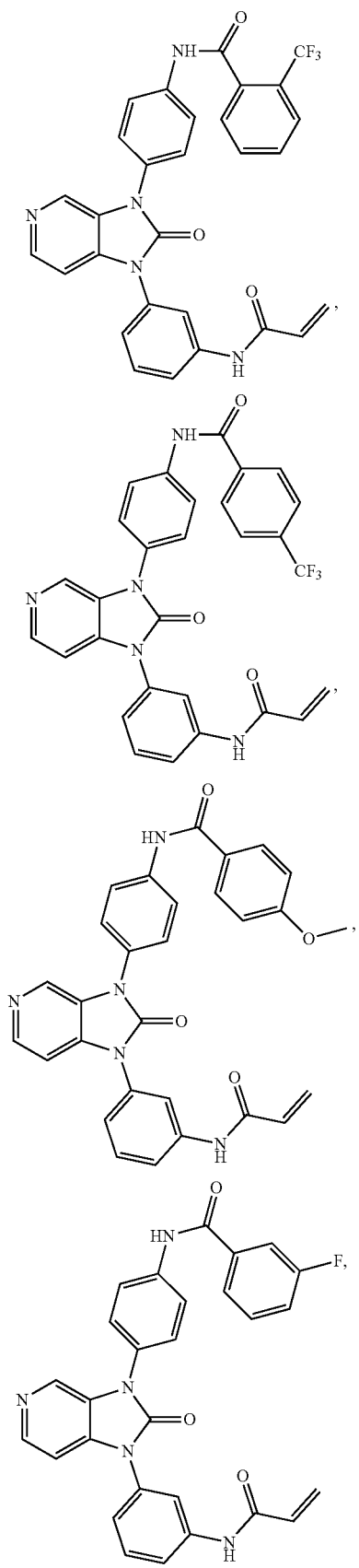
322
-continued
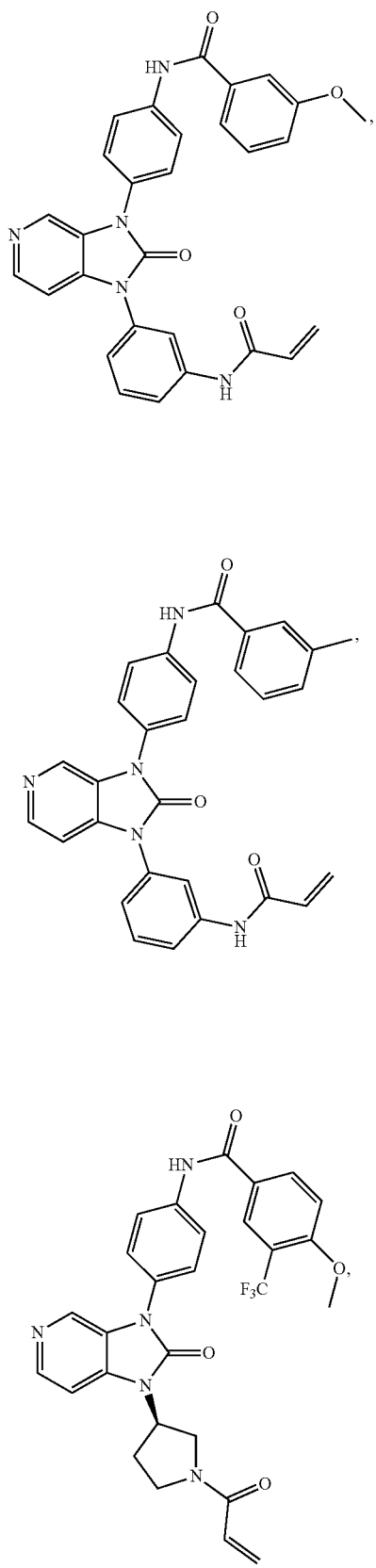

323
-continued
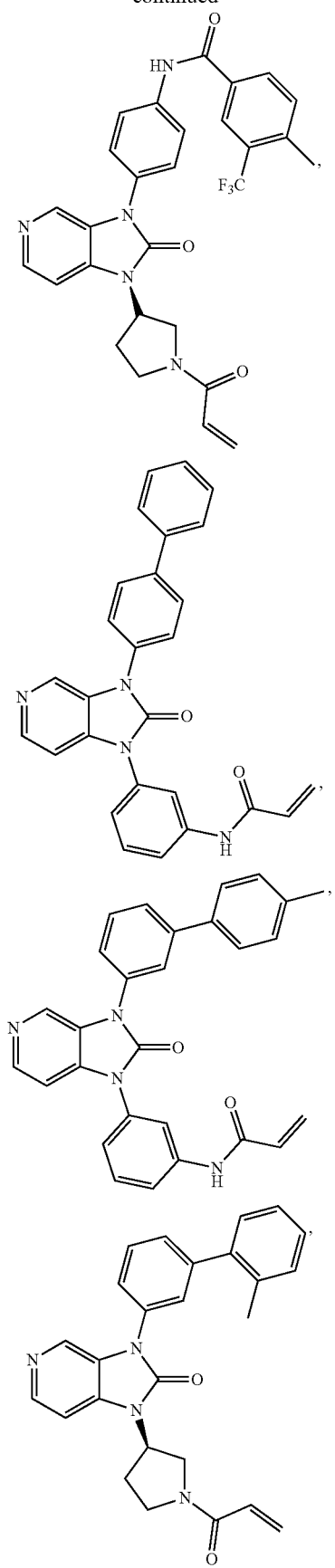
324
-continued
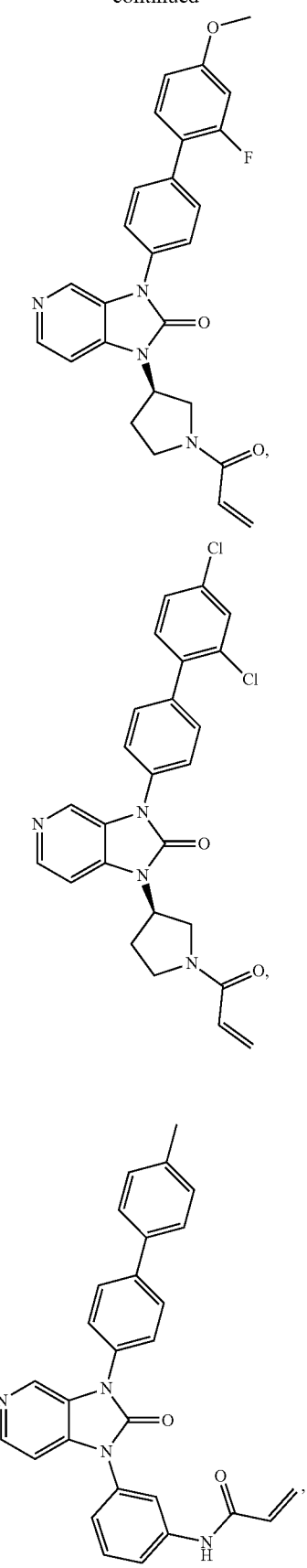

-continued
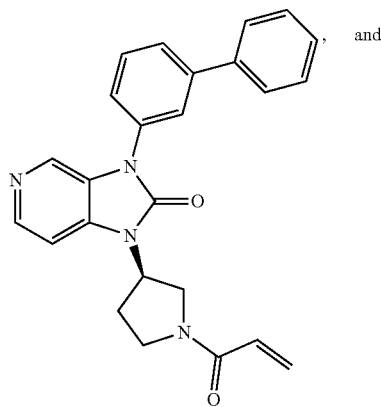, and
-continued
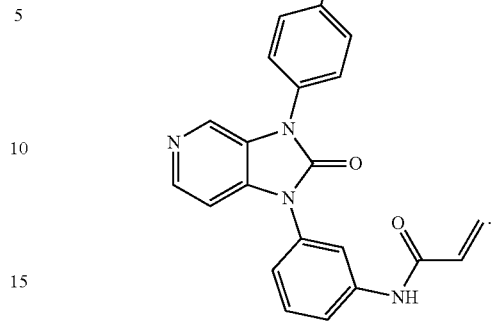.
6. A pharmaceutical composition comprising a therapeutically effective amount of the compound of claim 5, and a pharmaceutically acceptable excipient.
* * * * *